United States Patent
Brakenhoff et al.

(10) Patent No.: US 10,174,314 B2
(45) Date of Patent: Jan. 8, 2019

(54) MIRNA FOR TREATING HEAD AND NECK CANCER

(71) Applicants: INTERNA TECHNOLOGIES B.V., Nijmegen (NL); Vereniging Voor Christelijk Hoger Onderwijs, Wetenschappelijk Onderzoek En Patientenzorg, Amsterdam (NL)

(72) Inventors: Rudolf Henrikus Brakenhoff, Doorn (NL); Marlon Van Der Plas, Woerden (NL); Sanne Rosaly De Kemp, Woerden (NL); Willemijn Maria Gommans, Voorschoten (NL); Grégoire Pierre André Prevost, Antony (FR); Roeland Quirinus Jozef Schaapveld, Bussum (NL); Francesco Cerisoli, Rotterdam (NL)

(73) Assignees: INTERNA TECHNOLOGIES B.V., Nijmegen (NL); VERENIGING VOOR CHRISTELIJK HOGER ONDERWIJS, WETENSCHAPPELIJK ONDERZOEK EN PATIENTENZORG, Amsterdam (NL)

(*) Notice: Subject to any disclaimer, the term of this patent is extended or adjusted under 35 U.S.C. 154(b) by 223 days.

(21) Appl. No.: 14/367,837

(22) PCT Filed: Dec. 20, 2012

(86) PCT No.: PCT/NL2012/050905
§ 371 (c)(1),
(2) Date: Jun. 20, 2014

(87) PCT Pub. No.: WO2013/095132
PCT Pub. Date: Jun. 27, 2013

(65) Prior Publication Data
US 2015/0225716 A1    Aug. 13, 2015

Related U.S. Application Data

(60) Provisional application No. 61/579,191, filed on Dec. 22, 2011, provisional application No. 61/579,162, (Continued)

(30) Foreign Application Priority Data

Dec. 22, 2011    (EP) .................................... 11195240

(51) Int. Cl.
*C12N 15/11*    (2006.01)
*A61K 48/00*    (2006.01)
(Continued)

(52) U.S. Cl.
CPC .......... *C12N 15/113* (2013.01); *C12Q 1/6886* (2013.01); *C12N 2310/141* (2013.01);
(Continued)

(58) Field of Classification Search
CPC ............ C12N 15/113; C12N 2310/141; C12N 2320/31
(Continued)

(56) References Cited

U.S. PATENT DOCUMENTS

2012/0088687 A1*    4/2012    Goel ................... C12Q 1/6886
                                                                506/9

FOREIGN PATENT DOCUMENTS

WO    WO-2008008430 A2 *    1/2008    .......... C12Q 1/6809
WO    WO 2009/070653 A1 *    6/2009

OTHER PUBLICATIONS

Jiang et al. (Nucleic Acids Research, 2005 vol. 33:5394-5403, plus supplementary data).*
(Continued)

*Primary Examiner* — Terra C Gibbs
(74) *Attorney, Agent, or Firm* — Polsinelli PC; Christopher M. Cabral

(57) ABSTRACT

The invention relates to the diagnostic and therapeutic uses of a miRNA-323, miRNA-342, miRNA-326, miRNA-371, miRNA-3157 and/or miRNA-345 molecule, an equivalent or a source thereof in a disease and condition associated with
(Continued)

a squamous cell carcinoma such as head and neck cancer or a preneoplastic mucosal change.

2 Claims, 18 Drawing Sheets

Specification includes a Sequence Listing.

Related U.S. Application Data filed on Dec. 22, 2011, provisional application No. 61/579,229, filed on Dec. 22, 2011, provisional application No. 61/579,019, filed on Dec. 22, 2011, provisional application No. 61/579,160, filed on Dec. 22, 2011.

(51) Int. Cl.
*C07H 21/02* (2006.01)
*C07H 21/04* (2006.01)
*C12N 15/113* (2010.01)
*C12Q 1/6886* (2018.01)

(52) U.S. Cl.
CPC .  *C12Q 2600/136* (2013.01); *C12Q 2600/158* (2013.01); *C12Q 2600/178* (2013.01)

(58) Field of Classification Search
USPC .......................................... 514/44; 536/24.5
See application file for complete search history.

(56) References Cited

OTHER PUBLICATIONS

Ramdas et al. (Head Neck, 2009. vol. 31:642-654).*
Bandrés et al. (Mol Cancer. Jul. 19, 2006;5:29, pp. 1-10).*
Florida Hospital. Prevention of Glioma. Downloaded from https://www.floridahospital.com/glioma/prevention-glioma on Jul. 11, 2018.*
American Cancer Society. Can Colorectal Cancer Be Prevented? Downloaded from https://www.cancer.org/cancer/colon-rectal-cancer/causes-risks-prevention/prevention.html on Jul. 11, 2018.*
Lindenbergh-van der Plas (Clin Cancer Res; 1-11. 2013 AACR.).*
MedicineNet.com. Colon Cancer Causes, Treatment, Symptoms & Survival Rate. Downloaded from https://www.medicinenet.com/colon_cancer/article.htm on Aug. 2, 2018.*
Wikipedia. Colorectal Cancer. Downloaded from https://en.wikipedia.org/wiki/Colorectal_cancer on Aug. 2, 2018.*
Colorectal Cancer Alliance. What is Colorectal Cancer? Downloaded from https://www.ccalliance.org/colorectal-cancer-information/what-is-colorectal-cancer on Aug. 2, 2018.*
MedlinePlus. Colorectal Cancer| Colon Cancer | Rectal Cancer. Downloaded from https://medlineplus.gov/colorectalcancer.html on Aug. 2, 2018.*
LifeScience. Colon Cancer: Causes, Symptoms and Treatments. Downloaded from https://www.livescience.com/34716-colon-cancer-symptoms-colonoscopy.html on Aug. 2, 2018.*
Babu, J., et al., "A miR-centric View of Head and Neck Cancers," Biochimica et Biophysica Acta (BBA)—Reviews on Cancer, vol. 1816, No. 1, pp. 67-72 (Aug. 2011).
Liu, X., et al., "MicroRNA-138 Suppresses Invasion and Promotes Apoptosis in Head and Neck Squamous Cell Carcinoma Cell Lines," Cancer Letters, vol. 286, No. 2, pp. 217-222 (Dec. 2009).
Perez-Sayas, M., et al., "Current Trends in miRNAs and Their Relationship with Oral Squamous Cell Carcinoma," Journal of Oral Pathology and Medicine, pp. 1-11 (Dec. 1, 2011).
Chen, L., et al., "MicroRNA as a Novel Modulator in Head and Neck Squamous Carcinoma", Journal of Oncology, vol. 2010, pp. 1-15 (Jan. 1, 2010).
Lo, W., et al., "MicroRNA-200c Attenuates Tumour Growth and Metastasis of Presumptive Head and Neck Squamous Cell Carcinoma Stem Cells," The Journal of Pathology, vol. 223, No. 4, pp. 482-495 (Mar. 1, 2011).
Shin, K., et al., "miR-181a Shows Tumor Suppressive Effect Against Oral Squamous Cell Carcinoma Cells by Downregulating K-ras," Biochemical and Biophysical Research Communications, vol. 404, No. 4, pp. 896-902 (2011).
International Search Report of PCT/NL2012/050905 dated May 15, 2013.

* cited by examiner

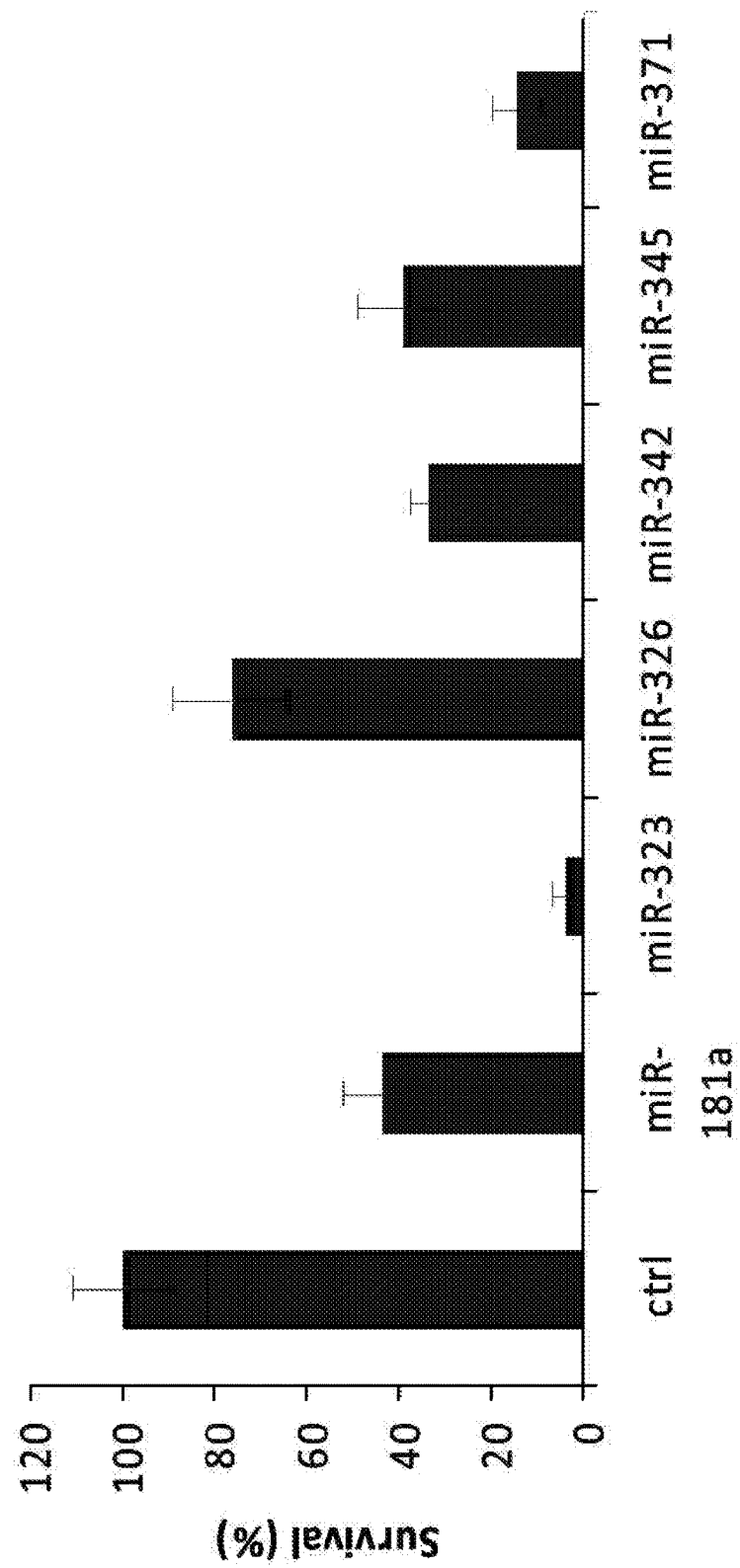

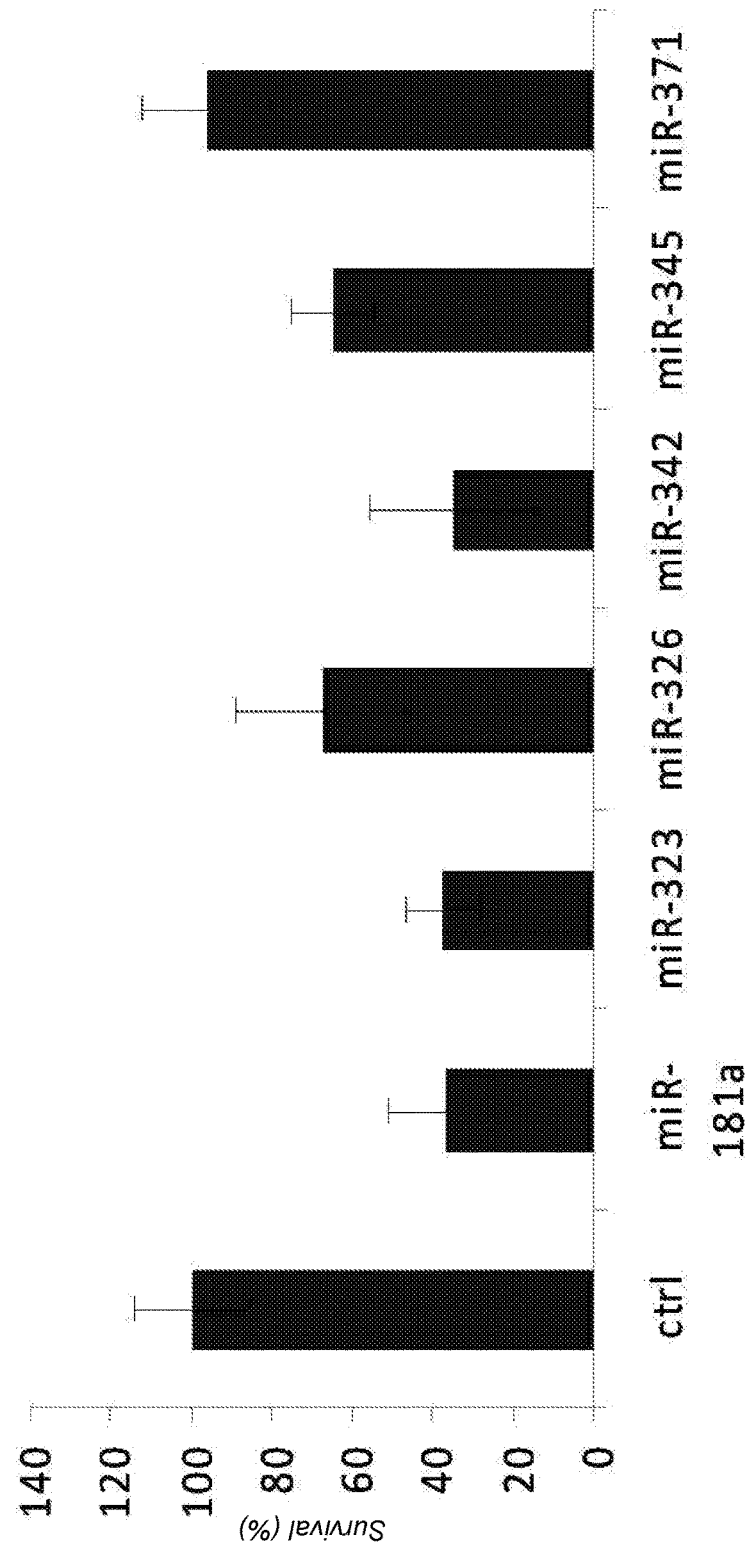

| | miR-181a | miR-326 | miR-371 | miR-345 | miR-323 | miR-342 |
|---|---|---|---|---|---|---|
| miR-181a | 1.000 | | | | | |
| miR-326 | 0.572 | 1.000 | | | | |
| miR-371 | 0.113 | 0.119 | 1.000 | | | |
| miR-345 | 0.373 | 0.573 | 0.158 | 1.000 | | |
| miR-323 | 0.099 | 0.087 | 0.602 | 0.170 | 1.000 | |
| miR-342 | 0.074 | 0.065 | 0.388 | 0.123 | 0.577 | 1.000 |

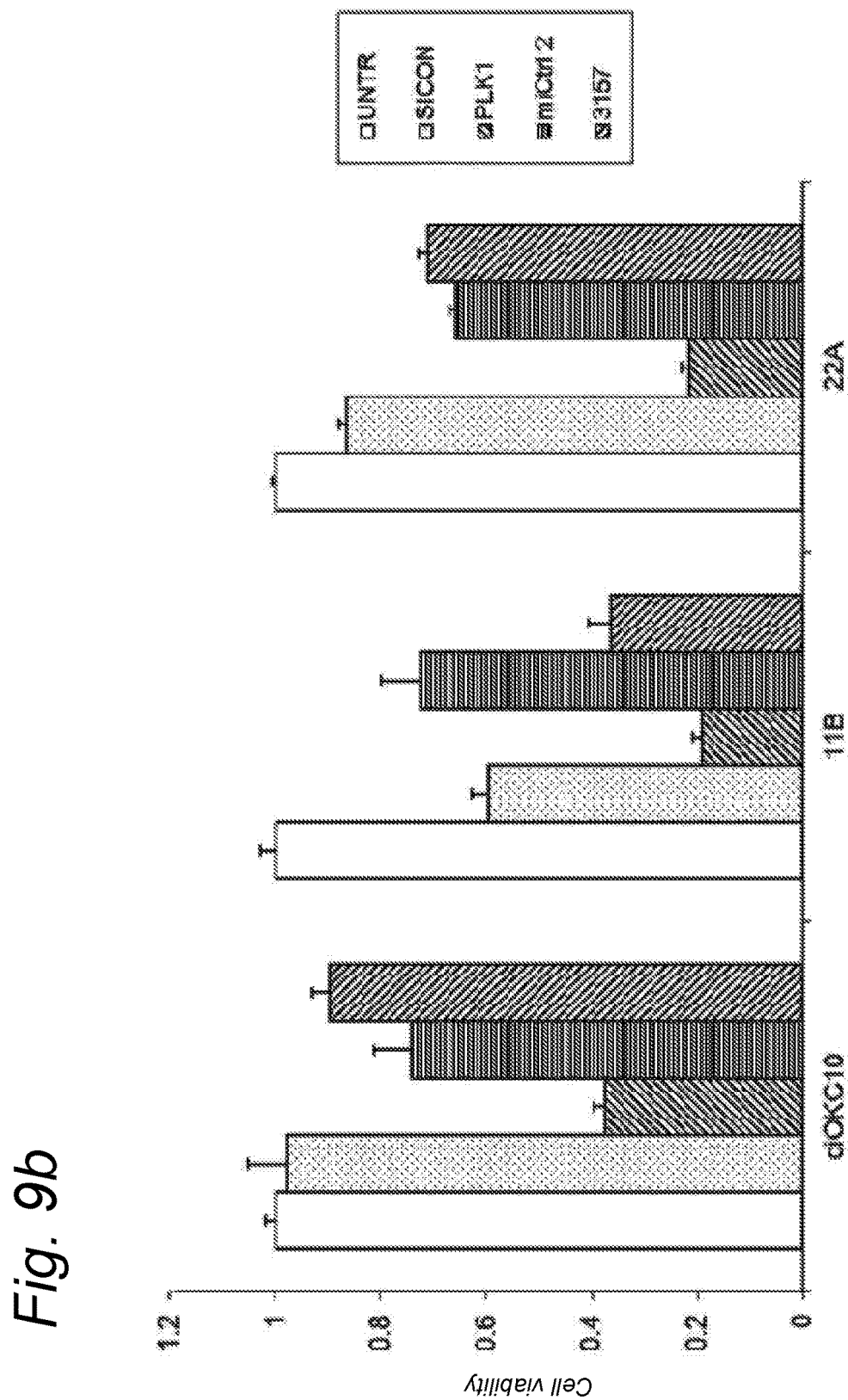

SEQUENCE LISTING

<160> NUMBER OF SEQ ID NOS: 372

<210> SEQ ID NO 1
<211> LENGTH: 110
<212> TYPE: RNA
<213> ORGANISM: Artificial
<220> FEATURE:
<223> OTHER INFORMATION: Precursor sequence

<400> SEQUENCE: 1
ugaguuuuga gguugcuuca gugaacauuc aacgcugucg gugaguuugg aauuaaaauc    60
aaaaccaucg accguugauu guacccuaug gcuaaccauc aucuacucca    110

<210> SEQ ID NO 2
<211> LENGTH: 110
<212> TYPE: RNA
<213> ORGANISM: Artificial
<220> FEATURE:
<223> OTHER INFORMATION: Precursor sequence

<400> SEQUENCE: 2
agaagggcua ucaggccagc cuucagagga cuccaaggaa cauucaacgc ugucggugag    60
uuugggauuu gaaaaaacca cugaccguug acuguaccuu gggguccuua    110

<210> SEQ ID NO 3
<211> LENGTH: 86
<212> TYPE: RNA
<213> ORGANISM: Artificial
<220> FEATURE:
<223> OTHER INFORMATION: Precursor sequence

<400> SEQUENCE: 3
uugguacuug gagagaggug guccguggcg cguucgcuuu auuuauggcg cacauuacac    60
ggucgaccuc uuugcaguau cuaauc    86

<210> SEQ ID NO 4
<211> LENGTH: 95
<212> TYPE: RNA
<213> ORGANISM: Artificial
<220> FEATURE:
<223> OTHER INFORMATION: Precursor sequence

<400> SEQUENCE: 4
cucaucuguc uguugggcug gaggcagggc cuuugugaag gcgggugguu cucagaucgc    60

```
cucugggccc uuccuccagc cccgaggcgg auuca                                95
```

<210> SEQ ID NO 5
<211> LENGTH: 99
<212> TYPE: RNA
<213> ORGANISM: Artificial
<220> FEATURE:
<223> OTHER INFORMATION: Precursor sequence

<400> SEQUENCE: 5

```
gaaacugggc ucaaggugag gggugcuauc ugugauugag ggacaugguu aauggaauug    60
ucucacacag aaaucgcacc cgucaccuug gccuacuua                           99
```

<210> SEQ ID NO 6
<211> LENGTH: 98
<212> TYPE: RNA
<213> ORGANISM: Artificial
<220> FEATURE:
<223> OTHER INFORMATION: Precursor sequence

<400> SEQUENCE: 6

```
acccaaaccc uaggucugcu gacuccuagu ccagggcucg ugauggcugg ugggcccuga    60
acgagggguc uggaggccug gguuugaaua ucgacagc                            98
```

<210> SEQ ID NO 7
<211> LENGTH: 67
<212> TYPE: RNA
<213> ORGANISM: Artificial
<220> FEATURE:
<223> OTHER INFORMATION: Precursor sequence

<400> SEQUENCE: 7

```
guggcacuca aacugugggg gcacuuucug cucucuggug aaagugccgc caucuuuuga    60
guguuac                                                              67
```

<210> SEQ ID NO 8
<211> LENGTH: 7
<212> TYPE: RNA
<213> ORGANISM: Artificial
<220> FEATURE:
<223> OTHER INFORMATION: Seed sequence

<400> SEQUENCE: 8

```
acauuca                                                               7
```

<210> SEQ ID NO 9
<211> LENGTH: 7
<212> TYPE: RNA
<213> ORGANISM: Artificial
<220> FEATURE:
<223> OTHER INFORMATION: Seed sequence

<400> SEQUENCE: 9

```
ccaucga                                                               7
```

<210> SEQ ID NO 10
<211> LENGTH: 7
<212> TYPE: RNA
<213> ORGANISM: Artificial
<220> FEATURE:
<223> OTHER INFORMATION: Seed sequence

<400> SEQUENCE: 10

```
ccacuga                                                               7
```

```
<210> SEQ ID NO 11
<211> LENGTH: 7
<212> TYPE: RNA
<213> ORGANISM: Artificial
<220> FEATURE:
<223> OTHER INFORMATION: Seed sequence

<400> SEQUENCE: 11 ggugguc                                                                    7

<210> SEQ ID NO 12
<211> LENGTH: 7
<212> TYPE: RNA
<213> ORGANISM: Artificial
<220> FEATURE:
<223> OTHER INFORMATION: Seed sequence

<400> SEQUENCE: 12 acauuac                                                                    7

<210> SEQ ID NO 13
<211> LENGTH: 7
<212> TYPE: RNA
<213> ORGANISM: Artificial
<220> FEATURE:
<223> OTHER INFORMATION: Seed sequence

<400> SEQUENCE: 13 cucuggg                                                                    7

<210> SEQ ID NO 14
<211> LENGTH: 7
<212> TYPE: RNA
<213> ORGANISM: Artificial
<220> FEATURE:
<223> OTHER INFORMATION: Seed sequence

<400> SEQUENCE: 14 ggggugc                                                                    7

<210> SEQ ID NO 15
<211> LENGTH: 7
<212> TYPE: RNA
<213> ORGANISM: Artificial
<220> FEATURE:
<223> OTHER INFORMATION: Seed sequence

<400> SEQUENCE: 15 cucacac                                                                    7

<210> SEQ ID NO 16
<211> LENGTH: 7
<212> TYPE: RNA
<213> ORGANISM: Artificial
<220> FEATURE:
<223> OTHER INFORMATION: Seed sequence

<400> SEQUENCE: 16 cugacuc                                                                    7

<210> SEQ ID NO 17
<211> LENGTH: 7
<212> TYPE: RNA
<213> ORGANISM: Artificial
<220> FEATURE:
```

```
<223> OTHER INFORMATION: Seed sequence

<400> SEQUENCE: 17 cucaaac                                                                  7

<210> SEQ ID NO 18
<211> LENGTH: 7
<212> TYPE: RNA
<213> ORGANISM: Artificial
<220> FEATURE:
<223> OTHER INFORMATION: Seed sequence

<400> SEQUENCE: 18 agugccg                                                                  7

<210> SEQ ID NO 19
<211> LENGTH: 23
<212> TYPE: RNA
<213> ORGANISM: Artificial
<220> FEATURE:
<223> OTHER INFORMATION: Mature sequence

<400> SEQUENCE: 19
aacauucaac gcugucggug agu                                               23

<210> SEQ ID NO 20
<211> LENGTH: 22
<212> TYPE: RNA
<213> ORGANISM: Artificial
<220> FEATURE:
<223> OTHER INFORMATION: Mature sequence

<400> SEQUENCE: 20
accaucgacc guugauugua cc                                                22

<210> SEQ ID NO 21
<211> LENGTH: 22
<212> TYPE: RNA
<213> ORGANISM: Artificial
<220> FEATURE:
<223> OTHER INFORMATION: Mature sequence

<400> SEQUENCE: 21
accacugacc guugacugua cc                                                22

<210> SEQ ID NO 22
<211> LENGTH: 22
<212> TYPE: RNA
<213> ORGANISM: Artificial
<220> FEATURE:
<223> OTHER INFORMATION: Mature sequence

<400> SEQUENCE: 22
aggugguccg uggcgcguuc gc                                                22

<210> SEQ ID NO 23
<211> LENGTH: 21
<212> TYPE: RNA
<213> ORGANISM: Artificial
<220> FEATURE:
<223> OTHER INFORMATION: Mature sequence

<400> SEQUENCE: 23
cacauuacac ggucgaccuc u                                                 21
```

```
<210> SEQ ID NO 24
<211> LENGTH: 20
<212> TYPE: RNA
<213> ORGANISM: Artificial
<220> FEATURE:
<223> OTHER INFORMATION: Mature sequence

<400> SEQUENCE: 24
ccucugggcc cuuccuccag                                               20

<210> SEQ ID NO 25
<211> LENGTH: 21
<212> TYPE: RNA
<213> ORGANISM: Artificial
<220> FEATURE:
<223> OTHER INFORMATION: Mature sequence

<400> SEQUENCE: 25
aggggugcua ucugugauug a                                             21

<210> SEQ ID NO 26
<211> LENGTH: 23
<212> TYPE: RNA
<213> ORGANISM: Artificial
<220> FEATURE:
<223> OTHER INFORMATION: Mature sequence

<400> SEQUENCE: 26
ucucacacag aaaucgcacc cgu                                           23

<210> SEQ ID NO 27
<211> LENGTH: 22
<212> TYPE: RNA
<213> ORGANISM: Artificial
<220> FEATURE:
<223> OTHER INFORMATION: Mature sequence

<400> SEQUENCE: 27
gcugacuccu aguccagggc uc                                            22

<210> SEQ ID NO 28
<211> LENGTH: 20
<212> TYPE: RNA
<213> ORGANISM: Artificial
<220> FEATURE:
<223> OTHER INFORMATION: Mature sequence

<400> SEQUENCE: 28
acucaaacug uggggggcacu                                              20

<210> SEQ ID NO 29
<211> LENGTH: 23
<212> TYPE: RNA
<213> ORGANISM: Artificial
<220> FEATURE:
<223> OTHER INFORMATION: Mature sequence

<400> SEQUENCE: 29
aagugccgcc aucuuuugag ugu                                           23

<210> SEQ ID NO 30
<211> LENGTH: 486
<212> TYPE: DNA
<213> ORGANISM: Artificial
<220> FEATURE:
<223> OTHER INFORMATION: Sequence cloned in lentiviral vector
```

<400> SEQUENCE: 30

```
ctgcacagtc tatcccacag ttcattagtt ctctgctgca cacaaattga ttttataatt      60
taaatactct cgacttgaaa cccagagagg aatgtaagag catccatcag cggtggtctc     120
actgctcact ggttcttggg atgtggatgg gagaatgaag aagggctatc aggccagcct     180
tcagaggact ccaaggaaca ttcaacgctg tcggtgagtt tgggatttga aaaaaccact     240
gaccgttgac tgtaccttgg ggtccttaca gacgacacta catttcctga agcaaaagag     300
caagctgtac cttcacatgt cacatgagtt caccagaaat ggtcctgcaa tcccccaaat     360
gtggtccagt gaattttatt cctactgctc actgttcctt gctttctgtt gtgtgtttta     420
ttattatttg tttgttttta caaaaaagt gtttcatttc aacaaggtaa ggagcagtcc     480
atgatg                                                                486
```

<210> SEQ ID NO 31
<211> LENGTH: 483
<212> TYPE: DNA
<213> ORGANISM: Artificial
<220> FEATURE:
<223> OTHER INFORMATION: Sequence cloned in lentiviral vector

<400> SEQUENCE: 31

```
ttcctggtat ttgaagatgc ggttgaccat ggtgtgtacg ctttatttgt gacgtaggac      60
acatggtcta cttcttctca atatcacatc tcgccttgga agacttccag gaggtgatat     120
cagctttgcg gaagagccac tgtcctggtg tcagtacggc tgctgcttgg tacttggaga     180
gaggtggtcc gtggcgcgtt cgctttttt atggcgcaca ttacacggtc gacctctttg      240
cagtatctaa tcccgccttg caagctttcc tggagctaac atcaactgcg gggtgggg      300
ccactaggtc tgcgctcagt gcgacccagc ggggtttgtg atgtgtctgt cttgtgtgtg     360
acgataactc acgtgtggca gccctcttct cagcacactg ctctggcttg gcagcagggt     420
taacttgcgg acgaggagcg tggtgtcagc acgtgcctgg atacatgaga tggttgacca     480
gag                                                                   483
```

<210> SEQ ID NO 32
<211> LENGTH: 438
<212> TYPE: DNA
<213> ORGANISM: Artificial
<220> FEATURE:
<223> OTHER INFORMATION: Sequence cloned in lentiviral vector

<400> SEQUENCE: 32

```
cgtccggcca gatctgcttc ttctgaaacc atggcaagag aaagacagac agacttggac      60
ctactgcagg gagggttaag tagcagcggg actcccatca agaagaagga atgtcttccg     120
gagcctcatc tgtctgttgg gctggaggca gggcctttgt gaaggcgggt ggtgctcaga     180
tcgcctctgg gccttcctc cagccccgag gcggattcac catgaggctg atgcagcttc     240
agcttccagc ccttcacgct ccagggccct ttccaaggcc tagcaatgtg tccatgtgct     300
caggggtttt gtgaaatttg caaaggaaa ttattttgt actcttttt ttttaaaaca       360
aacaaacaaa caaaaaaaaa ccttccaagc tctgtaagct ttaggcgccc aagcccagct     420
ctgccctgct gtggcaag                                                   438
```

<210> SEQ ID NO 33
<211> LENGTH: 488
<212> TYPE: DNA
<213> ORGANISM: Artificial

<220> FEATURE:
<223> OTHER INFORMATION: Sequence cloned in lentiviral vector

<400> SEQUENCE: 33

```
cctgaagaga gactgacaca tcagaggtgt cyggtgactg aacaagctcc cagcttgcgc    60
ccatgtcata ttgtgtgcct ctcatagcct ggcacttcct gccattgcat ccttctctgc   120
agactaagat ggagttcctg aaccaagacc gcttgctggc caacctgtga aactgggctc   180
aaggtgaggg gtgctatctg tgattgaggg acatggttaa tggaattgtc tcacacagaa   240
atcgcacccg tcaccttggc ctacttatca ccaccccaaa cagaggaaca cgccttctcc   300
agccacagcc tatggaaggg ccttcagctg ctgtggcccc gaggtgtgca tactgtggaa   360
ggaacttcgg acgtgaactc ggatctggtt ccagtaccag ctgtgccagg agtgcccttg   420
ggcatgtcac tgacctaaga ctcagtttcg ccatctgtga aatggctgaa tcagactcac   480
ctcacagg                                                            488
```

<210> SEQ ID NO 34
<211> LENGTH: 467
<212> TYPE: DNA
<213> ORGANISM: Artificial
<220> FEATURE:
<223> OTHER INFORMATION: Sequnece cloned in lentiviral vector

<400> SEQUENCE: 34

```
cggtttaggg tcacatggtt cttttatcca aattccagtg ggtacctacc tcctggaggt    60
gcaggtcgaa aggttctgtg tatttggtac taggacacac aggtaggtgt tgtcagtagt   120
gcagcctggt gctaggggca ggggtcccca gtgctcatgt tagtttcctt ttagagtcta   180
agtagaatgt taagcagaga cccaaaccct aggtctgctg actcctagtc cagggctcgt   240
gatggctggt gggccctgaa cgaggggtct ggaggcctgg gtttgaatat cgacagcctc   300
tctgacccac ttggttgcct cagggaggca ggtgtgcgga tgggggagag tggcccatgg   360
gccagaaaag cagtggtatg ggggccccaa gagaagccca gacccaaaag ggcaggagct   420
ggctgtgggg ctactcaggt ggctggaggc ctcctgcaga cacagtg                 467
```

<210> SEQ ID NO 35
<211> LENGTH: 504
<212> TYPE: DNA
<213> ORGANISM: Artificial
<220> FEATURE:
<223> OTHER INFORMATION: Sequence cloned in lentiviral vector

<400> SEQUENCE: 35

```
ttggatctgg aggctatggg cgggggagtg ctttgaatat ctatacgtgg aaagccttgt    60
tttttacttt ttaagaaagg gtcgttaaat tcgtgctttg tagaccttca acagctcatc   120
aagggctact ctccacctcc ttgcttaaag gcctcttctg atgggtaagt gcttccactt   180
gcgatcgccg ccttgccgca tcccctcagc ctgtggcact caaactgtgg gggcactttc   240
tgctctctgg tgaaagtgcc gccatctttt gagtgttacc gcttgagaag actcaacctg   300
cggagaagat accattttga ttgggtgagg gggcgggtag caggatggcc ctagaccctg   360
cctatggccg cttcctcgtg atataaattt cttggccggg gctcttgcag atggagctgc   420
tcaccctgtg ggcctcaaat gtggagcact attctgatgt ccaagtggaa agtgctgcga   480
atttgagcgt caccggtgac gccc                                          504
```

<210> SEQ ID NO 36

```
<211> LENGTH: 7
<212> TYPE: RNA
<213> ORGANISM: Artificial
<220> FEATURE:
<223> OTHER INFORMATION: Seed sequence

<400> SEQUENCE: 36 cauucaa                                                              7

<210> SEQ ID NO 37
<211> LENGTH: 7
<212> TYPE: RNA
<213> ORGANISM: Artificial
<220> FEATURE:
<223> OTHER INFORMATION: Seed sequence

<400> SEQUENCE: 37 auucaac                                                              7

<210> SEQ ID NO 38
<211> LENGTH: 7
<212> TYPE: RNA
<213> ORGANISM: Artificial
<220> FEATURE:
<223> OTHER INFORMATION: Seed sequence

<400> SEQUENCE: 38 uucaacg                                                              7

<210> SEQ ID NO 39
<211> LENGTH: 7
<212> TYPE: RNA
<213> ORGANISM: Artificial
<220> FEATURE:
<223> OTHER INFORMATION: Seed sequence

<400> SEQUENCE: 39 aacauuc                                                              7

<210> SEQ ID NO 40
<211> LENGTH: 7
<212> TYPE: RNA
<213> ORGANISM: Artificial
<220> FEATURE:
<223> OTHER INFORMATION: Seed sequence

<400> SEQUENCE: 40 ucaacgc                                                              7

<210> SEQ ID NO 41
<211> LENGTH: 7
<212> TYPE: RNA
<213> ORGANISM: Artificial
<220> FEATURE:
<223> OTHER INFORMATION: Seed sequence

<400> SEQUENCE: 41 caacgcu                                                              7

<210> SEQ ID NO 42
<211> LENGTH: 7
<212> TYPE: RNA
<213> ORGANISM: Artificial
<220> FEATURE:
<223> OTHER INFORMATION: Seed sequence

<400> SEQUENCE: 42
``` ccuucag 7

<210> SEQ ID NO 43
<211> LENGTH: 7
<212> TYPE: RNA
<213> ORGANISM: Artificial
<220> FEATURE:
<223> OTHER INFORMATION: Seed sequence

<400> SEQUENCE: 43 aacgcug 7

<210> SEQ ID NO 44
<211> LENGTH: 7
<212> TYPE: RNA
<213> ORGANISM: Artificial
<220> FEATURE:
<223> OTHER INFORMATION: Seed sequence

<400> SEQUENCE: 44 acgcugu 7

<210> SEQ ID NO 45
<211> LENGTH: 7
<212> TYPE: RNA
<213> ORGANISM: Artificial
<220> FEATURE:
<223> OTHER INFORMATION: Seed sequence

<400> SEQUENCE: 45 cuucaga 7

<210> SEQ ID NO 46
<211> LENGTH: 7
<212> TYPE: RNA
<213> ORGANISM: Artificial
<220> FEATURE:
<223> OTHER INFORMATION: Seed sequence

<400> SEQUENCE: 46 gccagcc 7

<210> SEQ ID NO 47
<211> LENGTH: 7
<212> TYPE: RNA
<213> ORGANISM: Artificial
<220> FEATURE:
<223> OTHER INFORMATION: Seed sequence

<400> SEQUENCE: 47 accaucg 7

<210> SEQ ID NO 48
<211> LENGTH: 7
<212> TYPE: RNA
<213> ORGANISM: Artificial
<220> FEATURE:
<223> OTHER INFORMATION: Seed sequence

<400> SEQUENCE: 48 aaccauc 7

<210> SEQ ID NO 49
<211> LENGTH: 7
<212> TYPE: RNA

```
<213> ORGANISM: Artificial
<220> FEATURE:
<223> OTHER INFORMATION: Seed sequence

<400> SEQUENCE: 49 caucgac                                                                        7

<210> SEQ ID NO 50
<211> LENGTH: 7
<212> TYPE: RNA
<213> ORGANISM: Artificial
<220> FEATURE:
<223> OTHER INFORMATION: Seed sequence

<400> SEQUENCE: 50 aaaccau                                                                        7

<210> SEQ ID NO 51
<211> LENGTH: 7
<212> TYPE: RNA
<213> ORGANISM: Artificial
<220> FEATURE:
<223> OTHER INFORMATION: Seed sequence

<400> SEQUENCE: 51 ucgaccg                                                                        7

<210> SEQ ID NO 52
<211> LENGTH: 7
<212> TYPE: RNA
<213> ORGANISM: Artificial
<220> FEATURE:
<223> OTHER INFORMATION: Seed sequence

<400> SEQUENCE: 52 ucaaaac                                                                        7

<210> SEQ ID NO 53
<211> LENGTH: 7
<212> TYPE: RNA
<213> ORGANISM: Artificial
<220> FEATURE:
<223> OTHER INFORMATION: Seed sequence

<400> SEQUENCE: 53 caaaacc                                                                        7

<210> SEQ ID NO 54
<211> LENGTH: 7
<212> TYPE: RNA
<213> ORGANISM: Artificial
<220> FEATURE:
<223> OTHER INFORMATION: Seed sequence

<400> SEQUENCE: 54 accacug                                                                        7

<210> SEQ ID NO 55
<211> LENGTH: 7
<212> TYPE: RNA
<213> ORGANISM: Artificial
<220> FEATURE:
<223> OTHER INFORMATION: Seed sequence

<400> SEQUENCE: 55 cacugac                                                                        7
```

```
<210> SEQ ID NO 56
<211> LENGTH: 7
<212> TYPE: RNA
<213> ORGANISM: Artificial
<220> FEATURE:
<223> OTHER INFORMATION: Seed sequence

<400> SEQUENCE: 56 acugacc                                                              7

<210> SEQ ID NO 57
<211> LENGTH: 7
<212> TYPE: RNA
<213> ORGANISM: Artificial
<220> FEATURE:
<223> OTHER INFORMATION: Seed sequence

<400> SEQUENCE: 57 cugaccg                                                              7

<210> SEQ ID NO 58
<211> LENGTH: 7
<212> TYPE: RNA
<213> ORGANISM: Artificial
<220> FEATURE:
<223> OTHER INFORMATION: Seed sequence

<400> SEQUENCE: 58 uggggguc                                                             7

<210> SEQ ID NO 59
<211> LENGTH: 7
<212> TYPE: RNA
<213> ORGANISM: Artificial
<220> FEATURE:
<223> OTHER INFORMATION: Seed sequence

<400> SEQUENCE: 59 aaaaaac                                                              7

<210> SEQ ID NO 60
<211> LENGTH: 7
<212> TYPE: RNA
<213> ORGANISM: Artificial
<220> FEATURE:
<223> OTHER INFORMATION: Seed sequence

<400> SEQUENCE: 60 aaaaacc                                                              7

<210> SEQ ID NO 61
<211> LENGTH: 7
<212> TYPE: RNA
<213> ORGANISM: Artificial
<220> FEATURE:
<223> OTHER INFORMATION: Seed sequence

<400> SEQUENCE: 61 cacauua                                                              7

<210> SEQ ID NO 62
<211> LENGTH: 7
<212> TYPE: RNA
<213> ORGANISM: Artificial
<220> FEATURE:
```

```
<223> OTHER INFORMATION: Seed sequence

<400> SEQUENCE: 62 cauuaca                                                              7

<210> SEQ ID NO 63
<211> LENGTH: 7
<212> TYPE: RNA
<213> ORGANISM: Artificial
<220> FEATURE:
<223> OTHER INFORMATION: Seed sequence

<400> SEQUENCE: 63 auuacac                                                              7

<210> SEQ ID NO 64
<211> LENGTH: 7
<212> TYPE: RNA
<213> ORGANISM: Artificial
<220> FEATURE:
<223> OTHER INFORMATION: Seed sequence

<400> SEQUENCE: 64 uauggcg                                                              7

<210> SEQ ID NO 65
<211> LENGTH: 7
<212> TYPE: RNA
<213> ORGANISM: Artificial
<220> FEATURE:
<223> OTHER INFORMATION: Seed sequence

<400> SEQUENCE: 65 gcacauu                                                              7

<210> SEQ ID NO 66
<211> LENGTH: 7
<212> TYPE: RNA
<213> ORGANISM: Artificial
<220> FEATURE:
<223> OTHER INFORMATION: Seed sequence

<400> SEQUENCE: 66 cugcuug                                                              7

<210> SEQ ID NO 67
<211> LENGTH: 7
<212> TYPE: RNA
<213> ORGANISM: Artificial
<220> FEATURE:
<223> OTHER INFORMATION: Seed sequence

<400> SEQUENCE: 67 ugcuugg                                                              7

<210> SEQ ID NO 68
<211> LENGTH: 7
<212> TYPE: RNA
<213> ORGANISM: Artificial
<220> FEATURE:
<223> OTHER INFORMATION: Seed sequence

<400> SEQUENCE: 68 gcugcuu                                                              7
```

```
<210> SEQ ID NO 69
<211> LENGTH: 7
<212> TYPE: RNA
<213> ORGANISM: Artificial
<220> FEATURE:
<223> OTHER INFORMATION: Seed sequence

<400> SEQUENCE: 69 agguggu                                                                    7

<210> SEQ ID NO 70
<211> LENGTH: 7
<212> TYPE: RNA
<213> ORGANISM: Artificial
<220> FEATURE:
<223> OTHER INFORMATION: Seed sequence

<400> SEQUENCE: 70 guggucc                                                                    7

<210> SEQ ID NO 71
<211> LENGTH: 7
<212> TYPE: RNA
<213> ORGANISM: Artificial
<220> FEATURE:
<223> OTHER INFORMATION: Seed sequence

<400> SEQUENCE: 71 ccucauc                                                                    7

<210> SEQ ID NO 72
<211> LENGTH: 7
<212> TYPE: RNA
<213> ORGANISM: Artificial
<220> FEATURE:
<223> OTHER INFORMATION: Seed sequence

<400> SEQUENCE: 72 cucaucu                                                                    7

<210> SEQ ID NO 73
<211> LENGTH: 7
<212> TYPE: RNA
<213> ORGANISM: Artificial
<220> FEATURE:
<223> OTHER INFORMATION: Seed sequence

<400> SEQUENCE: 73 gccucau                                                                    7

<210> SEQ ID NO 74
<211> LENGTH: 7
<212> TYPE: RNA
<213> ORGANISM: Artificial
<220> FEATURE:
<223> OTHER INFORMATION: Seed sequence

<400> SEQUENCE: 74 ucaucug                                                                    7

<210> SEQ ID NO 75
<211> LENGTH: 7
<212> TYPE: RNA
<213> ORGANISM: Artificial
<220> FEATURE:
<223> OTHER INFORMATION: Seed sequence
```

```
<400> SEQUENCE: 75 caucugu                                                              7

<210> SEQ ID NO 76
<211> LENGTH: 7
<212> TYPE: RNA
<213> ORGANISM: Artificial
<220> FEATURE:
<223> OTHER INFORMATION: Seed sequence

<400> SEQUENCE: 76 cccgagg                                                              7

<210> SEQ ID NO 77
<211> LENGTH: 7
<212> TYPE: RNA
<213> ORGANISM: Artificial
<220> FEATURE:
<223> OTHER INFORMATION: Seed sequence

<400> SEQUENCE: 77 gaggcag                                                              7

<210> SEQ ID NO 78
<211> LENGTH: 7
<212> TYPE: RNA
<213> ORGANISM: Artificial
<220> FEATURE:
<223> OTHER INFORMATION: Seed sequence

<400> SEQUENCE: 78 ugaaggc                                                              7

<210> SEQ ID NO 79
<211> LENGTH: 7
<212> TYPE: RNA
<213> ORGANISM: Artificial
<220> FEATURE:
<223> OTHER INFORMATION: Seed sequence

<400> SEQUENCE: 79 cacacag                                                              7

<210> SEQ ID NO 80
<211> LENGTH: 7
<212> TYPE: RNA
<213> ORGANISM: Artificial
<220> FEATURE:
<223> OTHER INFORMATION: Seed sequence

<400> SEQUENCE: 80 ucacaca                                                              7

<210> SEQ ID NO 81
<211> LENGTH: 7
<212> TYPE: RNA
<213> ORGANISM: Artificial
<220> FEATURE:
<223> OTHER INFORMATION: Seed sequence

<400> SEQUENCE: 81 acacaga                                                              7

<210> SEQ ID NO 82
<211> LENGTH: 7
```

```
<212> TYPE: RNA
<213> ORGANISM: Artificial
<220> FEATURE:
<223> OTHER INFORMATION: Seed sequence

<400> SEQUENCE: 82 cacagaa                                                                  7

<210> SEQ ID NO 83
<211> LENGTH: 7
<212> TYPE: RNA
<213> ORGANISM: Artificial
<220> FEATURE:
<223> OTHER INFORMATION: Seed sequence

<400> SEQUENCE: 83 cagaaau                                                                  7

<210> SEQ ID NO 84
<211> LENGTH: 7
<212> TYPE: RNA
<213> ORGANISM: Artificial
<220> FEATURE:
<223> OTHER INFORMATION: Seed sequence

<400> SEQUENCE: 84 acagaaa                                                                  7

<210> SEQ ID NO 85
<211> LENGTH: 7
<212> TYPE: RNA
<213> ORGANISM: Artificial
<220> FEATURE:
<223> OTHER INFORMATION: Seed sequence

<400> SEQUENCE: 85 ucucaca                                                                  7

<210> SEQ ID NO 86
<211> LENGTH: 7
<212> TYPE: RNA
<213> ORGANISM: Artificial
<220> FEATURE:
<223> OTHER INFORMATION: Seed sequence

<400> SEQUENCE: 86 gggugcu                                                                  7

<210> SEQ ID NO 87
<211> LENGTH: 7
<212> TYPE: RNA
<213> ORGANISM: Artificial
<220> FEATURE:
<223> OTHER INFORMATION: Seed sequence

<400> SEQUENCE: 87 gcuaucu                                                                  7

<210> SEQ ID NO 88
<211> LENGTH: 7
<212> TYPE: RNA
<213> ORGANISM: Artificial
<220> FEATURE:
<223> OTHER INFORMATION: Seed sequence

<400> SEQUENCE: 88
```

-continued

```
ggugcua                                                              7

<210> SEQ ID NO 89
<211> LENGTH: 7
<212> TYPE: RNA
<213> ORGANISM: Artificial
<220> FEATURE:
<223> OTHER INFORMATION: Seed sequence

<400> SEQUENCE: 89 ugugaaa                                                              7

<210> SEQ ID NO 90
<211> LENGTH: 7
<212> TYPE: RNA
<213> ORGANISM: Artificial
<220> FEATURE:
<223> OTHER INFORMATION: Seed sequence

<400> SEQUENCE: 90 gugcuau                                                              7

<210> SEQ ID NO 91
<211> LENGTH: 7
<212> TYPE: RNA
<213> ORGANISM: Artificial
<220> FEATURE:
<223> OTHER INFORMATION: Seed sequence

<400> SEQUENCE: 91 ugaaacu                                                              7

<210> SEQ ID NO 92
<211> LENGTH: 7
<212> TYPE: RNA
<213> ORGANISM: Artificial
<220> FEATURE:
<223> OTHER INFORMATION: Seed sequence

<400> SEQUENCE: 92 cugugaa                                                              7

<210> SEQ ID NO 93
<211> LENGTH: 7
<212> TYPE: RNA
<213> ORGANISM: Artificial
<220> FEATURE:
<223> OTHER INFORMATION: Seed sequence

<400> SEQUENCE: 93 cuaucug                                                              7

<210> SEQ ID NO 94
<211> LENGTH: 7
<212> TYPE: RNA
<213> ORGANISM: Artificial
<220> FEATURE:
<223> OTHER INFORMATION: Seed sequence

<400> SEQUENCE: 94 ugcuauc                                                              7

<210> SEQ ID NO 95
<211> LENGTH: 7
<212> TYPE: RNA
<213> ORGANISM: Artificial
```

```
<220> FEATURE:
<223> OTHER INFORMATION: Seed sequence

<400> SEQUENCE: 95 augguua                                                                  7

<210> SEQ ID NO 96
<211> LENGTH: 7
<212> TYPE: RNA
<213> ORGANISM: Artificial
<220> FEATURE:
<223> OTHER INFORMATION: Seed sequence

<400> SEQUENCE: 96 aucugug                                                                  7

<210> SEQ ID NO 97
<211> LENGTH: 7
<212> TYPE: RNA
<213> ORGANISM: Artificial
<220> FEATURE:
<223> OTHER INFORMATION: Seed sequence

<400> SEQUENCE: 97 gaaacug                                                                  7

<210> SEQ ID NO 98
<211> LENGTH: 7
<212> TYPE: RNA
<213> ORGANISM: Artificial
<220> FEATURE:
<223> OTHER INFORMATION: Seed sequence

<400> SEQUENCE: 98 uaucugu                                                                  7

<210> SEQ ID NO 99
<211> LENGTH: 7
<212> TYPE: RNA
<213> ORGANISM: Artificial
<220> FEATURE:
<223> OTHER INFORMATION: Seed sequence

<400> SEQUENCE: 99 gugaaac                                                                  7

<210> SEQ ID NO 100
<211> LENGTH: 7
<212> TYPE: RNA
<213> ORGANISM: Artificial
<220> FEATURE:
<223> OTHER INFORMATION: Seed sequence

<400> SEQUENCE: 100 ugacucc                                                                  7

<210> SEQ ID NO 101
<211> LENGTH: 7
<212> TYPE: RNA
<213> ORGANISM: Artificial
<220> FEATURE:
<223> OTHER INFORMATION: Seed sequence

<400> SEQUENCE: 101 gacuccu                                                                  7
```

```
<210> SEQ ID NO 102
<211> LENGTH: 7
<212> TYPE: RNA
<213> ORGANISM: Artificial
<220> FEATURE:
<223> OTHER INFORMATION: Seed sequence

<400> SEQUENCE: 102 cccugaa                                                                    7

<210> SEQ ID NO 103
<211> LENGTH: 7
<212> TYPE: RNA
<213> ORGANISM: Artificial
<220> FEATURE:
<223> OTHER INFORMATION: Seed sequence

<400> SEQUENCE: 103 ccugaac                                                                    7

<210> SEQ ID NO 104
<211> LENGTH: 7
<212> TYPE: RNA
<213> ORGANISM: Artificial
<220> FEATURE:
<223> OTHER INFORMATION: Seed sequence

<400> SEQUENCE: 104 gugccgc                                                                    7

<210> SEQ ID NO 105
<211> LENGTH: 7
<212> TYPE: RNA
<213> ORGANISM: Artificial
<220> FEATURE:
<223> OTHER INFORMATION: Seed sequence

<400> SEQUENCE: 105 ugccgcc                                                                    7

<210> SEQ ID NO 106
<211> LENGTH: 7
<212> TYPE: RNA
<213> ORGANISM: Artificial
<220> FEATURE:
<223> OTHER INFORMATION: Seed sequence

<400> SEQUENCE: 106 gccgcca                                                                    7

<210> SEQ ID NO 107
<211> LENGTH: 7
<212> TYPE: RNA
<213> ORGANISM: Artificial
<220> FEATURE:
<223> OTHER INFORMATION: Seed sequence

<400> SEQUENCE: 107 ucaaacu                                                                    7

<210> SEQ ID NO 108
<211> LENGTH: 25
<212> TYPE: RNA
<213> ORGANISM: Artificial
<220> FEATURE:
<223> OTHER INFORMATION: IsomiR sequence
```

-continued

<400> SEQUENCE: 108
aacauucaac gcugucggug aguuu					25

<210> SEQ ID NO 109
<211> LENGTH: 24
<212> TYPE: RNA
<213> ORGANISM: Artificial
<220> FEATURE:
<223> OTHER INFORMATION: IsomiR sequence

<400> SEQUENCE: 109
aacauucaac gcugucggug aguu					24

<210> SEQ ID NO 110
<211> LENGTH: 20
<212> TYPE: RNA
<213> ORGANISM: Artificial
<220> FEATURE:
<223> OTHER INFORMATION: IsomiR sequence

<400> SEQUENCE: 110
aacauucaac gcugucggug					20

<210> SEQ ID NO 111
<211> LENGTH: 21
<212> TYPE: RNA
<213> ORGANISM: Artificial
<220> FEATURE:
<223> OTHER INFORMATION: IsomiR sequence

<400> SEQUENCE: 111
aacauucaac gcugucggug a					21

<210> SEQ ID NO 112
<211> LENGTH: 22
<212> TYPE: RNA
<213> ORGANISM: Artificial
<220> FEATURE:
<223> OTHER INFORMATION: IsomiR sequence

<400> SEQUENCE: 112
aacauucaac gcugucggug ag					22

<210> SEQ ID NO 113
<211> LENGTH: 19
<212> TYPE: RNA
<213> ORGANISM: Artificial
<220> FEATURE:
<223> OTHER INFORMATION: IsomiR sequence

<400> SEQUENCE: 113
aacauucaac gcugucggu					19

<210> SEQ ID NO 114
<211> LENGTH: 26
<212> TYPE: RNA
<213> ORGANISM: Artificial
<220> FEATURE:
<223> OTHER INFORMATION: IsomiR sequence

<400> SEQUENCE: 114
aacauucaac gcugucggug aguuug					26

<210> SEQ ID NO 115

```
<211> LENGTH: 24
<212> TYPE: RNA
<213> ORGANISM: Artificial
<220> FEATURE:
<223> OTHER INFORMATION: IsomiR sequence

<400> SEQUENCE: 115
acauucaacg cugucgguga guuu                                              24

<210> SEQ ID NO 116
<211> LENGTH: 22
<212> TYPE: RNA
<213> ORGANISM: Artificial
<220> FEATURE:
<223> OTHER INFORMATION: IsomiR sequence

<400> SEQUENCE: 116
acauucaacg cugucgguga gu                                                22

<210> SEQ ID NO 117
<211> LENGTH: 18
<212> TYPE: RNA
<213> ORGANISM: Artificial
<220> FEATURE:
<223> OTHER INFORMATION: IsomiR sequence

<400> SEQUENCE: 117
aacauucaac gcugucgg                                                     18

<210> SEQ ID NO 118
<211> LENGTH: 23
<212> TYPE: RNA
<213> ORGANISM: Artificial
<220> FEATURE:
<223> OTHER INFORMATION: IsomiR sequence

<400> SEQUENCE: 118
acauucaacg cugucgguga guu                                               23

<210> SEQ ID NO 119
<211> LENGTH: 21
<212> TYPE: RNA
<213> ORGANISM: Artificial
<220> FEATURE:
<223> OTHER INFORMATION: IsomiR sequence

<400> SEQUENCE: 119
acauucaacg cugucgguga g                                                 21

<210> SEQ ID NO 120
<211> LENGTH: 19
<212> TYPE: RNA
<213> ORGANISM: Artificial
<220> FEATURE:
<223> OTHER INFORMATION: IsomiR sequence

<400> SEQUENCE: 120
acauucaacg cugucggug                                                    19

<210> SEQ ID NO 121
<211> LENGTH: 20
<212> TYPE: RNA
<213> ORGANISM: Artificial
<220> FEATURE:
<223> OTHER INFORMATION: IsomiR sequence

<400> SEQUENCE: 121
```

```
acauucaacg cugucgguga                                              20

<210> SEQ ID NO 122
<211> LENGTH: 18
<212> TYPE: RNA
<213> ORGANISM: Artificial
<220> FEATURE:
<223> OTHER INFORMATION: IsomiR sequence

<400> SEQUENCE: 122
acauucaacg cugucggu                                                18

<210> SEQ ID NO 123
<211> LENGTH: 23
<212> TYPE: RNA
<213> ORGANISM: Artificial
<220> FEATURE:
<223> OTHER INFORMATION: IsomiR sequence

<400> SEQUENCE: 123
cauucaacgc ugucggugag uuu                                          23

<210> SEQ ID NO 124
<211> LENGTH: 22
<212> TYPE: RNA
<213> ORGANISM: Artificial
<220> FEATURE:
<223> OTHER INFORMATION: IsomiR sequence

<400> SEQUENCE: 124
auucaacgcu gucggugagu uu                                           22

<210> SEQ ID NO 125
<211> LENGTH: 21
<212> TYPE: RNA
<213> ORGANISM: Artificial
<220> FEATURE:
<223> OTHER INFORMATION: IsomiR sequence

<400> SEQUENCE: 125
cauucaacgc ugucggugag u                                            21

<210> SEQ ID NO 126
<211> LENGTH: 20
<212> TYPE: RNA
<213> ORGANISM: Artificial
<220> FEATURE:
<223> OTHER INFORMATION: IsomiR sequence

<400> SEQUENCE: 126
cauucaacgc ugucggugag                                              20

<210> SEQ ID NO 127
<211> LENGTH: 20
<212> TYPE: RNA
<213> ORGANISM: Artificial
<220> FEATURE:
<223> OTHER INFORMATION: IsomiR sequence

<400> SEQUENCE: 127
auucaacgcu gucggugagu                                              20

<210> SEQ ID NO 128
<211> LENGTH: 22
<212> TYPE: RNA
```

```
<213> ORGANISM: Artificial
<220> FEATURE:
<223> OTHER INFORMATION: IsomiR sequence

<400> SEQUENCE: 128
gaacauucaa cgcugucggu ga                                              22

<210> SEQ ID NO 129
<211> LENGTH: 20
<212> TYPE: RNA
<213> ORGANISM: Artificial
<220> FEATURE:
<223> OTHER INFORMATION: IsomiR sequence

<400> SEQUENCE: 129
gaacauucaa cgcugucggu                                                 20

<210> SEQ ID NO 130
<211> LENGTH: 22
<212> TYPE: RNA
<213> ORGANISM: Artificial
<220> FEATURE:
<223> OTHER INFORMATION: IsomiR sequence

<400> SEQUENCE: 130
cauucaacgc ugucggugag uu                                              22

<210> SEQ ID NO 131
<211> LENGTH: 21
<212> TYPE: RNA
<213> ORGANISM: Artificial
<220> FEATURE:
<223> OTHER INFORMATION: IsomiR sequence

<400> SEQUENCE: 131
gaacauucaa cgcugucggu g                                               21

<210> SEQ ID NO 132
<211> LENGTH: 19
<212> TYPE: RNA
<213> ORGANISM: Artificial
<220> FEATURE:
<223> OTHER INFORMATION: IsomiR sequence

<400> SEQUENCE: 132
auucaacgcu gucggugag                                                  19

<210> SEQ ID NO 133
<211> LENGTH: 21
<212> TYPE: RNA
<213> ORGANISM: Artificial
<220> FEATURE:
<223> OTHER INFORMATION: IsomiR sequence

<400> SEQUENCE: 133
uucaacgcug ucggugaguu u                                               21

<210> SEQ ID NO 134
<211> LENGTH: 28
<212> TYPE: RNA
<213> ORGANISM: Artificial
<220> FEATURE:
<223> OTHER INFORMATION: IsomiR sequence

<400> SEQUENCE: 134
aacauucaac gcugucggug aguuugga                                        28
```

```
<210> SEQ ID NO 135
<211> LENGTH: 20
<212> TYPE: RNA
<213> ORGANISM: Artificial
<220> FEATURE:
<223> OTHER INFORMATION: IsomiR sequence

<400> SEQUENCE: 135
ucaacgcugu cggugaguuu                                               20

<210> SEQ ID NO 136
<211> LENGTH: 18
<212> TYPE: RNA
<213> ORGANISM: Artificial
<220> FEATURE:
<223> OTHER INFORMATION: IsomiR sequence

<400> SEQUENCE: 136
cauucaacgc ugucggug                                                 18

<210> SEQ ID NO 137
<211> LENGTH: 19
<212> TYPE: RNA
<213> ORGANISM: Artificial
<220> FEATURE:
<223> OTHER INFORMATION: IsomiR sequence

<400> SEQUENCE: 137
ucaacgcugu cggugaguu                                                19

<210> SEQ ID NO 138
<211> LENGTH: 23
<212> TYPE: RNA
<213> ORGANISM: Artificial
<220> FEATURE:
<223> OTHER INFORMATION: IsomiR sequence

<400> SEQUENCE: 138
gaacauucaa cgcugucggu gag                                           23

<210> SEQ ID NO 139
<211> LENGTH: 27
<212> TYPE: RNA
<213> ORGANISM: Artificial
<220> FEATURE:
<223> OTHER INFORMATION: IsomiR sequence

<400> SEQUENCE: 139
aacauucaac gcugucggug aguuugg                                       27

<210> SEQ ID NO 140
<211> LENGTH: 19
<212> TYPE: RNA
<213> ORGANISM: Artificial
<220> FEATURE:
<223> OTHER INFORMATION: IsomiR sequence

<400> SEQUENCE: 140
caacgcuguc ggugaguuu                                                19

<210> SEQ ID NO 141
<211> LENGTH: 18
<212> TYPE: RNA
<213> ORGANISM: Artificial
<220> FEATURE:
```

```
<223> OTHER INFORMATION: IsomiR sequence

<400> SEQUENCE: 141
aacgcugucg gugaguuu                                                 18

<210> SEQ ID NO 142
<211> LENGTH: 19
<212> TYPE: RNA
<213> ORGANISM: Artificial
<220> FEATURE:
<223> OTHER INFORMATION: IsomiR sequence

<400> SEQUENCE: 142
uucaacgcug ucggugagu                                                19

<210> SEQ ID NO 143
<211> LENGTH: 18
<212> TYPE: RNA
<213> ORGANISM: Artificial
<220> FEATURE:
<223> OTHER INFORMATION: IsomiR sequence

<400> SEQUENCE: 143
uucaacgcug ucggugag                                                 18

<210> SEQ ID NO 144
<211> LENGTH: 21
<212> TYPE: RNA
<213> ORGANISM: Artificial
<220> FEATURE:
<223> OTHER INFORMATION: IsomiR sequence

<400> SEQUENCE: 144
auucaacgcu gucggugagu u                                             21

<210> SEQ ID NO 145
<211> LENGTH: 18
<212> TYPE: RNA
<213> ORGANISM: Artificial
<220> FEATURE:
<223> OTHER INFORMATION: IsomiR sequence

<400> SEQUENCE: 145
ucaacgcugu cggugagu                                                 18

<210> SEQ ID NO 146
<211> LENGTH: 18
<212> TYPE: RNA
<213> ORGANISM: Artificial
<220> FEATURE:
<223> OTHER INFORMATION: IsomiR sequence

<400> SEQUENCE: 146
auucaacgcu gucgguga                                                 18

<210> SEQ ID NO 147
<211> LENGTH: 20
<212> TYPE: RNA
<213> ORGANISM: Artificial
<220> FEATURE:
<223> OTHER INFORMATION: IsomiR sequence

<400> SEQUENCE: 147
uucaacgcug ucggugaguu                                               20
```

```
<210> SEQ ID NO 148
<211> LENGTH: 19
<212> TYPE: RNA
<213> ORGANISM: Artificial
<220> FEATURE:
<223> OTHER INFORMATION: IsomiR sequence

<400> SEQUENCE: 148
cauucaacgc ugucgguga                                                 19

<210> SEQ ID NO 149
<211> LENGTH: 25
<212> TYPE: RNA
<213> ORGANISM: Artificial
<220> FEATURE:
<223> OTHER INFORMATION: IsomiR sequence

<400> SEQUENCE: 149
acauucaacg cugucgguga guuug                                          25

<210> SEQ ID NO 150
<211> LENGTH: 22
<212> TYPE: RNA
<213> ORGANISM: Artificial
<220> FEATURE:
<223> OTHER INFORMATION: IsomiR sequence

<400> SEQUENCE: 150
ucaacgcugu cggugaguuu gg                                             22

<210> SEQ ID NO 151
<211> LENGTH: 18
<212> TYPE: RNA
<213> ORGANISM: Artificial
<220> FEATURE:
<223> OTHER INFORMATION: IsomiR sequence

<400> SEQUENCE: 151
caacgcuguc ggugaguu                                                  18

<210> SEQ ID NO 152
<211> LENGTH: 21
<212> TYPE: RNA
<213> ORGANISM: Artificial
<220> FEATURE:
<223> OTHER INFORMATION: IsomiR sequence

<400> SEQUENCE: 152
ucaacgcugu cggugaguuu g                                              21

<210> SEQ ID NO 153
<211> LENGTH: 24
<212> TYPE: RNA
<213> ORGANISM: Artificial
<220> FEATURE:
<223> OTHER INFORMATION: IsomiR sequence

<400> SEQUENCE: 153
gaacauucaa cgcugucggu gagu                                           24

<210> SEQ ID NO 154
<211> LENGTH: 20
<212> TYPE: RNA
<213> ORGANISM: Artificial
<220> FEATURE:
<223> OTHER INFORMATION: IsomiR sequence
```

<400> SEQUENCE: 154
gccuucagag gacuccaagg                                               20

<210> SEQ ID NO 155
<211> LENGTH: 19
<212> TYPE: RNA
<213> ORGANISM: Artificial
<220> FEATURE:
<223> OTHER INFORMATION: IsomiR sequence

<400> SEQUENCE: 155
ccuucagagg acuccaagg                                                19

<210> SEQ ID NO 156
<211> LENGTH: 29
<212> TYPE: RNA
<213> ORGANISM: Artificial
<220> FEATURE:
<223> OTHER INFORMATION: IsomiR sequence

<400> SEQUENCE: 156
aacauucaac gcugucggug aguuuggga                                     29

<210> SEQ ID NO 157
<211> LENGTH: 25
<212> TYPE: RNA
<213> ORGANISM: Artificial
<220> FEATURE:
<223> OTHER INFORMATION: IsomiR sequence

<400> SEQUENCE: 157
ggccagccuu cagaggacuc caagg                                         25

<210> SEQ ID NO 158
<211> LENGTH: 20
<212> TYPE: RNA
<213> ORGANISM: Artificial
<220> FEATURE:
<223> OTHER INFORMATION: IsomiR sequence

<400> SEQUENCE: 158
accaucgacc guugauugua                                               20

<210> SEQ ID NO 159
<211> LENGTH: 21
<212> TYPE: RNA
<213> ORGANISM: Artificial
<220> FEATURE:
<223> OTHER INFORMATION: IsomiR sequence

<400> SEQUENCE: 159
accaucgacc guugauugua c                                             21

<210> SEQ ID NO 160
<211> LENGTH: 19
<212> TYPE: RNA
<213> ORGANISM: Artificial
<220> FEATURE:
<223> OTHER INFORMATION: IsomiR sequence

<400> SEQUENCE: 160
accaucgacc guugauugu                                                19

<210> SEQ ID NO 161
<211> LENGTH: 21

-continued

<212> TYPE: RNA
<213> ORGANISM: Artificial
<220> FEATURE:
<223> OTHER INFORMATION: IsomiR sequence

<400> SEQUENCE: 161
aaccaucgac cguugauugu a                                              21

<210> SEQ ID NO 162
<211> LENGTH: 22
<212> TYPE: RNA
<213> ORGANISM: Artificial
<220> FEATURE:
<223> OTHER INFORMATION: IsomiR sequence

<400> SEQUENCE: 162
aaaccaucga ccguugauug ua                                             22

<210> SEQ ID NO 163
<211> LENGTH: 20
<212> TYPE: RNA
<213> ORGANISM: Artificial
<220> FEATURE:
<223> OTHER INFORMATION: IsomiR sequence

<400> SEQUENCE: 163
aaccaucgac cguugauugu                                                20

<210> SEQ ID NO 164
<211> LENGTH: 18
<212> TYPE: RNA
<213> ORGANISM: Artificial
<220> FEATURE:
<223> OTHER INFORMATION: IsomiR sequence

<400> SEQUENCE: 164
accaucgacc guugauug                                                  18

<210> SEQ ID NO 165
<211> LENGTH: 22
<212> TYPE: RNA
<213> ORGANISM: Artificial
<220> FEATURE:
<223> OTHER INFORMATION: IsomiR sequence

<400> SEQUENCE: 165
aaccaucgac cguugauugu ac                                             22

<210> SEQ ID NO 166
<211> LENGTH: 21
<212> TYPE: RNA
<213> ORGANISM: Artificial
<220> FEATURE:
<223> OTHER INFORMATION: IsomiR sequence

<400> SEQUENCE: 166
aaaccaucga ccguugauug u                                              21

<210> SEQ ID NO 167
<211> LENGTH: 23
<212> TYPE: RNA
<213> ORGANISM: Artificial
<220> FEATURE:
<223> OTHER INFORMATION: IsomiR sequence

<400> SEQUENCE: 167
aaaccaucga ccguugauug uac                                         23

<210> SEQ ID NO 168
<211> LENGTH: 21
<212> TYPE: RNA
<213> ORGANISM: Artificial
<220> FEATURE:
<223> OTHER INFORMATION: IsomiR sequence

<400> SEQUENCE: 168
ccaucgaccg uugauuguac c                                           21

<210> SEQ ID NO 169
<211> LENGTH: 19
<212> TYPE: RNA
<213> ORGANISM: Artificial
<220> FEATURE:
<223> OTHER INFORMATION: IsomiR sequence

<400> SEQUENCE: 169
ccaucgaccg uugauugua                                              19

<210> SEQ ID NO 170
<211> LENGTH: 22
<212> TYPE: RNA
<213> ORGANISM: Artificial
<220> FEATURE:
<223> OTHER INFORMATION: IsomiR sequence

<400> SEQUENCE: 170
aaaaccaucg accguugauu gu                                          22

<210> SEQ ID NO 171
<211> LENGTH: 20
<212> TYPE: RNA
<213> ORGANISM: Artificial
<220> FEATURE:
<223> OTHER INFORMATION: IsomiR sequence

<400> SEQUENCE: 171
ccaucgaccg uugauuguac                                             20

<210> SEQ ID NO 172
<211> LENGTH: 19
<212> TYPE: RNA
<213> ORGANISM: Artificial
<220> FEATURE:
<223> OTHER INFORMATION: IsomiR sequence

<400> SEQUENCE: 172
aucgaccguu gauuguacc                                              19

<210> SEQ ID NO 173
<211> LENGTH: 21
<212> TYPE: RNA
<213> ORGANISM: Artificial
<220> FEATURE:
<223> OTHER INFORMATION: IsomiR sequence

<400> SEQUENCE: 173
aucaaaacca ucgaccguug a                                           21

<210> SEQ ID NO 174
<211> LENGTH: 25
<212> TYPE: RNA
<213> ORGANISM: Artificial

```
<220> FEATURE:
<223> OTHER INFORMATION: IsomiR sequence

<400> SEQUENCE: 174
ucaaaaccau cgaccguuga uugua                                          25

<210> SEQ ID NO 175
<211> LENGTH: 19
<212> TYPE: RNA
<213> ORGANISM: Artificial
<220> FEATURE:
<223> OTHER INFORMATION: IsomiR sequence

<400> SEQUENCE: 175
aaccaucgac cguugauug                                                 19

<210> SEQ ID NO 176
<211> LENGTH: 20
<212> TYPE: RNA
<213> ORGANISM: Artificial
<220> FEATURE:
<223> OTHER INFORMATION: IsomiR sequence

<400> SEQUENCE: 176
aaaccaucga ccguugauug                                                20

<210> SEQ ID NO 177
<211> LENGTH: 18
<212> TYPE: RNA
<213> ORGANISM: Artificial
<220> FEATURE:
<223> OTHER INFORMATION: IsomiR sequence

<400> SEQUENCE: 177
aaaccaucga ccguugau                                                  18

<210> SEQ ID NO 178
<211> LENGTH: 21
<212> TYPE: RNA
<213> ORGANISM: Artificial
<220> FEATURE:
<223> OTHER INFORMATION: IsomiR sequence

<400> SEQUENCE: 178
accacugacc guugacugua c                                              21

<210> SEQ ID NO 179
<211> LENGTH: 20
<212> TYPE: RNA
<213> ORGANISM: Artificial
<220> FEATURE:
<223> OTHER INFORMATION: IsomiR sequence

<400> SEQUENCE: 179
accacugacc guugacugua                                                20

<210> SEQ ID NO 180
<211> LENGTH: 19
<212> TYPE: RNA
<213> ORGANISM: Artificial
<220> FEATURE:
<223> OTHER INFORMATION: IsomiR sequence

<400> SEQUENCE: 180
accacugacc guugacugu                                                 19
```

```
<210> SEQ ID NO 181
<211> LENGTH: 22
<212> TYPE: RNA
<213> ORGANISM: Artificial
<220> FEATURE:
<223> OTHER INFORMATION: IsomiR sequence

<400> SEQUENCE: 181
aaccacugac cguugacugu ac                                              22

<210> SEQ ID NO 182
<211> LENGTH: 21
<212> TYPE: RNA
<213> ORGANISM: Artificial
<220> FEATURE:
<223> OTHER INFORMATION: IsomiR sequence

<400> SEQUENCE: 182
aaccacugac cguugacugu a                                               21

<210> SEQ ID NO 183
<211> LENGTH: 20
<212> TYPE: RNA
<213> ORGANISM: Artificial
<220> FEATURE:
<223> OTHER INFORMATION: IsomiR sequence

<400> SEQUENCE: 183
aaccacugac cguugacugu                                                 20

<210> SEQ ID NO 184
<211> LENGTH: 23
<212> TYPE: RNA
<213> ORGANISM: Artificial
<220> FEATURE:
<223> OTHER INFORMATION: IsomiR sequence

<400> SEQUENCE: 184
accacugacc guugacugua ccu                                             23

<210> SEQ ID NO 185
<211> LENGTH: 20
<212> TYPE: RNA
<213> ORGANISM: Artificial
<220> FEATURE:
<223> OTHER INFORMATION: IsomiR sequence

<400> SEQUENCE: 185
ccacugaccg uugacuguac                                                 20

<210> SEQ ID NO 186
<211> LENGTH: 18
<212> TYPE: RNA
<213> ORGANISM: Artificial
<220> FEATURE:
<223> OTHER INFORMATION: IsomiR sequence

<400> SEQUENCE: 186
accacugacc guugacug                                                   18

<210> SEQ ID NO 187
<211> LENGTH: 23
<212> TYPE: RNA
<213> ORGANISM: Artificial
<220> FEATURE:
<223> OTHER INFORMATION: IsomiR sequence
```

-continued

<400> SEQUENCE: 187
aaccacugac cguugacugu acc                                       23

<210> SEQ ID NO 188
<211> LENGTH: 21
<212> TYPE: RNA
<213> ORGANISM: Artificial
<220> FEATURE:
<223> OTHER INFORMATION: IsomiR sequence

<400> SEQUENCE: 188
ccacugaccg uugacuguac c                                         21

<210> SEQ ID NO 189
<211> LENGTH: 19
<212> TYPE: RNA
<213> ORGANISM: Artificial
<220> FEATURE:
<223> OTHER INFORMATION: IsomiR sequence

<400> SEQUENCE: 189
cacugaccgu ugacuguac                                            19

<210> SEQ ID NO 190
<211> LENGTH: 18
<212> TYPE: RNA
<213> ORGANISM: Artificial
<220> FEATURE:
<223> OTHER INFORMATION: IsomiR sequence

<400> SEQUENCE: 190
cacugaccgu ugacugua                                             18

<210> SEQ ID NO 191
<211> LENGTH: 24
<212> TYPE: RNA
<213> ORGANISM: Artificial
<220> FEATURE:
<223> OTHER INFORMATION: IsomiR sequence

<400> SEQUENCE: 191
aaccacugac cguugacugu accu                                      24

<210> SEQ ID NO 192
<211> LENGTH: 19
<212> TYPE: RNA
<213> ORGANISM: Artificial
<220> FEATURE:
<223> OTHER INFORMATION: IsomiR sequence

<400> SEQUENCE: 192
ccacugaccg uugacugua                                            19

<210> SEQ ID NO 193
<211> LENGTH: 21
<212> TYPE: RNA
<213> ORGANISM: Artificial
<220> FEATURE:
<223> OTHER INFORMATION: IsomiR sequence

<400> SEQUENCE: 193
uugggguccu uacagacgac a                                         21

<210> SEQ ID NO 194

```
<211> LENGTH: 19
<212> TYPE: RNA
<213> ORGANISM: Artificial
<220> FEATURE:
<223> OTHER INFORMATION: IsomiR sequence

<400> SEQUENCE: 194
acugaccguu gacuguacc                                                        19

<210> SEQ ID NO 195
<211> LENGTH: 18
<212> TYPE: RNA
<213> ORGANISM: Artificial
<220> FEATURE:
<223> OTHER INFORMATION: IsomiR sequence

<400> SEQUENCE: 195
acugaccguu gacuguac                                                         18

<210> SEQ ID NO 196
<211> LENGTH: 22
<212> TYPE: RNA
<213> ORGANISM: Artificial
<220> FEATURE:
<223> OTHER INFORMATION: IsomiR sequence

<400> SEQUENCE: 196
ccacugaccg uugacuguac cu                                                    22

<210> SEQ ID NO 197
<211> LENGTH: 20
<212> TYPE: RNA
<213> ORGANISM: Artificial
<220> FEATURE:
<223> OTHER INFORMATION: IsomiR sequence

<400> SEQUENCE: 197
cacugaccgu ugacuguacc                                                       20

<210> SEQ ID NO 198
<211> LENGTH: 25
<212> TYPE: RNA
<213> ORGANISM: Artificial
<220> FEATURE:
<223> OTHER INFORMATION: IsomiR sequence

<400> SEQUENCE: 198
gaaaaaacca cugaccguug acugu                                                 25

<210> SEQ ID NO 199
<211> LENGTH: 24
<212> TYPE: RNA
<213> ORGANISM: Artificial
<220> FEATURE:
<223> OTHER INFORMATION: IsomiR sequence

<400> SEQUENCE: 199
aaaaaaccac ugaccguuga cugu                                                  24

<210> SEQ ID NO 200
<211> LENGTH: 19
<212> TYPE: RNA
<213> ORGANISM: Artificial
<220> FEATURE:
<223> OTHER INFORMATION: IsomiR sequence

<400> SEQUENCE: 200
```
aaccacugac cguugacug                                            19

<210> SEQ ID NO 201
<211> LENGTH: 25
<212> TYPE: RNA
<213> ORGANISM: Artificial
<220> FEATURE:
<223> OTHER INFORMATION: IsomiR sequence

<400> SEQUENCE: 201
aaaaaaccac ugaccguuga cugua                                     25

<210> SEQ ID NO 202
<211> LENGTH: 25
<212> TYPE: RNA
<213> ORGANISM: Artificial
<220> FEATURE:
<223> OTHER INFORMATION: IsomiR sequence

<400> SEQUENCE: 202
accacugacc guugacugua ccuug                                     25

<210> SEQ ID NO 203
<211> LENGTH: 22
<212> TYPE: RNA
<213> ORGANISM: Artificial
<220> FEATURE:
<223> OTHER INFORMATION: IsomiR sequence

<400> SEQUENCE: 203
gcacauuaca cggucgaccu cu                                        22

<210> SEQ ID NO 204
<211> LENGTH: 20
<212> TYPE: RNA
<213> ORGANISM: Artificial
<220> FEATURE:
<223> OTHER INFORMATION: IsomiR sequence

<400> SEQUENCE: 204
gcacauuaca cggucgaccu                                           20

<210> SEQ ID NO 205
<211> LENGTH: 21
<212> TYPE: RNA
<213> ORGANISM: Artificial
<220> FEATURE:
<223> OTHER INFORMATION: IsomiR sequence

<400> SEQUENCE: 205
gcacauuaca cggucgaccu c                                         21

<210> SEQ ID NO 206
<211> LENGTH: 23
<212> TYPE: RNA
<213> ORGANISM: Artificial
<220> FEATURE:
<223> OTHER INFORMATION: IsomiR sequence

<400> SEQUENCE: 206
gcacauuaca cggucgaccu cuu                                       23

<210> SEQ ID NO 207
<211> LENGTH: 20
<212> TYPE: RNA

```
<213> ORGANISM: Artificial
<220> FEATURE:
<223> OTHER INFORMATION: IsomiR sequence

<400> SEQUENCE: 207
cacauuacac ggucgaccuc                                              20

<210> SEQ ID NO 208
<211> LENGTH: 20
<212> TYPE: RNA
<213> ORGANISM: Artificial
<220> FEATURE:
<223> OTHER INFORMATION: IsomiR sequence

<400> SEQUENCE: 208
acauuacacg gucgaccucu                                              20

<210> SEQ ID NO 209
<211> LENGTH: 19
<212> TYPE: RNA
<213> ORGANISM: Artificial
<220> FEATURE:
<223> OTHER INFORMATION: IsomiR sequence

<400> SEQUENCE: 209
gcacauuaca cggucgacc                                               19

<210> SEQ ID NO 210
<211> LENGTH: 25
<212> TYPE: RNA
<213> ORGANISM: Artificial
<220> FEATURE:
<223> OTHER INFORMATION: IsomiR sequence

<400> SEQUENCE: 210
gcacauuaca cggucgaccu cuuug                                        25

<210> SEQ ID NO 211
<211> LENGTH: 22
<212> TYPE: RNA
<213> ORGANISM: Artificial
<220> FEATURE:
<223> OTHER INFORMATION: IsomiR sequence

<400> SEQUENCE: 211
cacauuacac ggucgaccuc uu                                           22

<210> SEQ ID NO 212
<211> LENGTH: 18
<212> TYPE: RNA
<213> ORGANISM: Artificial
<220> FEATURE:
<223> OTHER INFORMATION: IsomiR sequence

<400> SEQUENCE: 212
gcacauuaca cggucgac                                                18

<210> SEQ ID NO 213
<211> LENGTH: 19
<212> TYPE: RNA
<213> ORGANISM: Artificial
<220> FEATURE:
<223> OTHER INFORMATION: IsomiR sequence

<400> SEQUENCE: 213
cacauuacac ggucgaccu                                               19
```

```
<210> SEQ ID NO 214
<211> LENGTH: 24
<212> TYPE: RNA
<213> ORGANISM: Artificial
<220> FEATURE:
<223> OTHER INFORMATION: IsomiR sequence

<400> SEQUENCE: 214
gcacauuaca cggucgaccu cuuu                                          24

<210> SEQ ID NO 215
<211> LENGTH: 18
<212> TYPE: RNA
<213> ORGANISM: Artificial
<220> FEATURE:
<223> OTHER INFORMATION: IsomiR sequence

<400> SEQUENCE: 215
cacauuacac ggucgacc                                                 18

<210> SEQ ID NO 216
<211> LENGTH: 19
<212> TYPE: RNA
<213> ORGANISM: Artificial
<220> FEATURE:
<223> OTHER INFORMATION: IsomiR sequence

<400> SEQUENCE: 216
cauuacacgg ucgaccucu                                                19

<210> SEQ ID NO 217
<211> LENGTH: 22
<212> TYPE: RNA
<213> ORGANISM: Artificial
<220> FEATURE:
<223> OTHER INFORMATION: IsomiR sequence

<400> SEQUENCE: 217
uuauggcgca cauuacacgg uc                                            22

<210> SEQ ID NO 218
<211> LENGTH: 23
<212> TYPE: RNA
<213> ORGANISM: Artificial
<220> FEATURE:
<223> OTHER INFORMATION: IsomiR sequence

<400> SEQUENCE: 218
cgcacauuac acggucgacc ucu                                           23

<210> SEQ ID NO 219
<211> LENGTH: 20
<212> TYPE: RNA
<213> ORGANISM: Artificial
<220> FEATURE:
<223> OTHER INFORMATION: IsomiR sequence

<400> SEQUENCE: 219
aggugguccg uggcgcguuc                                               20

<210> SEQ ID NO 220
<211> LENGTH: 21
<212> TYPE: RNA
<213> ORGANISM: Artificial
<220> FEATURE:
```

<223> OTHER INFORMATION: IsomiR sequence

<400> SEQUENCE: 220
aggugguccg uggcgcguuc g                                         21

<210> SEQ ID NO 221
<211> LENGTH: 20
<212> TYPE: RNA
<213> ORGANISM: Artificial
<220> FEATURE:
<223> OTHER INFORMATION: IsomiR sequence

<400> SEQUENCE: 221
gcugcuuggu acuuggagag                                           20

<210> SEQ ID NO 222
<211> LENGTH: 19
<212> TYPE: RNA
<213> ORGANISM: Artificial
<220> FEATURE:
<223> OTHER INFORMATION: IsomiR sequence

<400> SEQUENCE: 222
aggugguccg uggcgcguu                                            19

<210> SEQ ID NO 223
<211> LENGTH: 19
<212> TYPE: RNA
<213> ORGANISM: Artificial
<220> FEATURE:
<223> OTHER INFORMATION: IsomiR sequence

<400> SEQUENCE: 223
cugcuuggua cuuggagag                                            19

<210> SEQ ID NO 224
<211> LENGTH: 21
<212> TYPE: RNA
<213> ORGANISM: Artificial
<220> FEATURE:
<223> OTHER INFORMATION: IsomiR sequence

<400> SEQUENCE: 224
ugcugcuugg uacuuggaga g                                         21

<210> SEQ ID NO 225
<211> LENGTH: 21
<212> TYPE: RNA
<213> ORGANISM: Artificial
<220> FEATURE:
<223> OTHER INFORMATION: IsomiR sequence

<400> SEQUENCE: 225
gagguggucc guggcgcguu c                                         21

<210> SEQ ID NO 226
<211> LENGTH: 23
<212> TYPE: RNA
<213> ORGANISM: Artificial
<220> FEATURE:
<223> OTHER INFORMATION: IsomiR sequence

<400> SEQUENCE: 226
aggugguccg uggcgcguuc gcu                                       23

```
<210> SEQ ID NO 227
<211> LENGTH: 18
<212> TYPE: RNA
<213> ORGANISM: Artificial
<220> FEATURE:
<223> OTHER INFORMATION: IsomiR sequence

<400> SEQUENCE: 227
ggugguccgu ggcgcguu                                                 18

<210> SEQ ID NO 228
<211> LENGTH: 18
<212> TYPE: RNA
<213> ORGANISM: Artificial
<220> FEATURE:
<223> OTHER INFORMATION: IsomiR sequence

<400> SEQUENCE: 228
aggugguccg uggcgcgu                                                 18

<210> SEQ ID NO 229
<211> LENGTH: 20
<212> TYPE: RNA
<213> ORGANISM: Artificial
<220> FEATURE:
<223> OTHER INFORMATION: IsomiR sequence

<400> SEQUENCE: 229
gagguggucc guggcgcguu                                               20

<210> SEQ ID NO 230
<211> LENGTH: 21
<212> TYPE: RNA
<213> ORGANISM: Artificial
<220> FEATURE:
<223> OTHER INFORMATION: IsomiR sequence

<400> SEQUENCE: 230 gcccucaucug ucuguugggc u                                            21

<210> SEQ ID NO 231
<211> LENGTH: 20
<212> TYPE: RNA
<213> ORGANISM: Artificial
<220> FEATURE:
<223> OTHER INFORMATION: IsomiR sequence

<400> SEQUENCE: 231
ccucaucugu cuguugggcu                                               20

<210> SEQ ID NO 232
<211> LENGTH: 22
<212> TYPE: RNA
<213> ORGANISM: Artificial
<220> FEATURE:
<223> OTHER INFORMATION: IsomiR sequence

<400> SEQUENCE: 232 agcccucaucu gucuguuggg cu                                           22

<210> SEQ ID NO 233
<211> LENGTH: 19
<212> TYPE: RNA
<213> ORGANISM: Artificial
<220> FEATURE:
<223> OTHER INFORMATION: IsomiR sequence
```

```
<400> SEQUENCE: 233
cucaucuguc uguugggcu                                              19

<210> SEQ ID NO 234
<211> LENGTH: 18
<212> TYPE: RNA
<213> ORGANISM: Artificial
<220> FEATURE:
<223> OTHER INFORMATION: IsomiR sequence

<400> SEQUENCE: 234
ucaucugucu guugggcu                                               18

<210> SEQ ID NO 235
<211> LENGTH: 23
<212> TYPE: RNA
<213> ORGANISM: Artificial
<220> FEATURE:
<223> OTHER INFORMATION: IsomiR sequence

<400> SEQUENCE: 235
ccccgaggcg gauucaccau gag                                         23

<210> SEQ ID NO 236
<211> LENGTH: 21
<212> TYPE: RNA
<213> ORGANISM: Artificial
<220> FEATURE:
<223> OTHER INFORMATION: IsomiR sequence

<400> SEQUENCE: 236
ccucugggcc cuuccuccag c                                           21

<210> SEQ ID NO 237
<211> LENGTH: 18
<212> TYPE: RNA
<213> ORGANISM: Artificial
<220> FEATURE:
<223> OTHER INFORMATION: IsomiR sequence

<400> SEQUENCE: 237
ccccgaggcg gauucacc                                               18

<210> SEQ ID NO 238
<211> LENGTH: 20
<212> TYPE: RNA
<213> ORGANISM: Artificial
<220> FEATURE:
<223> OTHER INFORMATION: IsomiR sequence

<400> SEQUENCE: 238
gccucaucug ucuguugggc                                             20

<210> SEQ ID NO 239
<211> LENGTH: 19
<212> TYPE: RNA
<213> ORGANISM: Artificial
<220> FEATURE:
<223> OTHER INFORMATION: IsomiR sequence

<400> SEQUENCE: 239
ccucaucugu cuguugggc                                              19

<210> SEQ ID NO 240
<211> LENGTH: 23
```

<212> TYPE: RNA
<213> ORGANISM: Artificial
<220> FEATURE:
<223> OTHER INFORMATION: IsomiR sequence

<400> SEQUENCE: 240
gugaaggcgg guggugcuca gau                                        23

<210> SEQ ID NO 241
<211> LENGTH: 19
<212> TYPE: RNA
<213> ORGANISM: Artificial
<220> FEATURE:
<223> OTHER INFORMATION: IsomiR sequence

<400> SEQUENCE: 241
gccucaucug ucuguuggg                                             19

<210> SEQ ID NO 242
<211> LENGTH: 26
<212> TYPE: RNA
<213> ORGANISM: Artificial
<220> FEATURE:
<223> OTHER INFORMATION: IsomiR sequence

<400> SEQUENCE: 242
ggaggcaggg ccuuugugaa ggcggg                                     26

<210> SEQ ID NO 243
<211> LENGTH: 20
<212> TYPE: RNA
<213> ORGANISM: Artificial
<220> FEATURE:
<223> OTHER INFORMATION: IsomiR sequence

<400> SEQUENCE: 243
agccucaucu gucuguuggg                                            20

<210> SEQ ID NO 244
<211> LENGTH: 20
<212> TYPE: RNA
<213> ORGANISM: Artificial
<220> FEATURE:
<223> OTHER INFORMATION: IsomiR sequence

<400> SEQUENCE: 244
ccccgaggcg gauucaccau                                            20

<210> SEQ ID NO 245
<211> LENGTH: 24
<212> TYPE: RNA
<213> ORGANISM: Artificial
<220> FEATURE:
<223> OTHER INFORMATION: IsomiR sequence

<400> SEQUENCE: 245
ucucacacag aaaucgcacc cguc                                       24

<210> SEQ ID NO 246
<211> LENGTH: 22
<212> TYPE: RNA
<213> ORGANISM: Artificial
<220> FEATURE:
<223> OTHER INFORMATION: IsomiR sequence

<400> SEQUENCE: 246
ucucacacag aaaucgcacc cg         22

<210> SEQ ID NO 247
<211> LENGTH: 23
<212> TYPE: RNA
<213> ORGANISM: Artificial
<220> FEATURE:
<223> OTHER INFORMATION: IsomiR sequence

<400> SEQUENCE: 247
ucacacagaa aucgcacccg uca         23

<210> SEQ ID NO 248
<211> LENGTH: 25
<212> TYPE: RNA
<213> ORGANISM: Artificial
<220> FEATURE:
<223> OTHER INFORMATION: IsomiR sequence

<400> SEQUENCE: 248
ucucacacag aaaucgcacc cguca         25

<210> SEQ ID NO 249
<211> LENGTH: 20
<212> TYPE: RNA
<213> ORGANISM: Artificial
<220> FEATURE:
<223> OTHER INFORMATION: IsomiR sequence

<400> SEQUENCE: 249
ucucacacag aaaucgcacc         20

<210> SEQ ID NO 250
<211> LENGTH: 22
<212> TYPE: RNA
<213> ORGANISM: Artificial
<220> FEATURE:
<223> OTHER INFORMATION: IsomiR sequence

<400> SEQUENCE: 250
ucacacagaa aucgcacccg uc         22

<210> SEQ ID NO 251
<211> LENGTH: 21
<212> TYPE: RNA
<213> ORGANISM: Artificial
<220> FEATURE:
<223> OTHER INFORMATION: IsomiR sequence

<400> SEQUENCE: 251
ucacacagaa aucgcacccg u         21

<210> SEQ ID NO 252
<211> LENGTH: 22
<212> TYPE: RNA
<213> ORGANISM: Artificial
<220> FEATURE:
<223> OTHER INFORMATION: IsomiR sequence

<400> SEQUENCE: 252
cucacacaga aaucgcaccc gu         22

<210> SEQ ID NO 253
<211> LENGTH: 21
<212> TYPE: RNA
<213> ORGANISM: Artificial

```
<220> FEATURE:
<223> OTHER INFORMATION: IsomiR sequence

<400> SEQUENCE: 253
ucucacacag aaaucgcacc c                                              21

<210> SEQ ID NO 254
<211> LENGTH: 23
<212> TYPE: RNA
<213> ORGANISM: Artificial
<220> FEATURE:
<223> OTHER INFORMATION: IsomiR sequence

<400> SEQUENCE: 254
cucacacaga aaucgcaccc guc                                            23

<210> SEQ ID NO 255
<211> LENGTH: 22
<212> TYPE: RNA
<213> ORGANISM: Artificial
<220> FEATURE:
<223> OTHER INFORMATION: IsomiR sequence

<400> SEQUENCE: 255
cacacagaaa ucgcacccgu ca                                             22

<210> SEQ ID NO 256
<211> LENGTH: 20
<212> TYPE: RNA
<213> ORGANISM: Artificial
<220> FEATURE:
<223> OTHER INFORMATION: IsomiR sequence

<400> SEQUENCE: 256
ucacacagaa aucgcacccg                                                20

<210> SEQ ID NO 257
<211> LENGTH: 21
<212> TYPE: RNA
<213> ORGANISM: Artificial
<220> FEATURE:
<223> OTHER INFORMATION: IsomiR sequence

<400> SEQUENCE: 257
cucacacaga aaucgcaccc g                                              21

<210> SEQ ID NO 258
<211> LENGTH: 24
<212> TYPE: RNA
<213> ORGANISM: Artificial
<220> FEATURE:
<223> OTHER INFORMATION: IsomiR sequence

<400> SEQUENCE: 258
cucacacaga aaucgcaccc guca                                           24

<210> SEQ ID NO 259
<211> LENGTH: 19
<212> TYPE: RNA
<213> ORGANISM: Artificial
<220> FEATURE:
<223> OTHER INFORMATION: IsomiR sequence

<400> SEQUENCE: 259
ucucacacag aaaucgcac                                                 19
```

<210> SEQ ID NO 260
<211> LENGTH: 21
<212> TYPE: RNA
<213> ORGANISM: Artificial
<220> FEATURE:
<223> OTHER INFORMATION: IsomiR sequence

<400> SEQUENCE: 260
cacacagaaa ucgcacccgu c                                              21

<210> SEQ ID NO 261
<211> LENGTH: 19
<212> TYPE: RNA
<213> ORGANISM: Artificial
<220> FEATURE:
<223> OTHER INFORMATION: IsomiR sequence

<400> SEQUENCE: 261
acacagaaau cgcacccgu                                                 19

<210> SEQ ID NO 262
<211> LENGTH: 20
<212> TYPE: RNA
<213> ORGANISM: Artificial
<220> FEATURE:
<223> OTHER INFORMATION: IsomiR sequence

<400> SEQUENCE: 262
cacacagaaa ucgcacccgu                                                20

<210> SEQ ID NO 263
<211> LENGTH: 20
<212> TYPE: RNA
<213> ORGANISM: Artificial
<220> FEATURE:
<223> OTHER INFORMATION: IsomiR sequence

<400> SEQUENCE: 263
cucacacaga aaucgcaccc                                                20

<210> SEQ ID NO 264
<211> LENGTH: 18
<212> TYPE: RNA
<213> ORGANISM: Artificial
<220> FEATURE:
<223> OTHER INFORMATION: IsomiR sequence

<400> SEQUENCE: 264
acagaaaucg cacccguc                                                  18

<210> SEQ ID NO 265
<211> LENGTH: 19
<212> TYPE: RNA
<213> ORGANISM: Artificial
<220> FEATURE:
<223> OTHER INFORMATION: IsomiR sequence

<400> SEQUENCE: 265
acagaaaucg cacccguca                                                 19

<210> SEQ ID NO 266
<211> LENGTH: 19
<212> TYPE: RNA
<213> ORGANISM: Artificial
<220> FEATURE:
<223> OTHER INFORMATION: IsomiR sequence

<400> SEQUENCE: 266
ucacacagaa aucgcaccc                                                    19

<210> SEQ ID NO 267
<211> LENGTH: 18
<212> TYPE: RNA
<213> ORGANISM: Artificial
<220> FEATURE:
<223> OTHER INFORMATION: IsomiR sequence

<400> SEQUENCE: 267
ucucacacag aaaucgca                                                     18

<210> SEQ ID NO 268
<211> LENGTH: 22
<212> TYPE: RNA
<213> ORGANISM: Artificial
<220> FEATURE:
<223> OTHER INFORMATION: IsomiR sequence

<400> SEQUENCE: 268
gucucacaca gaaaucgcac cc                                                22

<210> SEQ ID NO 269
<211> LENGTH: 21
<212> TYPE: RNA
<213> ORGANISM: Artificial
<220> FEATURE:
<223> OTHER INFORMATION: IsomiR sequence

<400> SEQUENCE: 269
acacagaaau cgcacccguc a                                                 21

<210> SEQ ID NO 270
<211> LENGTH: 18
<212> TYPE: RNA
<213> ORGANISM: Artificial
<220> FEATURE:
<223> OTHER INFORMATION: IsomiR sequence

<400> SEQUENCE: 270
cacagaaauc gcacccgu                                                     18

<210> SEQ ID NO 271
<211> LENGTH: 24
<212> TYPE: RNA
<213> ORGANISM: Artificial
<220> FEATURE:
<223> OTHER INFORMATION: IsomiR sequence

<400> SEQUENCE: 271
ucacacagaa aucgcacccg ucac                                              24

<210> SEQ ID NO 272
<211> LENGTH: 18
<212> TYPE: RNA
<213> ORGANISM: Artificial
<220> FEATURE:
<223> OTHER INFORMATION: IsomiR sequence

<400> SEQUENCE: 272
ucacacagaa aucgcacc                                                     18

<210> SEQ ID NO 273

```
<211> LENGTH: 19
<212> TYPE: RNA
<213> ORGANISM: Artificial
<220> FEATURE:
<223> OTHER INFORMATION: IsomiR sequence

<400> SEQUENCE: 273
cacagaaauc gcacccguc                                                    19

<210> SEQ ID NO 274
<211> LENGTH: 26
<212> TYPE: RNA
<213> ORGANISM: Artificial
<220> FEATURE:
<223> OTHER INFORMATION: IsomiR sequence

<400> SEQUENCE: 274
ggggugcuau cugugauuga gggaca                                            26

<210> SEQ ID NO 275
<211> LENGTH: 25
<212> TYPE: RNA
<213> ORGANISM: Artificial
<220> FEATURE:
<223> OTHER INFORMATION: IsomiR sequence

<400> SEQUENCE: 275
ggggugcuau cugugauuga gggac                                             25

<210> SEQ ID NO 276
<211> LENGTH: 24
<212> TYPE: RNA
<213> ORGANISM: Artificial
<220> FEATURE:
<223> OTHER INFORMATION: IsomiR sequence

<400> SEQUENCE: 276
ggggugcuau cugugauuga ggga                                              24

<210> SEQ ID NO 277
<211> LENGTH: 22
<212> TYPE: RNA
<213> ORGANISM: Artificial
<220> FEATURE:
<223> OTHER INFORMATION: isomiR sequence

<400> SEQUENCE: 277
ggggugcuau cugugauuga gg                                                22

<210> SEQ ID NO 278
<211> LENGTH: 22
<212> TYPE: RNA
<213> ORGANISM: Artificial
<220> FEATURE:
<223> OTHER INFORMATION: IsomiR sequence

<400> SEQUENCE: 278
ugcuaucugu gauugaggga ca                                                22

<210> SEQ ID NO 279
<211> LENGTH: 23
<212> TYPE: RNA
<213> ORGANISM: Artificial
<220> FEATURE:
<223> OTHER INFORMATION: IsomiR sequence

<400> SEQUENCE: 279
```

```
aggggugcua ucugugauug agg                                             23

<210> SEQ ID NO 280
<211> LENGTH: 23
<212> TYPE: RNA
<213> ORGANISM: Artificial
<220> FEATURE:
<223> OTHER INFORMATION: IsomiR sequence

<400> SEQUENCE: 280
ggggugcuau cugugauuga ggg                                             23

<210> SEQ ID NO 281
<211> LENGTH: 27
<212> TYPE: RNA
<213> ORGANISM: Artificial
<220> FEATURE:
<223> OTHER INFORMATION: IsomiR sequence

<400> SEQUENCE: 281
aggggugcua ucugugauug agggaca                                         27

<210> SEQ ID NO 282
<211> LENGTH: 25
<212> TYPE: RNA
<213> ORGANISM: Artificial
<220> FEATURE:
<223> OTHER INFORMATION: IsomiR sequence

<400> SEQUENCE: 282
aggggugcua ucugugauug aggga                                           25

<210> SEQ ID NO 283
<211> LENGTH: 20
<212> TYPE: RNA
<213> ORGANISM: Artificial
<220> FEATURE:
<223> OTHER INFORMATION: IsomiR sequence

<400> SEQUENCE: 283
ggggugcuau cugugauuga                                                 20

<210> SEQ ID NO 284
<211> LENGTH: 21
<212> TYPE: RNA
<213> ORGANISM: Artificial
<220> FEATURE:
<223> OTHER INFORMATION: IsomiR sequence

<400> SEQUENCE: 284
ugcuaucugu gauugaggga c                                               21

<210> SEQ ID NO 285
<211> LENGTH: 23
<212> TYPE: RNA
<213> ORGANISM: Artificial
<220> FEATURE:
<223> OTHER INFORMATION: IsomiR sequence

<400> SEQUENCE: 285
gggugcuauc ugugauugag gga                                             23

<210> SEQ ID NO 286
<211> LENGTH: 24
<212> TYPE: RNA
```

```
<213> ORGANISM: Artificial
<220> FEATURE:
<223> OTHER INFORMATION: IsomiR sequence

<400> SEQUENCE: 286
aggggugcua ucugugauug aggg                                              24

<210> SEQ ID NO 287
<211> LENGTH: 24
<212> TYPE: RNA
<213> ORGANISM: Artificial
<220> FEATURE:
<223> OTHER INFORMATION: IsomiR sequence

<400> SEQUENCE: 287
gggugcuauc ugugauugag ggac                                              24

<210> SEQ ID NO 288
<211> LENGTH: 22
<212> TYPE: RNA
<213> ORGANISM: Artificial
<220> FEATURE:
<223> OTHER INFORMATION: IsomiR sequence

<400> SEQUENCE: 288
aggggugcua ucugugauug ag                                                22

<210> SEQ ID NO 289
<211> LENGTH: 22
<212> TYPE: RNA
<213> ORGANISM: Artificial
<220> FEATURE:
<223> OTHER INFORMATION: IsomiR sequence

<400> SEQUENCE: 289
gggugcuauc ugugauugag gg                                                22

<210> SEQ ID NO 290
<211> LENGTH: 21
<212> TYPE: RNA
<213> ORGANISM: Artificial
<220> FEATURE:
<223> OTHER INFORMATION: IsomiR sequence

<400> SEQUENCE: 290
gggugcuauc ugugauugag g                                                 21

<210> SEQ ID NO 291
<211> LENGTH: 20
<212> TYPE: RNA
<213> ORGANISM: Artificial
<220> FEATURE:
<223> OTHER INFORMATION: IsomiR sequence

<400> SEQUENCE: 291
ugcuaucugu gauugaggga                                                   20

<210> SEQ ID NO 292
<211> LENGTH: 25
<212> TYPE: RNA
<213> ORGANISM: Artificial
<220> FEATURE:
<223> OTHER INFORMATION: IsomiR sequence

<400> SEQUENCE: 292
gggugcuauc ugugauugag ggaca                                             25
```

```
<210> SEQ ID NO 293
<211> LENGTH: 26
<212> TYPE: RNA
<213> ORGANISM: Artificial
<220> FEATURE:
<223> OTHER INFORMATION: IsomiR sequence

<400> SEQUENCE: 293
aggggugcua ucugugauug agggac                                         26

<210> SEQ ID NO 294
<211> LENGTH: 22
<212> TYPE: RNA
<213> ORGANISM: Artificial
<220> FEATURE:
<223> OTHER INFORMATION: IsomiR sequence

<400> SEQUENCE: 294
cugugaaacu gggcucaagg ug                                             22

<210> SEQ ID NO 295
<211> LENGTH: 20
<212> TYPE: RNA
<213> ORGANISM: Artificial
<220> FEATURE:
<223> OTHER INFORMATION: IsomiR sequence

<400> SEQUENCE: 295
aggggugcua ucugugauug                                                20

<210> SEQ ID NO 296
<211> LENGTH: 21
<212> TYPE: RNA
<213> ORGANISM: Artificial
<220> FEATURE:
<223> OTHER INFORMATION: IsomiR sequence

<400> SEQUENCE: 296
ggggugcuau cugugauuga g                                              21

<210> SEQ ID NO 297
<211> LENGTH: 23
<212> TYPE: RNA
<213> ORGANISM: Artificial
<220> FEATURE:
<223> OTHER INFORMATION: IsomiR sequence

<400> SEQUENCE: 297
ugcuaucugu gauugaggga cau                                            23

<210> SEQ ID NO 298
<211> LENGTH: 23
<212> TYPE: RNA
<213> ORGANISM: Artificial
<220> FEATURE:
<223> OTHER INFORMATION: IsomiR sequence

<400> SEQUENCE: 298
cugugaaacu gggcucaagg uga                                            23

<210> SEQ ID NO 299
<211> LENGTH: 23
<212> TYPE: RNA
<213> ORGANISM: Artificial
<220> FEATURE:
```

<223> OTHER INFORMATION: IsomiR sequence

<400> SEQUENCE: 299
ggugcuaucu gugauugagg gac                                    23

<210> SEQ ID NO 300
<211> LENGTH: 20
<212> TYPE: RNA
<213> ORGANISM: Artificial
<220> FEATURE:
<223> OTHER INFORMATION: IsomiR sequence

<400> SEQUENCE: 300
gugaaacugg gcucaaggug                                        20

<210> SEQ ID NO 301
<211> LENGTH: 20
<212> TYPE: RNA
<213> ORGANISM: Artificial
<220> FEATURE:
<223> OTHER INFORMATION: IsomiR sequence

<400> SEQUENCE: 301
gggugcuauc ugugauugag                                        20

<210> SEQ ID NO 302
<211> LENGTH: 19
<212> TYPE: RNA
<213> ORGANISM: Artificial
<220> FEATURE:
<223> OTHER INFORMATION: IsomiR sequence

<400> SEQUENCE: 302
ggggugcuau cugugauug                                         19

<210> SEQ ID NO 303
<211> LENGTH: 21
<212> TYPE: RNA
<213> ORGANISM: Artificial
<220> FEATURE:
<223> OTHER INFORMATION: IsomiR sequence

<400> SEQUENCE: 303
gcuaucugug auugagggac a                                      21

<210> SEQ ID NO 304
<211> LENGTH: 23
<212> TYPE: RNA
<213> ORGANISM: Artificial
<220> FEATURE:
<223> OTHER INFORMATION: IsomiR sequence

<400> SEQUENCE: 304
ccugugaaac ugggcucaag gug                                    23

<210> SEQ ID NO 305
<211> LENGTH: 22
<212> TYPE: RNA
<213> ORGANISM: Artificial
<220> FEATURE:
<223> OTHER INFORMATION: IsomiR sequence

<400> SEQUENCE: 305
gugcuaucug ugauugaggg ac                                     22

```
<210> SEQ ID NO 306
<211> LENGTH: 28
<212> TYPE: RNA
<213> ORGANISM: Artificial
<220> FEATURE:
<223> OTHER INFORMATION: IsomiR sequence

<400> SEQUENCE: 306 agggugcua ucugugauug agggacau                                        28

<210> SEQ ID NO 307
<211> LENGTH: 19
<212> TYPE: RNA
<213> ORGANISM: Artificial
<220> FEATURE:
<223> OTHER INFORMATION: IsomiR sequence

<400> SEQUENCE: 307
ugcuaucugu gauugaggg                                                 19

<210> SEQ ID NO 308
<211> LENGTH: 18
<212> TYPE: RNA
<213> ORGANISM: Artificial
<220> FEATURE:
<223> OTHER INFORMATION: IsomiR sequence

<400> SEQUENCE: 308
gggugcuauc ugugauug                                                  18

<210> SEQ ID NO 309
<211> LENGTH: 19
<212> TYPE: RNA
<213> ORGANISM: Artificial
<220> FEATURE:
<223> OTHER INFORMATION: IsomiR sequence

<400> SEQUENCE: 309
caugguuaau ggaauuguc                                                 19

<210> SEQ ID NO 310
<211> LENGTH: 27
<212> TYPE: RNA
<213> ORGANISM: Artificial
<220> FEATURE:
<223> OTHER INFORMATION: IsomiR sequence

<400> SEQUENCE: 310
ggggugcuau cugugauuga gggacau                                        27

<210> SEQ ID NO 311
<211> LENGTH: 19
<212> TYPE: RNA
<213> ORGANISM: Artificial
<220> FEATURE:
<223> OTHER INFORMATION: IsomiR sequence

<400> SEQUENCE: 311
gggugcuauc ugugauuga                                                 19

<210> SEQ ID NO 312
<211> LENGTH: 19
<212> TYPE: RNA
<213> ORGANISM: Artificial
<220> FEATURE:
<223> OTHER INFORMATION: IsomiR sequence
```

```
<400> SEQUENCE: 312
uaucugugau ugagggaca                                              19

<210> SEQ ID NO 313
<211> LENGTH: 21
<212> TYPE: RNA
<213> ORGANISM: Artificial
<220> FEATURE:
<223> OTHER INFORMATION: IsomiR sequence

<400> SEQUENCE: 313
gugaaacugg gcucaaggug a                                           21

<210> SEQ ID NO 314
<211> LENGTH: 24
<212> TYPE: RNA
<213> ORGANISM: Artificial
<220> FEATURE:
<223> OTHER INFORMATION: IsomiR sequence

<400> SEQUENCE: 314
ccugugaaac ugggcucaag guga                                        24

<210> SEQ ID NO 315
<211> LENGTH: 20
<212> TYPE: RNA
<213> ORGANISM: Artificial
<220> FEATURE:
<223> OTHER INFORMATION: IsomiR sequence

<400> SEQUENCE: 315
ggugcuaucu gugauugagg                                             20

<210> SEQ ID NO 316
<211> LENGTH: 20
<212> TYPE: RNA
<213> ORGANISM: Artificial
<220> FEATURE:
<223> OTHER INFORMATION: IsomiR sequence

<400> SEQUENCE: 316
cuaucuguga uugagggaca                                             20

<210> SEQ ID NO 317
<211> LENGTH: 19
<212> TYPE: RNA
<213> ORGANISM: Artificial
<220> FEATURE:
<223> OTHER INFORMATION: IsomiR sequence

<400> SEQUENCE: 317
ugaaacuggg cucaaggug                                              19

<210> SEQ ID NO 318
<211> LENGTH: 22
<212> TYPE: RNA
<213> ORGANISM: Artificial
<220> FEATURE:
<223> OTHER INFORMATION: IsomiR sequence

<400> SEQUENCE: 318
ugugaaacug ggcucaaggu ga                                          22

<210> SEQ ID NO 319
<211> LENGTH: 21
```

```
<212> TYPE: RNA
<213> ORGANISM: Artificial
<220> FEATURE:
<223> OTHER INFORMATION: IsomiR sequence

<400> SEQUENCE: 319
gcugacuccu aguccagggc u                                          21

<210> SEQ ID NO 320
<211> LENGTH: 20
<212> TYPE: RNA
<213> ORGANISM: Artificial
<220> FEATURE:
<223> OTHER INFORMATION: IsomiR sequence

<400> SEQUENCE: 320
gcugacuccu aguccagggc                                            20

<210> SEQ ID NO 321
<211> LENGTH: 18
<212> TYPE: RNA
<213> ORGANISM: Artificial
<220> FEATURE:
<223> OTHER INFORMATION: IsomiR sequence

<400> SEQUENCE: 321
gcugacuccu aguccagg                                              18

<210> SEQ ID NO 322
<211> LENGTH: 19
<212> TYPE: RNA
<213> ORGANISM: Artificial
<220> FEATURE:
<223> OTHER INFORMATION: IsomiR sequence

<400> SEQUENCE: 322
gcugacuccu aguccaggg                                             19

<210> SEQ ID NO 323
<211> LENGTH: 24
<212> TYPE: RNA
<213> ORGANISM: Artificial
<220> FEATURE:
<223> OTHER INFORMATION: IsomiR sequence

<400> SEQUENCE: 323
gcugacuccu aguccagggc ucgu                                       24

<210> SEQ ID NO 324
<211> LENGTH: 23
<212> TYPE: RNA
<213> ORGANISM: Artificial
<220> FEATURE:
<223> OTHER INFORMATION: IsomiR sequence

<400> SEQUENCE: 324
gcugacuccu aguccagggc ucg                                        23

<210> SEQ ID NO 325
<211> LENGTH: 20
<212> TYPE: RNA
<213> ORGANISM: Artificial
<220> FEATURE:
<223> OTHER INFORMATION: IsomiR sequence

<400> SEQUENCE: 325
```

-continued

| | |
|---|---|
| cugacuccua guccagggcu | 20 |

<210> SEQ ID NO 326
<211> LENGTH: 19
<212> TYPE: RNA
<213> ORGANISM: Artificial
<220> FEATURE:
<223> OTHER INFORMATION: IsomiR sequence

<400> SEQUENCE: 326

| | |
|---|---|
| cugacuccua guccagggc | 19 |

<210> SEQ ID NO 327
<211> LENGTH: 21
<212> TYPE: RNA
<213> ORGANISM: Artificial
<220> FEATURE:
<223> OTHER INFORMATION: IsomiR sequence

<400> SEQUENCE: 327

| | |
|---|---|
| cugacuccua guccagggcu c | 21 |

<210> SEQ ID NO 328
<211> LENGTH: 21
<212> TYPE: RNA
<213> ORGANISM: Artificial
<220> FEATURE:
<223> OTHER INFORMATION: IsomiR sequence

<400> SEQUENCE: 328

| | |
|---|---|
| ugacuccuag uccagggcuc g | 21 |

<210> SEQ ID NO 329
<211> LENGTH: 19
<212> TYPE: RNA
<213> ORGANISM: Artificial
<220> FEATURE:
<223> OTHER INFORMATION: IsomiR sequence

<400> SEQUENCE: 329

| | |
|---|---|
| ugacuccuag uccagggcu | 19 |

<210> SEQ ID NO 330
<211> LENGTH: 20
<212> TYPE: RNA
<213> ORGANISM: Artificial
<220> FEATURE:
<223> OTHER INFORMATION: IsomiR sequence

<400> SEQUENCE: 330

| | |
|---|---|
| ugacuccuag uccagggcuc | 20 |

<210> SEQ ID NO 331
<211> LENGTH: 22
<212> TYPE: RNA
<213> ORGANISM: Artificial
<220> FEATURE:
<223> OTHER INFORMATION: IsomiR sequence

<400> SEQUENCE: 331

| | |
|---|---|
| gcccugaacg aggggucugg ag | 22 |

<210> SEQ ID NO 332
<211> LENGTH: 21
<212> TYPE: RNA
<213> ORGANISM: Artificial

```
<220> FEATURE:
<223> OTHER INFORMATION: IsomiR sequence

<400> SEQUENCE: 332
cccugaacga ggggucugga g                                              21

<210> SEQ ID NO 333
<211> LENGTH: 21
<212> TYPE: RNA
<213> ORGANISM: Artificial
<220> FEATURE:
<223> OTHER INFORMATION: IsomiR sequence

<400> SEQUENCE: 333
gcccugaacg agggguucugg a                                             21

<210> SEQ ID NO 334
<211> LENGTH: 22
<212> TYPE: RNA
<213> ORGANISM: Artificial
<220> FEATURE:
<223> OTHER INFORMATION: IsomiR sequence

<400> SEQUENCE: 334
agugccgcca ucuuuugagu gu                                             22

<210> SEQ ID NO 335
<211> LENGTH: 21
<212> TYPE: RNA
<213> ORGANISM: Artificial
<220> FEATURE:
<223> OTHER INFORMATION: IsomiR sequence

<400> SEQUENCE: 335
gugccgccau cuuuugagug u                                              21

<210> SEQ ID NO 336
<211> LENGTH: 21
<212> TYPE: RNA
<213> ORGANISM: Artificial
<220> FEATURE:
<223> OTHER INFORMATION: IsomiR sequence

<400> SEQUENCE: 336
aagugccgcc aucuuuugag u                                              21

<210> SEQ ID NO 337
<211> LENGTH: 20
<212> TYPE: RNA
<213> ORGANISM: Artificial
<220> FEATURE:
<223> OTHER INFORMATION: IsomiR sequence

<400> SEQUENCE: 337
agugccgcca ucuuuugagu                                                20

<210> SEQ ID NO 338
<211> LENGTH: 22
<212> TYPE: RNA
<213> ORGANISM: Artificial
<220> FEATURE:
<223> OTHER INFORMATION: IsomiR sequence

<400> SEQUENCE: 338
aagugccgcc aucuuuugag ug                                             22
```

<210> SEQ ID NO 339
<211> LENGTH: 20
<212> TYPE: RNA
<213> ORGANISM: Artificial
<220> FEATURE:
<223> OTHER INFORMATION: IsomiR sequence

<400> SEQUENCE: 339
gugccgccau cuuuugagug                                                   20

<210> SEQ ID NO 340
<211> LENGTH: 20
<212> TYPE: RNA
<213> ORGANISM: Artificial
<220> FEATURE:
<223> OTHER INFORMATION: IsomiR sequence

<400> SEQUENCE: 340
ugccgccauc uuuugagugu                                                   20

<210> SEQ ID NO 341
<211> LENGTH: 23
<212> TYPE: RNA
<213> ORGANISM: Artificial
<220> FEATURE:
<223> OTHER INFORMATION: IsomiR sequence

<400> SEQUENCE: 341
agugccgcca ucuuuugagu guu                                               23

<210> SEQ ID NO 342
<211> LENGTH: 19
<212> TYPE: RNA
<213> ORGANISM: Artificial
<220> FEATURE:
<223> OTHER INFORMATION: IsomiR sequence

<400> SEQUENCE: 342
gugccgccau cuuuugagu                                                    19

<210> SEQ ID NO 343
<211> LENGTH: 22
<212> TYPE: RNA
<213> ORGANISM: Artificial
<220> FEATURE:
<223> OTHER INFORMATION: IsomiR sequence

<400> SEQUENCE: 343
acucaaacug uggggggcacu uu                                               22

<210> SEQ ID NO 344
<211> LENGTH: 23
<212> TYPE: RNA
<213> ORGANISM: Artificial
<220> FEATURE:
<223> OTHER INFORMATION: IsomiR sequence

<400> SEQUENCE: 344
acucaaacug uggggggcacu uuc                                              23

<210> SEQ ID NO 345
<211> LENGTH: 21
<212> TYPE: RNA
<213> ORGANISM: Artificial
<220> FEATURE:
<223> OTHER INFORMATION: IsomiR sequence

```
<400> SEQUENCE: 345
acucaaacug uggggcacu u                                                    21

<210> SEQ ID NO 346
<211> LENGTH: 24
<212> TYPE: RNA
<213> ORGANISM: Artificial
<220> FEATURE:
<223> OTHER INFORMATION: IsomiR sequence

<400> SEQUENCE: 346
acucaaacug uggggcacu uucu                                                 24

<210> SEQ ID NO 347
<211> LENGTH: 22
<212> TYPE: RNA
<213> ORGANISM: Artificial
<220> FEATURE:
<223> OTHER INFORMATION: IsomiR sequence

<400> SEQUENCE: 347
cucaaacugu gggggcacuu uc                                                  22

<210> SEQ ID NO 348
<211> LENGTH: 19
<212> TYPE: RNA
<213> ORGANISM: Artificial
<220> FEATURE:
<223> OTHER INFORMATION: IsomiR sequence

<400> SEQUENCE: 348
acucaaacug uggggcac                                                       19

<210> SEQ ID NO 349
<211> LENGTH: 23
<212> TYPE: RNA
<213> ORGANISM: Artificial
<220> FEATURE:
<223> OTHER INFORMATION: IsomiR sequence

<400> SEQUENCE: 349
cucaaacugu gggggcacuu ucu                                                 23

<210> SEQ ID NO 350
<211> LENGTH: 21
<212> TYPE: RNA
<213> ORGANISM: Artificial
<220> FEATURE:
<223> OTHER INFORMATION: IsomiR sequence

<400> SEQUENCE: 350
cucaaacugu gggggcacuu u                                                   21

<210> SEQ ID NO 351
<211> LENGTH: 18
<212> TYPE: RNA
<213> ORGANISM: Artificial
<220> FEATURE:
<223> OTHER INFORMATION: IsomiR sequence

<400> SEQUENCE: 351
acucaaacug uggggca                                                        18

<210> SEQ ID NO 352
```

```
<211> LENGTH: 20
<212> TYPE: RNA
<213> ORGANISM: Artificial
<220> FEATURE:
<223> OTHER INFORMATION: IsomiR sequence

<400> SEQUENCE: 352
cucaaacugu gggggcacuu                                              20

<210> SEQ ID NO 353
<211> LENGTH: 18
<212> TYPE: RNA
<213> ORGANISM: Artificial
<220> FEATURE:
<223> OTHER INFORMATION: IsomiR sequence

<400> SEQUENCE: 353
cucaaacugu gggggcac                                                18

<210> SEQ ID NO 354
<211> LENGTH: 19
<212> TYPE: RNA
<213> ORGANISM: Artificial
<220> FEATURE:
<223> OTHER INFORMATION: IsomiR sequence

<400> SEQUENCE: 354
cucaaacugu gggggcacu                                               19

<210> SEQ ID NO 355
<211> LENGTH: 58
<212> TYPE: DNA
<213> ORGANISM: Artificial
<220> FEATURE:
<223> OTHER INFORMATION: Sequence complementary to ATM mRNA

<400> SEQUENCE: 355
ccggcctgcc aacatacttt aagtactcga gtacttaaag tatgttggca ggttttttg      58

<210> SEQ ID NO 356
<211> LENGTH: 58
<212> TYPE: DNA
<213> ORGANISM: Artificial
<220> FEATURE:
<223> OTHER INFORMATION: Sequence complementary to ATM mRNA

<400> SEQUENCE: 356
ccgggcactg aaagaggatc gtaaactcga gtttacgatc ctctttcagt gcttttttg      58

<210> SEQ ID NO 357
<211> LENGTH: 58
<212> TYPE: DNA
<213> ORGANISM: Artificial
<220> FEATURE:
<223> OTHER INFORMATION: Sequence complementary to ATM mRNA

<400> SEQUENCE: 357
ccggcgtgtc ttaatgagac tacaactcga gttgtagtct cattaagaca cgtttttg       58

<210> SEQ ID NO 358
<211> LENGTH: 58
<212> TYPE: DNA
<213> ORGANISM: Artificial
<220> FEATURE:
<223> OTHER INFORMATION: Sequence complementary to ATM mRNA

<400> SEQUENCE: 358
```

```
ccgggccata attcagggta gtttactcga gtaaactacc ctgaattatg gcttttttg      58
```

<210> SEQ ID NO 359
<211> LENGTH: 58
<212> TYPE: DNA
<213> ORGANISM: Artificial
<220> FEATURE:
<223> OTHER INFORMATION: Sequence complementary to ATM mRNA

<400> SEQUENCE: 359

```
ccgggccgtc aactagaaca tgatactcga gtatcatgtt ctagttgacg gcttttttg      58
```

<210> SEQ ID NO 360
<211> LENGTH: 9385
<212> TYPE: DNA
<213> ORGANISM: Homo sapiens

<400> SEQUENCE: 360

```
gcgagaggag tcgggatctg cgctgcagcc accgccgcgg ttgatactac tttgaccttc      60
cgagtgcagt gaggcataca tcacaatttg gaattatgca ttggtttatc aatttacttg     120
tttattgtca ccctgctgcc cagatatgac ttcatgagga cagtgatgtg tgttctgaaa     180
ttgtgaacca tgagtctagt acttaatgat ctgcttatct gctgccgtca actagaacat     240
gatagagcta cagaacgaaa gaaagaagtt gagaaattta agcgcctgat tcgagatcct     300
gaaacaatta acatctaga tcggcattca gattccaaac aaggaaaata tttgaattgg     360
gatgctgttt ttagattttt acagaaatat attcagaaag aaacagaatg tctgagaata     420
gcaaaaccaa atgtatcagc ctcaacacaa gcctccaggc agaaaaagat gcaggaaatc     480
agtagtttgg tcaaatactt catcaaatgt gcaaacagaa gagcacctag gctaaaatgt     540
caagaactct taaattatat catggataca gtgaaagatt catctaatgg tgctatttac     600
ggagctgatt gtagcaacat actactcaaa gacattcttt ctgtgagaaa atactggtgt     660
gaaatatctc agcaacagtg gttagaattg ttctctgtgt acttcaggct ctatctgaaa     720
ccttcacaag atgttcatag agttttagtg gctagaataa ttcatgctgt taccaaagga     780
tgctgttctc agactgacgg attaaaattcc aaattttttgg acttttttttc caaggctatt     840
cagtgtgcga gacaagaaaa gagctcttca ggtctaaatc atatcttagc agctcttact     900
atcttcctca agactttggc tgtcaacttt cgaattcgag tgtgtgaatt aggagatgaa     960
attcttccca ctttgctttta tattggact caacataggc ttaatgattc tttaaaagaa    1020
gtcattattg aattatttca actgcaaatt tatatccatc atccgaaagg agccaaaacc    1080
caagaaaaag gtgcttatga atcaacaaaa tggagaagta ttttatacaa cttatatgat    1140
ctgctagtga atgagataag tcatatagga agtagaggaa agtattcttc aggatttcgt    1200
aatattgccg tcaaagaaaa tttgattgaa ttgatggcag atatctgtca ccaggttttt    1260
aatgaagata ccagatcctt ggagatttct caatcttaca ctactacaca aagagaatct    1320
agtgattaca gtgtcccttg caaaaggaag aaaatagaac taggctggga agtaataaaa    1380
gatcaccttc agaagtcaca gaatgatttt gatcttgtgc cttggctaca gattgcaacc    1440
caattaatat caagtatcc tgcaagtttta cctaactgtg agctgtctcc attactgatg    1500
atactatctc agcttctacc ccaacagcga catgggaac gtacaccata tgtgttacga    1560
tgccttacgg aagttgcatt gtgtcaagac aagaggtcaa acctagaaag ctcacaaaag    1620
tcagatttat taaaactctg gaataaaatt tggtgtatta ccttttcgtgg tataagttct    1680
```

```
gagcaaatac aagctgaaaa ctttggctta cttggagcca taattcaggg tagtttagtt    1740
gaggttgaca gagaattctg gaagttattt actgggtcag cctgcagacc ttcatgtcct    1800
gcagtatgct gtttgacttt ggcactgacc accagtatag ttccaggagc ggtaaaaatg    1860
ggaatagagc aaaatatgtg tgaagtaaat agaagctttt ctttaaagga atcaataatg    1920
aaatggctct tattctatca gttagagggt gacttagaaa atagcacaga agtgcctcca    1980
attcttcaca gtaattttcc tcatcttgta ctggagaaaa ttcttgtgag tctcactatg    2040
aaaaactgta aagctgcaat gaattttttc caaagcgtgc cagaatgtga acaccaccaa    2100
aaagataaag aagaactttc attctcagaa gtagaagaac tatttcttca gacaactttt    2160
gacaagatgg acttttaac cattgtgaga gaatgtggta tagaaaagca ccagtccagt     2220
attggcttct ctgtccacca gaatctcaag gaatcactgg atcgctgtct ctgggatta    2280 tcagaacagc ttctgaataa ttactcatct gagattacaa attcagaaac tcttgtccgg    2340
tgttcacgtc ttttggtggg tgtccttggc tgctactgtt acatgggtgt aatagctgaa    2400
gaggaagcat ataagtcaga attattccag aaagccaact ctctaatgca atgtgcagga    2460
gaaagtatca ctctgtttaa aaataagaca aatgaggaat tcagaattgg ttccttgaga    2520
aatatgatgc agctatgtac acgttgcttg agcaactgta ccaagaagag tccaaataag    2580
attgcatctg cttttttcct gcgattgtta acatcaaagc taatgaatga cattgcagat    2640
atttgtaaaa gtttagcatc cttcatcaaa aagccatttg accgtggaga agtagaatca    2700
atggaagatg atactaatgg aaatctaatg gaggtggagg atcagtcatc catgaatcta    2760
tttaacgatt accctgatag tagtgttagt gatgcaaacg aacctggaga gagccaaagt    2820
accataggtg ccattaatcc tttagctgaa gaatatctgt caaagcaaga tctacttttc    2880
ttagacatgc tcaagttctt gtgtttgtgt gtaactactg ctcagaccaa tactgtgtcc    2940
tttagggcag ctgatattcg gaggaaattg ttaatgttaa ttgattctag cacgctagaa    3000
cctaccaaat ccctccacct gcatatgtat ctaatgcttt taaaggagct tcctggagaa    3060 gagtaccct tgccaatgga agatgttctt gaacttctga accactatc caatgtgtgt     3120 tctttgtatc gtcgtgacca agatgtttgt aaaactattt taaaccatgt ccttcatgta    3180
gtgaaaaacc taggtcaaag caatatggac tctgagaaca caagggatgc tcaaggacag    3240
tttcttacag taattggagc attttggcat ctaacaaagg agaggaaata tatattctct    3300
gtaagaatgg ccctagtaaa ttgccttaaa actttgcttg aggctgatcc ttattcaaaa    3360
tgggccattc ttaatgtaat gggaaaagac tttcctgtaa atgaagtatt tacacaattt    3420
cttgctgaca atcatcacca agttcgcatg ttggctgcag agtcaatcaa tagattgttc    3480
caggacacga agggagattc ttccaggtta ctgaaagcac ttcctttgaa gcttcagcaa    3540
acagcttttg aaaatgcata cttgaaagct caggaaggaa tgagagaaat gtcccatagt    3600
gctgagaacc ctgaaacttt ggatgaaatt tataatagaa aatctgtttt actgacgttg    3660
atagctgtgg ttttatcctg tagccctatc tgcgaaaaac aggctttgtt tgccctgtgt    3720
aaatctgtga agagaatgga attagaacct caccttgtga aaaggtttt agagaaagtt    3780 tctgaaactt ttggatatag acgtttagaa gactttatgg catctcatt agattatctg     3840 gttttggaat ggctaaatct tcaagatact gaatacaact tatcttcttt tccttttatt    3900
ttattaaact acacaaatat tgaggatttc tatagatctt gttataaggt tttgattcca    3960
catctggtga ttagaagtca ttttgatgag gtgaagtcca ttgctaatca gattcaagag    4020
gactggaaaa gtcttctaac agactgcttt ccaaagattc ttgtaaatat tcttccttat    4080
```

```
tttgcctatg agggtaccag agacagtggg atggcacagc aaagagagac tgctaccaag    4140
gtctatgata tgcttaaaag tgaaaactta ttgggaaaac agattgatca cttattcatt    4200
agtaatttac cagagattgt ggtggagtta ttgatgacgt tacatgagcc agcaaattct    4260
agtgccagtc agagcactga cctctgtgac ttttcagggg atttggatcc tgctcctaat    4320
ccacctcatt ttccatcgca tgtgattaaa gcaacatttg cctatatcag caattgtcat    4380
aaaaccaagt taaaaagcat tttagaaatt ctttccaaaa gccctgattc ctatcagaaa    4440
attcttcttg ccatatgtga gcaagcagct gaaacaaata atgtttataa gaagcacaga    4500
attcttaaaa tatatcacct gtttgttagt ttattactga aagatataaa aagtggctta    4560
ggaggagctt gggcctttgt tcttcgagac gttatttata ctttgattca ctatatcaac    4620
caaaggcctt cttgtatcat ggatgtgtca ttacgtagct tctcccttttg ttgtgactta    4680 ttaagtcagg tttgccagac agccgtgact tactgtaagg atgctctaga aaccatctt    4740 catgttattg ttggtacact tatacccctt gtgtatgagc aggtggaggt tcagaaacag    4800
gtattggact tgttgaaata cttagtgata gataacaagg ataatgaaaa cctctatatc    4860
acgattaagc ttttagatcc ttttcctgac catgttgttt ttaaggatttt gcgtattact    4920 cagcaaaaaa tcaaatacag tagaggaccc ttttcactct tggaggaaat taaccatttt    4980
ctctcagtaa gtgtttatga tgcacttcca ttgacaagac ttgaaggact aaaggatctt    5040
cgaagacaac tggaactaca taaagatcag atggtggaca ttatgagagc ttctcaggat    5100
aatccgcaag atgggattat ggtgaaacta gttgtcaatt tgttgcagtt atccaagatg    5160
gcaataaacc acactggtga aaaagaagtt ctagaggctg ttggaagctg cttgggagaa    5220
gtgggtccta tagatttctc taccatagct atacaacata gtaaagatgc atcttatacc    5280
aaggccctta agttatttga agataaagaa cttcagtgga ccttcataat gctgacctac    5340
ctgaataaca cactggtaga agattgtgtc aaagttcgat cagcagctgt tacctgtttg    5400
aaaaacattt tagccacaaa gactggacat agtttctggg agatttataa gatgacaaca    5460
gatccaatgc tggcctatct acagccttttt agaacatcaa gaaaaaagtt tttagaagta    5520
cccagatttg acaaagaaaa ccctttttgaa ggcctggatg atataaatct gtggattcct    5580
ctaagtgaaa atcatgacat ttggataaag acactgactt gtgcttttttt ggacagtgga    5640 ggcacaaaat gtgaaattct tcaattatta aagccaatgt gtgaagtgaa aactgactt    5700 tgtcagactg tacttccata cttgattcat gatattttac tccaagatac aaatgaatca    5760
tggagaaatc tgcttttctac acatgttcag ggattttttca ccagctgtct tcgacacttc    5820
tcgcaaacga gccgatccac aaccctgca aacttggatt cagagtcaga gcactttttc    5880
cgatgctgtt tggataaaaa atcacaaaga acaatgcttg ctgttgtgga ctacatgaga    5940
agacaaaaga gaccttcttc aggaacaatt tttaatgatg ctttctggct ggatttaaat    6000
tatctagaag ttgccaaggt agctcagtct tgtgctgctc actttacagc tttactctat    6060
gcagaaatct atgcagataa gaaaagtatg gatgatcaag agaaaagaag tcttgcattt    6120
gaagaaggaa gccagagtac aactatttct agcttgagtg aaaaaagtaa agaagaaact    6180
ggaataagtt tacaggatct tctcttagaa atctacagaa gtataggggga gccagatagt    6240 ttgtatggct gtggtggagg gaagatgtta caacccatta ctagactacg aacatatgaa    6300
cacgaagcaa tgtggggcaa agccctagta acatatgacc tcgaaacagc aatcccctca    6360
tcaacacgcc aggcaggaat cattcaggcc ttgcagaatt tgggactctg ccatattctt    6420
```

```
tccgtctatt taaaaggatt ggattatgaa aataaagact ggtgtcctga actagaagaa    6480
cttcattacc aagcagcatg gaggaatatg cagtgggacc attgcacttc cgtcagcaaa    6540
gaagtagaag gaaccagtta ccatgaatca ttgtacaatg ctctacaatc tctaagagac    6600
agagaattct ctacatttta tgaaagtctc aaatatgcca gagtaaaaga agtggaagag    6660
atgtgtaagc gcagccttga gtctgtgtat tcgctctatc ccacacttag caggttgcag    6720
gccattggag agctggaaag cattggggag cttttctcaa gatcagtcac acatagacaa    6780
ctctctgaag tatatattaa gtggcagaaa cactcccagc ttctcaagga cagtgatttt    6840
agttttcagg agcctatcat ggctctacgc acagtcattt tggagatcct gatggaaaag    6900
gaaatggaca actcacaaag agaatgtatt aaggacattc tcaccaaaca ccttgtagaa    6960
ctctctatac tggccagaac tttcaagaac actcagctcc ctgaaagggc aatatttcaa    7020
attaaacagt acaattcagt tagctgtgga gtctctgagt ggcagctgga agaagcacaa    7080
gtattctggg caaaaaagga gcagagtctt gccctgagta ttctcaagca aatgatcaag    7140
aagttggatg ccagctgtgc agcgaacaat cccagcctaa aacttacata cacagaatgt    7200
ctgagggttt gtggcaactg gttagcagaa acgtgcttag aaaatcctgc ggtcatcatg    7260
cagacctatc tagaaaaggc agtagaagtt gctggaaatt atgatggaga aagtagtgat    7320
gagctaagaa atggaaaaat gaaggcattt ctctcattag cccggttttc agatactcaa    7380
taccaaagaa ttgaaaacta catgaaatca tcggaatttg aaaacaagca agctctcctg    7440
aaaagagcca agaggaagt aggtctcctt agggaacata aaattcagac aaacagatac    7500
acagtaaagg ttcagcgaga gctggagttg gatgaattag ccctgcgtgc actgaaaagag   7560 gatcgtaaac gcttcttatg taaagcagtt gaaaattata tcaactgctt attaagtgga    7620
gaagaacatg atatgtgggt attccggctt tgttccctct ggcttgaaaa ttctggagtt    7680
tctgaagtca atggcatgat gaagagagac ggaatgaaga ttccaacata taaattttg    7740 cctcttatgt accaattggc tgctagaatg gggaccaaga tgatgggagg cctaggattt    7800
catgaagtcc tcaataatct aatctctaga atttcaatgg atcaccccca tcacactttg    7860
tttattatac tggccttagc aaatgcaaac agagatgaat ttctgactaa accagaggta    7920
gccagaagaa gcagaataac taaaaatgtg cctaaacaaa gctctcagct tgatgaggat    7980
cgaacagagg ctgcaaatag aataatatgt actatcagaa gtaggagacc tcagatggtc    8040
agaagtgttg aggcactttg tgatgcttat attatattag caaacttaga tgccactcag    8100
tggaagactc agagaaaagg cataaatatt ccagcagacc agccaattac taaacttaag    8160
aatttagaag atgttgttgt ccctactatg gaaattaagg tggaccacac aggagaatat    8220
ggaaatctgg tgactataca gtcatttaaa gcagaatttc gcttagcagg aggtgtaaat    8280
ttaccaaaaa taatagattg tgtaggttcc gatggcaagg agaggagaca gcttgttaag    8340
ggccgtgatg acctgagaca agatgctgtc atgcaacagg tcttccagat gtgtaataca    8400
ttactgcaga gaaacacgga aactaggaag aggaaattaa ctatctgtac ttataaggtg    8460
gttcccctct ctcagcgaag tggtgttctt gaatggtgca caggaactgt ccccattggt    8520
gaatttcttg ttaacaatga agatggtgct cataaaagat acaggccaaa tgatttcagt    8580
gcctttcagt gccaaagaa aatgatggag gtgcaaaaaa agtcttttga agagaaatat    8640
gaagtcttca tggatgtttg ccaaaatttt caaccagttt tccgttactt ctgcatggaa    8700
aaattcttgg atccagctat ttggtttgag aagcgattgg cttatacgcg cagtgtagct    8760
acttcttcta ttgttggtta catacttgga cttggtgata gacatgtaca gaatatcttg    8820
```

-continued

```
ataaatgagc agtcagcaga acttgtacat atagatctag gtgttgcttt tgaacagggc    8880
aaaatccttc ctactcctga gacagttcct tttagactca ccagagatat tgtggatggc    8940
atgggcatta cgggtgttga aggtgtcttc agaagatgct gtgagaaaac catggaagtg    9000
atgagaaact ctcaggaaac tctgttaacc attgtagagg tccttctata tgatccactc    9060
tttgactgga ccatgaatcc tttgaaagct ttgtatttac agcagaggcc ggaagatgaa    9120
actgagcttc accctactct gaatgcagat gaccaagaat gcaaacgaaa tctcagtgat    9180
attgaccaga gtttcgacaa agtagctgaa cgtgtcttaa tgagactaca agagaaactg    9240
aaaggagtgg aagaaggcac tgtgctcagt gttggtggac aggtgaattt gctcatacag    9300
caggccatag accccaaaaa tctcagccga ctttccccag gatggaaagc ttgggtgtga    9360
tcttcagtat atgaattacc ctttc                                          9385
```

<210> SEQ ID NO 361
<211> LENGTH: 6112
<212> TYPE: PRT
<213> ORGANISM: Homo sapiens

<400> SEQUENCE: 361

```
Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
    50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Leu Tyr Ile Trp Thr Gln His Arg Leu Asn
            260                 265                 270
```

-continued

```
Asp Ser Leu Lys Glu Val Ile Ile Glu Leu Phe Gln Leu Gln Ile Tyr
        275                 280                 285

Ile His His Pro Lys Gly Ala Lys Thr Gln Glu Lys Gly Ala Tyr Glu
        290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
                340                 345                 350

Cys His Gln Val Phe Asn Glu Asp Thr Arg Ser Leu Glu Ile Ser Gln
        355                 360                 365

Ser Tyr Thr Thr Thr Gln Arg Glu Ser Ser Asp Tyr Ser Val Pro Cys
370                 375                 380

Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
                405                 410                 415

Thr Gln Leu Ile Ser Lys Tyr Pro Ala Ser Leu Pro Asn Cys Glu Leu
        420                 425                 430

Ser Pro Leu Leu Met Ile Leu Ser Gln Leu Leu Pro Gln Gln Arg His
        435                 440                 445

Gly Glu Arg Thr Pro Tyr Val Leu Arg Cys Leu Thr Glu Val Ala Leu
        450                 455                 460

Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Ile Gln Ala Glu Asn Phe Gly Leu Leu Gly Ala Ile Ile
                500                 505                 510

Gln Gly Ser Leu Val Glu Val Asp Arg Glu Phe Trp Lys Leu Phe Thr
        515                 520                 525

Gly Ser Ala Cys Arg Pro Ser Cys Pro Ala Val Cys Cys Leu Thr Leu
        530                 535                 540

Ala Leu Thr Thr Ser Ile Val Pro Gly Ala Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
                580                 585                 590

Thr Glu Val Pro Pro Ile Leu His Ser Asn Phe Pro His Leu Val Leu
        595                 600                 605

Glu Lys Ile Leu Val Ser Leu Thr Met Lys Asn Cys Lys Ala Ala Met
        610                 615                 620

Asn Phe Phe Gln Ser Val Pro Glu Cys Glu His Gln Lys Asp Lys
625                 630                 635                 640

Glu Glu Leu Ser Phe Ser Glu Val Glu Leu Phe Leu Gln Thr Thr
                645                 650                 655

Phe Asp Lys Met Asp Phe Leu Thr Ile Val Arg Glu Cys Gly Ile Glu
                660                 665                 670

Lys His Gln Ser Ser Ile Gly Phe Ser Val His Gln Asn Leu Lys Glu
        675                 680                 685
```

```
Ser Leu Asp Arg Cys Leu Leu Gly Leu Ser Glu Gln Leu Leu Asn Asn
    690                 695                 700

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Asn Ser Leu
            740                 745                 750

Met Gln Cys Ala Gly Glu Ser Ile Thr Leu Phe Lys Asn Lys Thr Asn
        755                 760                 765

Glu Glu Phe Arg Ile Gly Ser Leu Arg Asn Met Met Gln Leu Cys Thr
    770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
            820                 825                 830

Gly Glu Val Glu Ser Met Glu Asp Asp Thr Asn Gly Asn Leu Met Glu
        835                 840                 845

Val Glu Asp Gln Ser Ser Met Asn Leu Phe Asn Asp Tyr Pro Asp Ser
    850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
                885                 890                 895

Phe Leu Asp Met Leu Lys Phe Leu Cys Leu Cys Val Thr Thr Ala Gln
            900                 905                 910

Thr Asn Thr Val Ser Phe Arg Ala Ala Asp Ile Arg Arg Lys Leu Leu
        915                 920                 925

Met Leu Ile Asp Ser Ser Thr Leu Glu Pro Thr Lys Ser Leu His Leu
    930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
            980                 985                 990

His Val Leu His Val Val Lys Asn Leu Gly Gln Ser Asn Met Asp Ser
        995                 1000                1005

Glu Asn Thr Arg Asp Ala Gln Gly Gln Phe Leu Thr Val Ile Gly
    1010                1015                1020

Ala Phe Trp His Leu Thr Lys Glu Arg Lys Tyr Ile Phe Ser Val
    1025                1030                1035

Arg Met Ala Leu Val Asn Cys Leu Lys Thr Leu Leu Glu Ala Asp
    1040                1045                1050

Pro Tyr Ser Lys Trp Ala Ile Leu Asn Val Met Gly Lys Asp Phe
    1055                1060                1065

Pro Val Asn Glu Val Phe Thr Gln Phe Leu Ala Asp Asn His His
    1070                1075                1080

Gln Val Arg Met Leu Ala Ala Glu Ser Ile Asn Arg Leu Phe Gln
    1085                1090                1095

Asp Thr Lys Gly Asp Ser Ser Arg Leu Leu Lys Ala Leu Pro Leu
```

-continued

```
                1100                1105                1110
Lys Leu Gln Gln Thr Ala Phe Glu Asn Ala Tyr Leu Lys Ala Gln
    1115                1120                1125
Glu Gly Met Arg Glu Met Ser His Ser Ala Glu Asn Pro Glu Thr
    1130                1135                1140
Leu Asp Glu Ile Tyr Asn Arg Lys Ser Val Leu Leu Thr Leu Ile
    1145                1150                1155
Ala Val Val Leu Ser Cys Ser Pro Ile Cys Glu Lys Gln Ala Leu
    1160                1165                1170
Phe Ala Leu Cys Lys Ser Val Lys Glu Asn Gly Leu Glu Pro His
    1175                1180                1185
Leu Val Lys Lys Val Leu Glu Lys Val Ser Glu Thr Phe Gly Tyr
    1190                1195                1200
Arg Arg Leu Glu Asp Phe Met Ala Ser His Leu Asp Tyr Leu Val
    1205                1210                1215
Leu Glu Trp Leu Asn Leu Gln Asp Thr Glu Tyr Asn Leu Ser Ser
    1220                1225                1230
Phe Pro Phe Ile Leu Leu Asn Tyr Thr Asn Ile Glu Asp Phe Tyr
    1235                1240                1245
Arg Ser Cys Tyr Lys Val Leu Ile Pro His Leu Val Ile Arg Ser
    1250                1255                1260
His Phe Asp Glu Val Lys Ser Ile Ala Asn Gln Ile Gln Glu Asp
    1265                1270                1275
Trp Lys Ser Leu Leu Thr Asp Cys Phe Pro Lys Ile Leu Val Asn
    1280                1285                1290
Ile Leu Pro Tyr Phe Ala Tyr Glu Gly Thr Arg Asp Ser Gly Met
    1295                1300                1305
Ala Gln Gln Arg Glu Thr Ala Thr Lys Val Tyr Asp Met Leu Lys
    1310                1315                1320
Ser Glu Asn Leu Leu Gly Lys Gln Ile Asp His Leu Phe Ile Ser
    1325                1330                1335
Asn Leu Pro Glu Ile Val Val Glu Leu Leu Met Thr Leu His Glu
    1340                1345                1350
Pro Ala Asn Ser Ser Ala Ser Gln Ser Thr Asp Leu Cys Asp Phe
    1355                1360                1365
Ser Gly Asp Leu Asp Pro Ala Pro Asn Pro Pro His Phe Pro Ser
    1370                1375                1380
His Val Ile Lys Ala Thr Phe Ala Tyr Ile Ser Asn Cys His Lys
    1385                1390                1395
Thr Lys Leu Lys Ser Ile Leu Glu Ile Leu Ser Lys Ser Pro Asp
    1400                1405                1410
Ser Tyr Gln Lys Ile Leu Leu Ala Ile Cys Glu Gln Ala Ala Glu
    1415                1420                1425
Thr Asn Asn Val Tyr Lys Lys His Arg Ile Leu Lys Ile Tyr His
    1430                1435                1440
Leu Phe Val Ser Leu Leu Leu Lys Asp Ile Lys Ser Gly Leu Gly
    1445                1450                1455
Gly Ala Trp Ala Phe Val Leu Arg Asp Val Ile Tyr Thr Leu Ile
    1460                1465                1470
His Tyr Ile Asn Gln Arg Pro Ser Cys Ile Met Asp Val Ser Leu
    1475                1480                1485
Arg Ser Phe Ser Leu Cys Cys Asp Leu Leu Ser Gln Val Cys Gln
    1490                1495                1500
```

```
Thr Ala Val Thr Tyr Cys Lys Asp Ala Leu Glu Asn His Leu His
1505                1510                1515

Val Ile Val Gly Thr Leu Ile Pro Leu Val Tyr Glu Gln Val Glu
1520                1525                1530

Val Gln Lys Gln Val Leu Asp Leu Leu Lys Tyr Leu Val Ile Asp
1535                1540                1545

Asn Lys Asp Asn Glu Asn Leu Tyr Ile Thr Ile Lys Leu Leu Asp
1550                1555                1560

Pro Phe Pro Asp His Val Val Phe Lys Asp Leu Arg Ile Thr Gln
1565                1570                1575

Gln Lys Ile Lys Tyr Ser Arg Gly Pro Phe Ser Leu Leu Glu Glu
1580                1585                1590

Ile Asn His Phe Leu Ser Val Ser Val Tyr Asp Ala Leu Pro Leu
1595                1600                1605

Thr Arg Leu Glu Gly Leu Lys Asp Leu Arg Arg Gln Leu Glu Leu
1610                1615                1620

His Lys Asp Gln Met Val Asp Ile Met Arg Ala Ser Gln Asp Asn
1625                1630                1635

Pro Gln Asp Gly Ile Met Val Lys Leu Val Val Asn Leu Leu Gln
1640                1645                1650

Leu Ser Lys Met Ala Ile Asn His Thr Gly Glu Lys Glu Val Leu
1655                1660                1665

Glu Ala Val Gly Ser Cys Leu Gly Glu Val Gly Pro Ile Asp Phe
1670                1675                1680

Ser Thr Ile Ala Ile Gln His Ser Lys Asp Ala Ser Tyr Thr Lys
1685                1690                1695

Ala Leu Lys Leu Phe Glu Asp Lys Glu Leu Gln Trp Thr Phe Ile
1700                1705                1710

Met Leu Thr Tyr Leu Asn Asn Thr Leu Val Glu Asp Cys Val Lys
1715                1720                1725

Val Arg Ser Ala Ala Val Thr Cys Leu Lys Asn Ile Leu Ala Thr
1730                1735                1740

Lys Thr Gly His Ser Phe Trp Glu Ile Tyr Lys Met Thr Thr Asp
1745                1750                1755

Pro Met Leu Ala Tyr Leu Gln Pro Phe Arg Thr Ser Arg Lys Lys
1760                1765                1770

Phe Leu Glu Val Pro Arg Phe Asp Lys Glu Asn Pro Phe Glu Gly
1775                1780                1785

Leu Asp Asp Ile Asn Leu Trp Ile Pro Leu Ser Glu Asn His Asp
1790                1795                1800

Ile Trp Ile Lys Thr Leu Thr Cys Ala Phe Leu Asp Ser Gly Gly
1805                1810                1815

Thr Lys Cys Glu Ile Leu Gln Leu Leu Lys Pro Met Cys Glu Val
1820                1825                1830

Lys Thr Asp Phe Cys Gln Thr Val Leu Pro Tyr Leu Ile His Asp
1835                1840                1845

Ile Leu Leu Gln Asp Thr Asn Glu Ser Trp Arg Asn Leu Leu Ser
1850                1855                1860

Thr His Val Gln Gly Phe Phe Thr Ser Cys Leu Arg His Phe Ser
1865                1870                1875

Gln Thr Ser Arg Ser Thr Thr Pro Ala Asn Leu Asp Ser Glu Ser
1880                1885                1890
```

```
Glu His Phe Phe Arg Cys Cys Leu Asp Lys Lys Ser Gln Arg Thr
    1895                1900                1905

Met Leu Ala Val Val Asp Tyr Met Arg Arg Gln Lys Arg Pro Ser
    1910                1915                1920

Ser Gly Thr Ile Phe Asn Asp Ala Phe Trp Leu Asp Leu Asn Tyr
    1925                1930                1935

Leu Glu Val Ala Lys Val Ala Gln Ser Cys Ala Ala His Phe Thr
    1940                1945                1950

Ala Leu Leu Tyr Ala Glu Ile Tyr Ala Asp Lys Lys Ser Met Asp
    1955                1960                1965

Asp Gln Glu Lys Arg Ser Leu Ala Phe Glu Gly Ser Gln Ser
    1970                1975                1980

Thr Thr Ile Ser Ser Leu Ser Glu Lys Ser Lys Glu Glu Thr Gly
    1985                1990                1995

Ile Ser Leu Gln Asp Leu Leu Leu Glu Ile Tyr Arg Ser Ile Gly
    2000                2005                2010

Glu Pro Asp Ser Leu Tyr Gly Cys Gly Gly Gly Lys Met Leu Gln
    2015                2020                2025

Pro Ile Thr Arg Leu Arg Thr Tyr Glu His Glu Ala Met Trp Gly
    2030                2035                2040

Lys Ala Leu Val Thr Tyr Asp Leu Glu Thr Ala Ile Pro Ser Ser
    2045                2050                2055

Thr Arg Gln Ala Gly Ile Ile Gln Ala Leu Gln Asn Leu Gly Leu
    2060                2065                2070

Cys His Ile Leu Ser Val Tyr Leu Lys Gly Leu Asp Tyr Glu Asn
    2075                2080                2085

Lys Asp Trp Cys Pro Glu Leu Glu Glu Leu His Tyr Gln Ala Ala
    2090                2095                2100

Trp Arg Asn Met Gln Trp Asp His Cys Thr Ser Val Ser Lys Glu
    2105                2110                2115

Val Glu Gly Thr Ser Tyr His Glu Ser Leu Tyr Asn Ala Leu Gln
    2120                2125                2130

Ser Leu Arg Asp Arg Glu Phe Ser Thr Phe Tyr Glu Ser Leu Lys
    2135                2140                2145

Tyr Ala Arg Val Lys Glu Val Glu Glu Met Cys Lys Arg Ser Leu
    2150                2155                2160

Glu Ser Val Tyr Ser Leu Tyr Pro Thr Leu Ser Arg Leu Gln Ala
    2165                2170                2175

Ile Gly Glu Leu Glu Ser Ile Gly Glu Leu Phe Ser Arg Ser Val
    2180                2185                2190

Thr His Arg Gln Leu Ser Glu Val Tyr Ile Lys Trp Gln Lys His
    2195                2200                2205

Ser Gln Leu Leu Lys Asp Ser Asp Phe Ser Phe Gln Glu Pro Ile
    2210                2215                2220

Met Ala Leu Arg Thr Val Ile Leu Glu Ile Leu Met Glu Lys Glu
    2225                2230                2235

Met Asp Asn Ser Gln Arg Glu Cys Ile Lys Asp Ile Leu Thr Lys
    2240                2245                2250

His Leu Val Glu Leu Ser Ile Leu Ala Arg Thr Phe Lys Asn Thr
    2255                2260                2265

Gln Leu Pro Glu Arg Ala Ile Phe Gln Ile Lys Gln Tyr Asn Ser
    2270                2275                2280

Val Ser Cys Gly Val Ser Glu Trp Gln Leu Glu Glu Ala Gln Val
```

2285                2290                2295

Phe Trp Ala Lys Lys Glu Gln Ser Leu Ala Leu Ser Ile Leu Lys
            2300                2305           2310

Gln Met Ile Lys Lys Leu Asp Ala Ser Cys Ala Ala Asn Asn Pro
        2315                2320           2325

Ser Leu Lys Leu Thr Tyr Thr Glu Cys Leu Arg Val Cys Gly Asn
        2330                2335           2340

Trp Leu Ala Glu Thr Cys Leu Glu Asn Pro Ala Val Ile Met Gln
        2345                2350           2355

Thr Tyr Leu Glu Lys Ala Val Glu Val Ala Gly Asn Tyr Asp Gly
        2360                2365           2370

Glu Ser Ser Asp Glu Leu Arg Asn Gly Lys Met Lys Ala Phe Leu
        2375                2380           2385

Ser Leu Ala Arg Phe Ser Asp Thr Gln Tyr Gln Arg Ile Glu Asn
        2390                2395           2400

Tyr Met Lys Ser Ser Glu Phe Glu Asn Lys Gln Ala Leu Leu Lys
        2405                2410           2415

Arg Ala Lys Glu Glu Val Gly Leu Leu Arg Glu His Lys Ile Gln
        2420                2425           2430

Thr Asn Arg Tyr Thr Val Lys Val Gln Arg Glu Leu Glu Leu Asp
        2435                2440           2445

Glu Leu Ala Leu Arg Ala Leu Lys Glu Asp Arg Lys Arg Phe Leu
        2450                2455           2460

Cys Lys Ala Val Glu Asn Tyr Ile Asn Cys Leu Leu Ser Gly Glu
        2465                2470           2475

Glu His Asp Met Trp Val Phe Arg Leu Cys Ser Leu Trp Leu Glu
        2480                2485           2490

Asn Ser Gly Val Ser Glu Val Asn Gly Met Met Lys Arg Asp Gly
        2495                2500           2505

Met Lys Ile Pro Thr Tyr Lys Phe Leu Pro Leu Met Tyr Gln Leu
        2510                2515           2520

Ala Ala Arg Met Gly Thr Lys Met Met Gly Gly Leu Gly Phe His
        2525                2530           2535

Glu Val Leu Asn Asn Leu Ile Ser Arg Ile Ser Met Asp His Pro
        2540                2545           2550

His His Thr Leu Phe Ile Ile Leu Ala Leu Ala Asn Ala Asn Arg
        2555                2560           2565

Asp Glu Phe Leu Thr Lys Pro Glu Val Ala Arg Arg Ser Arg Ile
        2570                2575           2580

Thr Lys Asn Val Pro Lys Gln Ser Ser Gln Leu Asp Glu Asp Arg
        2585                2590           2595

Thr Glu Ala Ala Asn Arg Ile Ile Cys Thr Ile Arg Ser Arg Arg
        2600                2605           2610

Pro Gln Met Val Arg Ser Val Glu Ala Leu Cys Asp Ala Tyr Ile
        2615                2620           2625

Ile Leu Ala Asn Leu Asp Ala Thr Gln Trp Lys Thr Gln Arg Lys
        2630                2635           2640

Gly Ile Asn Ile Pro Ala Asp Gln Pro Ile Thr Lys Leu Lys Asn
        2645                2650           2655

Leu Glu Asp Val Val Val Pro Thr Met Glu Ile Lys Val Asp His
        2660                2665           2670

Thr Gly Glu Tyr Gly Asn Leu Val Thr Ile Gln Ser Phe Lys Ala
        2675                2680           2685

```
Glu Phe Arg Leu Ala Gly Gly Val Asn Leu Pro Lys Ile Ile Asp
2690                2695                2700

Cys Val Gly Ser Asp Gly Lys Glu Arg Arg Gln Leu Val Lys Gly
2705                2710                2715

Arg Asp Asp Leu Arg Gln Asp Ala Val Met Gln Gln Val Phe Gln
2720                2725                2730

Met Cys Asn Thr Leu Leu Gln Arg Asn Thr Glu Thr Arg Lys Arg
2735                2740                2745

Lys Leu Thr Ile Cys Thr Tyr Lys Val Val Pro Leu Ser Gln Arg
2750                2755                2760

Ser Gly Val Leu Glu Trp Cys Thr Gly Thr Val Pro Ile Gly Glu
2765                2770                2775

Phe Leu Val Asn Asn Glu Asp Gly Ala His Lys Arg Tyr Arg Pro
2780                2785                2790

Asn Asp Phe Ser Ala Phe Gln Cys Gln Lys Lys Met Met Glu Val
2795                2800                2805

Gln Lys Lys Ser Phe Glu Glu Lys Tyr Glu Val Phe Met Asp Val
2810                2815                2820

Cys Gln Asn Phe Gln Pro Val Phe Arg Tyr Phe Cys Met Glu Lys
2825                2830                2835

Phe Leu Asp Pro Ala Ile Trp Phe Glu Lys Arg Leu Ala Tyr Thr
2840                2845                2850

Arg Ser Val Ala Thr Ser Ser Ile Val Gly Tyr Ile Leu Gly Leu
2855                2860                2865

Gly Asp Arg His Val Gln Asn Ile Leu Ile Asn Glu Gln Ser Ala
2870                2875                2880

Glu Leu Val His Ile Asp Leu Gly Val Ala Phe Glu Gln Gly Lys
2885                2890                2895

Ile Leu Pro Thr Pro Glu Thr Val Pro Phe Arg Leu Thr Arg Asp
2900                2905                2910

Ile Val Asp Gly Met Gly Ile Thr Gly Val Glu Gly Val Phe Arg
2915                2920                2925

Arg Cys Cys Glu Lys Thr Met Glu Val Met Arg Asn Ser Gln Glu
2930                2935                2940

Thr Leu Leu Thr Ile Val Glu Val Leu Leu Tyr Asp Pro Leu Phe
2945                2950                2955

Asp Trp Thr Met Asn Pro Leu Lys Ala Leu Tyr Leu Gln Gln Arg
2960                2965                2970

Pro Glu Asp Glu Thr Glu Leu His Pro Thr Leu Asn Ala Asp Asp
2975                2980                2985

Gln Glu Cys Lys Arg Asn Leu Ser Asp Ile Asp Gln Ser Phe Asp
2990                2995                3000

Lys Val Ala Glu Arg Val Leu Met Arg Leu Gln Glu Lys Leu Lys
3005                3010                3015

Gly Val Glu Glu Gly Thr Val Leu Ser Val Gly Gly Gln Val Asn
3020                3025                3030

Leu Leu Ile Gln Gln Ala Ile Asp Pro Lys Asn Leu Ser Arg Leu
3035                3040                3045

Phe Pro Gly Trp Lys Ala Trp Val Met Ser Leu Val Leu Asn Asp
3050                3055                3060

Leu Leu Ile Cys Cys Arg Gln Leu Glu His Asp Arg Ala Thr Glu
3065                3070                3075
```

-continued

```
Arg Lys Lys Glu Val Glu Lys Phe Lys Arg Leu Ile Arg Asp Pro
    3080            3085            3090

Glu Thr Ile Lys His Leu Asp Arg His Ser Asp Ser Lys Gln Gly
    3095            3100            3105

Lys Tyr Leu Asn Trp Asp Ala Val Phe Arg Phe Leu Gln Lys Tyr
    3110            3115            3120

Ile Gln Lys Glu Thr Glu Cys Leu Arg Ile Ala Lys Pro Asn Val
    3125            3130            3135

Ser Ala Ser Thr Gln Ala Ser Arg Gln Lys Lys Met Gln Glu Ile
    3140            3145            3150

Ser Ser Leu Val Lys Tyr Phe Ile Lys Cys Ala Asn Arg Arg Ala
    3155            3160            3165

Pro Arg Leu Lys Cys Gln Glu Leu Leu Asn Tyr Ile Met Asp Thr
    3170            3175            3180

Val Lys Asp Ser Ser Asn Gly Ala Ile Tyr Gly Ala Asp Cys Ser
    3185            3190            3195

Asn Ile Leu Leu Lys Asp Ile Leu Ser Val Arg Lys Tyr Trp Cys
    3200            3205            3210

Glu Ile Ser Gln Gln Gln Trp Leu Glu Leu Phe Ser Val Tyr Phe
    3215            3220            3225

Arg Leu Tyr Leu Lys Pro Ser Gln Asp Val His Arg Val Leu Val
    3230            3235            3240

Ala Arg Ile Ile His Ala Val Thr Lys Gly Cys Cys Ser Gln Thr
    3245            3250            3255

Asp Gly Leu Asn Ser Lys Phe Leu Asp Phe Phe Ser Lys Ala Ile
    3260            3265            3270

Gln Cys Ala Arg Gln Glu Lys Ser Ser Ser Gly Leu Asn His Ile
    3275            3280            3285

Leu Ala Ala Leu Thr Ile Phe Leu Lys Thr Leu Ala Val Asn Phe
    3290            3295            3300

Arg Ile Arg Val Cys Glu Leu Gly Asp Glu Ile Leu Pro Thr Leu
    3305            3310            3315

Leu Tyr Ile Trp Thr Gln His Arg Leu Asn Asp Ser Leu Lys Glu
    3320            3325            3330

Val Ile Ile Glu Leu Phe Gln Leu Gln Ile Tyr Ile His His Pro
    3335            3340            3345

Lys Gly Ala Lys Thr Gln Glu Lys Gly Ala Tyr Glu Ser Thr Lys
    3350            3355            3360

Trp Arg Ser Ile Leu Tyr Asn Leu Tyr Asp Leu Leu Val Asn Glu
    3365            3370            3375

Ile Ser His Ile Gly Ser Arg Gly Lys Tyr Ser Ser Gly Phe Arg
    3380            3385            3390

Asn Ile Ala Val Lys Glu Asn Leu Ile Glu Leu Met Ala Asp Ile
    3395            3400            3405

Cys His Gln Val Phe Asn Glu Asp Thr Arg Ser Leu Glu Ile Ser
    3410            3415            3420

Gln Ser Tyr Thr Thr Thr Gln Arg Glu Ser Ser Asp Tyr Ser Val
    3425            3430            3435

Pro Cys Lys Arg Lys Lys Ile Glu Leu Gly Trp Glu Val Ile Lys
    3440            3445            3450

Asp His Leu Gln Lys Ser Gln Asn Asp Phe Asp Leu Val Pro Trp
    3455            3460            3465

Leu Gln Ile Ala Thr Gln Leu Ile Ser Lys Tyr Pro Ala Ser Leu
```

```
                3470            3475            3480
Pro Asn Cys Glu Leu Ser Pro Leu Leu Met Ile Leu Ser Gln Leu
        3485            3490            3495
Leu Pro Gln Gln Arg His Gly Glu Arg Thr Pro Tyr Val Leu Arg
        3500            3505            3510
Cys Leu Thr Glu Val Ala Leu Cys Gln Asp Lys Arg Ser Asn Leu
        3515            3520            3525
Glu Ser Ser Gln Lys Ser Asp Leu Leu Lys Leu Trp Asn Lys Ile
        3530            3535            3540
Trp Cys Ile Thr Phe Arg Gly Ile Ser Ser Gln Ile Gln Ala
        3545            3550            3555
Glu Asn Phe Gly Leu Leu Gly Ala Ile Ile Gln Gly Ser Leu Val
        3560            3565            3570
Glu Val Asp Arg Glu Phe Trp Lys Leu Phe Thr Gly Ser Ala Cys
        3575            3580            3585
Arg Pro Ser Cys Pro Ala Val Cys Cys Leu Thr Leu Ala Leu Thr
        3590            3595            3600
Thr Ser Ile Val Pro Gly Ala Val Lys Met Gly Ile Glu Gln Asn
        3605            3610            3615
Met Cys Glu Val Asn Arg Ser Phe Ser Leu Lys Glu Ser Ile Met
        3620            3625            3630
Lys Trp Leu Leu Phe Tyr Gln Leu Glu Gly Asp Leu Glu Asn Ser
        3635            3640            3645
Thr Glu Val Pro Pro Ile Leu His Ser Asn Phe Pro His Leu Val
        3650            3655            3660
Leu Glu Lys Ile Leu Val Ser Leu Thr Met Lys Asn Cys Lys Ala
        3665            3670            3675
Ala Met Asn Phe Phe Gln Ser Val Pro Glu Cys Glu His His Gln
        3680            3685            3690
Lys Asp Lys Glu Glu Leu Ser Phe Ser Glu Val Glu Glu Leu Phe
        3695            3700            3705
Leu Gln Thr Thr Phe Asp Lys Met Asp Phe Leu Thr Ile Val Arg
        3710            3715            3720
Glu Cys Gly Ile Glu Lys His Gln Ser Ser Ile Gly Phe Ser Val
        3725            3730            3735
His Gln Asn Leu Lys Glu Ser Leu Asp Arg Cys Leu Leu Gly Leu
        3740            3745            3750
Ser Glu Gln Leu Leu Asn Asn Tyr Ser Ser Glu Ile Thr Asn Ser
        3755            3760            3765
Glu Thr Leu Val Arg Cys Ser Arg Leu Leu Val Gly Val Leu Gly
        3770            3775            3780
Cys Tyr Cys Tyr Met Gly Val Ile Ala Glu Glu Ala Tyr Lys
        3785            3790            3795
Ser Glu Leu Phe Gln Lys Ala Asn Ser Leu Met Gln Cys Ala Gly
        3800            3805            3810
Glu Ser Ile Thr Leu Phe Lys Asn Lys Thr Asn Glu Glu Phe Arg
        3815            3820            3825
Ile Gly Ser Leu Arg Asn Met Met Gln Leu Cys Thr Arg Cys Leu
        3830            3835            3840
Ser Asn Cys Thr Lys Lys Ser Pro Asn Lys Ile Ala Ser Gly Phe
        3845            3850            3855
Phe Leu Arg Leu Leu Thr Ser Lys Leu Met Asn Asp Ile Ala Asp
        3860            3865            3870
```

-continued

```
Ile Cys Lys Ser Leu Ala Ser Phe Ile Lys Lys Pro Phe Asp Arg
3875             3880             3885

Gly Glu Val Glu Ser Met Glu Asp Thr Asn Gly Asn Leu Met
3890             3895             3900

Glu Val Glu Asp Gln Ser Ser Met Asn Leu Phe Asn Asp Tyr Pro
3905             3910             3915

Asp Ser Ser Val Ser Asp Ala Asn Glu Pro Gly Glu Ser Gln Ser
3920             3925             3930

Thr Ile Gly Ala Ile Asn Pro Leu Ala Glu Glu Tyr Leu Ser Lys
3935             3940             3945

Gln Asp Leu Leu Phe Leu Asp Met Leu Lys Phe Leu Cys Leu Cys
3950             3955             3960

Val Thr Thr Ala Gln Thr Asn Thr Val Ser Phe Arg Ala Ala Asp
3965             3970             3975

Ile Arg Arg Lys Leu Leu Met Leu Ile Asp Ser Ser Thr Leu Glu
3980             3985             3990

Pro Thr Lys Ser Leu His Leu His Met Tyr Leu Met Leu Leu Lys
3995             4000             4005

Glu Leu Pro Gly Glu Glu Tyr Pro Leu Pro Met Glu Asp Val Leu
4010             4015             4020

Glu Leu Leu Lys Pro Leu Ser Asn Val Cys Ser Leu Tyr Arg Arg
4025             4030             4035

Asp Gln Asp Val Cys Lys Thr Ile Leu Asn His Val Leu His Val
4040             4045             4050

Val Lys Asn Leu Gly Gln Ser Asn Met Asp Ser Glu Asn Thr Arg
4055             4060             4065

Asp Ala Gln Gly Gln Phe Leu Thr Val Ile Gly Ala Phe Trp His
4070             4075             4080

Leu Thr Lys Glu Arg Lys Tyr Ile Phe Ser Val Arg Met Ala Leu
4085             4090             4095

Val Asn Cys Leu Lys Thr Leu Leu Glu Ala Asp Pro Tyr Ser Lys
4100             4105             4110

Trp Ala Ile Leu Asn Val Met Gly Lys Asp Phe Pro Val Asn Glu
4115             4120             4125

Val Phe Thr Gln Phe Leu Ala Asp Asn His His Gln Val Arg Met
4130             4135             4140

Leu Ala Ala Glu Ser Ile Asn Arg Leu Phe Gln Asp Thr Lys Gly
4145             4150             4155

Asp Ser Ser Arg Leu Leu Lys Ala Leu Pro Leu Lys Leu Gln Gln
4160             4165             4170

Thr Ala Phe Glu Asn Ala Tyr Leu Lys Ala Gln Glu Gly Met Arg
4175             4180             4185

Glu Met Ser His Ser Ala Glu Asn Pro Glu Thr Leu Asp Glu Ile
4190             4195             4200

Tyr Asn Arg Lys Ser Val Leu Leu Thr Leu Ile Ala Val Val Leu
4205             4210             4215

Ser Cys Ser Pro Ile Cys Glu Lys Gln Ala Leu Phe Ala Leu Cys
4220             4225             4230

Lys Ser Val Lys Glu Asn Gly Leu Glu Pro His Leu Val Lys Lys
4235             4240             4245

Val Leu Glu Lys Val Ser Glu Thr Phe Gly Tyr Arg Arg Leu Glu
4250             4255             4260
```

-continued

Asp Phe Met Ala Ser His Leu Asp Tyr Leu Val Leu Glu Trp Leu
4265                4270                4275

Asn Leu Gln Asp Thr Glu Tyr Asn Leu Ser Ser Phe Pro Phe Ile
4280                4285                4290

Leu Leu Asn Tyr Thr Asn Ile Glu Asp Phe Tyr Arg Ser Cys Tyr
4295                4300                4305

Lys Val Leu Ile Pro His Leu Val Ile Arg Ser His Phe Asp Glu
4310                4315                4320

Val Lys Ser Ile Ala Asn Gln Ile Gln Glu Asp Trp Lys Ser Leu
4325                4330                4335

Leu Thr Asp Cys Phe Pro Lys Ile Leu Val Asn Ile Leu Pro Tyr
4340                4345                4350

Phe Ala Tyr Glu Gly Thr Arg Asp Ser Gly Met Ala Gln Gln Arg
4355                4360                4365

Glu Thr Ala Thr Lys Val Tyr Asp Met Leu Lys Ser Glu Asn Leu
4370                4375                4380

Leu Gly Lys Gln Ile Asp His Leu Phe Ile Ser Asn Leu Pro Glu
4385                4390                4395

Ile Val Val Glu Leu Leu Met Thr Leu His Glu Pro Ala Asn Ser
4400                4405                4410

Ser Ala Ser Gln Ser Thr Asp Leu Cys Asp Phe Ser Gly Asp Leu
4415                4420                4425

Asp Pro Ala Pro Asn Pro Pro His Phe Pro Ser His Val Ile Lys
4430                4435                4440

Ala Thr Phe Ala Tyr Ile Ser Asn Cys His Lys Thr Lys Leu Lys
4445                4450                4455

Ser Ile Leu Glu Ile Leu Ser Lys Ser Pro Asp Ser Tyr Gln Lys
4460                4465                4470

Ile Leu Leu Ala Ile Cys Glu Gln Ala Ala Glu Thr Asn Asn Val
4475                4480                4485

Tyr Lys Lys His Arg Ile Leu Lys Ile Tyr His Leu Phe Val Ser
4490                4495                4500

Leu Leu Leu Lys Asp Ile Lys Ser Gly Leu Gly Gly Ala Trp Ala
4505                4510                4515

Phe Val Leu Arg Asp Val Ile Tyr Thr Leu Ile His Tyr Ile Asn
4520                4525                4530

Gln Arg Pro Ser Cys Ile Met Asp Val Ser Leu Arg Ser Phe Ser
4535                4540                4545

Leu Cys Cys Asp Leu Leu Ser Gln Val Cys Gln Thr Ala Val Thr
4550                4555                4560

Tyr Cys Lys Asp Ala Leu Glu Asn His Leu His Val Ile Val Gly
4565                4570                4575

Thr Leu Ile Pro Leu Val Tyr Glu Gln Val Glu Val Gln Lys Gln
4580                4585                4590

Val Leu Asp Leu Leu Lys Tyr Leu Val Ile Asp Asn Lys Asp Asn
4595                4600                4605

Glu Asn Leu Tyr Ile Thr Ile Lys Leu Leu Asp Pro Phe Pro Asp
4610                4615                4620

His Val Val Phe Lys Asp Leu Arg Ile Thr Gln Gln Lys Ile Lys
4625                4630                4635

Tyr Ser Arg Gly Pro Phe Ser Leu Leu Glu Glu Ile Asn His Phe
4640                4645                4650

Leu Ser Val Ser Val Tyr Asp Ala Leu Pro Leu Thr Arg Leu Glu

```
                4655                4660                4665
    Gly Leu Lys Asp Leu Arg Arg Gln Leu Glu Leu His Lys Asp Gln
            4670                4675                4680

Met Val Asp Ile Met Arg Ala Ser Gln Asp Asn Pro Gln Asp Gly
            4685                4690                4695

Ile Met Val Lys Leu Val Val Asn Leu Leu Gln Leu Ser Lys Met
            4700                4705                4710

Ala Ile Asn His Thr Gly Glu Lys Glu Val Leu Glu Ala Val Gly
            4715                4720                4725

Ser Cys Leu Gly Glu Val Gly Pro Ile Asp Phe Ser Thr Ile Ala
            4730                4735                4740

Ile Gln His Ser Lys Asp Ala Ser Tyr Thr Lys Ala Leu Lys Leu
            4745                4750                4755

Phe Glu Asp Lys Glu Leu Gln Trp Thr Phe Ile Met Leu Thr Tyr
            4760                4765                4770

Leu Asn Asn Thr Leu Val Glu Asp Cys Val Lys Val Arg Ser Ala
            4775                4780                4785

Ala Val Thr Cys Leu Lys Asn Ile Leu Ala Thr Lys Thr Gly His
            4790                4795                4800

Ser Phe Trp Glu Ile Tyr Lys Met Thr Thr Asp Pro Met Leu Ala
            4805                4810                4815

Tyr Leu Gln Pro Phe Arg Thr Ser Arg Lys Lys Phe Leu Glu Val
            4820                4825                4830

Pro Arg Phe Asp Lys Glu Asn Pro Phe Glu Gly Leu Asp Asp Ile
            4835                4840                4845

Asn Leu Trp Ile Pro Leu Ser Glu Asn His Asp Ile Trp Ile Lys
            4850                4855                4860

Thr Leu Thr Cys Ala Phe Leu Asp Ser Gly Gly Thr Lys Cys Glu
            4865                4870                4875

Ile Leu Gln Leu Leu Lys Pro Met Cys Glu Val Lys Thr Asp Phe
            4880                4885                4890

Cys Gln Thr Val Leu Pro Tyr Leu Ile His Asp Ile Leu Leu Gln
            4895                4900                4905

Asp Thr Asn Glu Ser Trp Arg Asn Leu Leu Ser Thr His Val Gln
            4910                4915                4920

Gly Phe Phe Thr Ser Cys Leu Arg His Phe Ser Gln Thr Ser Arg
            4925                4930                4935

Ser Thr Thr Pro Ala Asn Leu Asp Ser Glu Ser Glu His Phe Phe
            4940                4945                4950

Arg Cys Cys Leu Asp Lys Lys Ser Gln Arg Thr Met Leu Ala Val
            4955                4960                4965

Val Asp Tyr Met Arg Arg Gln Lys Arg Pro Ser Ser Gly Thr Ile
            4970                4975                4980

Phe Asn Asp Ala Phe Trp Leu Asp Leu Asn Tyr Leu Glu Val Ala
            4985                4990                4995

Lys Val Ala Gln Ser Cys Ala Ala His Phe Thr Ala Leu Leu Tyr
            5000                5005                5010

Ala Glu Ile Tyr Ala Asp Lys Lys Ser Met Asp Asp Gln Glu Lys
            5015                5020                5025

Arg Ser Leu Ala Phe Glu Glu Gly Ser Gln Ser Thr Thr Ile Ser
            5030                5035                5040

Ser Leu Ser Glu Lys Ser Lys Glu Glu Thr Gly Ile Ser Leu Gln
            5045                5050                5055
```

```
Asp Leu Leu Leu Glu Ile Tyr Arg Ser Ile Gly Glu Pro Asp Ser
            5060                5065                5070

Leu Tyr Gly Cys Gly Gly Lys Met Leu Gln Pro Ile Thr Arg
        5075                5080                5085

Leu Arg Thr Tyr Glu His Glu Ala Met Trp Gly Lys Ala Leu Val
            5090                5095                5100

Thr Tyr Asp Leu Glu Thr Ala Ile Pro Ser Ser Thr Arg Gln Ala
            5105                5110                5115

Gly Ile Ile Gln Ala Leu Gln Asn Leu Gly Leu Cys His Ile Leu
            5120                5125                5130

Ser Val Tyr Leu Lys Gly Leu Asp Tyr Glu Asn Lys Asp Trp Cys
            5135                5140                5145

Pro Glu Leu Glu Glu Leu His Tyr Gln Ala Ala Trp Arg Asn Met
            5150                5155                5160

Gln Trp Asp His Cys Thr Ser Val Ser Lys Glu Val Glu Gly Thr
            5165                5170                5175

Ser Tyr His Glu Ser Leu Tyr Asn Ala Leu Gln Ser Leu Arg Asp
            5180                5185                5190

Arg Glu Phe Ser Thr Phe Tyr Glu Ser Leu Lys Tyr Ala Arg Val
            5195                5200                5205

Lys Glu Val Glu Glu Met Cys Lys Arg Ser Leu Glu Ser Val Tyr
            5210                5215                5220

Ser Leu Tyr Pro Thr Leu Ser Arg Leu Gln Ala Ile Gly Glu Leu
            5225                5230                5235

Glu Ser Ile Gly Glu Leu Phe Ser Arg Ser Val Thr His Arg Gln
            5240                5245                5250

Leu Ser Glu Val Tyr Ile Lys Trp Gln Lys His Ser Gln Leu Leu
            5255                5260                5265

Lys Asp Ser Asp Phe Ser Phe Gln Glu Pro Ile Met Ala Leu Arg
            5270                5275                5280

Thr Val Ile Leu Glu Ile Leu Met Glu Lys Glu Met Asp Asn Ser
            5285                5290                5295

Gln Arg Glu Cys Ile Lys Asp Ile Leu Thr Lys His Leu Val Glu
            5300                5305                5310

Leu Ser Ile Leu Ala Arg Thr Phe Lys Asn Thr Gln Leu Pro Glu
            5315                5320                5325

Arg Ala Ile Phe Gln Ile Lys Gln Tyr Asn Ser Val Ser Cys Gly
            5330                5335                5340

Val Ser Glu Trp Gln Leu Glu Glu Ala Gln Val Phe Trp Ala Lys
            5345                5350                5355

Lys Glu Gln Ser Leu Ala Leu Ser Ile Leu Lys Gln Met Ile Lys
            5360                5365                5370

Lys Leu Asp Ala Ser Cys Ala Ala Asn Asn Pro Ser Leu Lys Leu
            5375                5380                5385

Thr Tyr Thr Glu Cys Leu Arg Val Cys Gly Asn Trp Leu Ala Glu
            5390                5395                5400

Thr Cys Leu Glu Asn Pro Ala Val Ile Met Gln Thr Tyr Leu Glu
            5405                5410                5415

Lys Ala Val Glu Val Ala Gly Asn Tyr Asp Gly Glu Ser Ser Asp
            5420                5425                5430

Glu Leu Arg Asn Gly Lys Met Lys Ala Phe Leu Ser Leu Ala Arg
            5435                5440                5445
```

```
Phe Ser Asp Thr Gln Tyr Gln Arg Ile Glu Asn Tyr Met Lys Ser
        5450                5455                5460
Ser Glu Phe Glu Asn Lys Gln Ala Leu Leu Lys Arg Ala Lys Glu
    5465                5470                5475
Glu Val Gly Leu Leu Arg Glu His Lys Ile Gln Thr Asn Arg Tyr
    5480                5485                5490
Thr Val Lys Val Gln Arg Glu Leu Glu Leu Asp Glu Leu Ala Leu
    5495                5500                5505
Arg Ala Leu Lys Glu Asp Arg Lys Arg Phe Leu Cys Lys Ala Val
    5510                5515                5520
Glu Asn Tyr Ile Asn Cys Leu Leu Ser Gly Glu Glu His Asp Met
    5525                5530                5535
Trp Val Phe Arg Leu Cys Ser Leu Trp Leu Glu Asn Ser Gly Val
    5540                5545                5550
Ser Glu Val Asn Gly Met Met Lys Arg Asp Gly Met Lys Ile Pro
    5555                5560                5565
Thr Tyr Lys Phe Leu Pro Leu Met Tyr Gln Leu Ala Ala Arg Met
    5570                5575                5580
Gly Thr Lys Met Met Gly Gly Leu Gly Phe His Glu Val Leu Asn
    5585                5590                5595
Asn Leu Ile Ser Arg Ile Ser Met Asp His Pro His His Thr Leu
    5600                5605                5610
Phe Ile Ile Leu Ala Leu Ala Asn Ala Asn Arg Asp Glu Phe Leu
    5615                5620                5625
Thr Lys Pro Glu Val Ala Arg Arg Ser Arg Ile Thr Lys Asn Val
    5630                5635                5640
Pro Lys Gln Ser Ser Gln Leu Asp Glu Asp Arg Thr Glu Ala Ala
    5645                5650                5655
Asn Arg Ile Ile Cys Thr Ile Arg Ser Arg Arg Pro Gln Met Val
    5660                5665                5670
Arg Ser Val Glu Ala Leu Cys Asp Ala Tyr Ile Ile Leu Ala Asn
    5675                5680                5685
Leu Asp Ala Thr Gln Trp Lys Thr Gln Arg Lys Gly Ile Asn Ile
    5690                5695                5700
Pro Ala Asp Gln Pro Ile Thr Lys Leu Lys Asn Leu Glu Asp Val
    5705                5710                5715
Val Val Pro Thr Met Glu Ile Lys Val Asp His Thr Gly Glu Tyr
    5720                5725                5730
Gly Asn Leu Val Thr Ile Gln Ser Phe Lys Ala Glu Phe Arg Leu
    5735                5740                5745
Ala Gly Gly Val Asn Leu Pro Lys Ile Ile Asp Cys Val Gly Ser
    5750                5755                5760
Asp Gly Lys Glu Arg Arg Gln Leu Val Lys Gly Arg Asp Asp Leu
    5765                5770                5775
Arg Gln Asp Ala Val Met Gln Gln Val Phe Gln Met Cys Asn Thr
    5780                5785                5790
Leu Leu Gln Arg Asn Thr Glu Thr Arg Lys Arg Lys Leu Thr Ile
    5795                5800                5805
Cys Thr Tyr Lys Val Val Pro Leu Ser Gln Arg Ser Gly Val Leu
    5810                5815                5820
Glu Trp Cys Thr Gly Thr Val Pro Ile Gly Glu Phe Leu Val Asn
    5825                5830                5835
Asn Glu Asp Gly Ala His Lys Arg Tyr Arg Pro Asn Asp Phe Ser
```

```
                5840                5845                5850

Ala Phe Gln Cys Gln Lys Lys Met Met Glu Val Gln Lys Lys Ser
        5855                5860                5865

Phe Glu Glu Lys Tyr Glu Val Phe Met Asp Val Cys Gln Asn Phe
        5870                5875                5880

Gln Pro Val Phe Arg Tyr Phe Cys Met Glu Lys Phe Leu Asp Pro
        5885                5890                5895

Ala Ile Trp Phe Glu Lys Arg Leu Ala Tyr Thr Arg Ser Val Ala
        5900                5905                5910

Thr Ser Ser Ile Val Gly Tyr Ile Leu Gly Leu Gly Asp Arg His
        5915                5920                5925

Val Gln Asn Ile Leu Ile Asn Glu Gln Ser Ala Glu Leu Val His
        5930                5935                5940

Ile Asp Leu Gly Val Ala Phe Glu Gln Gly Lys Ile Leu Pro Thr
        5945                5950                5955

Pro Glu Thr Val Pro Phe Arg Leu Thr Arg Asp Ile Val Asp Gly
        5960                5965                5970

Met Gly Ile Thr Gly Val Glu Gly Val Phe Arg Arg Cys Cys Glu
        5975                5980                5985

Lys Thr Met Glu Val Met Arg Asn Ser Gln Glu Thr Leu Leu Thr
        5990                5995                6000

Ile Val Glu Val Leu Leu Tyr Asp Pro Leu Phe Asp Trp Thr Met
        6005                6010                6015

Asn Pro Leu Lys Ala Leu Tyr Leu Gln Gln Arg Pro Glu Asp Glu
        6020                6025                6030

Thr Glu Leu His Pro Thr Leu Asn Ala Asp Asp Gln Glu Cys Lys
        6035                6040                6045

Arg Asn Leu Ser Asp Ile Asp Gln Ser Phe Asp Lys Val Ala Glu
        6050                6055                6060

Arg Val Leu Met Arg Leu Gln Glu Lys Leu Lys Gly Val Glu Glu
        6065                6070                6075

Gly Thr Val Leu Ser Val Gly Gly Gln Val Asn Leu Leu Ile Gln
        6080                6085                6090

Gln Ala Ile Asp Pro Lys Asn Leu Ser Arg Leu Phe Pro Gly Trp
        6095                6100                6105

Lys Ala Trp Val
        6110

<210> SEQ ID NO 362
<211> LENGTH: 85
<212> TYPE: RNA
<213> ORGANISM: Artificial
<220> FEATURE:
<223> OTHER INFORMATION: Precursor sequence

<400> SEQUENCE: 362
gggaagggcu ucagccaggc uagugcaguc ugcuuugugc caacacuggg gugaugacug    60
cccuagucua gcugaagcuu uuccc                                         85

<210> SEQ ID NO 363
<211> LENGTH: 7
<212> TYPE: RNA
<213> ORGANISM: Artificial
<220> FEATURE:
<223> OTHER INFORMATION: Seed sequence

<400> SEQUENCE: 363
```

```
ucagcca                                                               7

<210> SEQ ID NO 364
<211> LENGTH: 22
<212> TYPE: RNA
<213> ORGANISM: Artificial
<220> FEATURE:
<223> OTHER INFORMATION: Mature sequence

<400> SEQUENCE: 364
uucagccagg cuagugcagu cu                                             22

<210> SEQ ID NO 365
<211> LENGTH: 240
<212> TYPE: DNA
<213> ORGANISM: Artificial
<220> FEATURE:
<223> OTHER INFORMATION: Sequence cloned in lentiviral vector

<400> SEQUENCE: 365
acaacttctc aatgagtctg ccctcactgt ccaacaattg agctgagaat ataagaaggg     60
aagggcttca gccaggctag tgcagtctgc tttgtgccaa cactgggtg atgactgccc    120 tagtctagct gaagcttttc ccttctttct acacccagct caagtcccag gtccataaaa   180
cctttagaaa ctcttcagaa actctttaga gcttcagaag ctcttgagaa ttggaagatg   240

<210> SEQ ID NO 366
<211> LENGTH: 7
<212> TYPE: RNA
<213> ORGANISM: Artificial
<220> FEATURE:
<223> OTHER INFORMATION: Seed sequence

<400> SEQUENCE: 366 uucagcc                                                               7

<210> SEQ ID NO 367
<211> LENGTH: 7
<212> TYPE: RNA
<213> ORGANISM: Artificial
<220> FEATURE:
<223> OTHER INFORMATION: Seed sequence

<400> SEQUENCE: 367 cagccag                                                               7

<210> SEQ ID NO 368
<211> LENGTH: 21
<212> TYPE: RNA
<213> ORGANISM: Artificial
<220> FEATURE:
<223> OTHER INFORMATION: IsomiR sequence

<400> SEQUENCE: 368
uucagccagg cuagugcagu c                                              21

<210> SEQ ID NO 369
<211> LENGTH: 22
<212> TYPE: RNA
<213> ORGANISM: Artificial
<220> FEATURE:
<223> OTHER INFORMATION: IsomiR sequence

<400> SEQUENCE: 369
```

```
cuucagccag gcuagugcag uc                                              22

<210> SEQ ID NO 370
<211> LENGTH: 21
<212> TYPE: RNA
<213> ORGANISM: Artificial
<220> FEATURE:
<223> OTHER INFORMATION: IsomiR sequence

<400> SEQUENCE: 370
ucagccaggc uagugcaguc u                                               21

<210> SEQ ID NO 371
<211> LENGTH: 20
<212> TYPE: RNA
<213> ORGANISM: Artificial
<220> FEATURE:
<223> OTHER INFORMATION: IsomiR sequence

<400> SEQUENCE: 371
uucagccagg cuagugcagu                                                 20

<210> SEQ ID NO 372
<211> LENGTH: 24
<212> TYPE: RNA
<213> ORGANISM: Artificial
<220> FEATURE:
<223> OTHER INFORMATION: IsomiR sequence

<400> SEQUENCE: 372
cuucagccag gcuagugcag ucug                                            24
```

MIRNA FOR TREATING HEAD AND NECK CANCER

CROSS REFERENCE TO RELATED APPLICATIONS

The present application is the 35 U.S.C. 371 National Stage of International Application Number PCT/NL2012/050905, filed Dec. 20, 2012, which claims the benefit of U.S. Provisional Application Nos. 61/579,191, 61/579,162, 61/579,229, 61/579,019 and 61/579,160, all filed Dec. 22, 2011 and claims priority from European patent application 11195240.4, filed Dec. 22, 2011, the contents of each of which are incorporated herein by reference.

SEQUENCE LISTING SUBMISSION VIA EFS-WEB

A computer readable text file, entitled "031902-5013-US-Sequence-Listing.txt", created on or about Jun. 20, 2014, with a file size of about 134 KB contains the sequence listing for this application and is hereby incorporated by reference in its entirety

FIELD OF THE INVENTION

The invention relates to a diagnostic use of a miRNA molecule, equivalent or source thereof and therapeutic use of said miRNA molecule, equivalent or source thereof in diseases and conditions associated with a squamous cell carcinoma such as head and neck cancer or a preneoplastic mucosal change.

BACKGROUND OF THE INVENTION

Head and neck squamous cell carcinoma (HNSCC) develops in the mucosal linings of the upper aerodigestive tract and contributes to approximately 5% of all cancers in the Western world. Well-known risk factors for HNSCC are tobacco smoking, excessive consumption of alcohol and infection with human papillomavirus (HPV). About one third of the patients present with early stage tumours and receive single modality treatment (surgery or radiotherapy). The five-year-survival rate for this patient group is 90%. Unfortunately the majority of patients presents with advanced stages of the disease. These patients are often treated with a combination of surgery and radiotherapy or chemoradiation, the concurrent application of systemic cisplatin chemotherapy and locoregional radiotherapy. Despite major improvements in HNSCC treatment, the long term survival has only moderately improved during the last 20 years. Patients still frequently develop locoregional recurrences, distant metastasis and second primary tumours which results in a five-year-survival rate of less than 60%. Therefore, the development of new anti-cancer agents, which improve patient survival, is most desirable.

Several lines of evidence indicate that head and neck cancers are preceded by preneoplastic fields in the mucosal epithelium characterized by cancer-associated genetic changes. These fields are mostly not visible to the naked eye and remain frequently behind when the tumor is excised or otherwise treated, causing frequent recurrences and second primary tumors (Leemans C. R., et al. 2011). There is at present no treatment for these fields.

Several studies have shown the importance of miRNAs in HNSCC in general. Altered miRNA expression profiles were described in both HNSCC cell lines and tumours when compared to normal controls. A number of miRNAs that had been identified as being differentially expressed were shown to be associated with worse prognosis, such as miR-21 and miR-211. Interestingly, recent studies have described some miRNAs acting as tumour suppressors by targeting certain oncogenes. For example, the miR-16 family has shown antiproliferative effects by negatively regulating cell cycle progression and induction of apoptosis via the silencing of BCL2. Ectopic expression of miR-181a resulted in decreased proliferation via targeting of the oncogene K-RAS. However no new treatment has been yet been developed using a miRNA molecule as active ingredient.

DESCRIPTION OF THE INVENTION

The invention encompasses several uses of a miRNA molecule, equivalent, mimic, isomiR or source thereof as identified herein. The invention also encompasses each of the newly identified miRNA molecules equivalent, mimic, isomiR per se.

In a first aspect, there is provided a miRNA-323, miRNA-342, miRNA-326, miRNA-371, miRNA-345 and/or miRNA-3157 molecule, an equivalent, mimic, isomiR, or a source thereof or a composition comprising said miRNA molecule, said equivalent or said source thereof, preferably for use as a medicament for preventing, treating, reverting, curing and/or delaying a disease or a condition associated with a squamous cell carcinoma such as head and neck cancer or a preneoplastic mucosal change. Other diseases and conditions are also encompassed by the invention as later explained herein as colorectal cancer, colon cancer, glioblastoma, brain tumour, breast cancer, cervix cancer.

MicroRNAs (miRNAs) are small RNAs of 17-25 nucleotides, which function as regulators of gene expression in eukaryotes. miRNAs are initially expressed in the nucleus as part of long primary transcripts called primary miRNAs (pri-miRNAs). Inside the nucleus, pri-miRNAs are partially digested by the enzyme Drosha, to form 65-120 nucleotide-long hairpin precursor miRNAs (pre-miRNAs) that are exported to the cytoplasm for further processing by Dicer into shorter, mature miRNAs, which are the active molecules. In animals, these short RNAs comprise a 5' proximal "seed" region (nucleotides 2 to 8) which appears to be the primary determinant of the pairing specificity of the miRNA to the 3' untranslated region (3'-UTR) of a target mRNA. A more detailed explanation is given in the part dedicated to general definitions.

Each of the definitions given below concerning a miRNA molecule, a miRNA equivalent, a miRNA mimic or a miRNA isomiR, or a mimic or an isomiR or a miRNA source is to be used for each of the identified miRNAs or miRNA equivalent or miRNA sources of this application: miRNA-345, miRNA-323, miRNA-371, miRNA-342, miRNA-326, miRNA-181a, miRNA-3157 and sources thereof. Preferred mature or mimic sequences (as identified in Table 3 as SEQ ID NO: 19-29, 364), seed sequences (as identified in Tables 3 and 5 as SEQ ID NO: 8-18, 363 and 36-107, 366, 367), isomiR sequences (as identified in Table 5 as SEQ ID NO: 108-354, 368-372) or source sequences (as identified in Tables 2 (RNA precursor as SEQ ID NO: 1-7, 362) or 4 (DNA encoding a RNA precursor as SEQ ID NO: 30-35, 365)) of said miRNA molecule or equivalent thereof respectively are identified in corresponding tables. Within the whole text of the application unless otherwise indicated, a miRNA may also be named a miRNA molecule, a miR, or an equivalent thereof or a source or a precursor thereof. A preferred equivalent is an isomiR or a mimic. Each sequence identified herein may be identified as being SEQ ID NO as used in the text of the application or as corresponding SEQ ID NO in the sequence listing. The nomenclature as defined in http://www.mirbase.org/help/nomenclature.shtml has been used herein.

In the context of the invention, a miRNA molecule or an equivalent or a mimic or an isomiR thereof may be a synthetic or natural or recombinant or mature or part of a mature miRNA or a human miRNA or derived from a human miRNA as further defined in the part dedicated to the general definitions. A human miRNA molecule is a miRNA molecule which is found in a human cell, tissue, organ or body fluids (i.e. endogenous human miRNA molecule). A human miRNA molecule may also be a human miRNA molecule derived from an endogenous human miRNA molecule by substitution, deletion and/or addition of a nucleotide. A miRNA molecule or an equivalent or a mimic thereof may be a single stranded or double stranded RNA molecule.

Preferably a miRNA molecule or an equivalent, or a mimic thereof is from 6 to 30 nucleotides in length, preferably 12 to 30 nucleotides in length, preferably 15 to 28 nucleotides in length, more preferably said molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA molecule or equivalent or mimic or isomiR thereof comprises at least 6 of the 7 nucleotides present in the seed sequence of said miRNA molecule or equivalent or mimic or isomiR thereof (Tables 3 and 5 show preferred seed sequence of each of the miRNAs molecule identified herein as SEQ ID NO: 8-18, 363 and 36-107, 366, 367). Preferably in this embodiment, a miRNA molecule or an equivalent or a mimic or isomiR thereof is from 6 to 30 nucleotides in length and more preferably comprises at least 6 of the 7 nucleotides present in the seed sequence of said miRNA molecule or equivalent thereof. Even more preferably a miRNA molecule or an equivalent or a mimic or isomiR thereof is from 15 to 28 nucleotides in length and more preferably comprises at least 6 of the 7 nucleotides present in the seed sequence, even more preferably a miRNA molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-345 molecule or equivalent or mimic or isomiR thereof comprises at least 6 of the 7 nucleotides present in the seed sequence identified as SEQ ID NO: 16 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-323 molecule or equivalent or mimic or isomiR thereof comprises at least 6 of the 7 nucleotides present in the seed sequence identified as SEQ ID NO: 11 and/or 12 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

A more preferred miRNA-323 molecule or equivalent or mimic or isomiR thereof comprises at least 6 of the 7 nucleotides present in the seed sequence identified as SEQ ID NO: 11 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-371 molecule or equivalent or mimic or isomiR thereof comprises at least 6 of the 7 nucleotides present in the seed sequence identified as SEQ ID NO: 17 and/or 18 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

A more preferred miRNA-371 molecule or equivalent or mimic or isomiR thereof comprises at least 6 of the 7 nucleotides present in the seed sequence identified as SEQ ID NO: 18 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-342 molecule or equivalent or mimic or isomiR thereof comprises at least 6 of the 7 nucleotides present in the seed sequence identified as SEQ ID NO: 14 and/or 15 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

A more preferred miRNA-342 molecule or equivalent or mimic or isomiR thereof comprises at least 6 of the 7 nucleotides present in the seed sequence identified as SEQ ID NO: 14 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-326 molecule or equivalent or mimic or isomiR thereof comprises at least 6 of the 7 nucleotides present in the seed sequence identified as SEQ ID NO: 13 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-3157 molecule or equivalent or mimic or isomiR thereof comprises at least 6 of the 7 nucleotides present in the seed sequence identified as SEQ ID NO: 363 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a more preferred embodiment, a miRNA-181a molecule or equivalent or mimic or isomiR thereof comprises at least 6 of the 7 nucleotides present in the seed sequence identified as SEQ ID NO: 8, 9, and/or 10 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

A more preferred embodiment, a miRNA-181a molecule or equivalent or mimic or isomiR thereof comprises at least 6 of the 7 nucleotides present in the seed sequence identified as SEQ ID NO: 8 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In another preferred embodiment, a miRNA molecule or an equivalent or mimic or isomiR thereof comprises at least 6 of the 7 nucleotides present in a given seed sequence as identified in tables 3 and 5 as SEQ ID NO: 8-18, 363 and 36-107, 366, 367 and has at least 70% identity over the whole mature sequence as identified in table 3 (Table 3 shows preferred mature or mimic sequences of each of the miRNAs identified herein as SEQ ID NO: 19-29, 364). Preferably, identity is at least 75%, 80%, 85%, 90%, 95%, 97%, 98%, 99% or 100%.

Accordingly a preferred miRNA-345 molecule or equivalent or mimic or isomiR thereof comprises at least 6 of the 7 nucleotides present in the seed sequence identified as SEQ ID NO: 16, 100, 101, 102, and/or 103 and/or has at least 70%, 75%, 80%, 85%, 90%, 95%, 97%, 98%, 99% or 100% identity over SEQ ID NO: 27, 319, 320, 321, 322, 323, 324, 325, 326, 327, 328, 329, 330, 331, 332 and/or 333.

Accordingly a preferred miRNA-323 molecule or equivalent or mimic or isomiR thereof comprises at least 6 of the 7 nucleotides present in the seed sequence identified as SEQ ID NO: 11, 12, 61, 62, 63, 64, 65, 66, 67, 68, 69 and/or 70 and/or has at least 70%, 75%, 80%, 85%, 90%, 95%, 97%, 98%, 99% or 100% identity over SEQ ID NO: 22, 23, 203, 204, 205, 206, 207, 208, 209, 210, 211, 212, 213, 214, 215, 216, 217, 218, 219, 220, 221 222, 223, 224, 225, 226, 227, 228 and/or 229.

A more preferred miRNA-323 molecule or equivalent or mimic or isomiR thereof comprises at least 6 of the 7 nucleotides present in the seed sequence identified as SEQ ID NO: 11, 66, 67, 68, 69 and/or 70 and/or has at least 70%, 75%, 80%, 85%, 90%, 95%, 97%, 98%, 99% or 100% identity over SEQ ID NO: 22, 219, 220, 221 222, 223, 224, 225, 226, 227, 228 and/or 229.

Accordingly a preferred miRNA-371 molecule or equivalent or mimic or isomiR thereof comprises at least 6 of the 7 nucleotides present in the seed sequence identified as SEQ ID NO: 17, 18, 104, 105, 106 and/or 107 and/or has at least 70%, 75%, 80%, 85%, 90%, 95%, 97%, 98%, 99% or 100% identity over SEQ ID NO: 28, 29, 334, 335, 336, 337, 338, 339, 340, 341, 342, 343, 344, 345, 346, 347, 348, 349, 350, 351, 352, 353 and/or 354.

A more preferred miRNA-371 molecule or equivalent or mimic or isomiR thereof comprises at least 6 of the 7 nucleotides present in the seed sequence identified as SEQ ID NO: 18, 104, 105 and/or 106 and/or has at least 70%, 75%, 80%, 85%, 90%, 95%, 97%, 98%, 99% or 100% identity over SEQ ID NO: 29, 334, 335, 336, 337, 338, 339, 340, 341 and/or 342.

Accordingly a preferred miRNA-342 molecule or equivalent or mimic or isomiR thereof comprises at least 6 of the 7 nucleotides present in the seed sequence identified as SEQ ID NO: 14, 15, 79, 80, 81, 82, 83, 84, 85, 86, 87, 88, 89, 90, 91, 92, 93, 94, 95, 96, 97, 98 and/or 99 and/or has at least 70%, 75%, 80%, 85%, 90%, 95%, 97%, 98%, 99% or 100% identity over SEQ ID NO: 25, 26, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317 and/or 318.

A more preferred miRNA-342 molecule or equivalent or mimic or isomiR thereof comprises at least 6 of the 7 nucleotides present in the seed sequence identified as SEQ ID NO: 14, 86, 87, 88, 89, 90, 91, 92, 93, 94, 95, 96, 97, 98 and/or 99 and/or has at least 70%, 75%, 80%, 85%, 90%, 95%, 97%, 98%, 99% or 100% identity over SEQ ID NO: 25, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317 and/or 318.

Accordingly a preferred miRNA-326 molecule or equivalent or mimic or isomiR thereof comprises at least 6 of the 7 nucleotides present in the seed sequence identified as SEQ ID NO: 13, 71, 72, 73, 74, 75, 76, 77 and/or 78 and/or has at least 70%, 75%, 80%, 85%, 90%, 95%, 97%, 98%, 99% or 100% identity over SEQ ID NO: 24, 230, 231, 232, 233, 234, 235, 236, 237, 238, 239, 240, 241, 242, 243 and/or 244.

Accordingly a preferred miRNA-3157 molecule or equivalent or mimic or isomiR thereof comprises at least 6 of the 7 nucleotides present in the seed sequence identified as SEQ ID NO: 363, 366 and/or 367 and/or has at least 70%, 75%, 80%, 85%, 90%, 95%, 97%, 98%, 99% or 100% identity over SEQ ID NO:364, 368, 369, 370, 371 and/or 372.

Accordingly a preferred miRNA-181a molecule or equivalent or mimic or isomiR thereof comprises at least 6 of the 7 nucleotides present in the seed sequence identified as SEQ ID NO: 8, 9, 10, 36, 37, 38, 39, 40, 41, 42, 43, 44, 45, 46, 47, 48, 49, 50, 51, 52, 53, 54, 55, 56, 57, 58, 59 and/or 60 has at least 70%, 75%, 80%, 85%, 90%, 95%, 97%, 98%, 99% or 100% identity over SEQ ID NO: 19, 20, 21, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201 and/or 202.

A more preferred miRNA-181a molecule or equivalent or mimic or isomiR thereof comprises at least 6 of the 7 nucleotides present in the seed sequence identified as SEQ ID NO: 8, 36, 37, 38, 39, 40, 41, 42, 43, 44, 45 and/or 46 has at least 70%, 75%, 80%, 85%, 90%, 95%, 97%, 98%, 99% or 100% identity over SEQ ID NO: 19, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and/or 157.

Preferably in this embodiment, a miRNA molecule or an equivalent or a mimic or an isomiR thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more, comprises at least 6 of the 7 nucleotides present in a given seed sequence as identified in tables 3 and 5 as SEQ ID NO: 8-18, 363 and 36-107, 366, 367 and has at least 70% identity over the whole mature sequence as identified in table 3 as SEQ ID NO: 19-29, 364 and 108-354, 368-372. Preferably, identity is at least 75%, 80%, 85%, 90%, 95%, 97%, 98%, 99% or 100%.

Alternatively, preferably in this embodiment, a miRNA molecule or an equivalent or a mimic or an isomiR thereof has a length of not more than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides, comprises at least 6 of the 7 nucleotides present in a given seed sequence as identified in tables 3 and 5 as SEQ ID NO: 8-18, 363 and 36-107, 366, 367 and has at least 70% identity over the whole mature sequence as identified in table 3 as SEQ ID NO: 19-29, 364 and 108-354, 368-372. Preferably, identity is at least 75%, 80%, 85%, 90%, 95%, 97%, 98%, 99% or 100%.

In another preferred embodiment, an isomiR of a miRNA molecule has at least 70% identity over the whole isomiR sequence (Table 5 shows preferred isomiR of each of the mature miRNAs identified as SEQ ID NO: 108-354, 368-372. Preferably, identity is at least 75%, 80%, 85%, 90%, 95% or higher. Preferably in this embodiment, an isomiR of a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-345 molecule or equivalent or mimic or isomiR thereof comprises at least 6 of the 7 nucleotides present in the seed sequence identified as SEQ ID NO: 16, 100, 101, 102, and/or 103 and/or has at least 70%, 75%, 80%, 85%, 90%, 95%, 97%, 98%, 99% or 100% identity over SEQ ID NO: 27, 319, 320, 321, 322, 323, 324, 325, 326, 327, 328, 329, 330, 331, 332 and/or 333 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-323 molecule or equivalent or mimic or isomiR thereof comprises at least 6 of the 7 nucleotides present in the seed sequence identified as SEQ ID NO: 11, 12, 61, 62, 63, 64, 65, 66, 67, 68, 69 and/or 70 and/or has at least 70%, 75%, 80%, 85%, 90%, 95%, 97%, 98%, 99% or 100% identity over SEQ ID NO: 22, 23, 203, 204, 205, 206, 207, 208, 209, 210, 211, 212, 213, 214, 215, 216, 217, 218, 219, 220, 221 222, 223, 224, 225, 226, 227, 228 and/or 229 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

A more preferred miRNA-323 molecule or equivalent or mimic or isomiR thereof comprises at least 6 of the 7 nucleotides present in the seed sequence identified as SEQ ID NO: 11, 66, 67, 68, 69 and/or 70 and/or has at least 70%, 75%, 80%, 85%, 90%, 95%, 97%, 98%, 99% or 100% identity over SEQ ID NO: 22, 219, 220, 221 222, 223, 224, 225, 226, 227, 228 and/or 229 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-371 molecule or equivalent or mimic or isomiR thereof comprises at least 6 of the 7 nucleotides present in the seed sequence identified as SEQ ID NO: 17, 18, 104, 105, 106 and/or 107 and/or has at least 70%, 75%, 80%, 85%, 90%, 95%, 97%, 98%, 99% or 100% identity over SEQ ID NO: 28, 29, 334, 335, 336, 337, 338, 339, 340, 341, 342, 343, 344, 345, 346, 347, 348, 349, 350, 351, 352, 353 and/or 354 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

A more preferred miRNA-371 molecule or equivalent or mimic or isomiR thereof comprises at least 6 of the 7 nucleotides present in the seed sequence identified as SEQ ID NO: 18, 104, 105 and/or 106 and/or has at least 70%, 75%, 80%, 85%, 90%, 95%, 97%, 98%, 99% or 100% identity over SEQ ID NO: 29, 334, 335, 336, 337, 338, 339, 340, 341 and/or 342 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-342 molecule or equivalent or mimic or isomiR thereof comprises at least 6 of the 7 nucleotides present in the seed sequence identified as SEQ ID NO: 14, 15, 79, 80, 81, 82, 83, 84, 85, 86, 87, 88, 89, 90, 91, 92, 93, 94, 95, 96, 97, 98 and/or 99 and/or has at least 70%, 75%, 80%, 85%, 90%, 95%, 97%, 98%, 99% or 100% identity over SEQ ID NO: 25, 26, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317 and/or 318 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

A more preferred miRNA-342 molecule or equivalent or mimic or isomiR thereof comprises at least 6 of the 7 nucleotides present in the seed sequence identified as SEQ ID NO: 14, 86, 87, 88, 89, 90, 91, 92, 93, 94, 95, 96, 97, 98 and/or 99 and/or has at least 70%, 75%, 80%, 85%, 90%, 95%, 97%, 98%, 99% or 100% identity over SEQ ID NO: 25, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317 and/or 318 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-326 molecule or equivalent or mimic or isomiR thereof comprises at least 6 of the 7 nucleotides present in the seed sequence identified as SEQ ID NO: 13, 71, 72, 73, 74, 75, 76, 77 and/or 78 has at least 70%, 75%, 80%, 85%, 90%, 95%, 97%, 98%, 99% or 100% identity over SEQ ID NO: 24, 230, 231, 232, 233, 234, 235, 236, 237, 238, 239, 240, 241, 242, 243 and/or 244 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-3157 molecule or equivalent or mimic or isomiR thereof comprises at least 6 of the 7 nucleotides present in the seed sequence identified as SEQ ID NO: 363, 366 and/or 367 has at least 70%, 75%, 80%, 85%, 90%, 95%, 97%, 98%, 99% or 100% identity over SEQ ID NO: 364, 368, 369, 370, 371 and/or 372 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a more preferred embodiment, a miRNA-181a molecule or equivalent or mimic or isomiR thereof comprises at least 6 of the 7 nucleotides present in the seed sequence identified as SEQ ID NO: 8, 9, 10, 36, 37, 38, 39, 40, 41, 42, 43, 44, 45, 46, 47, 48, 49, 50, 51, 52, 53, 54, 55, 56, 57, 58, 59 and/or 60 has at least 70%, 75%, 80%, 85%, 90%, 95%, 97%, 98%, 99% or 100% identity over SEQ ID NO: 19, 20, 21, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201 and/or 202 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In an even more preferred embodiment, a miRNA-181a molecule or equivalent or mimic or isomiR thereof comprises at least 6 of the 7 nucleotides present in the seed sequence identified as SEQ ID NO: 8, 36, 37, 38, 39, 40, 41, 42, 43, 44, 45 and/or 46 has at least 70%, 75%, 80%, 85%, 90%, 95%, 97%, 98%, 99% or 100% identity over SEQ ID NO: 19, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and/or 157 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Another preferred miRNA molecule or equivalent or mimic or an isomiR thereof has at least 60% identity with a seed sequence (as identified in Tables 3 and 5 as SEQ ID NO: 8-18, 363 and 36-107, 366-367 or with a mature sequence (as identified in Table 3 as SEQ ID NO: 19-29, 364 or with a precursor sequence (as identified in Table 2 as SEQ ID NO: 1-7, 362 or with a DNA encoding an RNA precursor (as identified in Table 4 as SEQ ID NO: 30-35, 365 or with an isomiR sequence (as identified in Table 5 as SEQ ID NO: 108-354, 368-372). Identity may be at least 65%, 70%, 75%, 80%, 85%, 90%, 95%, 99% or 100%. Identity is preferably assessed on the whole SEQ ID NO as identified in a given Table. However, identity may also be assessed on part of a given SEQ ID NO. Part may mean at least 50% of the length of the SEQ ID NO, at least 60%, at least 70%, at least 80%, at least 90% or 100%.

An equivalent of a miRNA molecule may be an isomiR or a mimic. A precursor sequence may result in more than one isomiR sequences depending on the maturation process (see for example miRNA-342 wherein certain tissues multiple isomiRs have been identified (Table 5). A mimic is a molecule which has a similar or identical activity with a miRNA molecule. In this context a similar activity is given the same meaning as an acceptable level of an activity.

Each of the miRNA molecules or equivalents or mimics or isomiRs thereof as identified herein has an acceptable level of an activity of a given miRNA they derive from. An acceptable level of an activity is preferably that said miRNA or equivalent or mimics or isomiRs thereof is still able to exhibit an acceptable level of said activity of said miRNA. An activity of a given miRNA or an equivalent thereof is for example the ability to exhibit a detectable anti-tumour activity in tumour cells as later defined herein. An acceptable level of an activity is preferably at least 30%, 40%, 50%, 60%, 70%, 80%, 90%, 95% or 100%, or more than 100%, such as 200% or 300% or more of the activity of the miRNA they derive from.

A preferred activity of any of the miRNA molecule or equivalent or isomiR or mimic thereof as identified herein (i.e. miRNA-345, miRNA-323, miRNA-371, miRNA-342, miRNA-326, miRNA-3157, miRNA-181a) is to exhibit or may comprise a detectable anti-tumour activity in tumour cells of a subject as later defined herein.

A source of a miRNA molecule or a source of an equivalent of a miRNA molecule, mimic, isomiR may be any molecule which is able to induce the production of a miRNA molecule or of an equivalent thereof such as a mimic or isomiR as identified herein and which comprises a hairpin-like structure and/or a double stranded nucleic acid molecule. The presence of a hairpin-like structure, may be assessed using the RNAshapes program (Steffen P. et al 2006) using sliding windows of 80, 100 and 120 nt or more. The hairpin-like structure is usually present in a natural or endogenous source of a miRNA molecule whereas a double-stranded nucleic acid molecule is usually present in a recombinant or synthetic source of a miRNA molecule or of an equivalent thereof.

A source of a miRNA molecule or of an equivalent or a mimic or an isomiR thereof may be a single stranded optionally within a hairpin like structure, a double stranded RNA or a partially double stranded RNA or may comprise three strands, an example of which is described in WO2008/10558. As used herein partially double stranded refers to double stranded structures that also comprise single stranded structures at the 5' and/or at the 3' end. It may occur when each strand of a miRNA molecule does not have the same length. In general, such partial double stranded miRNA molecule may have less than 75% double stranded structure and more than 25% single stranded structure, or less than 50% double stranded structure and more than 50% single stranded structure, or more preferably less than 25%, 20% or 15% double stranded structure and more than 75%, 80%, 85% single stranded structure.

Alternatively, a source of a miRNA molecule or of an equivalent or a mimic or an isomiR thereof is a DNA molecule encoding a precursor of a miRNA molecule or of an equivalent or a mimic or an isomiR thereof. Preferred DNA molecules in this context are identified in table 4 as SEQ ID NO: 30-35, 365. The invention encompasses the use of a DNA molecule encoding a precursor of a miRNA molecule that has at least 70% identity with said sequence as identified in table 4. Preferably, the identity is at least 75%, 80%, 85%, 90%, 95%, 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400 nucleotides or more and has at least 70% identity with a DNA sequence as identified in table 4 as SEQ ID NO: 30-35, 365.

The induction of the production of a given miRNA molecule or of an equivalent thereof or of a mimic or an isomiR thereof is preferably obtained when said source is introduced into a cell using one assay as defined below. Cells encompassed by the present invention are later on defined.

A preferred source of a miRNA molecule or of an equivalent thereof or of a mimic or an isomiR thereof is a precursor thereof, more preferably a nucleic acid encoding said miRNA molecule or an equivalent thereof or of a mimic or an isomiR thereof. A preferred precursor is a naturally-occurring precursor. A precursor may be a synthetic or recombinant precursor.

A preferred precursor of a given miRNA molecule is identified in table 2 as SEQ ID NO: 1-7, 362. The invention encompasses the use of a precursor of a miRNA molecule or of an equivalent thereof that has at least 70% identity with said sequence. Preferably, identity is at least 75%, 80%, 85%, 90%, 95%, 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400 nucleotides or more and has at least 70% identity with a sequence as identified in table 2 as SEQ ID NO: 1-7, 362.

Accordingly, a preferred source of a miRNA-345 molecule has at least 70%, 75%, 80%, 85%, 90%, 95%, 97%, 98%, 99% or 100% identity with SEQ ID NO: 6 and/or 34 and/or has a length of at least 50, 55, 60, 70, 75, 80, 85, 90, 95, 100, 130, 150, 200, 250, 300, 350, 400 nucleotides or more.

Accordingly, a preferred source of a miRNA-323 molecule has at least 70%, 75%, 80%, 85%, 90%, 95%, 97%, 98%, 99% or 100% identity with SEQ ID NO: 3 and/or 31 and/or has a length of at least 50, 55, 60, 70, 75, 80, 85, 90, 95, 100, 130, 150, 200, 250, 300, 350, 400 nucleotides or more.

Accordingly, a preferred source of a miRNA-371 molecule has at least 70%, 75%, 80%, 85%, 90%, 95%, 97%, 98%, 99% or 100% identity with SEQ ID NO: 7 and/or 35 and/or has a length of at least 50, 55, 60, 70, 75, 80, 85, 90, 95, 100, 130, 150, 200, 250, 300, 350, 400 nucleotides or more.

Accordingly, a preferred source of a miRNA-342 molecule has at least 70%, 75%, 80%, 85%, 90%, 95%, 97%, 98%, 99% or 100% identity with SEQ ID NO: 5 and/or 33 and/or has a length of at least 50, 55, 60, 70, 75, 80, 85, 90, 95, 100, 130, 150, 200, 250, 300, 350, 400 nucleotides or more.

Accordingly, a preferred source of a miRNA-326 molecule has at least 70%, 75%, 80%, 85%, 90%, 95%, 97%, 98%, 99% or 100% identity with SEQ ID NO: 4 and/or 32 and/or has a length of at least 50, 55, 60, 70, 75, 80, 85, 90, 95, 100, 130, 150, 200, 250, 300, 350, 400 nucleotides or more.

Accordingly, a preferred source of a miRNA-3157 molecule has at least 70%, 75%, 80%, 85%, 90%, 95%, 97%, 98%, 99% or 100% identity with SEQ ID NO: 362 and/or 365 and/or has a length of at least 50, 55, 60, 70, 75, 80, 85, 90, 95, 100, 130, 150, 200, 250, 300, 350, 400 nucleotides or more.

Accordingly, a preferred source of a miRNA-181a molecule has at least 70%, 75%, 80%, 85%, 90%, 95%, 97%, 98%, 99% or 100% identity with SEQ ID NO: 1, 2 and/or 30 and/or has a length of at least 50, 55, 60, 70, 75, 80, 85, 90, 95, 100, 130, 150, 200, 250, 300, 350, 400 nucleotides or more.

In this context, it is pointed that several precursors of a given mature miRNA molecule may lead to an identical miRNA molecule. For example, hsa-miRNA-181a may originate from precursors miRNA-181a-1 or miRNA-181a-2 (preferably identified as being SEQ ID NO:1 and 2).

Preferred sources or precursors have been defined later herein. A preferred source includes or comprises an expression construct comprising a nucleic acid, i.e. DNA encoding said precursor of said miRNA, more preferably said expression construct is a viral gene therapy vector selected from gene therapy vectors based on an adenovirus, an adeno-associated virus (AAV), a herpes virus, a pox virus and a retrovirus. A preferred viral gene therapy vector is an AAV or Lentiviral vector. Other preferred vectors are oncolytic viral vectors. Such vectors are further described herein below. Alternatively, a source may be a synthetic miRNA molecule or a chemical mimic as further defined in the part dedicated to general definitions.

The detection of the presence of a miRNA molecule or of an equivalent thereof such as a mimic or an isomiR of a miRNA molecule or equivalent thereof may be carried out using any technique known to the skilled person. The assessment of the expression level or of the presence of such molecule is preferably performed using classical molecular biology techniques such as (real time Polymerase Chain Reaction) qPCR, microarrays, bead arrays, RNAse protection analysis or Northern blot analysis or cloning and sequencing. The skilled person will understand that alternatively or in combination with the quantification of a miRNA molecule or of an equivalent thereof, the quantification of a substrate of a corresponding miRNA molecule or of an equivalent thereof of any compound known to be associated with a function of said miRNA molecule or of said equivalent thereof or the quantification of a function or activity of said miRNA molecule or of said equivalent thereof using a specific assay is encompassed within the scope of the invention.

Preferred compositions and formulations are all defined later herein. A miRNA molecule or an equivalent thereof or a mimic or an isomiR thereof may be used as such as a naked molecule, with or without chemical modifications, or encapsulated into a particle or conjugated to a moiety. A preferred composition comprises a miRNA molecule or an equivalent thereof or a mimic or an isomiR thereof encapsulated into a nanoparticle or a liposomal structure. A miRNA molecule or equivalent thereof or a mimic or an isomiR thereof may be an aptamer-miRNA hybrid. An aptamer-miRNA is defined as a miRNA linked to an RNA (or DNA) oligonucleotide, the latter adopting a conformation that targets the aptamer-miRNA hybrid molecule to a cell-surface protein (e.g. cyclic RGD peptide (cyclic arginine(R)-glycine(G)-aspartic acid (D) peptide). The aptamer-tagged miRNA can be linked to e.g. polyethylene glycol, which increases the chimera's circulating half-life (Dassie, J. P., et al. 2009).

An activity of a given miRNA or an equivalent thereof such as a mimic, isomiR or a corresponding source thereof all as defined herein is preferably the ability to exhibit a detectable anti-tumour activity or effect in tumour cells. Preferably, this anti-tumour activity or effect is only seen in a tumour cell, and therefore not in a corresponding healthy, non-tumour cell. Within the context of the invention, an anti-tumour activity or effect comprises at least one of the following:
a decrease of tumour cell viability or survival,
an induction of apoptosis in tumour cells or an induction of tumour cell death,
an inhibition of proliferation in tumour cells,
an inhibition or a delay of a tumour weight increase or a decrease of a tumour weight or a delayed tumour growth or an inhibition of a tumour growth and
a decrease of ATM (Ataxia Telangiectasia Mutated) expression in tumour cells.

Exhibiting such a detectable anti-tumour activity is crucial in the present invention in order to be able to prevent, delay, cure and/or any disease or condition associated with head and neck cancer. Any disease or condition associated with or comprising a squamous cell carcinoma such as head and neck cancer or a preneoplastic mucosal change is involved or associated may be prevented, delayed, cured and/or treated with a molecule as defined herein. Other diseases and conditions are also encompassed by the invention as later explained herein as colorectal cancer, colon cancer, glioblastoma, brain tumour, breast cancer, cervix cancer.

The assessment of an anti-tumour activity may be carried out periodically, e.g. each week, two weeks, three weeks, fours weeks, one month, two months, three months, four months, five months, six months or each year in a treated subject.

The increase/decrease of an anti-tumour activity may therefore be assessed periodically, e.g. each week, month. This assessment is preferably carried out at several time points for a given subject or at one or several time points for a given subject and a healthy control. Alternatively, such anti-tumour activity may be measured by comparing said anti-tumour activity in a tumour cell from a subject with the corresponding activity in a non-tumour or healthy cell from the same subject at a given time point after start of treatment.

When an anti-tumour activity has been detected at least once, twice, three times, a miRNA molecule, an equivalent, a mimic, an isomiR thereof a or a source thereof is said is exhibit a detectable an anti-tumour activity.

A detectable anti-tumour activity has therefore been preferably detected when for at least one time point, an anti-tumour activity has been detected. Preferably, such detectable anti-tumour activity has been detected for at least two, three, four, five time points. In a preferred embodiment, an anti-tumour activity is assessed in tumour cells of a subject. More preferably, said tumour cells are HNSCC cells (Head and Neck Squamous Cell Carcinoma), i.e. squamous cell carcinomas or mucosal or epithelium cells of the upper aerodigestive tract including the lip, inner lip, oral cavity (mouth), tongue, floor of mouth, gingiva, hard palate, nasal cavity (inside the nose), paranasal sinuses, pharynx, including the nasopharynx, oropharynx, hypopharynx and larynx (i.e. laryngeal cancer including glottic, supraglottic and subglottic cancer), trachea. Alternatively, said tumour cells may be colorectal cells, colon cells, brain cells, glioblastoma cells, breast cells, cervical cells.

A decrease of tumour cell viability or survival may be at least a decrease of at least 1%, 5%, 10%, 15%, 20%, 25%, 30%, 40%, 50%, 55%, 60%, 65%, 70% or 75%, or more. An induction of apoptosis in tumour cells or an induction of tumour cell death may be at least 1%, 5%, 10%, 15%, 20%, 25%, 30%, 40%, 50%, 55%, 60%, 65%, 70% or 75%, or more. Tumour cell viability or survival or death may be assessed using techniques known to the skilled person.

Tumour cell viability and death may be assessed using routine imaging methods such MRI, CT or PET, and derivatives thereof, or in biopsies. Tumour cell viability may be assessed by visualising the extension of the lesion at several time points. A decrease of 10%, 15%, 20%, 25%, 30%, 40%, 50%, 55%, 60%, 65%, 70% or 75%, or more of the lesion observed at least once will be seen as a decrease of tumour cell viability.

An inhibition of the proliferation of tumour cells may be at least 1%, 5%, 10%, 15%, 20%, 30%, 40%, 50%, 55%, 60%, 65%, 70% or 75%, or more. Proliferation of cells may be assessed using known techniques as a standard proliferation assay. Such a proliferation assay may use of vital stains such as Cell Titer Blue (Promega). This includes a substrate molecule that is converted into a fluorescent molecule by metabolic enzymes. The level of fluorescence then reflects the number of living and metabolically active cells. Alternatively, such proliferation assay may determine the mitotic index. The mitotic index is based on the number of tumor cells under proliferation stage compared to the number of total tumor cells. The labelling of proliferative cells can be performed by using the antibody Ki-67 and immunohistochemistry staining. An inhibition of the proliferation of tumours cells may be seen when the mitotic index is reduced by at least 20%, at least 30%, at least 50% or more (as described in Kearsley J. H., et al, 1990).

In certain embodiments, an inhibition or a decrease of a tumour weight or a delayed tumour growth or an inhibition of a tumour growth may be of at least 1%, 5%, 10%, 15%, 20%, 30%, 40%, 50%, 55%, 60%, 65%, 70% or 75%, or more. Tumour weight or tumour growth may be assessed using techniques known to the skilled person. The detection of tumour growth or the detection of the proliferation of tumour cells may be assessed in vivo by measuring changes in glucose utilization by positron emission tomography with the glucose analogue 2-[18F]-fluor-2-deoxy-D-glucose (FDG-PET) or [18F]-'3-fluoro-'3-deoxy-L-thymidine PET. An ex vivo alternative may be staining of a tumour biopsy with Ki67.

In a preferred embodiment, a decrease of ATM (Ataxia Telangiectasia Mutated) expression is detected in tumour cells. A decrease may mean a decrease of at least 1%, 5%, 10%, 15%, 20%, 30%, 40%, 50%, 55%, 60%, 65%, 70%, 75%, 80%, 85%, 90% or more. In an embodiment, there is no detectable expression of ATM. A preferred nucleic acid molecule coding for human ATM is represented by SEQ ID NO:360. A corresponding preferred encoded amino acid sequence of human ATM is represented by SEQ ID NO:361 (UGID:197106 Unigene Hs. 367437).

Preferably, a decrease of the expression level of ATM is assessed at the nucleic acid level, more preferably using qPCR, microarrays or Northern blot analysis. Primers used may be the ones from the kit from Applied Biosystems Hs01112326_m1. Alternatively according to another preferred embodiment, a decrease of the expression level of ATM is assessed at the amino acid level. A decrease of the expression level of ATM at the amino acid level may be detected using Western blotting or ELISA. Alternatively according to another preferred embodiment, a decrease of ATM is assessed as a decrease of an activity of ATM. An activity of ATM may be the phosphorylation of one of its substrates (Methods in molecular immunology, 2004). Phosphorylation may be assessed by Western blotting using an antibody specific for phosphorylated serine or threonine residues. Preferably said substrate is CHK2. Other suitable substrates include p53, BRCA1, NBS1 or BLM. A decrease of an ATM activity may mean a decrease of at least 1%, 5%, 10%, 15%, 20%, 30%, 40%, 50%, 55%, 60%, 65%, 70%, 75%, 80%, 85%, 90% or more of said phosphorylation activity on a substrate.

The invention provides a miRNA-323, miRNA-342, miRNA-326, miRNA-371, miRNA-345, and/or miRNA-3157 molecule, an equivalent or a source thereof or a composition comprising said miRNA-323, miRNA-342, miRNA-326, miRNA-371, miRNA-345, and/or miRNA-3157 molecule said equivalent or said source thereof, preferably, for use as a medicament for preventing, treating, reverting, curing and/or delaying a disease or a condition associated with a squamous cell carcinoma such as head and neck cancer or a preneoplastic mucosal change. Other diseases and conditions are also encompassed by the invention as later explained as colorectal cancer, colon cancer, glioblastoma, brain tumour, breast cancer or cervix cancer.

Preferably, a miRNA-323, miRNA-342, miRNA-326, miRNA-371, miRNA-345, and/or miRNA-3157 molecule or an equivalent or a source thereof is able to prevent, treat, revert, cure and/or delay a disease or a condition associated with a squamous cell carcinoma such as head and neck cancer or a preneoplastic mucosal change or colorectal cancer, colon cancer, glioblastoma, brain tumour, breast cancer or cervix cancer when said molecule exhibits a detectable anti-tumour activity as defined earlier herein.

A disease or a condition encompassed by the invention is involved or associated with a squamous cell carcinoma (SCC) or a preneoplastic mucosal change. A preferred SCC is head and neck cancer or HNSCC. Head and neck cancer refers to a group of biologically similar cancers that start in the upper aerodigestive tract, including the lip, inner lip, oral cavity (mouth), tongue, floor of mouth, gingiviae, hard palate, nasal cavity (inside the nose), paranasal sinuses, pharynx, including the nasopharynx, oropharynx (i.e. OSCC: Oropharyngeal Squamous Cell Carcinoma), hypopharynx and larynx (i.e. laryngeal cancer including glottic, supraglottic and subglottic cancer). Usually head and neck cancer originate from squamous cells, i.e. mucosal or epithelium cells of the upper aerodigestive tract. However, the invention is not limited to HNSCC. The invention also encompasses other SCCs (Squamous Cell Carcinoma). A SCC is a cancer originating in the mucosal linings or the skin. Besides the mucosal epithelium lining the head and neck regions (i.e. the upper aero- and digestive tract), this also includes the trachea and bronchi, the esophagus and the anogenital region. Such a cancer may be genetically characterised by a mutation of p53 and/or an inactivation of p16 as initiating events (Leemans C. R. et al 2011, and Kumar B, et al, 2008). The invention also encompasses any preneoplastic change or so called "field" in a mucosal epithelium. Such preneoplastic change include any mucosal cell or group of cells that contain cancer-associated genetic changes known to the skilled person. Many of these prenoplastic are morphologically abnormal under the microscope and referred to as dysplasia. Some are even visible by the naked eye as white or red mucosal changes referred to as leukoplakia and erythroplakia, respectively (Leemans C. R. et al Nature 2011).

In another embodiment, a disease or a condition encompassed by the invention is involved or associated with colorectal cancer or colon cancer. Colorectal cancer is known to be associated with uncontrolled cell growth (neoplasia) in the colon, rectum or vermiform.

In another embodiment, a disease or a condition encompassed by the invention is involved or associated with glioblastoma or brain tumour. A glioblastoma is known to be a tumour involving glial cells. In another embodiment, a disease or a condition encompassed by the invention is involved or associated with breast cancer.

In another embodiment, a disease or a condition encompassed by the invention is involved or associated with cervix cancer.

There are currently known medicaments that may be used for specifically preventing, treating, reverting, curing and/or delaying a disease or condition associated with a squamous cell carcinoma such as head and neck cancer or a preneoplastic mucosal change or other diseases and conditions as defined herein such in a subject. However, each of these medicaments is likely to display a therapeutic activity which is not sufficient to cure all patients or may induce resistance. Each of these features has been defined earlier herein. The invention provides a new medicament which is expected to add to the current treatment modalities. It could even be applied to eradicate prenoplastic mucosal changes or prevent malignant transformation. The invention encompasses to use a miRNA-323, miRNA-342, miRNA-326, miRNA-371, miRNA-345, and/or miRNA-3157 molecule, an equivalent or a source thereof or a composition comprising said miRNA molecule or equivalent thereof or a source thereof. This use includes increasing, preferably pharmacologically increasing an activity or the steady-state level of said miRNA-323, miRNA-342, miRNA-326, miRNA-371, miRNA-345, and/or miRNA-3157 molecule or equivalent thereof or of said source thereof in a subject, in a cell of said subject, in a tissue of said subject or in body fluid of said subject.

In this use, an activity or steady-state level of said miRNA-323, miRNA-342, miRNA-326, miRNA-371, miRNA-345, and/or miRNA-3157 molecule or equivalent thereof or source thereof is increased in order to exhibit a detectable anti-tumour activity. The assessment of an anti-tumour activity in a subject had been earlier defined herein.

An activity or steady-state level of said miRNA-323, miRNA-342, miRNA-326, miRNA-371, miRNA-345, and/or miRNA-3157 molecule, equivalent thereof; such as a mimic or isomiR thereof or source thereof may be increased at the level of said miRNA molecule (or equivalent thereof) itself, e.g. by providing said miRNA molecule or equivalent thereof to a subject, preferably to a cell of a subject, or to a tissue of said subject, or to an organ of said subject or to said subject said miRNA molecule or equivalent thereof being from an exogenous source. For provision of a miRNA molecule or equivalent thereof from an exogenous source, said miRNA molecule or equivalent thereof may conveniently be produced by expression of a nucleic acid encoding said miRNA molecule or equivalent thereof or encoding a source of said miRNA molecule or equivalent thereof in a suitable host cell as described below or as completely synthetic molecule by chemical synthesis.

Preferably, however, an activity or steady-state level of a miRNA molecule or equivalent thereof is increased by regulating the expression level of a nucleotide sequence encoding said miRNA molecule or equivalent thereof or encoding a source of said miRNA molecule or equivalent thereof. Preferably, the expression level of a nucleotide sequence is regulated in a cell of said subject or in a tissue of said subject or in the subject. The expression level of a miRNA molecule or equivalent thereof or a source of said miRNA molecule or equivalent thereof may be increased by introduction of a miRNA, and equivalent, or a source thereof, or an expression construct (or vector) into a cell, tissue, organ or body fluid of said subject, or in the subject whereby an expression vector comprises a nucleotide sequence comprising a miRNA molecule or equivalent thereof or comprising a source of said miRNA molecule or equivalent thereof, and whereby a nucleotide sequence is under control of a promoter capable of driving expression of a nucleotide sequence in said cell, tissue, organ, subject. The expression level of a miRNA molecule or equivalent thereof or source thereof may also be increased by introduction of an expression construct into a cell, tissue, organ, subject, whereby a construct comprises a nucleotide sequence encoding a factor capable of trans-activation of an endogenous nucleotide sequence encoding a miRNA molecule or equivalent thereof.

A use of the invention preferably comprises the step of administering to a subject a therapeutically effective amount of a pharmaceutical composition comprising a nucleic acid construct for increasing the activity or steady state level of miRNA-323, miRNA-342, miRNA-326, miRNA-371, miRNA-345, and/or miRNA-3157 molecule or equivalent as defined herein. A nucleic acid construct may be an expression construct as further specified herein. Preferably, an expression construct is a viral gene therapy vector selected from gene therapy vectors based on an adenovirus, an adeno-associated virus (AAV), a herpes virus, a pox virus, an oncolytic virus vector and a retrovirus. A preferred viral gene therapy vector is an AAV or Lentiviral vector. Alternatively, a use of the invention preferably comprises the step of administering to a subject a therapeutically effective amount of a pharmaceutical composition comprising a miRNA-323, miRNA-342, miRNA-326, miRNA-371, miRNA-345, and/or miRNA-3157 molecule, an equivalent or a source thereof as defined herein.

In a use of the invention, a cell, a tissue, an organ or body fluid is preferably from a subject suspected of having a disease or condition associated with a squamous cell carcinoma such as head and neck cancer or a preneoplastic mucosal change or other diseases or conditions as defined herein due for example to its age or its genetic background or to its diet or to its lifestyle including tobacco smoking, alcohol consumption, UV light. Alternatively, in another preferred embodiment, use of the invention is applied on a cell, tissue, organ or body fluid from a subject diagnosed as either having a predictive risk for developing later a disease or condition associated with a squamous cell carcinoma such head and neck cancer or a preneoplastic mucosal change or other diseases or conditions as defined herein. A diagnostic method used is preferably one of the inventions as described herein. Alternatively, a cell, a tissue or organ to be treated may be selected based on risk of progression of the disease or condition associated with a disease or condition associated with a squamous cell carcinoma such as head and neck cancer or a preneoplastic mucosal change or other diseases or conditions as defined herein. Such risk of progression may be assessed using classical clinic-pathological criteria or biomarker-based prognosis known to the skilled person. It is also encompassed by the invention to administer a miRNA-323, miRNA-342, miRNA-326, miRNA-371, miRNA-345, and/or miRNA-3157 molecule or equivalent thereof or a precursor thereof or a composition comprising said miRNA-323, miRNA-342, miRNA-326, miRNA-371, RNA-345, and/or miRNA-3157 molecule or equivalent thereof or source thereof into a tissue or organ or cell of said subject. The organ or tissue or cell may correspond to the organ or tissue or cell wherein a disease or condition associated with a squamous cell carcinoma such as head and neck cancer or a preneoplastic mucosal change or other diseases or conditions as defined herein had been diagnosed. Such organ or tissue or cell may comprise or contain or consist of or derive from or be in the vicinity of a tumor cell.

In the invention, a preferred organ or tissue or cell is an organ or tissue or cell found in the upper aerodigestive tract or in the vicinity thereof. In the invention, a preferred tissue or organ or cell comprises or is derived from the lip, inner lip, oral cavity (mouth), tongue, floor of mouth, gingivae, hard palate, nasal cavity (inside the nose), paranasal sinuses, pharynx, including the nasopharynx, oropharynx, hypopharynx and larynx, trachea.

Other preferred tissues or cells comprise or are derived from squamous cell carcinomas, i.e. mucosal or epithelium cells of the upper aerodigestive tract.

Other preferred tissues of cells comprise or are derived from colorectal cells, colon cells, glioblastoma cell, brain cell, breast cell or cervical cell.

A vicinity of a tumor or a vicinity of the aerodigestive tract in this context may mean up to a few centimeters.

An organ or a tissue or a cell may be an organ or a tissue or a cell wherein a pre-neoplastic change has occurred in the mucosa. A pre-neoplastic change may be a cancer-associated genetic change that is frequently found in head and neck cancers such as p53 mutation, 9p, 3p and 17p loss (Leemans C. R. et al, 2011).

A cell may be or comprise a tumor cell or a metastasized cell or a metastasized tumor cell. Such a cell usually originates from the head and neck area.

A metastatic site or tissue may be located in the lung, bone, liver, mediastinum and bone marrow.

In each case, a miRNA-323, miRNA-342, miRNA-326, miRNA-371, miRNA-345, and/or miRNA-3157 molecule or equivalent or source thereof or composition comprising said molecule, equivalent or source thereof is preferably administered to a cell present in said organ, tissue as identified above. Said miRNA-323, miRNA-342, miRNA-326, miRNA-371, miRNA-345, and/or miRNA-3157 molecule or equivalent or source thereof or composition comprising said molecule, equivalent or source thereof is preferably administered to an organ or tissue comprising 30%, 40%, 50%, 60%, 70%, 80%, 90%, 100% tumour cells. Said miRNA-323, miRNA-342, miRNA-326, miRNA-371, miRNA-345, and/or miRNA-3157 molecule or equivalent or source thereof or composition comprising said molecule, equivalent or source thereof may be targeted to tumour cells, e.g by coupling or conjugating the miRNA-323, miRNA-342, miRNA-326, miRNA-371, miRNA-345, and/or miRNA-3157 molecule or equivalent or source thereof or composition comprising said molecule, equivalent or source thereof with an antibody or other moiety binding to the tumor. Alternatively or in combination said miRNA-323, miRNA-342, miRNA-326, miRNA-371, miRNA-345, and/or miRNA-3157 molecule or equivalent or source thereof or composition comprising said molecule, equivalent or source thereof with may be locally delivered or injected using specific lipid-based formulation (as described in Oliveira S., et al, 2006). A treatment of a disease or condition associated with a squamous cell carcinoma such as head and neck cancer or a preneoplastic mucosal change or of any other disease or condition as identified herein may include a local treatment in or into a tumour tissue that contains tumour cells that have not yet metastasized or induces an anti-tumour activity around a tumour cell that has already formed metastases and/or is migrating from the primary tumour to distant sites in the body. In this preferred embodiment, tumour cells are HNSCC cells. In a preferred embodiment, a miRNA-323, miRNA-342, miRNA-326, miRNA-371, miRNA-345, and/or miRNA-3157 molecule, equivalent, mimic or source thereof or composition comprising said molecule, equivalent or source thereof is systemically administered. Alternatively, in another embodiment, the treatment is locally administered, more preferably by intra-tumoral injection, possibly combined with electroporation (Takei et al, 2008). In a preferred embodiment, a miRNA-323, miRNA-342, miRNA-326, miRNA-371, miRNA-345, and/or miRNA-3157 molecule or equivalent or mimic or source thereof or composition comprising said molecule, equivalent or source thereof is specifically targeted to said tumour, preferably HNSCC tumour cells by linking or conjugating said miRNA-323, miRNA-342, miRNA-326, miRNA-371, miRNA-345, and/or miRNA-3157 or equivalent or source thereof to a targeting part. A preferred targeting part is any molecule known to recognize or bind a molecule which is expressed on tumour cells. A preferred molecule expressed on tumour cells is the Ago-2 (Argonaute-2) protein (Sand M, 2011).

In another use, the invention mentioned herein may be combined with standard treatments of disease or condition associated with head and neck cancer or with any other diseases or conditions as identified herein such as chemotherapy, radiotherapy or surgery. A preferred chemotherapeutic agent is cisplatin.

Although gene therapy is a possibility for preventing, treating, reverting and/or delaying a condition or a disease associated with head and neck cancer, other possible treatments may also be envisaged. For example, treatment by "small molecule" drugs to steer certain molecular pathways in the desired direction, is also preferred. These small molecules are preferably identified by the screening method of the invention as defined later herein.

In the context of the invention, preventing, treating, reverting, curing and/or delaying a disease or condition associated with a squamous cell carcinoma such as head and neck cancer or a preneoplastic mucosal change or of any other diseases or conditions as identified herein may mean that:

The severity of at least one symptom of this disease or condition has been reduced, and/or At least a parameter associated with this disease or condition has been improved: preferably such parameter is associated with an anti-tumour activity or effect.

Such symptom or parameter is preferably identified in a subject as:

a delay in occurrence of metastases and/or of tumour cell migration and/or a prolongation of patient survival of at least one month, several months or more (compared to those not treated or treated with a control or compared with the subject at the onset of the treatment) and/or improvement of the quality of life and observed pain relief.

Criteria to judge therapeutic response are known as the RECIST (Wahl R. L. et al, 2009) criteria. In the context of the invention, a patient may survive and/or may be considered as remaining disease free for a longer time interval. Alternatively, the disease or condition may have been stopped or delayed. In the context of the invention, an improvement of quality of life and observed pain relief may mean that a patient may need less pain relief drugs than at the onset of the treatment. Alternatively or in combination with the consumption of less pain relief drugs, a patient may be less constipated than at the onset of the treatment. "Less" in this context may mean 5% less, 10% less, 20% less, 30% less, 40% less, 50% less, 60% less, 70% less, 80% less, 90% less. A patient may no longer need any pain relief drug. This improvement of quality of life and observed pain relief may be seen, detected or assessed after at least one week, two weeks, three weeks, fours weeks, one month, two months, three months, four months, five months, six months or more of treatment in a patient and compared to the quality of life and observed pain relief at the onset of the treatment of said patient.

A delay in occurrence of metastases and/or of tumour cell migration may be a delay of at least one week, one month, several months, one year or longer. The presence of metastases may be assessed using MRI, CT or Echography or techniques allowing the detection of circulating tumour cells (CTC). Examples of the latter tests are CellSearch CTC test (Vendex), an EpCam-based magnetic sorting of CTCs from peripheral blood. In certain embodiments, tumour growth may be delayed at least one week, one month, two months or more. In a certain embodiment, an occurrence of metastases is delayed at least one week, two weeks, three weeks, fours weeks, one months, two months, three months, four months, five months, six months or more.

In a further preferred embodiment, there is provided a composition further comprising another miRNA molecule which is: a miRNA-181a molecule an equivalent such as a mimic or an isomiR or a source thereof.

Since not each of the identified miRNAs molecules or equivalents thereof is expected to have the same target genes, it is assumed that the use of a miRNA-323, miRNA-342, miRNA-326, miRNA-371, miRNA-3157 and/or miRNA-345 molecule or equivalent thereof or source thereof optionally combined together and/or combined with one additional miRNAs molecule, or equivalent thereof or source thereof identified above allows a more effective treatment of a disease or condition associated with a squamous cell carcinoma such as head and neck cancer or a preneoplastic mucosal change or of any other diseases of conditions as identified herein. A tumour treated by a composition or a cocktail of at least a miRNA-323, miRNA-342, miRNA-326, miRNA-371, miRNA-3157, miRNA-345 and optionally a miRNA-181a molecule, or equivalent or source thereof is expected to have fewer possibilities to escape or to resist said treatment. In a further preferred embodiment, it is encompassed to diagnose the expression of each of the miRNA molecules or of their target genes as identified herein and depending on the outcome to adapt the identity of the miRNA molecules used for the treatment.

When the invention relates to a composition comprising more than one miRNA molecule or equivalent thereof or source thereof it is encompassed that each miRNA molecule or equivalent thereof or source thereof may be present each in a separate composition, each composition being sequentially or simultaneously administered to a subject. Alternatively, it is also encompassed that more than one miRNA molecules or equivalents thereof or sources thereof is present in a composition as defined herein. Preferred compositions of miRNA molecule or equivalent thereof or source thereof include the following miRNA molecule or equivalent thereof or source thereof:

miRNA-323 and miRNA-342,
miRNA-323 and miRNA-326,
miRNA-323 and miRNA-371,
miRNA-323 and miRNA-345,
miRNA-323 and miRNA-181a,
miRNA-323 and miRNA-3157,
miRNA-3157 and miRNA-342,
miRNA-3157 and miRNA-326,
miRNA-3157 and miRNA-371,
miRNA-3157 and miRNA-345,
miRNA-3157 and miRNA-181a,
miRNA-342 and miRNA-326,
miRNA-342 and miRNA-181a,
miRNA-342 and miRNA-371,
miRNA-342 and miRNA-345,
miRNA-326 and miRNA-181a,
miRNA-326 and miRNA-371,
miRNA-326 and miRNA-345,
miRNA-371 and miRNA-181a,
miRNA-371 and miRNA-345,
miRNA-345 and miRNA-181a.

Therefore the invention further encompasses to use a miRNA molecule, an equivalent or a source thereof or a composition comprising said miRNA molecule or equivalent thereof or a source thereof as identified herein.

This preferred use:
includes increasing, preferably pharmacologically increasing an activity or the steady-state level of said miRNA molecule or equivalent thereof or of said source thereof as identified herein in a subject, in a cell of said subject, in a tissue of said subject or in body fluid of said subject.

In this preferred use:
an activity or steady-state level of a miRNA molecule as defined herein may be increased in order to exhibit a detectable anti-tumour activity. The assessment of an anti-tumour activity in a subject had been earlier defined herein.

In a further aspect, there is provided the use of a miRNA-323, miRNA-342, miRNA-326, miRNA-371, miRNA-345, and/or miRNA-3157 molecule, an equivalent or a source thereof or a composition comprising said miRNA-323, miRNA-342, miRNA-326, miRNA-371, miRNA-345, and/or miRNA-3157, an equivalent or a source thereof preferably for the manufacture of a medicament for preventing, treating, reverting, curing and/or delaying a disease or a condition associated with a squamous cell carcinoma such as head and neck cancer or a preneoplastic mucosal change or of any disease or condition as identified herein. Each feature of this further aspect has already been described herein.

In a further aspect, there is provided a method for preventing, treating, reverting, curing and/or delaying a condition or disease associated with a squamous cell carcinoma such as head and neck cancer or a preneoplastic mucosal change or of any disease or condition as identified herein by administering a miRNA molecule or equivalent thereof or source thereof or a composition as earlier defined herein to a subject in the need thereof. Each feature of this further aspect has already been described herein.

In a further aspect, there is provided a method for diagnosing a disease or condition associated with a squamous cell carcinoma such as head and neck cancer or a preneoplastic mucosal change or of any disease or condition as identified herein in a subject, the method comprising the steps of:
(a) determining the expression level of a miRNA-323, miRNA-342, miRNA-326, miRNA-371, miRNA-345, and/or miRNA-3157 molecule, an equivalent or a source thereof in a subject, and optionally
(b) comparing the expression level of said molecule or equivalent thereof or source thereof as defined in (a) with a reference value for the expression level of said molecule, equivalent or source thereof, the reference value preferably being the average value for the expression level of said molecule, equivalent or source thereof in a healthy subject.

In the context of the invention, diagnosis means either a predictive risk assessment of a subject for developing a disease or a condition associated with a squamous cell carcinoma such as head and neck cancer or a preneoplastic mucosal change or of any disease or condition as identified herein. In the context of the invention, a subject may be an animal or a human being. Preferably, a subject is a human being. In the context of the invention, the reference value assessed in (b) and the expression level of a miRNA-323, miRNA-342, miRNA-326, miRNA-371, miRNA-345, and/or miRNA-3157 molecule, an equivalent or a source thereof assessed in (a) are assessed in a corresponding or similar tissue of both subjects.

Since the expression levels of these nucleotide sequences and/or amounts of corresponding miRNA molecule or equivalent thereof or source thereof may be difficult to be measured in a subject, a sample from a subject is preferably used. According to another preferred embodiment, the expression level (of a nucleotide sequence or miRNA molecule or equivalent or source thereof) is determined ex vivo in a sample obtained from a subject. The sample preferably comprises a body fluid of a subject. A sample may be a tissue biopsy or a tumor biopsy or a cancer tissue of a subject. A preferred tissue is either primary tumor tissue or metastasized tissue. A body fluid may comprise or be derived from blood, serum, sputum, plasma, CSF (Cerebrospinal Fluid), stool, urine. A preferred organ or tissue or cell is an organ or tissue or cell found in the upper aerodigestive tract. In the invention, a preferred tissue or organ or cell comprises or is derived from the lip, inner lip, oral cavity (mouth), tongue, floor of mouth, gingiviae, hard palate, nasal cavity (inside the nose), paranasal sinuses, pharynx, including the nasopharynx, oropharynx, hypopharynx and larynx, trachea. Other preferred tissues or cells comprise or are derived from squamous cell carcinomas, i.e. mucosal or epithelium cells of the upper aerodigestive tract.

Other preferred organ or tissue or cell is or derives from or comprises the colon, the brain, the breast or the cervix.

It is specifically contemplated that the invention can be used to evaluate or diagnose differences between stages of disease or condition associated with a squamous cell carcinoma such as head and neck cancer or a preneoplastic mucosal change or of any disease or condition as identified herein, or such as between pre-cancer and cancer, or between a primary tumor and a metastasized tumor.

An increase or decrease of the expression level of a nucleotide sequence (or steady state level of the encoded miRNA molecule or equivalent or source thereof) is preferably defined as being a detectable change of the expression level of a nucleotide (or steady state level of an encoded miRNA molecule or equivalent or source thereof or any detectable change in a biological activity of a miRNA molecule or equivalent or source thereof) using a method as defined earlier on as compared to the expression level of a corresponding nucleotide sequence (or steady state level of a corresponding encoded miRNA molecule or equivalent or source thereof) in a healthy subject. A preferred nucleotide sequence is a sequence encoding a precursor of a miRNA molecule or equivalent thereof. According to a preferred embodiment, an increase or decrease of a miRNA activity is quantified using a specific assay for a miRNA activity. A preferred assay is the assessment of an anti-tumour activity as earlier defined herein.

Preferably, a decrease of the expression level of a nucleotide sequence means a decrease of at least 10% of the expression level of the nucleotide sequence using arrays. More preferably, a decrease of the expression level of a nucleotide sequence means an decrease of at least 15%, even more preferably at least 20%, at least 30%, at least 40%, at least 50%, at least 70%, at least 90%, or 100%. In this case, there is no detectable expression.

Preferably, a decrease of the expression level of a miRNA molecule or equivalent or source thereof means a decrease of at least 10% of the expression level of the miRNA using qPCR, microarrays or Northern blot analysis. Preferably qPCR is stem-loop RT qPCR. More preferably, a decrease of the expression level of a miRNA molecule or equivalent or source thereof means a decrease of at least 15%, even more preferably at least 20%, at least 30%, at least 40%, at least 50%, at least 70%, at least 90%, or 100%. In this case, there is no detectable expression.

Preferably, a decrease of a miRNA activity means a decrease of at least 5% of a miRNA activity using a suitable assay. More preferably, a decrease of a miRNA activity means a decrease of at least 10%, even more preferably at least 20%, at least 30%, at least 40%, at least 50%, at least 70%, at least 90%, or 100%. In this case, there is no detectable activity.

Preferably, an increase of the expression level of a nucleotide sequence means an increase of at least 10% of the expression level of the nucleotide sequence using any of the techniques mentioned herein. More preferably, an increase of the expression level of a nucleotide sequence means an increase of at least 15%, even more preferably at least 20%, at least 30%, at least 40%, at least 50%, at least 70%, at least 90%, at least 150% or more.

Preferably, an increase of the expression level of a miRNA molecule or equivalent or source thereof means an increase of at least 10% of the expression level of the miRNA molecule or equivalent or source thereof using RT-qPCR, preferably stem-loop RT qPCR. More preferably, an increase of the expression level of a miRNA molecule or equivalent or source thereof means an increase of at least 15%, even more preferably at least 20%, at least 30%, at least 40%, at least 50%, at least 70%, at least 90%, at least 150% or more.

Preferably, an increase of a miRNA activity means an increase of at least 5% of a miRNA activity using a suitable assay. More preferably, an increase of a miRNA activity means an increase of at least 10%, even more preferably at least 20%, at least 30%, at least 40%, at least 50%, at least 70%, at least 90%, at least 150% or more.

Preferably, an expression level is determined ex vivo in a sample obtained from a subject. More preferably, the sample is as earlier defined herein and wherein subsequently, a given nucleotide sequence and/or miRNA molecule or equivalent or source thereof is extracted and purified using known methods to the skilled person. More preferably, the sample is or comprises or is derived from a tumor biopsy, blood, sputum, stool or urine.

In a diagnostic method of the invention preferably the expression level of more than one, more preferably of at least 1, 2, 3, 4, 5, 6, 7, 8, 9, 10, 11, 12, 13, 14, 15 miRNAs molecule or equivalent or source thereof and/or the steady state levels of the corresponding miRNAs molecule or equivalent or source thereof are determined.

Accordingly in a preferred method, in step (a) one determines the expression level of another miRNA molecule or equivalent or source thereof which is a miRNA-181a molecule an equivalent or a source thereof.

In a further preferred method, a disease or condition associated with a squamous cell carcinoma such as head and neck cancer or a preneoplastic mucosal change or of any disease or condition as identified herein is diagnosed when the comparison leads to the finding of a decrease of the expression level of said miRNA-323, miRNA-342, miRNA- 326, miRNA-371, miRNA-345, and/or miRNA-3157 molecule, equivalent or a source thereof.

In a further preferred method, a disease or condition associated with a squamous cell carcinoma such as head and neck cancer or a preneoplastic mucosal change or of any disease or condition as identified herein is diagnosed when the comparison leads to the finding of a decrease of the expression level of said miRNA-323, miRNA-342, miRNA-326, miRNA-371, miRNA-345, and/or miRNA-3157 molecule, equivalent or a source thereof and a decrease of the expression level of a miRNA-181a molecule an equivalent or a source thereof.

In a further preferred embodiment, a disease or condition associated with a squamous cell carcinoma such as head and neck cancer or a preneoplastic mucosal change or of any disease or condition as identified herein is diagnosed when the comparison leads to the finding of a decrease of the expression level of said miRNA-323, miRNA-342, miRNA-326, miRNA-371, miRNA-345, and/or miRNA-3157 molecule, equivalent or a source thereof and/or a decrease of the expression level of at an increase of the expression level of at least one of another miRNA as identified above.

In a further aspect, there is provided a method for identification of a substance or a molecule capable of preventing, treating, reverting, curing and/or delaying a condition or disease associated with a squamous cell carcinoma such as head and neck cancer or a preneoplastic mucosal change or of any disease or condition as identified herein in a subject, the method comprising the steps of:
(a) providing a test cell population capable of expressing a miRNA-323, miRNA-342, miRNA-326, miRNA-371, miRNA-345, and/or miRNA-3157 molecule or equivalent thereof or source thereof, preferably the test population comprises cancer cells and/or the test cell population comprises mammalian cells, and/or the test cell population comprises human cells;
(b) contacting the test cell population with the substance;
(c) determining the expression level of said miRNA-323, miRNA-342, miRNA-326, miRNA-371, miRNA-345, and/or miRNA-3157 molecule or equivalent thereof or source thereof or the activity or steady state level of said miRNA-323, miRNA-342, miRNA-326, miRNA-371, miRNA-345, and/or miRNA-3157 molecule or equivalent thereof or source thereof in the test cell population contacted with the substance;
(d) comparing the expression, activity or steady state level determined in (c) with the expression, activity or steady state level of said miRNA-323, miRNA-342, miRNA-326, miRNA-371, miRNA-345, and/or miRNA-3157 molecule or equivalent thereof or source thereof in a test cell population that is not contacted with the substance; and,
(e) identifying a substance that produces a difference in expression level, activity or steady state level of said miRNA-323, miRNA-342, miRNA-326, miRNA-371, miRNA-345, and/or miRNA-3157 molecule or equivalent thereof or source thereof, between the test cell population that is contacted with the substance and the test cell population that is not contacted with the substance.

Preferably, in step a), a test cell comprises a nucleic acid construct comprising a source or a precursor of a miRNA-323, miRNA-342, miRNA-326, miRNA-371, miRNA-345, and/or miRNA-3157 molecule or equivalent thereof or a precursor of said miRNA as identified earlier herein. Preferably, in a method the expression levels, an activity or steady state levels of more than one nucleotide sequence or more than one miRNA molecule, equivalent or source thereof are compared. Preferably, in a method, a test cell population comprises mammalian cells, more preferably human cells. More preferably, a test cell is a cell line derived from an head neck squamous cell carcinoma. A test cell may also be a colorectal cell, a colon cell, a glioblastoma cell, a brain tumour cell, a breast cancer cell or a cervical cancer cell. A cell line may also be used as VU-SCC-120. VU-SCC-120 is a HNSCC cell line previously described as 93VU120 (Hermsen et al., 1996). Other cell lines include HT29, U87, MCF7, Siha cells. A preferred test cell population does not express a miRNA-323, miRNA-342, miRNA-326, miRNA-371, miRNA-345, and/or miRNA-3157 molecule or equivalent thereof or source thereof or has a reduced expression compared to a normal counterpart. Alternatively or in addition to previous mentioned cells, in one aspect the invention also pertains to a substance that is identified in the aforementioned methods. In a preferred method, the expression levels, activities or steady state levels of another miRNA molecule or equivalent or source thereof is compared, preferably a miRNA-181a molecule an equivalent or a source thereof.

General Definitions and General Technologies Referred to Herein

MicroRNA molecules ("miRNAs") are generally 21 to 22 nucleotides in length, though lengths of 17 and up to 25 nucleotides have been reported. Any length of 17, 18, 19, 20, 21, 22, 23, 24, 25 is therefore encompassed within the present invention. The miRNAs are each processed from a longer precursor RNA molecule ("precursor miRNA"). Precursor miRNAs are transcribed from non-protein-encoding genes. A precursor may have a length of at least 50, 70, 75, 80, 85, 100, 150, 200 nucleotides ore more. The precursor miRNAs have two regions of complementarity that enables them to form a stem-loop- or fold-back-like structure, which is cleaved by enzymes called Dicer and Drosha in animals. Dicer and Drosha are ribonuclease Ill-like nucleases. The processed miRNA is typically a portion of the stem.

The processed miRNA (also referred to as "mature miRNA") becomes part of a large complex, known as the RNA-Induced Silencing Complex (RISC) complex, to (down)-regulate a particular target gene. Examples of animal miRNAs include those that perfectly or imperfectly basepair with the mRNA target, resulting in either mRNA degradation or inhibition of translation respectively (Olsen et al, 1999; Seggerson et al, 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al, 2003).

The study of endogenous miRNA molecules is described in U.S. Patent Application 60/575,743, which is hereby incorporated by reference in its entirety. A miRNA is apparently active in the cell when the mature, single-stranded RNA is bound by a protein complex that regulates the translation of mRNAs that hybridize to the miRNA. Introducing exogenous RNA molecules that affect cells in the same way as endogenously expressed miRNAs requires that a single-stranded RNA molecule of the same sequence as the endogenous mature miRNA be taken up by the protein complex that facilitates translational control. A variety of RNA molecule designs have been evaluated. Three general designs that maximize uptake of the desired single-stranded miRNA by the miRNA pathway have been identified. An RNA molecule with a miRNA sequence having at least one of the three designs may be referred to as a synthetic miRNA.

miRNA molecules of the invention can replace or supplement the gene silencing activity of an endogenous miRNA. An example of such molecules, preferred characteristics and modifications of such molecules and compositions comprising such molecules is described in WO2009/091982, which is hereby incorporated by reference in its entirety.

miRNA molecules of the invention or equivalents or source thereof comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand, is at least partially complementary to the active strand. The active and complementary strands are hybridized to create a double-stranded RNA, that is similar to the naturally occurring miRNA precursor that is bound by the protein complex immediately prior to miRNA activation in the cell. Maximizing activity of said miRNA requires maximizing uptake of the active strand and minimizing uptake of the complementary strand by the miRNA protein complex that regulates gene expression at the level of translation. The molecular designs that provide optimal miRNA activity involve modifications of the complementary strand.

Two designs incorporate chemical modifications of the complementary strand. The first modification involves creating a complementary RNA with a group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including NH2, NHCOCH3, biotin, and others. The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance miRNA activities.

The third miRNA design involves incorporating nucleotides in the 3' end of the complementary strand that are not complementary to the active strand.

Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathway in cells. The inventors have found that the judicious use of mismatches in the complementary RNA strand significantly enhances the activity of said miRNA.

MiRNA Libraries

A key application for the miRNAs as identified herein is the assessment or diagnosis of the presence of one individual or groups of miRNAs in a sample. Cell populations with each of the different miRNAs can then be assayed to identify miRNAs whose presence affects a cellular phenotype (i.e. proliferation and/or invasion). The number of different miRNAs in the libraries is variable. It is contemplated that there may be, be at least, or be at most 1, 2, 3, 4, 5, 6, 7, 8, 9, 10, 11, 12, 13, 14, 15, 16, 17, 18, 19, 20 or more, or any range derivable therein, different miRNA-specific molecules in the library. In specific embodiments, libraries have 1 to 20 different miRNA-specific molecules, or 5 to 20 different miRNA-specific molecules. "Different" miRNA-specific molecules refers to nucleic acids that specifically encode miRNAs with different sequences. miRNAs are contemplated to be made primarily of RNA, though in some embodiments, they may be RNA, nucleotide analogs, such as Locked nucleic acids (LNA) or Unlocked nucleic acids (UNA), DNA, or any combination of DNA, RNA, nucleotide analogs, and PNAs (Peptide Nucleic Acids). Accordingly, it is understood that the library contains one or more nucleic acids for these different miRNAs. In specific embodiments, the library is specific to human miRNAs, though libraries for multiple organisms are contemplated.

An RNA molecule of the invention has or comprises or consists of a miRNA region. In specific embodiments, a miRNA molecule or equivalent thereof has a sequence that derives from any of SEQ ID NOs: 19-29, 364 (Table 3). It is particularly contemplated that nucleic acid molecules of the invention may be derived from any of the mature miRNA sequences in SEQ ID NOs: 19-29, 364.

A miRNA molecule or equivalent thereof will include a sequence that extends at least 1 to 5 nucleotides of coding sequence upstream and/or downstream of the predicted miRNA sequence. In some embodiments, molecules have up to 1, 2, 3, 4, 5, 6, 7, or more contiguous nucleotides, or any range derivable therein, that flank the sequence encoding the predominant processed miRNA on one or both sides (5' and/or 3' end).

Libraries of the invention can contain miRNA sequences from any organism having miRNAs, specifically including but not limited to, mammals such as humans, non human primates, rats and mice. Specifically contemplated are libraries having, having at least, or having at most 1, 2, 3, 4, 5, 6, 7, 8, 9, 10, 11, 12, 13, 14, 15, 16, 17, 18, 19, 20 or more different miRNAs (that is, miRNA-specific molecules having different sequences derived from different miRNA genes). Specifically contemplated are such libraries described in the previous sentence with respect to any of SEQ ID NOs: 19-29, 364 particularly those corresponding to miRNA sequences (mature sequence).

Nucleic Acids

The present invention concerns nucleic acid molecules also called sources or precursors of miRNAs that can introduce miRNAs in cultured cells or into a subject. The nucleic acids may have been produced in cells or in vitro by purified enzymes though they are preferentially produced by chemical synthesis. They may be crude or purified. The term "miRNA," unless otherwise indicated, refers to the processed miRNA, after it has been cleaved from its precursor. Table 2 indicates which SEQ ID NO corresponds to a particular precursor sequence of a miRNA (SEQ ID NO: 1-7, 362) and Table 3 indicates which SEQ ID NO corresponds to the mature or mimic sequence of a miRNA (SEQ ID NO: 19-29, 364. Table 4 identifies the cloned DNA sequences into the retroviral library (SEQ ID NO: 30-35, 365 which were used in the functional screen as described in the examples. Tables 3 and 5 identify the preferred seed sequences (as SEQ ID NO: 8-18, 363 and 36-107, 366, 367) of each of the mature miRNAs of Table 3. The name of the miRNA is often abbreviated and referred to without the prefix and will be understood as such, depending on the context. Unless otherwise indicated, miRNAs referred to in the application are human sequences identified as mir-X or let-X, where X is a number and/or letter.

It is understood that a miRNA is derived from genomic sequences or a non-coding gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary.

As used herein, "hybridization", "hybridizes" or "capable of hybridizing" is understood to mean the forming of a double or triple stranded molecule or a molecule with partial double or triple stranded nature using techniques known to the skilled person such as southern blotting procedures. The term "anneal" as used herein is synonymous with "hybridize." The term "hybridization", "hybridize(s)" or "capable of hybridizing" may mean "low", "medium" or "high" hybridization conditions as defined below.

Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

Nucleic acids or derivatives thereof of the invention will comprise, in some embodiments the miRNA sequence of any miRNA described in SEQ ID NOs: 19-29, 364 or are described in SEQ ID NOs: 108-354, 368-372. It is contemplated that nucleic acids sequences of the invention derived from SEQ ID NO: 19-29, 364 and/or 108-354, 368-372 can have, have at least, or have at most 5, 6, 7, 8, 9, 10, 11, 12, 13, 14, 15, 16, 17, 18, 19, 20, 21, 22, 23, contiguous nucleotides from SEQ ID NOs: 19-29, 364 and/or 108-354, 368-372 (or any range derivable therein). In other embodiments, nucleic acids are, are at least, or are at most 80, 81, 82, 83, 84, 85, 86, 87, 88, 89, 90, 91, 92, 93, 94, 95, 96, 97, 98, 99, 100% identical to the miRNA sequence of SEQ ID NOs: 19-29, 364 or 108-354, 368-372 to the precursor sequence of any of SEQ ID NO: 1-7, 362 or 30-35, 365 any combination or range derivable therein.

Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moeity. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified T-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2' or 3' carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-0 position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and WO98/39352, WO99/14226, WO2003/95467 and WO2007/085485, which describe modified RNA nucleotides of which the ribose moiety is modified with an extra bridge connecting the 2' oxygen and 4' carbon. The locked ribose significantly increases the binding affinity and specificity; and WO2008/147824, which describes modified RNA nucleotides termed UNA (unlocked nucleic acid). UNA are acyclic analogues of RNA in which the bond between the C2' and C3' atoms has been cleaved, decreasing binding affinity towards a complementary strand. UNA are compatible with RNase H recognition and RNA cleavage and improves siRNA mediated gene silencing; WO2008/036127 which describes Morpholino nucleic acid analogues, which contain both uncharged and cationic intersubunit linkages; WO/2007/069092 and EP2075342 which describe Zip Nucleic Acids (ZNA), containing conjugating spermine derivatives as cationic moieties (Z units) to an oligonucleotide; U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'-deoxyguanosine nucleotides and nucleic acid analogs thereof).

The use of other analogs is specifically contemplated for use in the context of the present invention. Such analogs may be used in synthetic nucleic acid molecules of the invention, both throughout the molecule or at selected nucleotides. They include, but are not limited to, 1) ribose modifications (such as 2'F, 2' NH2, 2'N3,4'thio, or 2' O—CH3) and 2) phosphate modifications (such as those found in phosphorothioates, methyl phosphonates, and phosphoroborates).

Such analogs have been created to confer stability on RNAs by reducing or eliminating their capacity to be cleaved by ribonucleases. When these nucleotide analogs are present in RNAs, they can have profoundly positive effects on the stability of the RNAs in animals. It is contemplated that the use of nucleotide analogs can be used alone or in conjunction with any of the design modifications of a synthetic miRNA for any nucleic acid of the invention.

In a preferred embodiment, a phosphorothioated ssRNA (single stranded RNA) oligonucleotide is used. Such chemistry is attractive since such a ssRNA is assumed to mimic a corresponding double stranded duple (E. Swayze, Isis Pharmaceuticals, Copenhague, 7$^{th}$ Annual Meeting of the oligonucleotide, Therapeutics society, Sep. 8-10, 2011).

Modified Nucleotides miRNAs of the invention specifically contemplate the use of nucleotides that are modified to enhance their activities. Such nucleotides include those that are at the 5' or 3' terminus of the RNA as well as those that are internal within the molecule. Modified nucleotides used in the complementary strands of said miRNAs either block the 5'OH or phosphate of the RNA or introduce internal sugar modifications that enhance uptake of the active strand of the miRNA. Modifications for the miRNAs include internal sugar modifications that enhance hybridization as well as stabilize the molecules in cells and terminal modifications that further stabilize the nucleic acids in cells. Further contemplated are modifications that can be detected by microscopy or other methods to identify cells that contain the synthetic miRNAs.

Preparation of Nucleic Acid

A nucleic acid may be made by any technique known to one of ordinary skill in the art, such as for example, chemical synthesis, enzymatic production or biological production. Though miRNAs according to the invention could be produced using recombinant methods, it is preferred to produce miRNAs by chemical synthesis or enzymatic production. miRNAs can be produced by a number of methods, including methods involving recombinant DNA technology.

Nucleic acid synthesis is performed according to standard methods. See, for example, Itakura and Riggs (1980). Additionally, U.S. Pat. No. 4,704,362, U.S. Pat. No. 5,221,619, and U.S. Pat. No. 5,583,013 each describe various methods of preparing nucleic acids. Non-limiting examples of a nucleic acid (e.g., a oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester Method

The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purifications are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method.

This is an enzymatic method of DNA synthesis that can be used to synthesize many useful oligonucleotides (Gillam et al., 1978; Gillam et al, 1979). Under controlled conditions, polynucleotide phosphorylase adds predominantly a single nucleotide to a short oligonucleotide.

Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods.

Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference. In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

Design of miRNAs miRNAs typically comprise two strands, an active strand that is identical in sequence to the mature miRNA that is being studied and a complementary strand that is at least partially complementary to the active strand. The active strand is the biologically relevant molecule and should be preferentially taken up by the complex in cells that modulates translation either through mRNA degradation or translational control. Preferential uptake of the active strand has two profound results: (1) the observed activity of said miRNA increases dramatically and (2) non-intended effects induced by uptake and activation of the complementary strand are essentially eliminated. According to the invention, several miRNA designs can be used to ensure the preferential uptake of the active strand.

5' Blocking Agent.

The introduction of a stable moiety other than phosphate or hydroxyl at the 5' end of the complementary strand impairs its activity in the miRNA pathway. This ensures that only the active strand of the miRNA will be used to regulate translation in the cell. 5' modifications include, but are not limited to, NH2, biotin, an amine group, a lower alkylamine group, an acetyl group, 2' O-Me, DMTO, fluoroscein, a thiol, or acridine or any other group with this type of functionality.

Other sense strand modifications. The introduction of nucleotide modifications like 2'-O Me, 2'-deoxy, T-deoxy-2'-fluoro, 2'-O-methyl, 2'-O-methoxyethyl (2'-0-MOE), 2'-O-aminopropyl (2'-0-AP), 2'-O-dimethylaminoethyl (2'-O-DMAOE), 2'-0-dimethylaminopropyl (2'-O-DMAP), 2'-O-dimethylaminoethyloxyethyl (2'-0-DMAEOE), or 2'-O—N-methylacetamido (2'-0-NMA), NH2, biotin, an amine group, a lower alkylamine group, an acetyl group, DMTO, fluoroscein, a thiol, or acridine or any other group with this type of functionality in the complementary strand of the miRNA can eliminate the activity of the complementary strand and enhance uptake of the active strand of the miRNA.

Base mismatches in the sense strand. As with siRNAs (Schwarz 2003), the relative stability of the 5' and 3' ends of the active strand of the miRNA apparently determines the uptake and activation of the active by the miRNA pathway. Destabilizing the 5' end of the active strand of the miRNA by the strategic placement of base mismatches in the 3' end of the complementary strand of the synthetic miRNA enhances the activity of the active strand and essentially eliminates the activity of the complementary strand.

Host Cells and Target Cells

The cells wherein a miRNA or source thereof is introduced or wherein the presence of a miRNA is assessed may be derived from or contained in any organism. Preferably, the cell is a vertebrate cell. More preferably, the cell is a mammalian cell. Even more preferably, the cell is a human cell.

A mammalian cell may be from the germ line or somatic, totipotent or pluripotent, dividing or non-dividing, epithelium, immortalized or transformed, or the like. The cell may be an undifferentiated cell, such as a stem cell, or a differentiated cell, such as from a cell of an organ or tissue. Alternatively, cells may be from the upper aerodigestive tract. In the invention, a preferred tissue or organ or cell comprises or is derived from the lip, inner lip, oral cavity (mouth), tongue, floor of mouth, gingiviae, hard palate, nasal cavity (inside the nose), paranasal sinuses, pharynx, including the nasopharynx, oropharynx, hypopharynx and larynx, trachea. Other preferred tissues or cells comprise or are derived from squamous cell carcinomas, i.e. mucosal or epithelium cells of the upper aerodigestive tract. Other cells or tissues may comprise colorectal cells, colon cells, glioblastoma cells, brain tumour cells, breast cancer cells or cervical cancer cells.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding a reporter gene has been introduced. Therefore, recombinant cells are distinguishable from naturally occurring cells that do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to a tissue or cell found in the upper aerodigestive tract as the lip, inner lip, oral cavity (mouth), tongue, floor of mouth, gingivae, hard palate, nasal cavity (inside the nose), paranasal sinuses, pharynx, including the nasopharynx, oropharynx, hypopharynx and larynx, trachea. Other preferred tissues or cells comprise or are derived from squamous cell carcinomas, i.e. mucosal or epithelium cells of the upper aerodigestive tract. Other preferred tissues include colorectal, colon, brain, breast, cervix tissues.

In certain embodiments, the host cell or tissue may be comprised in at least one organism. In certain embodiments, the organism may be a mammal, a human, a primate or murine. One of skill in the art would further understand the conditions under which to incubate all of the above described host cells to maintain them and to permit their division to form progeny.

Delivery Methods

The present invention involves in some embodiments delivering a nucleic acid into a cell. This may be done as part of a screening method, or it may be related to a therapeutic or diagnostic application.

RNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, lentivirus, and plant viruses), and artificial chromosomes (e.g., YACs). One of skill in the art would be well equipped to construct a vector through standard recombinant techniques, which are described in Sambrook et al, 1989 and Ausubel et al, 1996, both incorporated herein by reference. In addition to encoding a modified polypeptide such as modified gelonin, a vector may encode non-modified polypeptide sequences such as a tag or targeting molecule. A targeting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). The expression vectors may contain an RNAi expression cassette comprising one promoter and one or more stem-loop structures separated by one or more spacer regions (WO2006/084209).

Another way of introducing expression vectors into cells, using avidin fusion proteins is described in U.S. Pat. No. 6,287,792.

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al, 1988) adeno-associated virus (AAV) (Ridgeway, 1988; Baichwal and Sugden, 1986; Hermonat and Muzycska, 1984), lentivirus (WO2008/071959, WO2004/054512), Hemaglutinating Virus of Japan (WO2004/035779), Baculovirus (WO2006/048662) and herpesviruses may be employed. They offer several attractive features for various mammalian cells (Friedmann, 1989; Ridgeway, 1988; Baichwal and Sugden, 1986; Coupar et al, 1988; Horwich et al, 1990).

Other suitable methods for nucleic acid delivery to affect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al, 1987); by liposome mediated transfection (Nicolau and Sene, 1982; Fraley et al., 1979; Nicolau et al, 1987; Wong et al, 1980; Kaneda et al., 1989; Kato et al., 1991); by photochemical internalization (WO2008/007073); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464, 765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

A review provides several ways of formulating a RNA molecule in order to optimize its internalisation into a cell (Kim S S, et al, Trends Mol. Med., 2009, 15: 491-500). The following other publications discloses alternative ways of formulating a RNA molecule in order to improve its internalisation into a cell, each incorporated herein by reference: WO 2007/095152, describing the use of PTD-DRBD (Peptide transduction domains linked to double stranded binding domain) for delivery of oligonucleotides, WO 2009/086558, describing the use of SNALP (Stable Nucleic Acid Lipid Particles) particles, comprising a mixture of cationic and fusogenic lipids that enable the cellular uptake and endosomal release of the particle's nucleic acid payload, WO 2009/149418, describing neutral phospholipid-oil-RNAi emulsions, WO 2007/121947, describing the use of a delivery vehicle based on lipoplex, WO 2009/132131, describing the use of novel lipids and nucleic acid-lipid particles that provide efficient encapsulation and efficient delivery of the encapsulated nucleic acid to cells, WO2004/091578 and WO2004/064805 describing cochleate technology of alternating layers of lipids that spiral around a nucleic acid molecule, WO2003/047494 and WO2003/047493 describing reverse micelles incorporating nucleic acids for oral and mucosal delivery, WO 2008/156702, describing bacteria and bacterial therapeutic particle (BTP), including oligonucleotides for as delivery vehicle to cells. Each of the formulations referred to or disclosed in these publications is encompassed by the present invention.

A variety of compounds have been attached to the ends of oligonucleotides to facilitate their transport across cell membranes. Short signal peptides found in the HIV TAT, HSV VP22, *Drosphila antennapedia*, and other proteins have been found to enable the rapid transfer of biomolecules across membranes (reviewed by Schwarze 2000). These signal peptides, referred to as Protein Transduction Domains (PTDs), have been attached to oligonucleotides to facilitate their delivery into cultured cells (Eguchi A, Dowdy S F, Trends Pharmacol Sci., 2009, 7:341-5). Cholesterols have been conjugated to oligonucleotides to improve their uptake into cells in animals (MacKellar 1992). The terminal cholesterol groups apparently interact with receptors or lipids on the surfaces of cells and facilitate the internalization of the modified oligonucleotides. Likewise, poly-L-lysine has been conjugated to oligonucleotides to decrease the net negative charge and improve uptake into cells (Leonetti 1990).

A variety of compounds have been developed that complex with nucleic acids, deliver them to surfaces of cells, and facilitate their uptake in and release from endosomes. Among these are: (1) a variety of lipids such as DOTAP (or other cationic lipid), DDAB, DHDEAB, and DOPE and (2) non-lipid-based polymers like polyethylenimine, polyamidoamine, and dendrimers of these and other polymers. In certain of these embodiments a combination of lipids is employed such as DOTAP and cholesterol or a cholesterol derivative (U.S. Pat. No. 6,770,291, which is hereby incorporated by reference). Several of these reagents have been shown to facilitate nucleic acid uptake in animals.

The cellular components involved in the miRNA pathway are becoming known. Proteins that stabilize and/or transport miRNAs within cells might enhance the stability and activity of miRNAs because they should protect and guide the bound miRNAs once they are in cells. Mixtures of miRNA-transporter proteins and miRNAs could enhance the efficacy of miRNA-based therapeutics. RNAs are hydrophilic molecules by virtue of their anionic phosphate and sugar backbone. Although the nucleobases are hydrophobic, hydrophilicity dominates owing to the extensive hydrogen bonding resulting from the phosphate and sugar residues. The hydrophilic character and anionic backbone reduces cellular permeation. Conjugation of lipophilic groups like cholesterol (Manoharan, 2002) and lauric and lithocholic acid derivatives with C32 functionality (Lorenz et al, 2004), have been shown to improve cellular uptake. Moreover binding of steroid conjugated oligonucleotides to different lipoproteins in the bloodstream, such as LDL, protect their integrity and govern their biodistribution (Rump et al, 2000). Cholesterol attached to anti-sense molecules (Bijsterbosch et al., 2001) and aptamers (Rusconi et al., 2004) has also been shown to stabilize oligonucleotides by allowing binding to lipoproteins. Cholesterol has been demonstrated to enhance uptake and serum stability of siRNAs in vitro (Lorenz et al., 2004) and in vivo (Soutschek et al., 2004). Additionally, a number of small molecules like SB-435495 (Blackie et al, (2002), Isradipine (Oravcova et al, 1994), amlodipine (Oravcova et al, 1994) and 2,2',4,4',5,5'-hexachlorobiphenyl (Borlakoglu et al, 1990) could enhance cellular uptake, and improve nuclease resistance by promoting lipoprotein association.

Screening with miRNA Libraries

As used in the patent application, screening is a process wherein multiple miRNA-specific reagents are delivered separately into individual cell populations or animals. At one or more designated times after delivery, the cell populations or animals are assayed for one or more phenotypes. Those cells or animals that have a significantly different phenotype than cells or animals in the negative control group are classified as positives. The miRNA that was being manipulated in the sample is defined as a hit. Hits represent targets for additional research and potential therapeutic development.

In some embodiments, there is a multi-step process for screening, in certain embodiments, there are four general steps:

(1) Develop Quantitative Assay to Monitor Cellular Process being Studied.

Assays that measure the intensity of a cellular phenotype range from microscopic assays that monitor cell size, cell cycle status, or antibody staining to enzymatic assays that assess the turnover of a specific substrate in a cell lysate to direct measurements of biomolecules or small molecules in lysates, on cells, or in medium.

Critical to the success of a screen is creating an assay that truly measures the cellular phenotype and maximizing the signal-to-noise ratio of the assay. Maximizing signal-to-noise involves testing variables like assay time, assay components, cell type, and length of time between transfection and assay. The greater the difference in the assay results between a positive phenotype and a negative control phenotype, the greater the spread will be in the screening results and the better the opportunity will be to identify interesting genes. Alternative screening methods exist using batch infection.

(2) Optimize Transfection Conditions for the Desired Cells.

The first step in this process is identifying a transfection reagent and plating conditions that maximize the uptake of synthetic miRNAs while maintaining high cell viability. We find it useful to test 2-5 different transfection reagents when using cell lines or 5-10 electroporation conditions when using primary or suspension cells. Transfection can be optimized for the reagent or electroporation condition that worked best among the conditions tested. Screening miRNA-specific libraries requires conditions for high-throughput transfection. In this type of screen, lentiviral introduction rather than transfection was used. This may require alternative optimization techniques.

(3) Screen

Once the assay and transfection process have been developed, a library of synthetic miRNAs or miRNAs expressed by viruses can be introduced sequentially into cells in a 24- or 96-well plate. Duplicate or Triplicate transfections for each reagent provide enough data for reasonable statistical analysis. MTS assay as carried out in the experimental part is an example of such a screen.

(4) Validate Hits

Validating a hit involves showing that the observed phenotype is due to the miRNA being targeted. Hits are typically confirmed by delivering a dilution series of the miRNA inhibitor or synthetic miRNA that registered as a hit into the cell that was originally assayed. Confirmation is slightly different from validation. Confirmation is a repeat of the miRNA-induced phenotype, whereas validation can also include reversal of the phenotype by antagonizing miRNA mediated phenotype.

Labeling and Labeling Techniques

In some embodiments, the present invention concerns miRNAs that are labeled, such as for screening assays to evaluate the therapeutic or diagnostic relevance of a particular miRNA species. It is contemplated that miRNA may first be isolated (either from a cell in which the miRNA is endogenous to the cell or from a cell in which miRNA is exogenous to the cell) and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

Moreover, miRNAs may be labeled as is described in U.S. Patent Application Ser. No. 60/649,584, which is hereby incorporated by reference. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Nucleotides for Labeling

Nucleotides for labelling are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and IDT. Functional groups may be prepared according to ways known to those of skill in the art, including the representative information found in U.S. Pat. Nos. 4,404,289; 4,405,711; 4,337,063 and 5,268,486, and Br. Pat. No. 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribonucleotides: 5-(3-aminoallyl)-UTP; 8-[(4-amino)butyl]-amino-ATP and 8-[(6-amino)butyl]-amino-ATP; $N^6$-(4-amino)butyl-ATP, $N^6$-(6-amino)butyl-ATP, $N^4$-[2,2-oxy-bis-(ethylamine)]-CTP; $N^6$-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N-(4-amino)butyl-dATP, $N^6$-(6-amino)butyl-dATP, $N^4$-[2,2-oxy-to-(ethylamine)]-dCTP; $N^6$-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to an miRNA, and the unlabeled nucleotide is modified with a chemical moiety that enables it to be subsequently labeled, in embodiments of the invention, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNAs is how to label the already existing molecule. To this end, we may use an enzyme capable of using a di- or tri-phosphate ribonucleotide or deoxyribonucleotide as a substrate for its addition to an miRNA, a small RNA molecule. Moreover, in specific embodiments, it involves using a modified di- or triphosphate ribonucleotide, which is added to the 3' end of an miRNA. The source of the enzyme is not limiting. Examples of sources for the enzymes include yeast, gram-negative bacteria such as E. coli, lactococcus lactis, and sheep pox virus.

Enzymes capable of adding such nucleotides include, but are not limited to, poly(A) polymerase, terminal transferase, and polynucleotide phosphorylase. In specific embodiments of the invention, ligase is contemplated as NOT being the enzyme used to add the label, and instead, a non-ligase enzyme is employed.

Poly(A) polymerase has been cloned from a number of organisms from plants to humans. It has been shown to catalyze the addition of homopolymer tracts to RNA (Martin et al, RNA, 4(2):226-30, 1998).

Terminal transferase catalyzes the addition of nucleotides to the 3' terminus of a nucleic acid.

Polynucleotide phosphorylase can polymerize nucleotide diphosphates without the need for a primer.

Labels and Tags miRNAs or miRNA probes may be labeled with a positron emitting (including radioactive), enzymatic, colorimetric (includes visible and UV spectrum, including fluorescent), luminescent or other label or tag for detection or isolation purposes. The label may be detected directly or indirectly. Radioactive labels include $^{125}I$, $^{32}P$, $^{33}P$, and $^{35}S$. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, AMCA, Alexa Fluor dyes, BODIPY dyes, such as BODIPY FL, BODIPY 630/650, BODIPY 650/665, BODIP Y-R6G, BODIPY-TRX; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye®; Marina Blue; Oregon Green; rhodamine dyes, such as rhodamine red, tetramethylrhodamine and rhodamine 6G; Texas Red;

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODEPY 530/550, BODEPY 558/568, BODIPY 564/570, BODDPY 576/589, BODIPY 581/591, BODEPY 630/650, BODIPY 650/655, BODIPY FL, BODIPY R6G, BODEPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODEPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP. Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODEPY FL-14-dUTP, Rhodamine Green-5-dUTP, Alexa Fluor 532-5-dUTP, BODEPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODEPY TR-14-dUTP, Alexa Fluor 594-5-dUTP, BODEPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. It is contemplated that nucleic acids may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference). Fluorescent energy transfer dyes, such as thiazole orange-ethidium heterodimer; and, TOTAB may be used. Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

Visualization Techniques

A number of techniques for visualizing or detecting labeled nucleic acids are readily available. The reference by Stanley T. Crooke, 2000 has a discussion of such techniques (Chapter 6), which is incorporated by reference. Such techniques include, microscopy, arrays, Fluorometry, Light cyclers or other real time PCR™ machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al, 1997, spectroscopy, capillary gel electrophoresis (Cummins et ah, 1996), spectroscopy; mass spectroscopy; radiological techniques; and mass balance techniques. Alternatively, nucleic acids may be labeled or tagged to allow for their efficient isolation. In other embodiments of the invention, nucleic acids are biotinylated.

When two or more differentially colored labels are employed, fluorescent resonance energy transfer (FRET) techniques may be employed to characterize the dsRNA. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule (Acumen [TTP Labtech] plate cytometer for example.

Sample Preparation

It is contemplated that the miRNA of a wide variety of samples can be analyzed using assays described herein. While endogenous miRNA is contemplated for use with some embodiments, recombinant or synthetic miRNA—including nucleic acids that are identical to endogenous miRNA or precursor miRNA—can also be handled and analyzed as described herein. Samples may be biological samples, in which case, they can be from blood, CSF, tissue, organs, tumor, semen, sputum, stool, urine, saliva, tears, other bodily fluid, hair follicles, skin, or any sample containing or constituting biological cells. Alternatively, the sample may not be a biological sample, but be a chemical mixture, such as a cell-free reaction mixture (which may contain one or more biological enzymes).

Cell Assays to Identify miRNAs with Ties to Disease

Specifically contemplated applications include identifying miRNAs that contribute to induce an anti-tumour activity that are themselves parts of a disease or conditions or might otherwise be associated with a particular disease state. Additionally, a contemplated application includes the identification of miRNAs that are able to induce an anti-tumour activity. Also, miRNA functions may be compared between a sample believed to be susceptible to a particular disease or condition associated with a squamous cell carcinoma such as head and neck cancer or a preneoplastic mucosal change and one believed to be not susceptible or resistant to that disease or condition. It is specifically contemplated that RNA molecules of the present invention can be used to treat any of the diseases or conditions discussed in the previous section or modulate any of the cellular pathways discussed in the previous section. Specifically contemplated applications include identifying miRNAs that induce an anti-tumour activity that are themselves parts of a disease or might otherwise be associated with a particular disease state. Also, miRNA functions may be compared between a sample believed to be susceptible to a particular disease or condition associated with neo-angiogenesis and one believed to be not susceptible or resistant to that disease or condition.

The efficacy of different therapeutic drugs may be altered, preferably enhanced by a miRNA molecule, equivalent, mimic or source thereof as defined herein and used according to the present invention. MiRNA molecule, equivalent or source thereof that induce an anti-tumour activity may enhance susceptibility to e.g. chemo and immunotherapy. Such therapeutic drugs include, but are not limited to, chemotherapeutic drugs. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. It is further contemplated that nucleic acids molecules of the invention can be employed in diagnostic and therapeutic methods with respect to any of the above pathways or factors. Thus, in some embodiments of the invention, a miRNA molecule, equivalent, mimic or source thereof inhibits, eliminate, activates, induces, increases, or otherwise modulates one or more of the above pathways or factors is contemplated as part of the invention. The nucleic acid can be used to diagnosis a disease or condition based on the relation of that miRNA to any of the pathways described above.

Other Assays

In addition to the use of arrays and microarrays, it is contemplated that a number of difference assays could be employed to analyze miRNAs, their activities and their effects. Such assays include, but are not limited to, RT-PCR, in situ hybridization, hybridization protection assay (HPA) (GenProbe), branched DNA (bDNA) assay (Collins, M. L. et al. (1997). Nucleic Acids Research 25: 2979-2984), rolling circle amplification (RCA), single molecule hybridization detection (US Genomics), Invader assay (ThirdWave Technologies), and Bridge Litigation Assay (Qiagen). It is contemplated that such methods may be used in the context of arrays, as well as in the context of diagnostic assays.

Therapeutic and Diagnostic Applications miRNAs that affect phenotypic traits provide intervention points for therapeutic applications as well as diagnostic applications (by screening for the presence or absence of a particular miRNA). It is specifically contemplated that RNA molecules of the present invention can be used to treat any of the diseases or conditions discussed in the previous section. Moreover, any of the methods described above can also be employed with respect to therapeutic and diagnostic aspects of the invention. For example, methods with respect to detecting miRNAs or screening for them can also be employed in a diagnostic context. In therapeutic applications, an effective amount of the miRNAs of the present invention is administered to a cell, which may or may not be in an animal. In some embodiments, a therapeutically effective amount of the miRNAs of the present invention is administered to an individual for the treatment of disease or condition. The term "effective amount" as used herein is defined as the amount of the molecules of the present invention that are necessary to result in the desired physiological change in the cell or tissue to which it is administered. The term "therapeutically effective amount" as used herein is defined as the amount of the molecules of the present invention that achieves a desired effect with respect to a disease or condition associated with head and neck cancer as earlier defined herein. A skilled artisan readily recognizes that in many cases the molecules may not provide a cure but may provide a partial benefit, such as alleviation or improvement of at least one symptom. In some embodiments, a physiological change having some benefit is also considered therapeutically beneficial. Thus, in some embodiments, an amount of molecules that provides a physiological change is considered an "effective amount" or a "therapeutically effective amount."

In some embodiments the molecule has a sequence that corresponds to the miRNA sequence from that particular animal, as opposed to from another animal. Thus, in some embodiments, a human sequence is utilized in the RNA molecules of the present invention. In in vivo experiments, a miRNA sequence may differ in the test animal as compared to the human sequence. In that case, a miRNA that differs from the human sequence might be used to demonstrate therapeutic effect in the animal. Results obtained with this sequence tested in an animal may be extrapolated expected results in human with a corresponding miRNA molecule.

Modes of Administration and Formulations

The nucleic acid molecules of the invention may be administered to a subject alone or in the form of a pharmaceutical composition for the treatment of a condition or disease. Pharmaceutical compositions may be formulated in conventional manner using one or more physiologically acceptable carriers, diluents, excipients or auxiliaries which facilitate processing of the miRNA into preparations which can be used pharmaceutically. Proper formulation is dependent upon the route of administration chosen. For topical administration the miRNAs of the invention may be formulated as solutions, gels, ointments, creams, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for constitution with a suitable vehicle, e.g., sterile pyrogen-free water, before use. For transmucosal administration, penetrants appropriate to the barrier to be permeated are used in the formulation. Such penetrants are generally known in the art. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The RNA molecules may also be formulated in rectal or vaginal compositions such as suppositories or retention enemas, e.g., containing conventional suppository bases such as cocoa butter or other glycerides.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt. Alternatively, other pharmaceutical delivery systems may be employed.

Liposomes and emulsions are well-known examples of delivery vehicles that may be used to deliver nucleic acids of the invention.

A nucleic acid of the invention may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP; cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects. The nucleic acids may also be administered in combination with a cationic amine such as poly-L-lysine.

Nucleic acids may also be conjugated to a chemical moiety, such as transferrin and cholesteryls. In addition, oligonucleotides may be targeted to certain organs or tissues by linking specific chemical groups to the oligonucleotide. For example, linking the oligonucleotide to a suitable array of mannose residues will target the oligonucleotide to the liver. Other targeting ligands are described in Liu B., Brief Funct. Genomic Proteomic 6:112-119, 2007. Additional examples are carbohydrate sugars such as galactose, N-acetylgalactosamine, mannose; vitamins such as folates; small molecules including naproxen, ibuprofen or other known protein-binding molecules, cyclodextrin, which targets the transferrin receptor, also called transferring modified cyclodextrin (Hu-Lieskovan et al., 2005), PEI (RGD-targeted PEG-PEI, Schiffelers et al. 2004), anisamide, RGD-peptide or RGD mimics, poly-arginin, anti-TfR single chain antibody fragment/TfRscFv, Annexin AS (targeting phosphatidylserine exposing membranes, Gamier B. et al., 2009, 11:2114-22), WO 2009/126933 describing compositions and methods for site-specific delivery of nucleic acids by combining them with targeting ligands and endosomolytic components. Targeting ligands that are preferentially suitable are endothelial-associated cell surface proteins. Targeting of nucleic acids may also be accomplished by using aptamer technology as described in WO2005/111238. Moreover, additional lipid moieties, such as PEG-lipids, cholesterol, endosomolytic helper lipids or peptides (WO2009/046220) or the overall morphology of the generated nanoparticles (characterized by charge and particle size) to the above mentioned delivery vehicles may confer targeting specificity to either cancer cells and/or tumor vasculature.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Alternatively, the molecules may be delivered using a coordination chemistry based delivery system as described in WO2007011217, which is specifically incorporated herein by reference.

In addition to the above, a molecule of the invention may be delivered using electroporation for local or targeted treatment. Electroporation methods are known to the skilled person and are for example described in Daud et al (2008) or Bodles-Brakhop (2009). Each of these publications is incorporated by reference.

Nucleic acids may be included in any of the above-described formulations as the free acids or bases or as pharmaceutically acceptable salts. Pharmaceutically acceptable salts are those salts that substantially retain the biological activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of one or more miRNA molecules dissolved or dispersed in a pharmaceutically acceptable carrier. The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The miRNAs may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal or a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise 2% to 75% of the weight of the unit, or 25% to 60%, for example, and any range derivable therein. In other non-limiting examples, a dose may also comprise less than 1 microgram/kg/body weight, or 1 microgram/kg/body weight, from 5 microgram/kg/body weight, 10 microgram/kg/body weight, 50 microgram/kg/body weight, 100 microgram/kg/body weight, 200 microgram/kg/body weight, 350 microgram/kg/body weight, 500 microgram/kg/body weight, 1 milligram/kg/body weight, 5 milligram/kg/body weight, 10 milligram/kg/body weight, 50 milligram/kg/body weight, 100 milligram/kg/body weight, 200 milligram/kg/body weight, 350 milligram/kg/body weight, or 500 milligram/kg/body weight, to 1000 mg/kg/body weight or more per administration, and any range derivable therein. In non-limiting examples of a derivable range from the numbers listed herein, a range of 5 mg/kg/body weight to 100 mg/kg/body weight, 5 microgram/kg/body weight to 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The molecules may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines. In certain embodiments, the molecules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Any embodiment discussed above with respect to delivery or transport to cells can also be employed with respect to implementing delivery of medicinal compounds discussed in this section.

Effective Dosages

The molecules of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the EC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from 0.01 to 0.1 mg/kg/day, or from 0.1 to 5 mg/kg/day, preferably from 0.5 to 1 mg/kg/day or more. Therapeutically effective serum levels may be achieved by administering multiple doses each day.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs or treatment (including surgery).

Toxicity

Preferably, a therapeutically effective dose of the molecules described herein will provide therapeutic benefit without causing substantial toxicity. Toxicity of the molecules described herein can be determined by standard pharmaceutical procedures in cell cultures or experimental animals, e.g., by determining the Maximal tolerated dose (Ann. Pharm, Fr, 2010, 291-300). The dose ratio between toxic and therapeutic effect is the therapeutic index. The data obtained from these cell culture assays and animal studies can be used in formulating a dosage range that is not toxic for use in human.

Pendant Groups

A "pendant group" may be attached or conjugated to the nucleic acid. Pendant groups may increase cellular uptake of the nucleic acid. Pendant groups can be linked to any portion of the nucleic acid but are commonly linked to the end(s) of the oligonucleotide chain. Examples of pendant groups include, but are not limited to: acridine derivatives (i.e. 2-methoxy-6-chloro-9-ammoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe (II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid is conjugated to a carbohydrate, sulfated carbohydrate, or glycan.

Kits

Any of the compositions described herein may be comprised in a kit. In a non-limiting example, individual miRNAs are included in a kit. The kit may further include one or more negative control synthetic miRNAs that can be used to control for the effects of synthetic miRNA delivery. The kit may further include water and hybridization buffer to facilitate hybridization of the two strands of the synthetic miRNAs. The kit may also include one or more transfection reagent(s) to facilitate delivery of the miRNA to cells.

In another non-limiting example, multiple synthetic miRNAs are included in a kit. The kit may further include one or more negative control synthetic miRNAs that can be used to control for the effects of synthetic miRNA delivery. The kit may also include one or more transfection reagents to facilitate delivery into cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent. The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: miRNA, library of miRNAs, combination library of miRNA, negative control miRNA, nuclease-free water;

RNase-free containers, such as 1.5 ml tubes; hybridization buffer; and transfection reagent(s).

It is contemplated that such reagents are embodiments of kits of the invention. Such kits, however, are not limited to the particular items identified above and may include any reagent used for the manipulation or characterization of miRNA.

Sequence Identity

"Sequence identity" is herein defined as a relationship between two or more nucleic acid (nucleotide, polynucleotide, RNA, DNA) sequences, as determined by comparing the sequences. In the art, "identity" also means the degree of sequence relatedness between nucleic acid sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). In an embodiment, identity is assessed on a whole length of a given SEQ ID NO.

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a miRNA, an equivalent, a mimic or a source thereof or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Figure 1A:
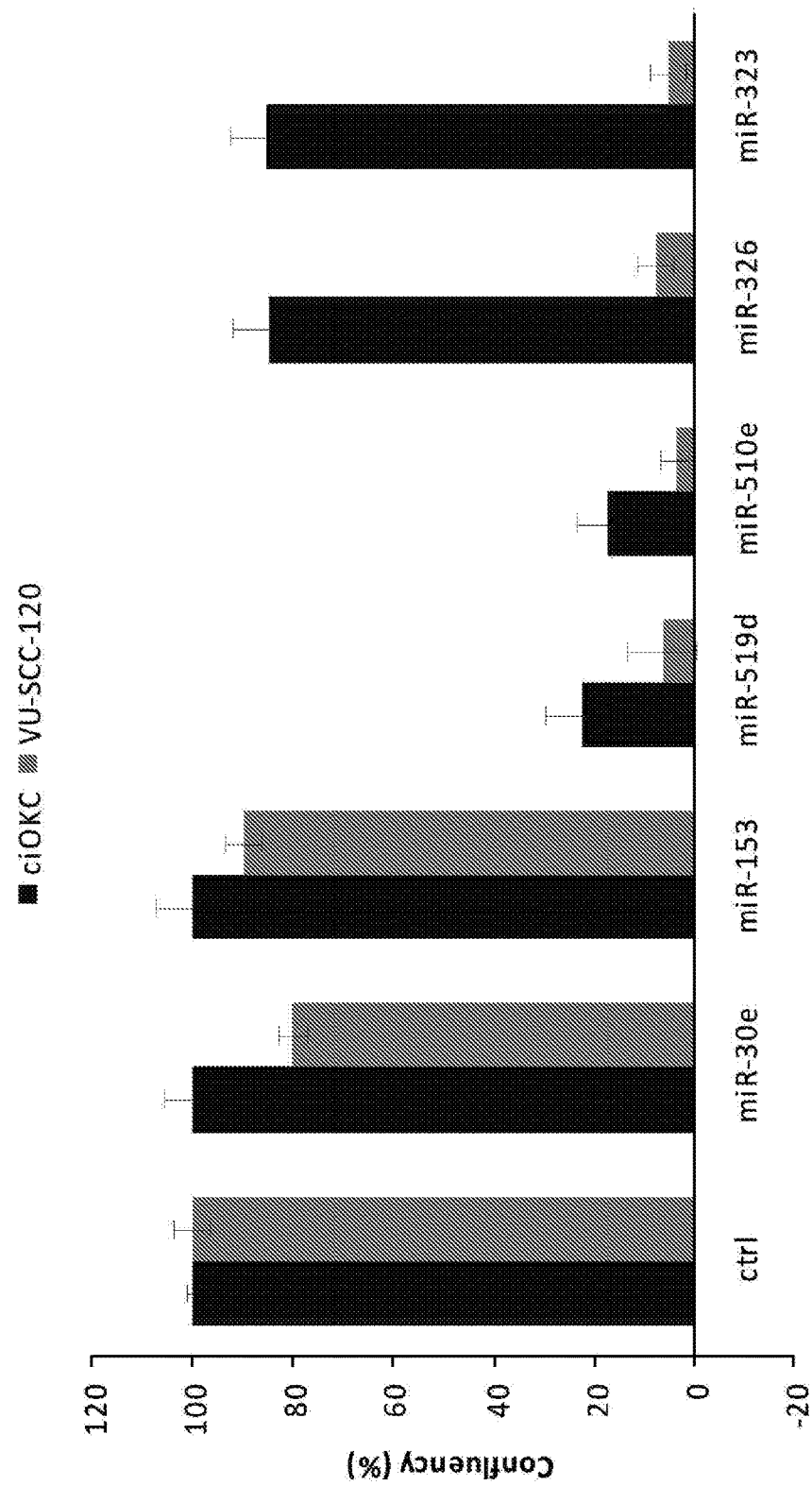
FIG. 1. Functional genetic screen identification of miR-NAs with potential tumor-specific lethal effect. (A) Representation of differences in survival for ciOKC (black bars) and VU-SCC-120 (grey bars) observed in the screen. Experiments were performed in duplicate. Confluency of the cultures was estimated by visual inspection. Averaged data are depicted with standard deviation as error bars. Only six examples are shown that have no effect (miR-30e, miR-153), a general toxic effect (miR-519d, miR-510e), or a tumor-specific lethal effect (miR-326, miR-323) (B) The effect of ectopic expression of the six miRNAs that showed a tumor-specific lethal effect on primary oral keratinocytes (black bars) and head and neck cancer cell lines VU-SCC-120 (dark grey bars), VU-SCC-OE (light grey bars) and UM-SCC-06 (white bars). Cell viability was quantified by the cell titer blue assay. The average value of triplicate experiments is depicted with standard deviations as error bars. These six miRs are lethal for three head and neck squamous tumor cell lines and not for primary mucosal keratinocytes.

A retroviral library has been prepared using known methods in the art. Briefly, genomic sequences of approximately 500 bp containing annotated microRNA sequences from mirbase were cloned into miR-Vec, a retroviral vector that expresses cloned sequences. Functionality of the library was tested as described in Voorhoeve et al, 2006. Details on vector construction and preparation of the library are described by Voorhoeve et al. 2006.

Example 1

Materials and Methods
Cell Culture

Normal oral keratinocytes were isolated and cultured as previously described (van Zeeburg et al., 2010). Conditionally immortalized oral keratinocytes (ciOKC) were cultured in Keratinocyte Serum Free Medium (KSFM; Invitrogen, Breda, The Netherlands) supplemented with 0.1% bovine serum albumin, 25 mg bovine pituitary extract, 2.5 µs human recombinant EGF, 250 µg Amphotericin B (MP biomedicals, San Francisco, United States of America) and 250 µg gentamycin (Sigma-Aldrich, Zwijndrecht, The Netherlands) at 32° C. (Smeets et al., 2011). Tumour cell lines VU-SCC-120, VU-SCC-OE, UM-SCC-6, MCF7, SiHa, U87, HT29 and Phoenix cells were cultured in DMEM, 5% FCS, 2 mM L-glutamine, 50 U/ml Penicillin and 50 µg/ml Streptomycin at 37° C. and 5% $CO_2$. The HNSCC cell lines used were all negative for the human papillomavirus and were sequenced for TP53 mutations. Cell line UM-SCC-6 was TP53 wild type, VU-SCC-120 contained two missense mutations (c.181_182CG>TT and c.527G>A) and VU-SCC-OE a truncating deletion (c.11_919del).

Human miRNA Library Screen

As previously described, amphotropic retroviral supernatants were produced for all 370 annotated and putative microRNAs included in the human miRNA expression library (miR-Lib) with miR-Vec-Ctrl (scrambled sequence) as negative control (Voorhoeve et al., 2006). As primary keratinocytes cannot be cultured at a scale to allow such a screen we used a model of conditionally immortalized oral keratinocytes (ciOKC) as described previously (Smeets et al., 2011). These were generated by transformation of primary keratinocytes with a temperature-sensitive SV40 large T-antigen. Both ciOKC and VU-SCC-120 cells (HNSCC cell line previously described as 93VU120 (Hermsen et al., 1996)) were transduced at two following days for four hours in the presence of 3 µg/ml polybrene (Sigma-Aldrich, Zwijndrecht, The Netherlands). After 48 hours the cells were subjected to blasticidin selection. For ciOKC this was two days 4 µg/ml and subsequently 5 days of 8 µg/ml blasticidin (Sigma-Aldrich). For VU-SCC-120 the selection was performed with 10 µg/ml for seven days. For the initial screen cell survival was assessed by visual inspection when miR-Vec-Ctrl (negative control) had reached 100% confluency, and expressed as estimated percentage of the control. For subsequent validation experiments cell viability was quantified using the CellTiter-Blue® cell viability assay (Promega, Leiden, The Netherlands). The conversion of resazurin to resorufin was measured using the Infinite 200 plate reader (Tecan Group Ltd, Männedorf, Switserland).

RNA Isolation from Formalin-Fixed Paraffin-Embedded Tissues

Normal oral mucosa was derived from three formalin-fixed paraffin-embedded (FFPE) specimens from patients who underwent uvulopalatopharyngoplasty. In addition, FFPE tumour biopsies were selected from five HNSCC patients. The mucosal epithelium or tumour cells were microdissected from the uvulas and tumour samples respectively, as previously described (Bremmer et al., 2005). Microdissected tissues were treated with 1 mg/ml of proteinase K for 17 hours at 56° C. in buffer containing 100 mM TRIS-HCL (pH 9.0), 10 mM NaCl, 1% sodium dodecyl sulphate and 5 mM EDTA (pH 8.2). RNA was isolated by phenol-choloform extraction using glycogen as carrier and precipitated by sodium acetate and ethanol according to standard protocols. After the RNA was washed with 70% ethanol, it was dissolved in RNAse-free water.

Lentiviral shRNA ATM Transduction

Lentiviral vectors with short-hairpin RNA sequences targeting ATM were obtained from the TRC short-hairpin library (Sigma-Aldrich, Zwijndrecht, the Netherlands) that is available at VU university medical center. Each shRNA sequence is complementary to an unique part of the ATM mRNA sequence.

```
                                                    (SEQ ID NO: 355)
5'-CCGGCCTGCCAACATACTTTAAGTACTCGAGTACTTAAAGTATGTT

GGCAGGTTTTTG-3'
                                                    (SEQ ID NO: 356)
5'-CCGGGCACTGAAAGAGGATCGTAAACTCGAGTTTACGATCCTCTTT

CAGTGCTTTTTG-3'
                                                    (SEQ ID NO: 357)
5'-CCGGCGTGTCTTAATGAGACTACAACTCGAGTTGTAGTCTCATTAA

GACACGTTTTTG-3'
                                                    (SEQ ID NO: 358)
5'-CCGGGCCATAATTCAGGGTAGTTTACTCGAGTAAACTACCCTGAAT

TATGGCTTTTTG-3'
                                                    (SEQ ID NO: 359)
5'-CCGGGCCGTCAACTAGAACATGATACTCGAGTATCATGTTCTAGTT

GACGGCTTTTTG-3'
```

Viral supernatants were produced by co-transfection of HEK239T cells using FuGENE® 6 (Roche diagnostics, Woerden, The Netherlands) with the pLKO.1 short-hairpin vector together with the packaging and envelop vectors. Both ciOKC and VU-SCC-120 (HNSCC cell line) were transduced with lentiviruses at two following days for four hours in the presence of 3 µg/ml polybrene (Sigma-Aldrich, Zwijndrecht, The Netherlands). In total 48 hours after transduction, cells were subjected to puromycin selection. For ciOKC this was two days 5 µg/ml and subsequently 5 days of 10 µg/ml puromycin (Sigma-Aldrich). For VU-SCC-120 the selection was performed with 1 µg/ml for seven days.

Quantitative Reverse Transcription-PCR

Total RNA was isolated using the mirVana™ miRNA isolation kit (Ambion, Nieuwerkerk aan den IJssel, The Netherlands) according to the instructions of the manufacturer with as only modification that the columns were eluted by 2×25 µl elution buffer. Expression of hsa-miR-181a, hsa-miR-323, hsa-miR-326, hsa-miR-342, hsa-miR-345 and hsa-miR-371 was analyzed by Taqman® microRNA assays following the instructions of the manufacturer (Applied biosystems, Nieuwerkerk aan den IJssel, The Netherlands). ATM expression was analysed by Taqman® gene expression assay. Relative expression was calculated via the comparative $C_T$ method using the small nucleolar RNA transcript RNU44 (for microRNA expression) or glucuronidase beta, BGUS (for ATM expression) as internal reference (Schmittgen and Livak, 2008). Quantitative RT-PCR reactions without reverse transcriptase were carried out in parallel for each RNA sample to exclude signal by contaminating DNA.

Primer used were from Applied Biosystems

| | |
|---|---|
| miR-181a | assayID000480 |
| miR-323 | assayID000538 |
| miR-326 | assayID000542 |
| miR-342 | assayID002147 |
| miR-345 | assayID002186 |
| miR-371 | assayID000559 |
| ATM | Hs01112326_m1 |

Gene Expression Profiling

The retroviral clones with miRNAs miR-181a, miR-323, miR-326, miR-342, miR-345 and miR-371 and negative control miR-Vec-Ctrl were transiently transfected in VU-SCC-120 by FuGENE® 6 (Roche diagnostics, Woerden, The Netherlands). Total RNA was isolated 72 hours after transfection using the mirVana™ miRNA isolation kit (Ambion). Microarray hybridization using the Agilent Low Input Quick Amplification labeling Kit and 4×44K Whole Human Genome Arrays was carried out according to the manufacturer (Agilent Technologies, Amstelveen, The Netherlands). The data were analyzed by Limma in the R-package using the miR-Vec-Ctrl as reference. Normalization of the gene expression data was done within the R statistical software, using the Limma-package and comprised of RMA background correction, loess within-array normalization and A-quantile between-array normalization. Then, missing values were imputed using the impute-package (impute.knn with default settings). Finally, the slide and dye effect were removed by gene-wise linear regression using the log-intensity values.

The log fold-changes between the reference group and each treated group were used to cluster the six treatments. This was done by means of hierarchical clustering with ward linkage and the similarity defined as the euclidean distance and as one minus the absolute value of the Spearman rank correlation measure. The grouping from hierarchical clustering was verified by means of principal component plots. Within each cluster the difference in gene expression between reference and treated samples were evaluated by means of a t-test. The multiplicity problem (many genes were tested) was addressed by application of the Benjamini-Hochberg procedure to the raw p-values to control the FDR (False Discovery Rate).

ATM Inhibitor Treatment

Both ciOKC and VU-SCC-120 cells were subjected to a concentration range of 40-0.075 µM ATM inhibitor CP466722 (Axon Medchem, Groningen, The Netherlands). After 72 hours cell viability was assessed with the CellTiter-Blue® cell viability assay.

ATM 3'UTR Reporter Luciferase Assay

CiOKC cells were transiently co-transfected with a luciferase reporter construct containing the 3'UTR sequence of ATM (GeneCopoeia Inc, Rockville, Md., United States of America) and one of the retroviral vectors containing the miR-181a, miR-323, miR-326 genes or negative control miR-Vec-Ctrl by FuGENE® 6. In total 72 hours after transfection, firefly and renilla luciferase activity was measured using the LucPair™ miR Dual Luciferase Assay Kit according to the instructions of the manufacturer (GeneCopoeia). Luciferase activity was measured using the Infinite 200 plate reader (Tecan Group Ltd, Männedorf, Switzerland).

Lethal Phenotype Rescue Experiment

VU-SCC-120 cells were transiently transfected with either pcDNA3.1(+)Flag-His-ATMwt (wild type ATM cDNA sequence, Addgene plasmid 31985) or pcDNA3.1(+) Flag-His-ATMkd (kinase dead ATM cDNA sequence, Addgene plasmid 31986) (23). Amphotropic retroviral supernatants were produced for miRNAs miR-181a, miR-326, miR-345 and miR-Vec-Ctrl (scrambled sequence) as negative control. VU-SCC-120-ATMwt, and VU-SCC-120-ATMkd cells were transduced with the microRNA expressing retroviruses at two following days for four hours in the presence of 3 µg/ml polybrene. After 72 hours cell viability was assessed by the CellTiter-Blue® cell viability assay (Promega).

Synthetic Mimic Transfection

Cells were plated and transfected with miRIDIAN microRNA mimics miR-181a, miR-181a*, miR-181a-2, miR-323-5p, miR-323-3p, miR-326-5p, miR-345-5p, miR-342-3p, miR-342-5p, miR-371-3p, miR-371-5p and non-targeting Mimic Negative Control#1 (Dharmacon, Thermo Fisher Scientific, Lafayette, Colo.) in 96-well flat bottom plates (Greiner Bio-One B.V., Alphen a/d Rijn, The Netherlands). MicroRNA mimic for miR-3157 was obtained from Ambion. The non-targeting siCONTROL#1, and the siRNA PLK1 SMARTpool (Dharmacon) were used as negative and positive controls, respectively. Cells were transfected with 30 nmol mimic/siRNA and cell line dependent amounts of DharmaFECT1 (Dharmacon) (Table 6). Cell viability was determined, 96 hours after transfection, by adding CellTiter-Blue reagent (Promega, Leiden, The Netherlands). After two hours of incubation at 37° C. fluorescence was analyzed at 540 nm excitation and 590 nm emission wavelength using an Infinite F200 microplate reader (Tecan, Giessen, The Netherlands).

TABLE 6

Transfection conditions used for the various cell lines

| Cell line | Cells/well | siRNA or mimic/well (nM) | DharmaFECT1/well (μl) |
|---|---|---|---|
| ciOKC10 | 3000 | 30 | 0.12 |
| VU-SCC-120 | 1000 | 30 | 0.03 |
| UM-SCC-22A | 4000 | 30 | 0.15 |
| VU-SCC-059 | 1000 | 30 | 0.05 |
| UM-SCC-11B | 2000 | 30 | 0.065 |
| UM-SCC-22B | 4000 | 30 | 0.15 |
| M3 | 2000 | 30 | 0.08 |

Results
Identification of miRNAs Lethal for HNSCC

To identify miRNAs that are lethal for head and neck cancer cells, we performed a functional genetic screen using the human miRNA expression library (miR-Lib). As a semi-normal control we used primary oral keratinocytes conditionally transformed by a temperature-sensitive SV40 large T-antigen (ciOKC). The library consisted of 370 annotated and putative miRNAs inserted in a retroviral vector, and was introduced in ciOKC and in the HNSCC cell line VU-SCC-120 in 24-well plates. All microRNAs were screened separately. The majority of miRNAs did not influence the survival of either tumour cells or ciOKC cells, or the lethal effect on both models was similar. However, a subset of 6 microRNAs (1.6%) specifically affected the head and neck cancer cell line, whereas the ciOKCs remained unaffected (Table 1, FIG. 1A and FIG. 1B).

Figure 1B:
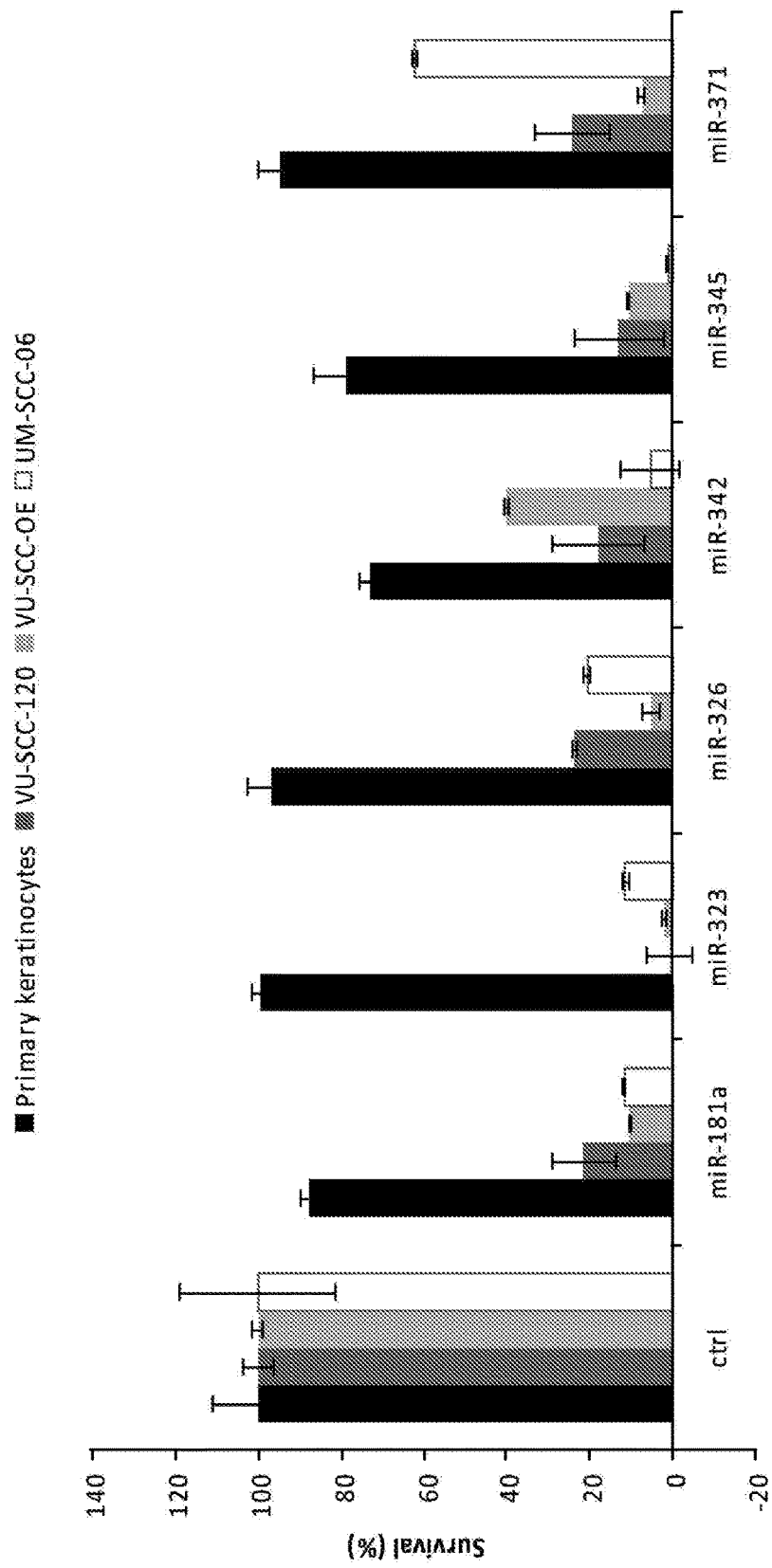

To verify these hits, we screened all 6 miRNAs identified in the initial screen in three HNSCC cell lines, being VU-SCC-120, VU-SCC-OE and UM-SCC-6, and we quantified the cell numbers (FIG. 1B). For the initial large scale screens we had to rely on the conditionally immortalized ciOKC cell model to study the effect of miRNAs. In the subsequent small scale validation experiments we also included primary oral keratinocytes (FIG. 1B). The miRNAs miR-323, miR-345, miR-371, miR-181a, miR-342, and miR-326 all showed a significant decrease in cell survival specifically in HNSCC cells, and not in primary keratinocytes (FIG. 1B). The sequence identity of all miRNAs was confirmed using sequence analysis (data not shown).

Figure 2A:
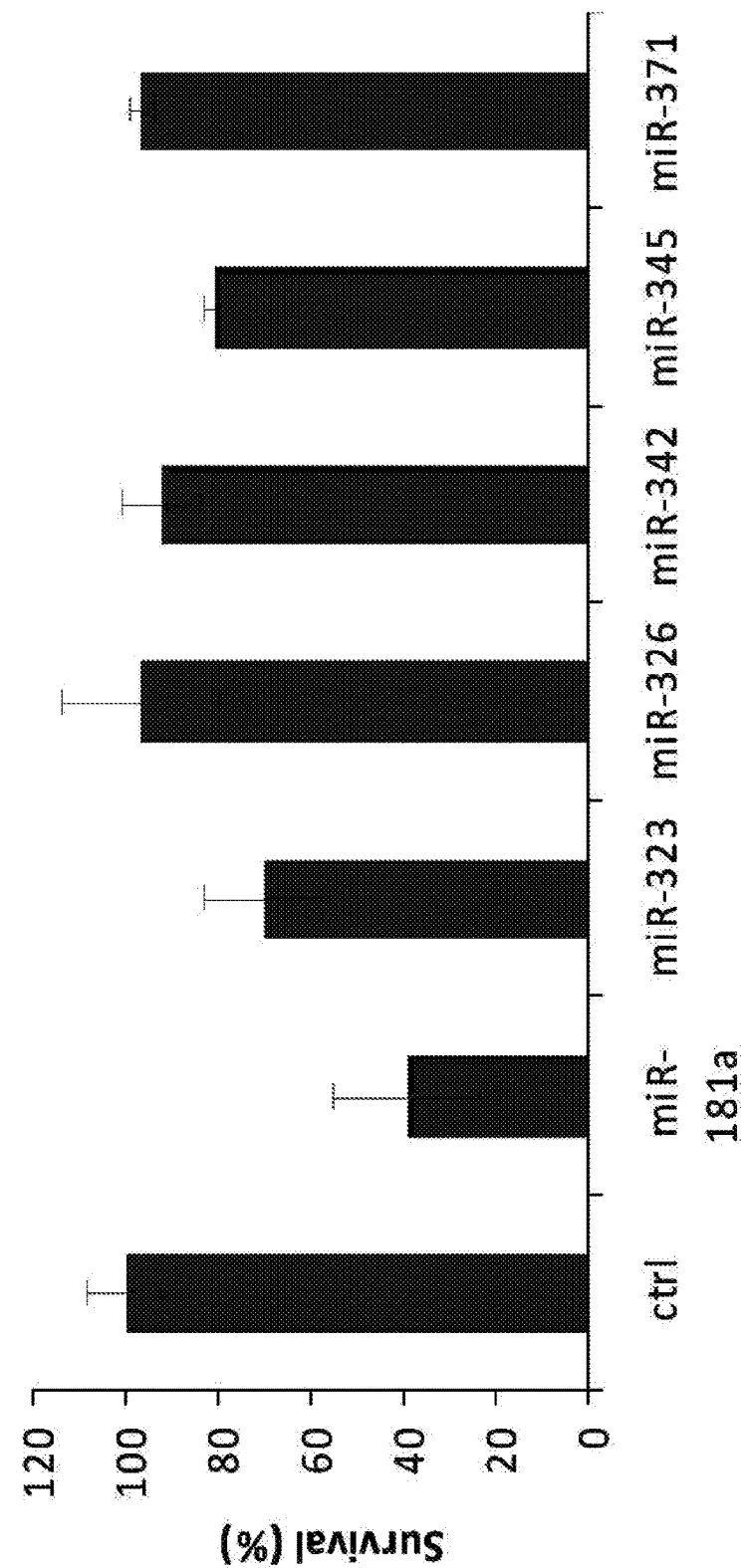
FIG. 2. Effect of the six miRNAs on cell lines derived from other cancer types. The effect of miRNAs on proliferation of (A) Siha, cervical cancer (B) MCF7, breast cancer (C) HT29, colon cancer and (D) U87, glioblastoma cell lines. Cell viability was quantified by the cell titer blue assay. The average value of triplicate experiments is depicted with standard deviations as error bars. These six miRs are lethal for some tumor cell lines.
Figure 2B:
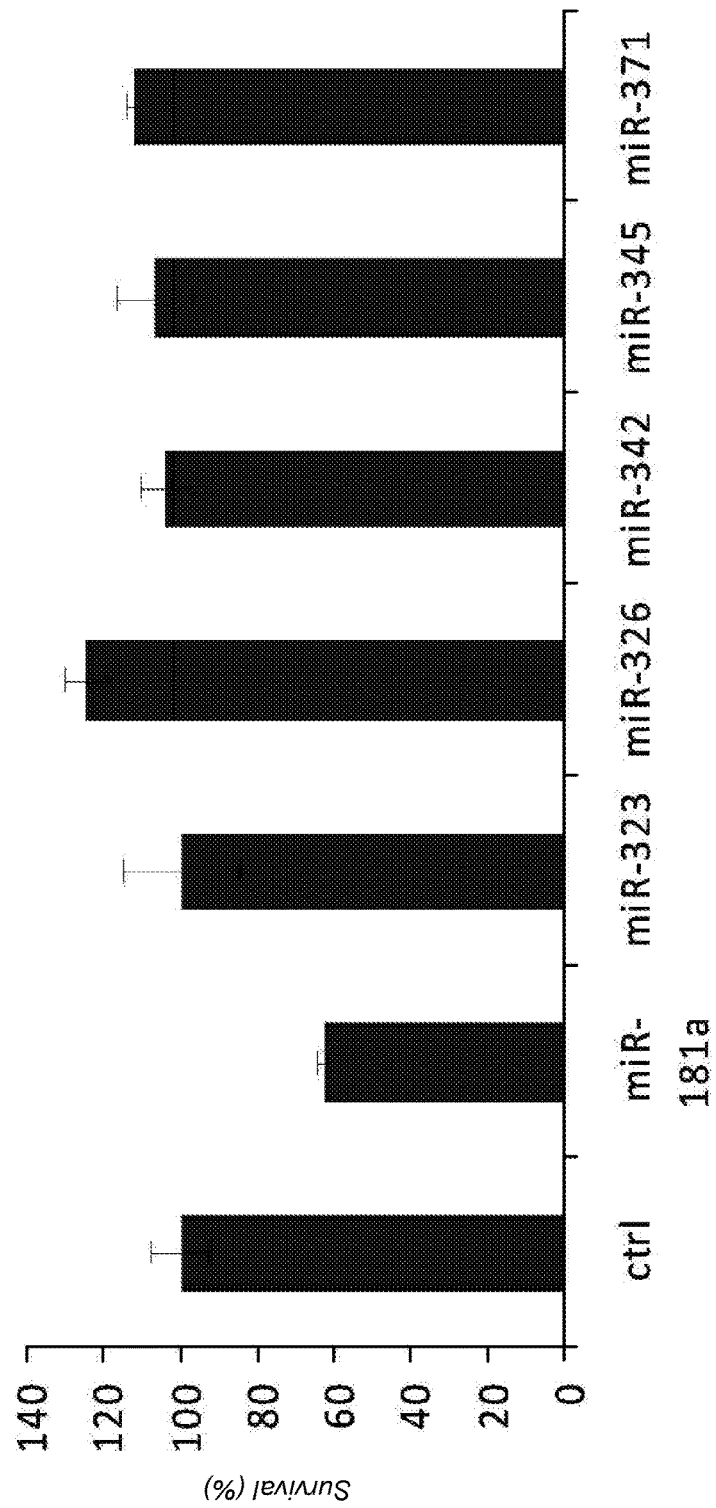

We then questioned whether the effect observed in the HNSCC cell lines was specific for HNSCC only. So we tested the six miRNAs with tumour-specific lethal effects in other cancer cell lines. The introduction of these miRNAs in cervical carcinoma cell line (SiHa) and breast carcinoma cell line (MCF7) had no lethal effect except for miRNA 181a (FIGS. 2A and 2B). When the miRNAs were introduced in colon adenocarcinoma cell line (HT29) or glioblastoma cell line (U87) a decrease in cell survival was observed, although with a less severe phenotype as compared to the tested HNSCC cell lines (FIGS. 2C and 2D). The effects observed depended on the specific microRNA. This strongly suggests lethal interactions in relation to the mutational status of specific cancer genes or deregulated signalling pathways in the various cell lines.

MiRNA Expression in HNSCC

Figure 3A:
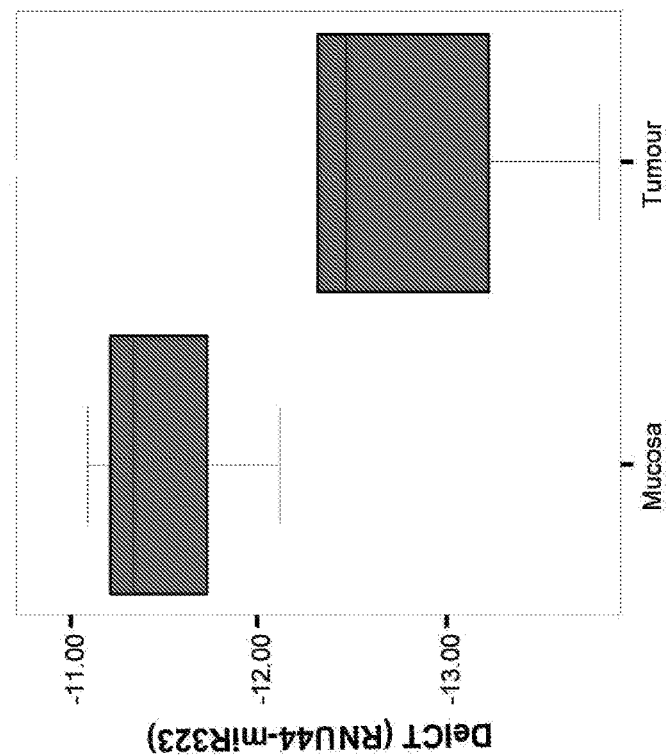
FIG. 3. Expression of tumour lethal miRNAs in HNSCC tumours and normal mucosal epihelium. MiRNA levels were determined using qRT-PCR analysis on RNA of microdissected formalin-fixed, paraffin embedded (FFPE) tumours and mucosal epithelium. Shown are deltaCT values, $Ct_{(miRNA)}-Ct_{(RNU44)}$ for (A) miR-181a (B) miR-323 (C) miR-326 (D) miR-342 and (E) miR-345. The data show the relative up- or down regulation, corrected for the RNA input by RNU44 expression. MiR-371 was not expressed, neither in mucosal epithelium nor in squamous tumor cells, and therefore not depicted.
Figure 3B:
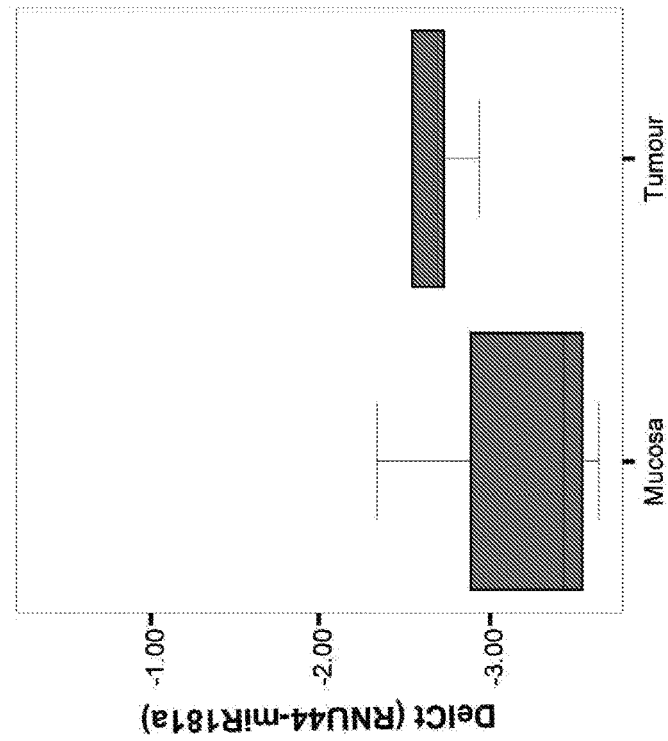
Figure 3C:
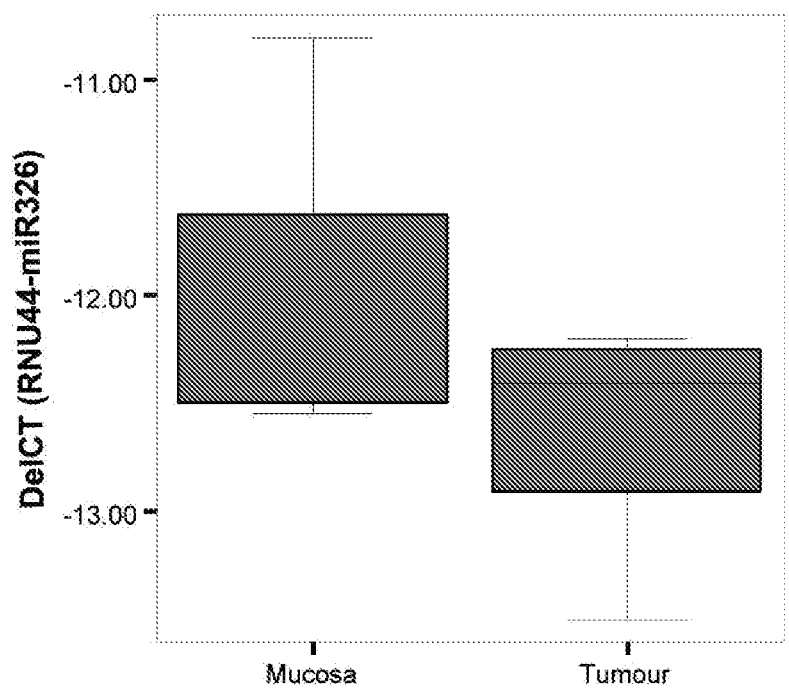
Figure 3E:
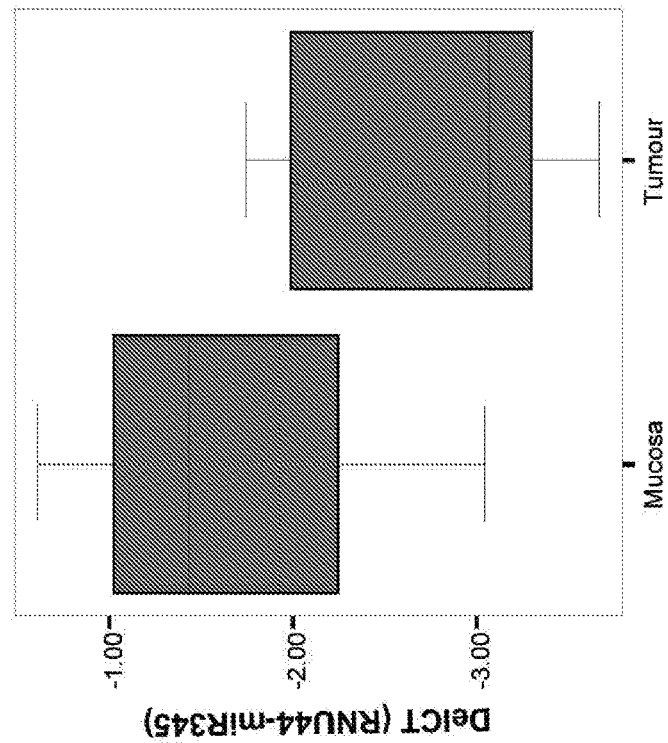
Figure 3D:
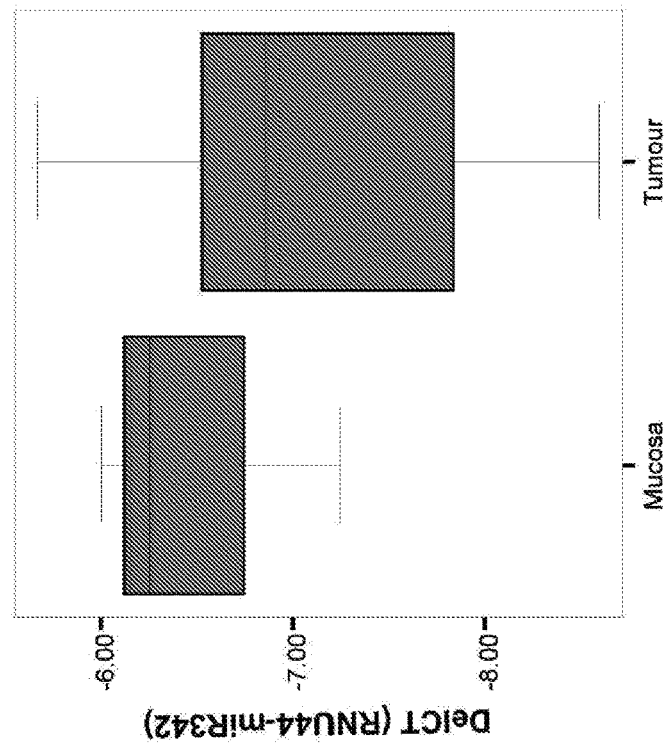

Since the ectopic expression of these six tumour lethal miRNAs had a lethal effect in tumour cell lines but not or less in mucosal keratinocytes, we were interested in the expression of these miRNAs in HNSCC tumours and normal oral mucosa. Thus we determined expression levels for the six miRNAs in RNA extracted from both microdissected tumour and oral mucosa samples. No expression was observed for miR-371, neither in normal mucosa nor in the five tumours analyzed (data not shown). For the other five miRNAs expression was observed in all tumour and mucosa samples (FIG. 3). The expression levels were in all cases below that of the RNU44 reference gene. In addition, only minimal differences in expression levels were observed between mucosa and tumour samples. The expression of miR-181a was slightly increased in tumours, but not significant (FIG. 3A). For miR-326 (FIG. 3C), miR-342 (FIG. 3D) and 345 (FIG. 3E) the expression level in tumour tissue was decreased when compared to normal mucosal epithelium, but not significant. Only the expression level of miR-323 (FIG. 3B) was significantly lower in tumour cells.

Tumor-Specific Lethal Phenotype in Cell Lines of Different Cancer Types

Figure 6:
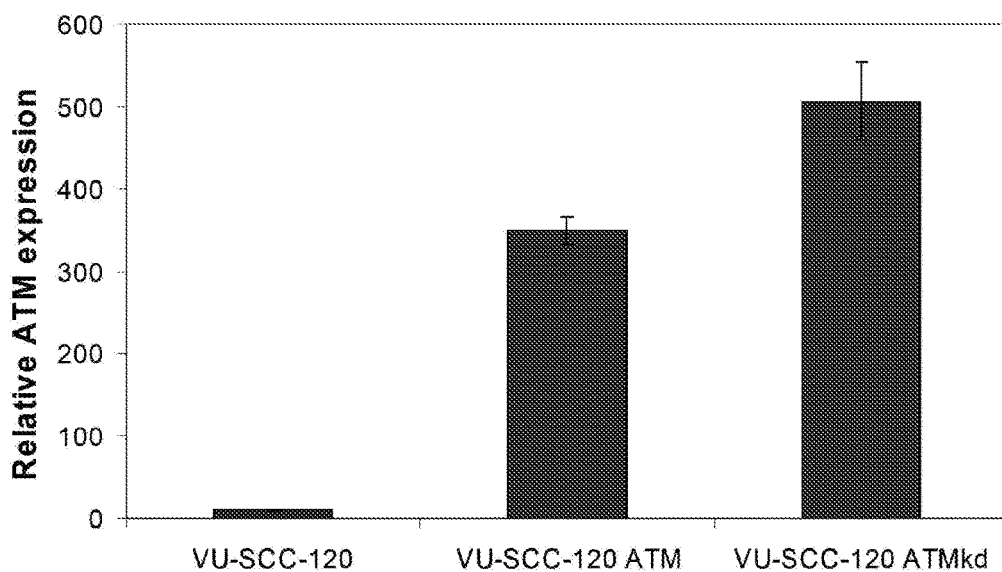
FIG. 6. ATM expression after transient transfection of expression constructs with ATM and a kinase-dead ATM mutant lacking the 3'UTR of ATM.

We next questioned whether the effect observed in the HNSCC cell lines was specific for HNSCC. Therefore we tested the six miRNAs with HNSCC-specific lethal effects in other cancer cell lines. The introduction of the various miRNAs in cervical carcinoma cell line (SiHa) and breast carcinoma cell line (MCF7) had no effect on proliferation except for miRNA 181a (FIGS. 6A and 6B). However, when the miRNAs were introduced in colon adenocarcinoma cell line (HT29) or glioblastoma cell line (U87) a decrease in cell proliferation was observed, although with a less severe phenotype as compared to the tested HNSCC cell lines (FIGS. 6C and 6D). The effects observed vary with the specific microRNA. This strongly suggests synthetic lethal interactions in relation to the mutational status of specific cancer genes or deregulated signalling pathways in the various cell lines of different tissue origin. The lethal interaction is likely not related to a mutation in TP53 as all miRNAs showed the tumor-selective lethal effect in all three HNSCC cell lines while one cell line was TP53 wild type, one showed two missense mutations and one a large deletion (see M&M above).

Target Gene Expression Analysis

Figure 4A:
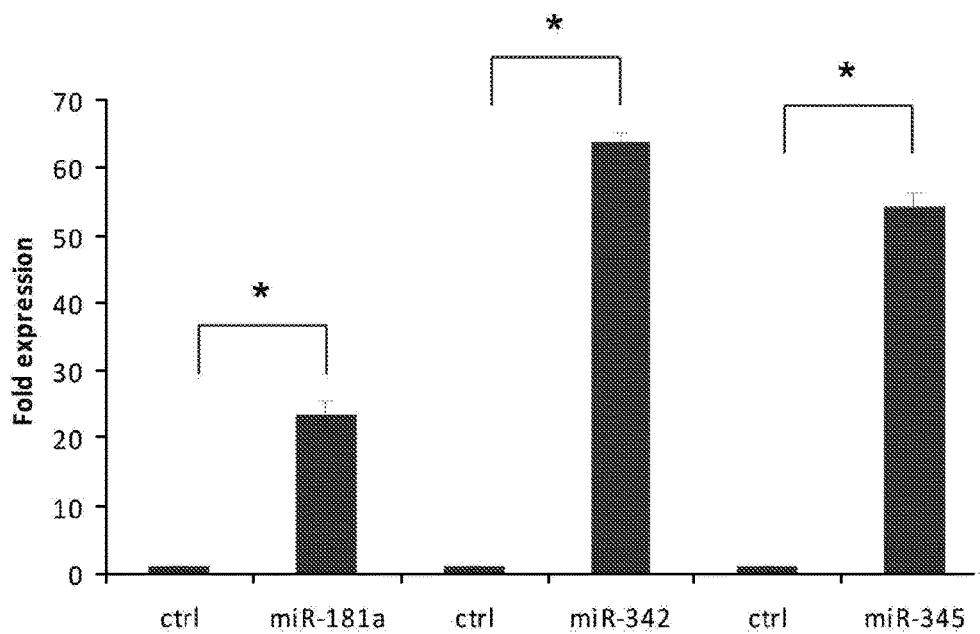
FIG. 4. Ectopic expression of specific miRNAs and their effect on gene expression. VU-SCC-120 cells were transiently transfected with the six different miRNA plasmids and expression was compared to miR-Vec-Ctrl transfected cells for (A) miR-345, miR-342 and miR-181a (B) miR-323, miR-326 and miR-371 (* $p<0.05$, t-test). The same RNA was used to analyze the expression profiles of the transfected cells using micro-array based gene expression analysis, to identify potential target genes. The profiles changed considerably by the transfected microRNAs and revealed correlations between different miRNAs (C) and two separate groups became apparent via cluster analysis (D). (* $p<0.05$, t-test). These data suggest that the tumor-specific lethal microRNAs within group A or B might (in part) target the same genes.
Figure 4B:
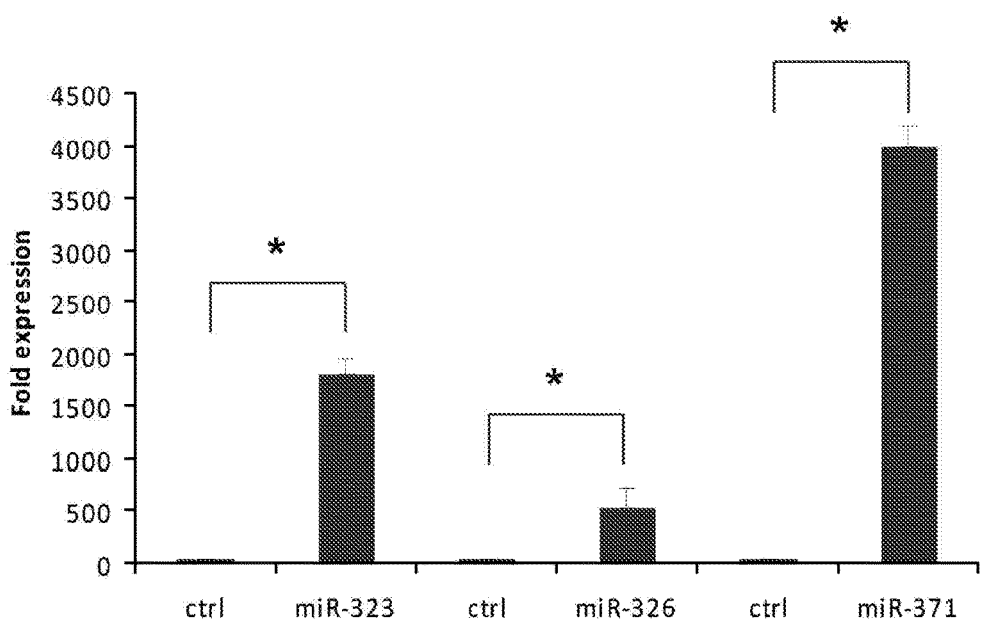
Figure 7:
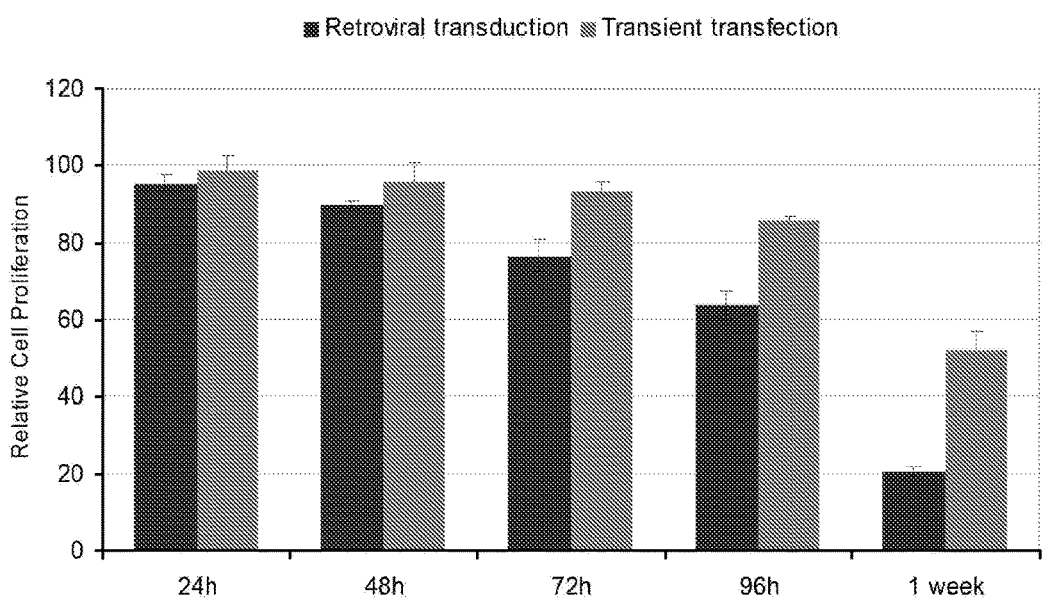
FIG. 7. Phenotypic effect of miR-181a over-expression in time, either when introduced by retroviral transduction or transient transfection in HNSCC cell line VU-SCC-120.

MiRNAs regulate gene expression at the post-transcriptional level, so we were interested in the downstream gene targets of these six miRNAs that are lethal for HNSCC cells but not for normal keratinocytes. Therefore we performed a micro-array based gene expression analysis to identify these candidate target genes. Since ectopic expression of these miRNAs caused a decrease in cell proliferation and cell death in HNSCC cell lines we were unable to analyse cells stably transduced with the miRNA in the retroviral vectors. We therefore decided to transiently transfect the cells with the retroviral vector plasmids instead of transduction with retroviral particles. Transient transfection is usually efficient, and expression can be observed almost immediately. Thus, VU-SCC-120 cells were transiently transfected, harvested and RNA was isolated 72 hours after transfection, the time point with high miRNA expression but before cell death was observed (FIG. 7). Overexpression of all miRNAs after transfection was compared to miR-Vec-Ctrl transfected cells. Depending on the endogenous expression of the microRNAs the overexpression ranged from 23-4,000 fold (FIGS. 4A and 4B).

Figures 4C, 4D:
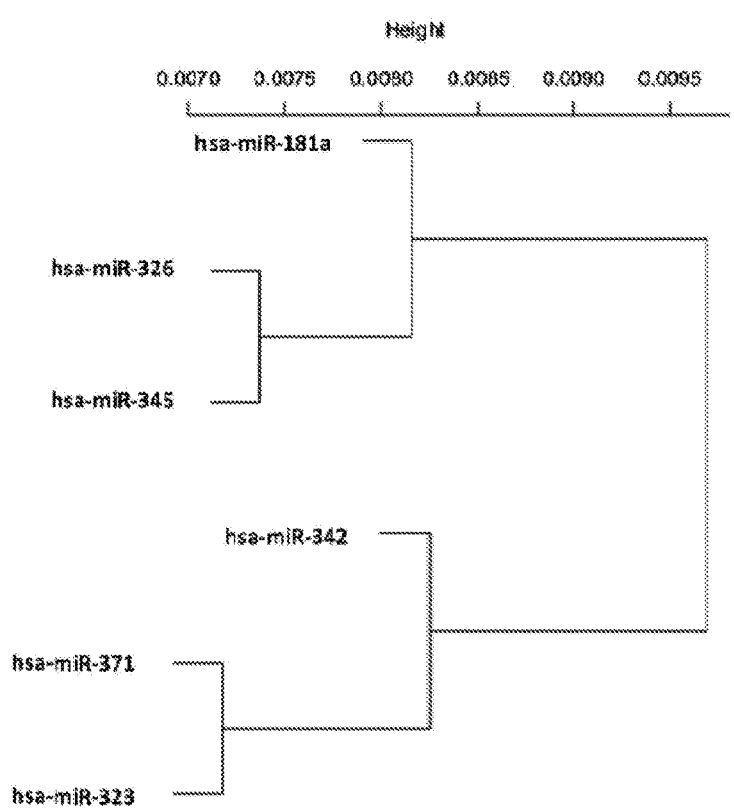

Next the RNA was labeled and hybridized for gene expression profiling. We hypothesized that it is most likely that some of these six miRNAs target the same genes, and we therefore focussed on a group-wise comparison. In the expression profiles we indeed observed significant correlations between certain miRNAs (FIG. 4C). Highly significant correlations were seen for hsa-miR-181a and miR-326 (r=0.572), hsa-miR-326 and hsa-miR-345 (r=0.573), hsa-miR-323 and hsa-miR-371 (r=0.602) and hsa-miR-342 and hsa-miR-323 (r=0.577). Cluster analysis revealed two groups of each three miRNAs with downstream target effects that showed significant correlations (FIG. 4D). The miRNAs miR-181a, miR-326 and miR-345 clustered together in group A and group B was composed of miR-342, miR-371 and miR-323. The profiles of these three microRNAs were grouped and analyzed against the empty vector control (in tetraplicate hybridized on the arrays) to detect significant differentially expressed genes. In total we observed 187 (FDR corrected p-value <0.1) significantly expressed genes in group A and 15 in group B. Subsequently, we applied several rankings on the differentially expressed genes in group A to distinguish primary effects from secondary effects. First, we ranked the genes for a negative effect (downregulation) as microRNAs are considered to downregulate expression of their target genes. Second, as for many genes multiple probes were present on the array, we subsequently ranked the genes for the number of probes per gene detected with an FDR corrected p-value <0.1 (not shown). One of the most striking target genes apparently regulated by the miRNAs from group A is the ataxia telangiectasia mutated (ATM) gene. First the differences are highly significant given the limited sample size (four controls versus three miRNAs of group A analyzed in duplicate) and the tight p-value adjustment. Second, in total 9/12 ATM probes were significantly regulated. We did not find such an apparent lead target for the microRNAs in group B.

Down Regulation of ATM Results in Tumour Specific Lethality

Figure 5A:
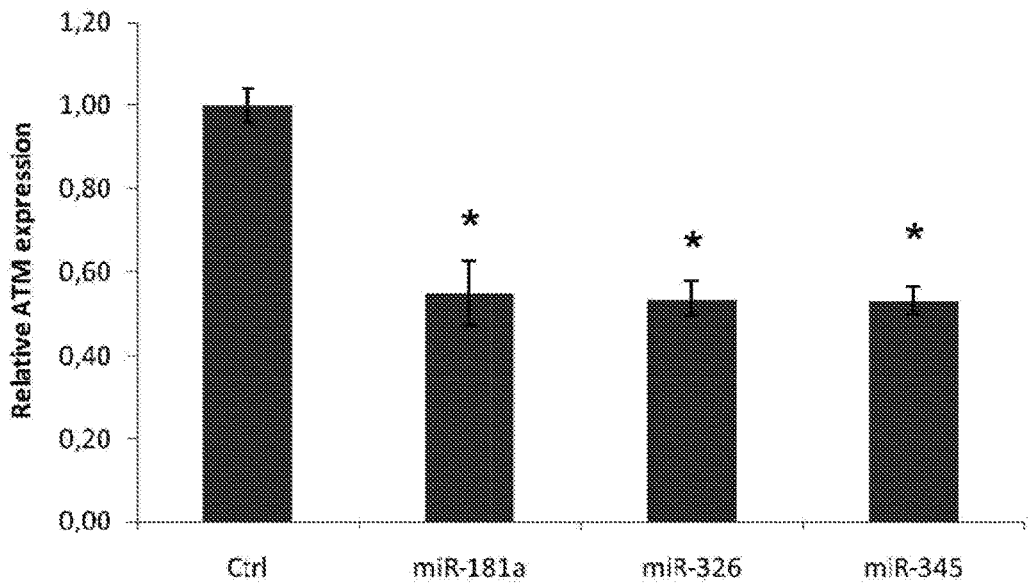
FIG. 5. ATM expression is regulated by miRNAs miR-181a, miR-326 and miR-345 from group A. (A) Endogenous ATM expression is shown in ciOKC cells either transiently transfected with miR-Vec-Ctrl or the indicated miRNA constructs. This shows that ATM is one of the likely targets of the miRs of group A, and knockdown of ATM might induce the same lethal phenotype. (B) Cell survival after ATM knockdown with five different shRNA constructs compared to a control vector (ctrl) in ciOKC (black bars) and VU-SCC-120 (grey bars). Indeed knockdown of ATM expression shows a similar (although not identical) tumor-specific lethal phenotype. (C) As control the knockdown of endogenous ATM expression after lentiviral transduction of ciOKC cells with either a control construct (Ctrl) or ATM shRNA constructs 1 to 5 was determined by qRT-PCR. The average of triplicate experiments is depicted with standard deviations as error bars. (* p<0.05, t-test). In (D) sensitivity of HNSCC cell lines VU-SCC-120 and ciOKC cells to the ATM drug CP466722 is determined. (E) Effect of the miRNAs of group A on ATM 3'UTR luciferase reporter construct. The 3'UTR of ATM was cloned behind the firefly luciferase. Firefly luciferase activity was normalized using renilla luciferase activity to correct for transfection efficiency. (F) Rescue experiments with ATM encoding expression constructs. Wild type ATM (ATM) or kinase-dead ATM (ATMkd) were transfected and the effect on the tumor-selective phenotype of miR-181a, miR-326, miR-345 or miR-Vec-Ctrl (miCtrl) compared to untransfected cells that have endogenous levels of ATM, but regulated by these miRNAs (ctrl). The average of triplicate experiments is shown with standard deviations as error bars. Significant differences are indicated with an asterisk* (p<0.05, Student's t-test).

ATM is a nuclear protein kinase that is activated upon DNA damage (Smith et al., 2010). To validate the observed decrease in expression we performed qRT-PCR for ATM in the same samples that were transiently transfected with the miRNAs and that were analysed by micro-array hybridization. Indeed we found that ectopic expression of all miRNAs of group A significantly inhibited ATM expression by ~50% (FIG. 5A).

Figure 5B:
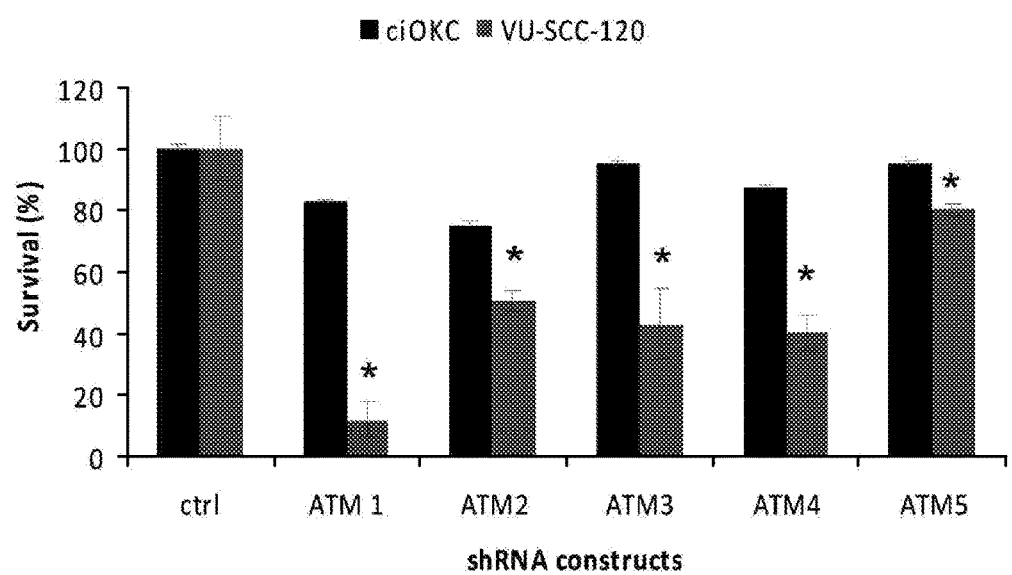

As ectopic expression of miR-181a, miR-326 and miR-345 results in tumour specific cell death and downregulation of ATM expression, we were interested to see whether down regulation of ATM is accompanied by tumour-specific cell death in HNSCC cells. Therefore we introduced five lentiviral shRNA constructs designed to specifically knockdown ATM expression. Each shRNA sequence was complementary to an unique part of the ATM mRNA sequence. Introduction of the ATM shRNAs resulted in some cell death in ciOKC compared to cells transduced with a control construct (ctrl), but significantly more cell death was observed in HNSCC cell line VU-SCC-120, ranging from 21-90% (FIG. 5B).

Figure 5C:
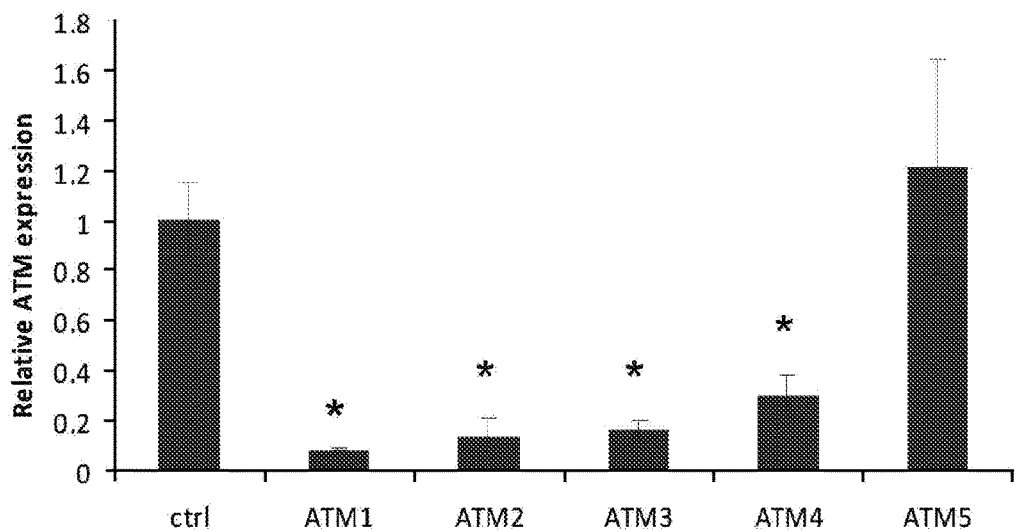

The maximum therapeutic window was observed with shRNA ATM1. It was at least 8 times more toxic in the tumour cell line as compared to the ciOKC cells. To check the knockdown of the various shRNA constructs we isolated RNA from the ciOKC cells transduced with either the control construct or the five different ATM shRNA constructs. ATM expression was analysed by qRT-PCR and expression levels were compared to the cells transduced with the control construct. Introduction of four out of five ATM shRNAs resulted in over 70% downregulation of ATM expression levels. Only in cells transduced with ATM shRNA number 5 no significant downregulation of ATM was observed (FIG. 5C).

Figure 5D:
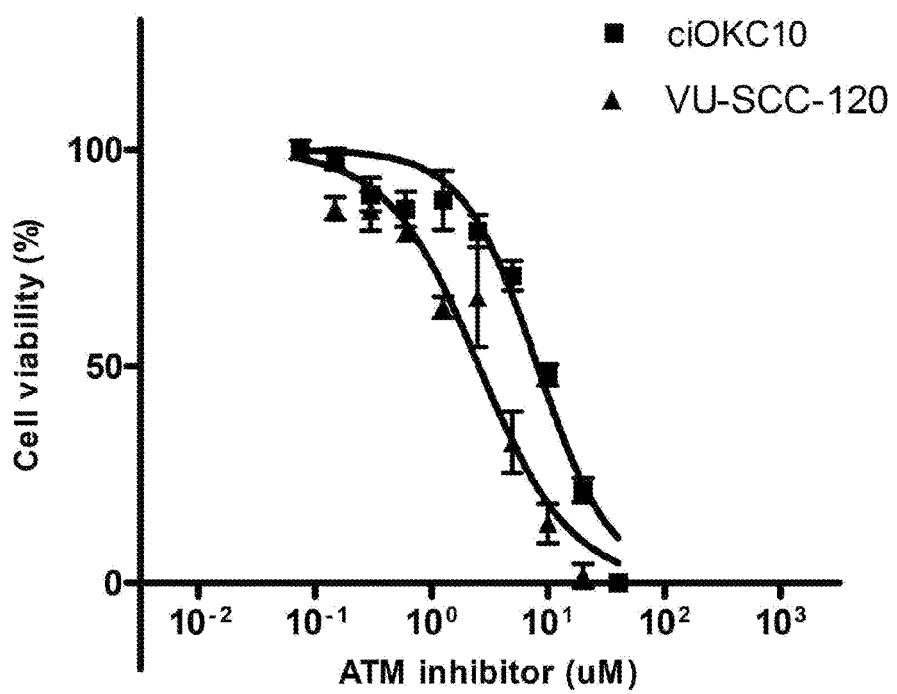

ATM is a kinase and druggable by kinase inhibitors. To confirm the tumour-specific decrease in cell viability by ATM inhibition, we also subjected ciOKC and HNSCC cells to different concentrations of the commercially available specific ATM inhibitor CP466722. Analysis of cell viability shows that HNSCC cells are more sensitive to the inhibitor compared to the ciOKC cells (FIG. 5D). The IC50 of 8.2 µM in ciOKC cells shifts to 2.6 µM in VU-SCC-120, a significant change of 3 fold (p-value <0.05 by T-testing).

Figure 5E:
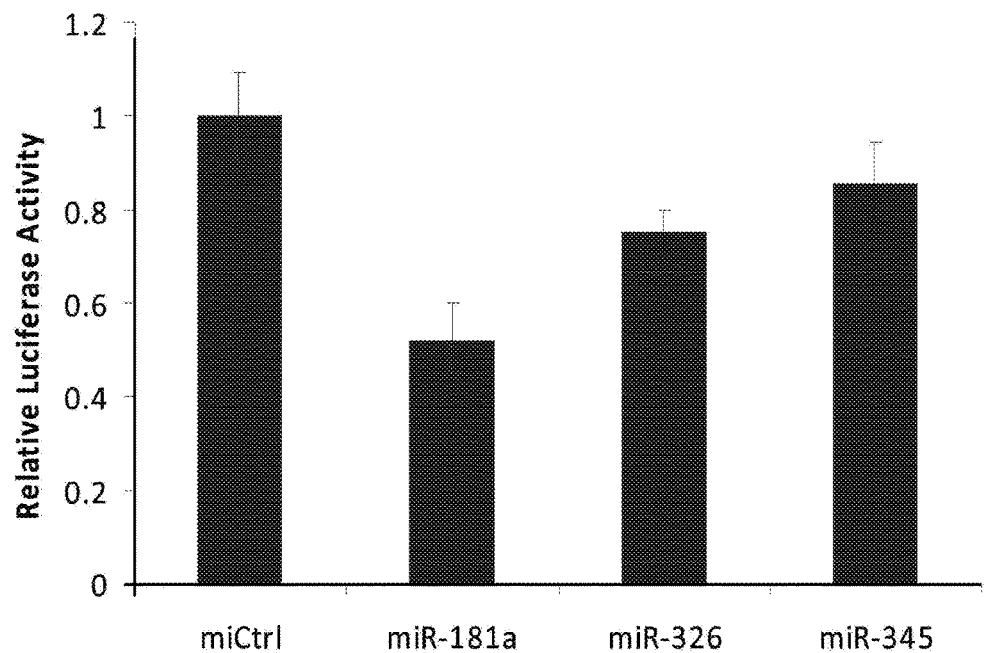

MiRNAs are known to regulate gene expression post-transcriptionally via binding to the 3'UTR of a mRNA sequence. To demonstrate an effect of miR-181a, miR-326 and miR-345 on the 3'UTR of the ATM gene miRNAs were cotransfected with a luciferase reporter construct cloned to the ATM 3'UTR sequence. Transfection of ciOKCs with miR-181a and miR-326 suppressed the activity of a luciferase reporter gene cloned to the 3'UTR of ATM. MiR-345 did show an effect, but not significant (FIG. 5E).

Figure 5F:
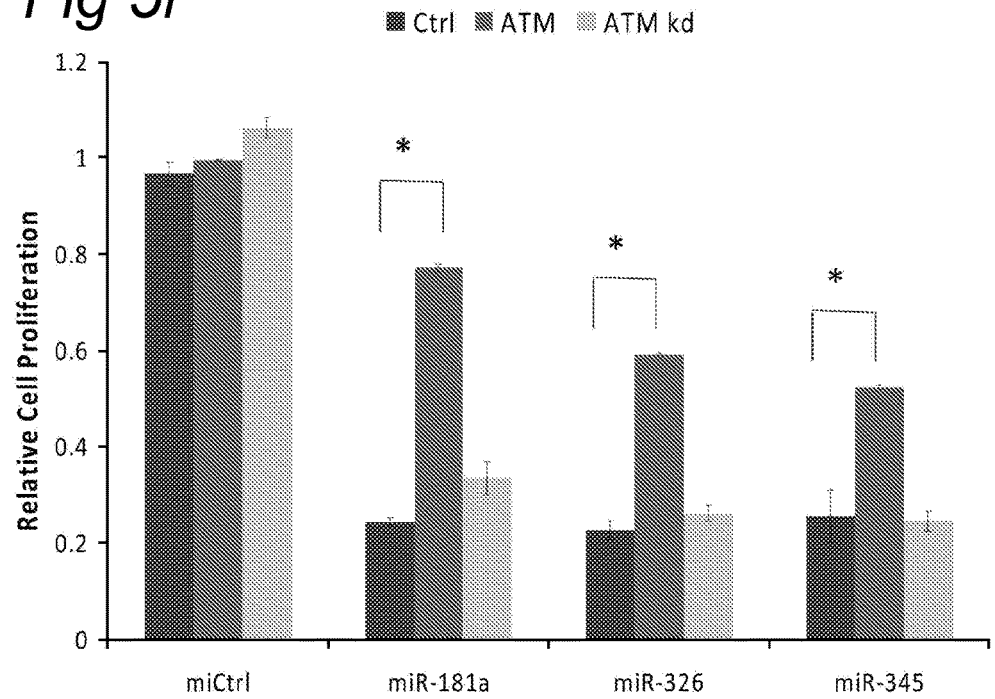
Figure 8:
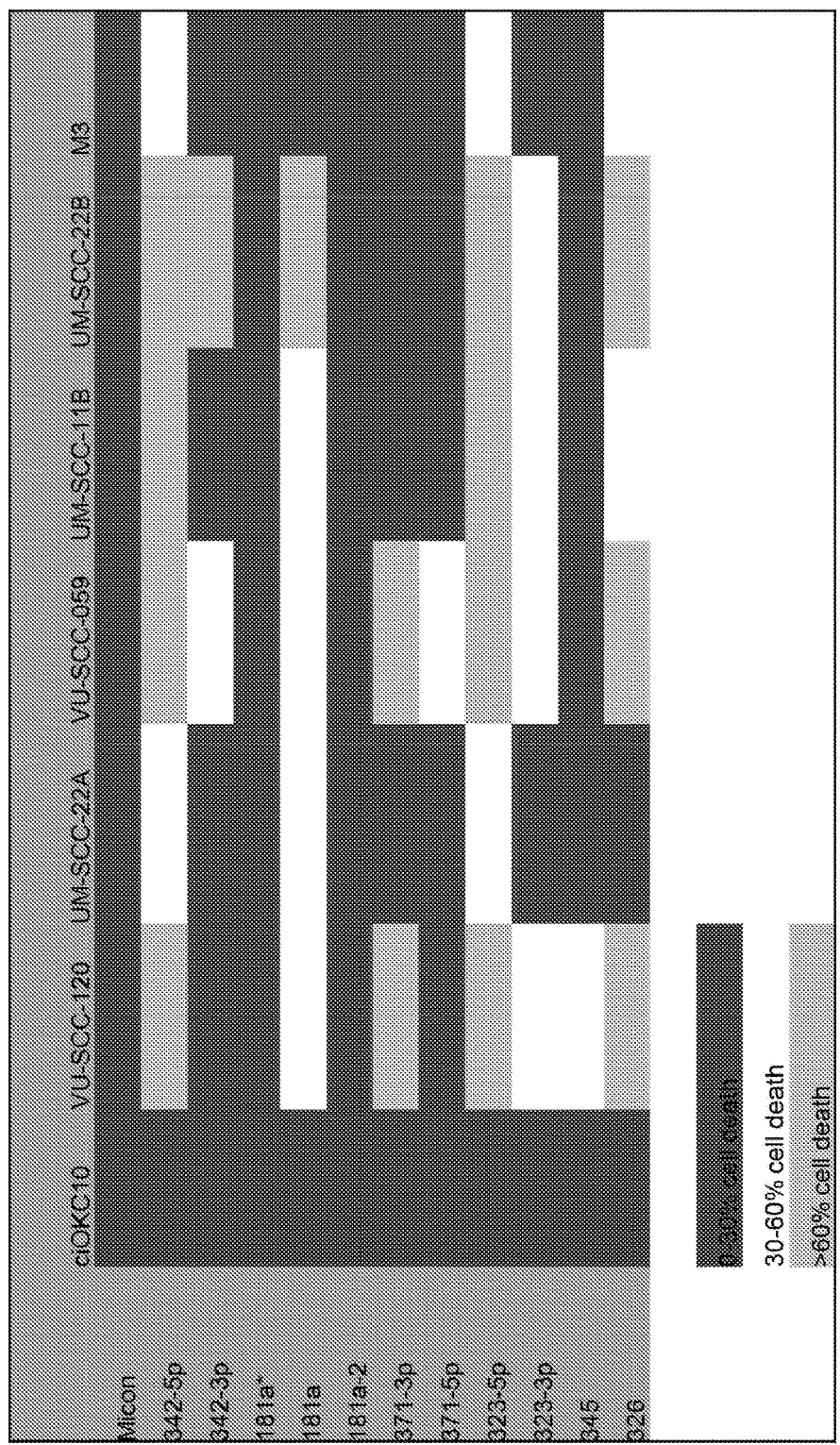
FIG. 8. Overview of the effect of miRNA mimics on cell viability on various cell lines.

Inhibition of ATM, either by microRNA overexpression, specific ATM shRNAs or kinase inhibitors results in a decrease in cell proliferation in HNSCC cells. When ATM is the direct effector, ectopic expression of ATM should rescue the HNSCC cells from cell death. To investigate this, VU-SCC-120 cells were transfected with either wild type ATM (ATMwt) or a kinase-dead mutant ATM (ATMkd) in an expression cassette that lacks the 3'UTR of ATM. Overexpression of ATMwt or ATMkd was confirmed by qRT-PCR (FIG. 8). Next miRNAs miR-181a, miR-326 and miR-345 were introduced in these two cell lines and compared to untransduced VU-SCC-120 (ctrl). The miRNAs all showed a decrease in cell proliferation in the untransduced VU-SCC-120 (FIG. 5F). However, in the cells with the ATMwt expression construct, cell proliferation was rescued up to ~80% (miR-181a) and ~50% (miR-326 and miR-345). Rescue was not observed when the kinase-dead mutant ATM was ectopically expressed in VU-SCC-120 cells. These data indicate that the miRNAs inhibit ATM expression, which elicits the tumor-selective lethal phenotype and it depends on the kinase activity of ATM.

Synthetic Mimic Transfection

The results of the mimic transfections are summarized in FIG. 8. The dark gray, white, and light gray colours indicate that the mimic causes maximum 30%, between 30% and maximum 60%, and more than 60% decrease in cell viability, respectively. Based on FIG. 8 it is indicated that some cell lines like UM-SCC-22A and precursor cell line M3 are responding less to the mimics. Whereas others like VU-SCC-120 and VU-SCC-059 and VU-SCC-22B are responding to certain mimics. From mimic perspective there are some mimics with little to no effect on all cell lines. However mimic 342-5p and 323-5p cause a decrease in all tumour cell lines and to a less extent in precursor line M3.

Systemic Transfection of HNSCC Cells with miRNA-3157 Mimic

Cell Culture and Proliferation:

Normal oral keratinocytes were isolated and cultured as previously described (van Zeeburg et al., 2010). Conditionally immortalized oral keratinocytes (ciOKC) were cultured in Keratinocyte Serum Free Medium (KSFM; Invitrogen, Breda, The Netherlands) supplemented with 0.1% bovine serum albumin, 25 mg bovine pituitary extract, 2.5 μs human recombinant EGF, 250 μg Amphotericin B (MP biomedicals, San Francisco, United States of America) and 250 μg gentamycin (Sigma-Aldrich, Zwijndrecht, The Netherlands) at 32° C. (Smeets et al., 2011). Tumor cell lines were cultured in DMEM, 5% FCS, 2 mM L-glutamine, 50 U/ml Penicillin and 50 μg/ml Streptomycin at 37° C. and 5% $CO_2$.

The cell proliferation has been assessed 96 hours after the transfection of nucleic acids using Dharmafect and the read-out based on the Alamar Blue (resazurin) fluorescent dye for the assessment of mammalian cell cytotoxicity.

Figure 9A:
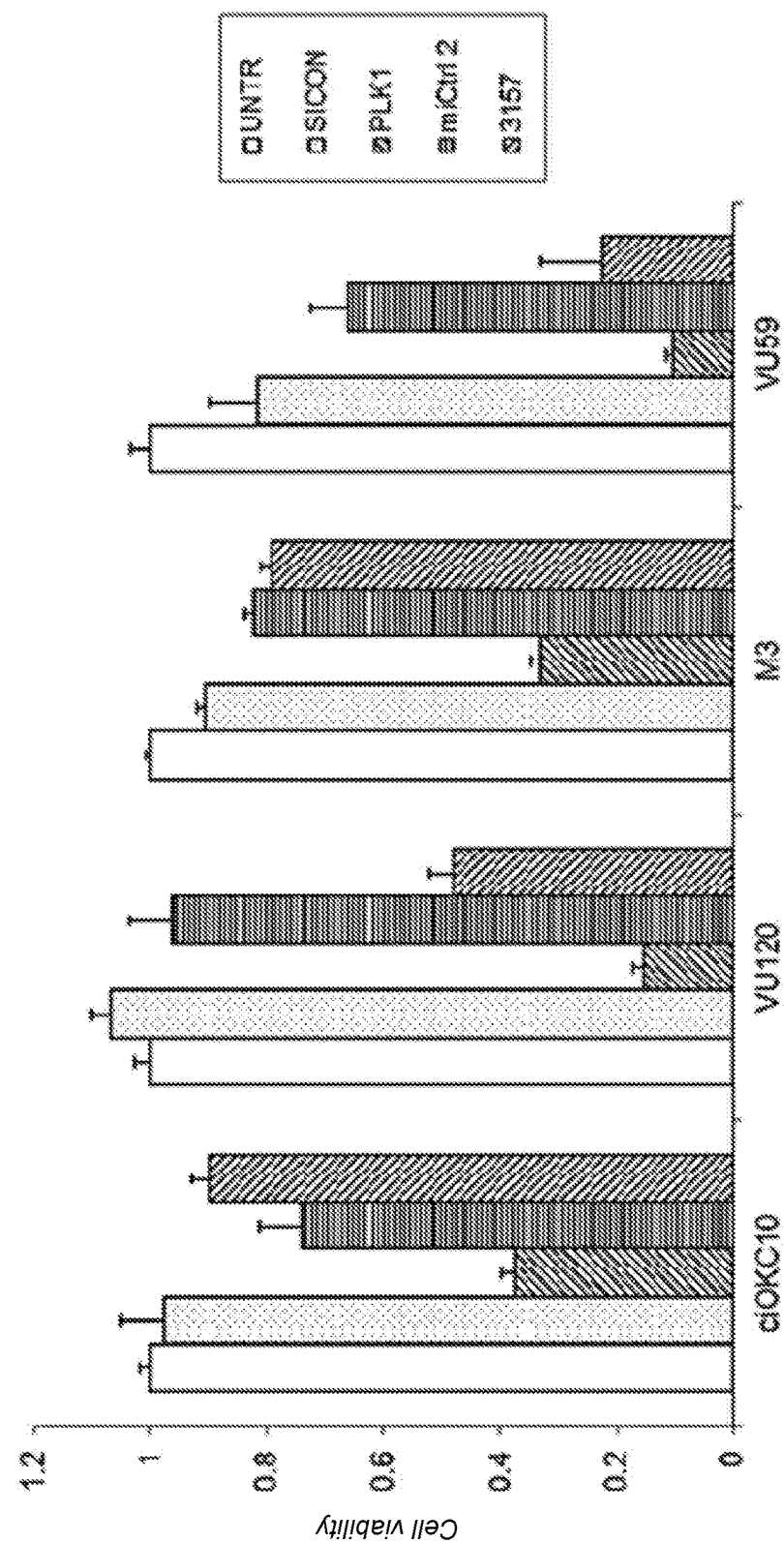
FIG. 9. Effect of miRNA-3157 on cell viability of various HNSCC cell lines. The effect of miRNA-3157 on proliferation of cells VU-SCC-120, VU-SCC-059, and precursor line M3 (A), UM-SCC-11B, UM-SCC-22A (B). Cell viability was quantified by the cell titer blue assay. siRNA against Polo Like Kinase 1 (PLK1, a kinase controlling cell proliferation) was used as positive control. miRNA-3157 is lethal for three out of four tumor cell lines, but not lethal in precursor line M3 and normal keratinocytes. siPLK1 is active in all cell lines.

By means of another miRNA screen (Poell et al. 2012) a miRNA was discovered that was lethal to melanoma or colorectal cancer cells. This miRNA, miR-3157, has been reported as a selective inhibitor of activated BRAF pathway in such cancer cells. In Head and Neck cancer, BRAF pathway is reported as a non activated pathway due to the absence of BRAF mutations. To investigate whether this miRNA is also lethal to other tumor types, miRNA-3157 was tested as mimic in various HNSCC cells. FIG. 9 surprisingly shows that miRNA-3157 (30 nM) inhibits cell viability of HNSCC cells VU-SCC-120, VU-SCC-059 and UM-SCC-11B, but not UM-SCC-22A and precursor line M3. Similar to the other lethal miRNAs, miRNA-3157 does not inhibit cell viability of normal keratinocytes, indicating that the induction of cell death is HNSCC cancer cell specific. Comparison of the activity of miRNA-3157 to that of the positive control siPLK1 (Polo Like Kinase 1, a kinase controlling cell proliferation) also shows that miRNA-3157 is selectively lethal to HNSCC tumor cells.

Taken together our data show that the over-expression of miRNAs such as miR-323, miR-345, miR-371, miR-181a, miR-342, miR-326, and miR-3157 may serve as a new treatment in HNSCC. Especially in head and neck cancer where access to the tumour is relatively easy, introduction of miRNAs via for instance intratumoral injection combined with electroporation may be a therapeutic possibility in the future (Takei et al., 2008). Also the application of ATM directed drugs might be a very interesting approach for trials specifically focused on HNSCC.

REFERENCE LIST

Bremmer, J. F., Braakhuis, B. J. M., Ruijter-Schippers, H. J., Brink, A., Duarte, H. M. B., Kuik, D. J., Bloemena, E., Leemans, C. R., van der Waal, I. C., and Brakenhoff, R. H. (2005). A noninvasive genetic screening test to detect oral preneoplastic lesions. Laboratory Investigation 85, 1481-1488.

Canman C E, Lim D S, Cimprich K A, Taya Y, Tamai K, Sakaguchi K, et al. Activation of the ATM kinase by ionizing radiation and phosphorylation of p53. Science 1998; 281:1677-9.

Cervigne, N. K., Reis, P. P., Machado, J., Sadikovic, B., Bradley, G., Galloni, N. N., Pintilie, M., Jurisica, I., Perez-Ordonez, B., Gilbert, R., Gullane, P., Irish, J., and Kamel-Reid, S. (2009). Identification of a microRNA signature associated with progression of leukoplakia to oral carcinoma. Hum. Mol Genet 18, 4818-4829.

Hermsen, M. A., Joenje, H., Arwert, F., Welters, M. J., Braakhuis, B. J., Bagnay, M., Westerveld, A., and Slater, R. (1996). Centromeric breakage as a major cause of cytogenetic abnormalities in oral squamous cell carcinoma. Genes Chromosomes Cancer 15, 1-9.

Kearsley J. H., et al, Br J Cancer. 1990 June; 61(6):821-7.

Kefas, B. (2010). Pyruvate kinase M2 is a target of the tumor-suppressive microRNA-326 and regulates the survival of glioma cells.

Kumar B, et al, J Clin Oncol. 2008 Jul. 1; 26(19):3128-37.

Leemans C R, Braakhuis B J M, Brakenhoff R H. Molecular biology of head and neckcancer. Nature Rev Cancer, 11: 9-21, 2011.

Sand, M., Skrygan, M., Georgas, D., Arenz, C., Gambichler, T., Sand, D., Altmeyer, P. and Bechara, F. G. (2011), Expression levels of the microRNA maturing microprocessor complex component DGCR8 and the RNA-induced silencing complex (RISC) components Argonaute-1, Argonaute-2, PACT, TARBP1, and TARBP2 in epithelial skin cancer. Molecular Carcinogenesis. doi: 10.1002/mc.20861

Poell J B, van Haastert R J, de Gunst T, Schultz I J, Gommans W M, Verheul M, Cerisoli F, van Noort P I, Prevost G P, Schaapveld R Q, Cuppen E. (2012) A functional screen identifies specific microRNAs capable of inhibiting human melanoma cell viability. PLoS One. 7(8):e43569, 2012

Methods in molecular immunology, volume 2, volume 281, page 171 year 2004, Humana Press, edited by Axel H. Schönthal.

Oliveira S., et al J Biomed Biotechnol. 2006, (4):63675.

Schmittgen, T. D. and Livak, K. J. (2008). Analyzing real-time PCR data by the comparative C(T) method. Nat. Protoc. 3, 1101-1108.

Shin, K. H., Bae, S. D., Hong, H. S., Kim, R. H., Kang, M. K., and Park, N. H. (2011). miR-181a shows tumor suppressive effect against oral squamous cell carcinoma cells by downregulating K-ras. Biochem. Biophys. Res Commun. 404, 896-902.

Smeets, S. J., van der, P. M., Schaaij-Visser, T. B., van Veen, E. A., van Meerloo, J., Braakhuis, B. J., Steenbergen, R. D., and Brakenhoff, R. H. (2011). Immortalization of oral keratinocytes by functional inactivation of the p53 and pRb pathways. Int J Cancer 128, 1596-1605.

Smith, J., Tho, L. M., Xu, N., and Gillespie, D. A. (2010). The ATM-Chk2 and ATR-Chk1 pathways in DNA damage signaling and cancer. Adv. Cancer Res 108, 73-112.

Takei, Y., Nemoto, T., Mu, P., Fujishima, T., Ishimoto, T., Hayakawa, Y., Yuzawa, Y., Matsuo, S., Muramatsu, T., and Kadomatsu, K. (2008). In vivo silencing of a molecular target by short interfering RNA electroporation: tumor vascularization correlates to delivery efficiency. Molecular Cancer Therapeutics 7, 211-221.

van Zeeburg, H. J., van Beusechem, V. W., Huizenga, A., Haisma, H. J., Korokhov, N., Gibbs, S., Leemans, C. R., and Brakenhoff, R. H. (2010). Adenovirus retargeting to surface expressed antigens on oral mucosa. J Gene Med 12, 365-376.

Voorhoeve, P. M., le Sage, C., Schrier, M., Gillis, A. J. M., Stoop, H., Nagel, R., Liu, Y. P., van Duijse, J., Drost, J., Griekspoor, A., Zlotorynski, E., Yabuta, N., De Vita, G., Nojima, H., Looijenga, L. H. J., and Agami, R. (2006). A Genetic Screen Implicates miRNA-372 and miRNA-373 As Oncogenes in Testicular Germ Cell Tumors. Cell 124, 1169-1181.

Wahl R. L. et al, J Nucl Med. 2009 May; 50 Suppl 1:122S-50S.

TABLE 1

List of 6 miRNAs with tumour-specific lethal effect in the initial screen.

MicroRNA hsa-mir-181a
hsa-mir-323
hsa-mir-326
hsa-mir-342
hsa-mir-345
hsa-mir-371

TABLE 2

Precursor sequences of miRNAs identified in screening or referred to in the application
List of miRNA precursor sequences (5' to 3' direction). All sequences were obtained from miRBase (release 16: Sep. 2010; www.mirbase.org).

| SEQ ID NO | miRNA | Precursor sequence |
|---|---|---|
| 1 | hsa-mir-181a-1 | UGAGUUUUGAGGUUGCUUCAGUGAACAUUCAACGCUGUCGGUGAGUUUGGAAUUAAAAUCAAAACCAUCGACCGUUGAUUGUACCCUAUGGCUAACCAUCAUCUACUCCA |
| 2 | hsa-mir-181a-2 | AGAAGGGCUAUCAGGCCAGCCUUCAGAGGACUCCAAGGAACAUUCAACGCUGUCGGUGAGUUUGGGAUUUGAAAAAACCACUGACCGUUGACUGUACCUUGGGGUCCUUA |
| 3 | hsa-mir-323 | UUGGUACUUGGAGAGAGGUGGUCCGUGGCGCGUUCGCUUUAUUUAUGGCGCACAUUACACGGUCGACCUCUUUGCAGUAUCUAAUC |
| 4 | hsa-mir-326 | CUCAUCUGUCUGUUGGGCUGGAGGCAGGGCCUUUGUGAAGGCGGGUGGUGCUCAGAUCGCCUCUGGGCCCUUCCUCCAGCCCCGAGGCGGAUUCA |
| 5 | hsa-mir-342 | GAAACUGGGCUCAAGGUGAGGGGUGCUAUCUGUGAUUGAGGACAUGGUUAAUGGAAUUGUCUCACACAGAAAUCGCACCCGUCACCUUGGCCUACUUA |
| 6 | hsa-mir-345 | ACCCAAACCCUAGGUCUGCUGACUCCUAGUCCAGGGCUCGUGAUGGCUGGUGGGCCCUGAACGAGGGGUCUGGAGGCCUGGGUUUGAAUAUCGACAGC |
| 7 | hsa-mir-371 | GUGGCACUCAAACUGUGGGGGCACUUUCUGCUCUCUGGUGAAAGUGCCGCCAUCUUUUGAGUGUUAC |
| 362 | hsa-mir-3157 | GGGAAGGGCUUCAGCCAGGCUAGUGCAGUCUGCUUUGUGCCAACACUGGGGUGAUGACUGCCCUAGUCUAGCUGAAGCUUUUCCC |

TABLE 3

Mature and mimic sequences of miRNAs identified in screening or referred to in the application
List of mature miRNA sequences (5' to 3' direction). All sequences were obtained from miRBase (release 16: Sep. 2010; www.mirbase.org).

| microRNA | mature miRNA | Seed (SEQ ID NO) | SEQ mature miRNA (SEQ ID) |
|---|---|---|---|
| hsa-mir-181a hsa-mir-181a-2 | hsa-miR-181a | ACAUUCA (8) | AACAUUCAACGCUGUCGGUGAGU (19) |
| hsa-mir-181a | hsa-miR-181a* | CCAUCGA (9) | ACCAUCGACCGUUGAUUGUACC (20) |
| hsa-mir-181a-2 | hsa-miR-181a-2* | CCACUGA (10) | ACCACUGACCGUUGACUGUACC (21) |
| hsa-mir-323 | hsa-miR-323-5p | GGUGGUC (11) | AGGUGGUCCGUGGCGCGUUCGC (22) |
| hsa-mir-323 | hsa-miR-323-3p | ACAUUAC (12) | CACAUUACACGGUCGACCUCU (23) |
| hsa-mir-326 | hsa-miR-326 | CUCUGGG (13) | CCUCUGGGCCCUUCCUCCAG (24) |
| hsa-mir-342 | hsa-miR-342-5p | GGGGUGC (14) | AGGGGUGCUAUCUGUGAUUGA (25) |
| hsa-mir-342 | hsa-miR-342-3p | CUCACAC (15) | UCUCACACAGAAAUCGCACCCGU (26) |
| hsa-mir-345 | hsa-miR-345 | CUGACUC (16) | GCUGACUCCUAGUCCAGGGCUC (27) |
| hsa-mir-371 | hsa-miR-371-5p | CUCAAAC (17) | ACUCAAACUGUGGGGGCACU (28) |

TABLE 3-continued

Mature and mimic sequences of miRNAs identified in screening or referred to in the application
List of mature miRNA sequences (5' to 3' direction). All sequences were obtained from miRBase (release 16: Sep. 2010; www.mirbase.org).

| microRNA | mature miRNA | Seed (SEQ ID NO) | SEQ mature miRNA (SEQ ID) |
|---|---|---|---|
| hsa-mir-371 | hsa-miR-371-3p | AGUGCCG (18) | AAGUGCCGCCAUCUUUUGAGUGU (29) |
| hsa-mir-3157 | hsa-miR-3157 | UCAGCCA (363) | UUCAGCCAGGCUAGUGCAGUCU (364) |

TABLE 4

DNA Sequences of miRNAs identified in screening (see table 1)

| Seq ID | miRNA | Cloned sequence in lentiviral vector |
|---|---|---|
| 30 | hsa-mir-181a-2 | CTGCACAGTCTATCCCACAGTTCATTAGTTCTCTGCTGCACACAAATTGATT<br>TTATAATTTAAATACTCTCGACTTGAAACCCAGAGAGGAATGTAAGAGCAT<br>CCATCAGCGGTGGTCTCACTGCTCACTGGTTCTTGGGATGTGGATGGGAG<br>AATGAAGAAGGGCTATCAGGCCAGCCTTCAGAGGACTCCAAGGAACATTC<br>AACGCTGTCGGTGAGTTTGGGATTTGAAAAAACCACTGACCGTTGACTGT<br>ACCTTGGGGTCCTTACAGACGACACTACATTTCCTGAAGCAAAAGAGCAA<br>GCTGTACCTTCACATGTCACATGAGTTCACCAGAAATGGTCCTGCAATCCC<br>CCAAATGTGGTCCAGTGAATTTTATTCCTACTGCTCACTGTTCCTTGCTTTC<br>TGTTGTGTGTTTTATTATTATTTGTTTGTTTTTACAAAAAAAGTGTTTCATTT<br>CAACAAGGTAAGGAGCAGTCCATGATG |
| 31 | hsa-mir-323 | TTCCTGGTATTTGAAGATGCGGTTGACCATGGTGTGTACGCTTTATTTGTG<br>ACGTAGGACACATGGTCTACTTCTTCTCAATATCACATCTCGCCTTGGAAG<br>ACTTCCAGGAGGTGATATCAGCTTTGCGGAAGAGCCACTGTCCTGGTGTC<br>AGTACGGCTGCTGCTTGGTACTTGGAGAGAGGTGGTCCGTGGCGCGTTC<br>GCTTTTTTTATGGCGCACATTACACGGTCGACCTCTTTGCAGTATCTAATCC<br>CGCCTTGCAAGCTTTCCTGGAGCTAACATCAACTGCGGGGGTGGGGGCCA<br>CTAGGTCTGCGCTCAGTGCGACCCAGCGGGGTTTGTGATGTGTCTGTCTT<br>GTGTGTGACGATAACTCACGTGTGGCAGCCCTCTTCTCAGCACACTGCTCT<br>GGCTTGGCAGCAGGGTTAACTTGCGGACGAGGAGCGTGGTGTCAGCACG<br>TGCCTGGATACATGAGATGGTTGACCAGAG |
| 32 | hsa-mir-326 | CGTCCGGCCAGATCTGCTTCTTCTGAAACCATGGCAAGAGAAAGACAGAC<br>AGACTTGGACCTACTGCAGGGAGGGTTAAGTAGCAGCGGGACTCCCATC<br>AAGAAGAAGGAATGTCTTCCGGAGCCTCATCTGTCTGTTGGGCTGGAGGC<br>AGGGCCTTTGTGAAGGCGGGTGGTGCTCAGATCGCCTCTGGGCCCTTCCT<br>CCAGCCCCGAGGCGGATTCACCATGAGGCTGATGCAGCTTCAGCTTCCAG<br>CCCTTCACGCTCCAGGGCCCTTTCCAAGGCCTAGCAATGTGTCCATGTGCT<br>CAGGGGTTTTGTGAAATTTGCAAAAGGAAATTATTTTTGTACTCTTTTTTTT<br>TTAAAACAAACAAACAAACAAAAAAAAACCTTCCAAGCTCTGTAAGCTTTA<br>GGCGCCCAAGCCCAGCTCTGCCCTGCTGTGGCAAG |
| 33 | hsa-mir-342 | CCTGAAGAGAGACTGACACATCAGAGGTGTCYGGTGACTGAACAAGCTCC<br>CAGCTTGCGCCCATGTCATATTGTGTGCCTCTCATAGCCTGGCACTTCCTG<br>CCATTGCATCCTTCTCTGCAGACTAAGATGGAGTTCCTGAACCAAGACCGC<br>TTGCTGGCCAACCTGTGAAACTGGGCTCAAGGTGAGGGGTGCTATCTGTG<br>ATTGAGGGACATGGTTAATGGAATTGTCTCACACAGAAATCGCACCCGTC<br>ACCTTGGCCTACTTATCACCACCCCAAACAGAGGAACACGCCTTCTCCAGC<br>CACAGCCTATGGAAGGGCCTTCAGCTGCTGTGGCCCCGAGGTGTGCATAC<br>TGTGGAAGGAACTTCGGACGTGAACTCGGATCTGGTTCCAGTACCAGCTG<br>TGCCAGGAGTGCCCTTGGGCATGTCACTGACCTAAGACTCAGTTTCGCCAT<br>CTGTGAAATGGCTGAATCAGACTCACCTCACAGG |
| 34 | hsa-mir-345 | CGGTTTAGGGTCACATGGTTCTTTTATCCAAATTCCAGTGGGTACCTACCT<br>CCTGGAGGTGCAGGTCGAAAGGTTCTGTGTATTTGGTACTAGGACACACA<br>GGTAGGTGTTGTCAGTAGTGCAGCCTGGTGCTAGGGGCAGGGGTCCCCA<br>GTGCTCATGTTAGTTTCCTTTTAGAGTCTAAGTAGAATGTTAAGCAGAGAC<br>CCAAACCCTAGGTCTGCTGACTCCTAGTCCAGGGCTCGTGATGGCTGGTG<br>GGCCCTGAACGAGGGGTCTGGAGGCCTGGGTTTGAATATCGACAGCCTCT<br>CTGACCCACTTGGTTGCCTCAGGGAGGCAGGTGTGCGGATGGGGAGAG<br>TGGCCCATGGGCCAGAAAAGCAGTGGTATGGGGGCCCCAAGAGAAGCCC<br>AGACCCAAAAGGGCAGGAGCTGGCTGTGGGGCTACTCAGGTGGCTGGA<br>GGCCTCCTGCAGACACAGTG |

TABLE 4-continued

DNA Sequences of miRNAs identified in screening (see table 1)

| Seq ID | miRNA | Cloned sequence in lentiviral vector |
|---|---|---|
| 35 | hsa-mir-371 | TTGGATCTGGAGGCTATGGGCGGGGGAGTGCTTTGAATATCTATACGTGG<br>AAAGCCTTGTTTTTACTTTTTAAGAAAGGGTCGTTAAATTCGTGCTTTGTA<br>GACCTTCAACAGCTCATCAAGGGCTACTCTCCACCTCCTTGCTTAAAGGCC<br>TCTTCTGATGGGTAAGTGCTTCCACTTGCGATCGCCGCCTTGCCGCATCCC<br>CTCAGCCTGTGGCACTCAAACTGTGGGGGCACTTTCTGCTCTCTGGTGAAA<br>GTGCCGCCATCTTTTGAGTGTTACCGCTTGAGAAGACTCAACCTGCGGAG<br>AAGATACCATTTTGATTGGGTGAGGGGCGGGTAGCAGGATGGCCCTAG<br>ACCCTGCCTATGGCCGCTTCCTCGTGATATAAATTTCTTGGCCGGGGCTCT<br>TGCAGATGGAGCTGCTCACCCTGTGGGCCTCAAATGTGGAGCACTATTCT<br>GATGTCCAAGTGGAAAGTGCTGCGAATTTGAGCGTCACCGGTGACGCCC |
| 365 | hsa-mir-3157 | ACAACTTCTCAATGAGTCTGCCCTCACTGTCCAACAATTGAGCTGAGAATA<br>TAAGAAGGGAAGGGCTTCAGCCAGGCTAGTGCAGTCTGCTTTGTGCCAAC<br>ACTGGGGTGATGACTGCCCTAGTCTAGCTGAAGCTTTTCCCTTCTTTCTAC<br>ACCCAGCTCAAGTCCCAGGTCCATAAAACCTTTAGAAACTCTTCAGAAACT<br>CTTTAGAGCTTCAGAAGCTCTTGAGAATTGGAAGATG |

TABLE 5

IsomiR and seed sequences of miRNAs identified in screening (see Table 1) or referred to in the application.
These isomiR sequences have been derived from smallRNA high-throughput deep sequencing analyses, and were obtained after combining the data of 87 human tissue samples.

| Mature miRNA | Seed (SEQ ID NO) | IsomiR sequence (SEQ ID NO) |
|---|---|---|
| hsa-miR-181a | CAUUCAA (36)<br>AUUCAAC (37)<br>UUCAACG (38)<br>AACAUUC (39)<br>UCAACGC (40)<br>CAACGCU (41)<br>CCUUCAG (42)<br>AACGCUG (43)<br>ACGCUGU (44)<br>CUUCAGA (45)<br>GCCAGCC (46) | AACAUUCAACGCUGUCGGUGAGUUU (108)<br>AACAUUCAACGCUGUCGGUGAGUU (109)<br>AACAUUCAACGCUGUCGGUG (110)<br>AACAUUCAACGCUGUCGGUGA (111)<br>AACAUUCAACGCUGUCGGUGAG (112)<br>AACAUUCAACGCUGUCGGU (113)<br>AACAUUCAACGCUGUCGGUGAGUUUG (114)<br>ACAUUCAACGCUGUCGGUGAGUUU (115)<br>ACAUUCAACGCUGUCGGUGAGU (116)<br>AACAUUCAACGCUGUCGG (117)<br>ACAUUCAACGCUGUCGGUGAGUU (118)<br>ACAUUCAACGCUGUCGGUGAG (119)<br>ACAUUCAACGCUGUCGGUG (120)<br>ACAUUCAACGCUGUCGGUGA (121)<br>ACAUUCAACGCUGUCGGU (122)<br>CAUUCAACGCUGUCGGUGAGUUU (123)<br>AUUCAACGCUGUCGGUGAGUUU (124)<br>CAUUCAACGCUGUCGGUGAGU (125)<br>CAUUCAACGCUGUCGGUGAG (126)<br>AUUCAACGCUGUCGGUGAGU (127)<br>GAACAUUCAACGCUGUCGGUGA (128)<br>GAACAUUCAACGCUGUCGGU (129)<br>CAUUCAACGCUGUCGGUGAGUU (130)<br>GAACAUUCAACGCUGUCGGUG (131)<br>AUUCAACGCUGUCGGUGAG (132)<br>UUCAACGCUGUCGGUGAGUUU (133)<br>AACAUUCAACGCUGUCGGUGAGUUUGGA (134)<br>UCAACGCUGUCGGUGAGUUU (135)<br>CAUUCAACGCUGUCGGUG (136)<br>UCAACGCUGUCGGUGAGUU (137)<br>GAACAUUCAACGCUGUCGGUGAG (138)<br>AACAUUCAACGCUGUCGGUGAGUUUGG (139)<br>CAACGCUGUCGGUGAGUUU (140)<br>AACGCUGUCGGUGAGUUU (141)<br>UUCAACGCUGUCGGUGAGU (142)<br>UUCAACGCUGUCGGUGAG (143)<br>AUUCAACGCUGUCGGUGAGUU (144)<br>UCAACGCUGUCGGUGAGU (145)<br>AUUCAACGCUGUCGGUGA (146)<br>UUCAACGCUGUCGGUGAGUU (147)<br>CAUUCAACGCUGUCGGUGA (148)<br>ACAUUCAACGCUGUCGGUGAGUUUG (149)<br>UCAACGCUGUCGGUGAGUUUGG (150)<br>CAACGCUGUCGGUGAGUU (151) |

TABLE 5-continued

IsomiR and seed sequences of miRNAs identified in screening (see Table 1) or referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
|---|---|---|
| | | UCAACGCUGUCGGUGAGUUUG (152) |
| | | GAACAUUCAACGCUGUCGGUGAGU (153) |
| | | GCCUUCAGAGGACUCCAAGG (154) |
| | | CCUUCAGAGGACUCCAAGG (155) |
| | | AACAUUCAACGCUGUCGGUGAGUUUGGGA (156) |
| | | GGCCAGCCUUCAGAGGACUCCAAGG (157) |
| hsa-miR-181a* | ACCAUCG (47) | ACCAUCGACCGUUGAUUGUA (158) |
| | AACCAUC (48) | ACCAUCGACCGUUGAUUGUAC (159) |
| | CAUCGAC (49) | ACCAUCGACCGUUGAUUGU (160) |
| | AAACCAU (50) | AACCAUCGACCGUUGAUUGUA (161) |
| | UCGACCG (51) | AAACCAUCGACCGUUGAUUGUA (162) |
| | UCAAAAC (52) | AACCAUCGACCGUUGAUUGU (163) |
| | CAAAACC (53) | ACCAUCGACCGUUGAUUG (164) |
| | | AACCAUCGACCGUUGAUUGUAC (165) |
| | | AAACCAUCGACCGUUGAUUGU (166) |
| | | AAACCAUCGACCGUUGAUUGUAC (167) |
| | | CCAUCGACCGUUGAUUGUACC (168) |
| | | CCAUCGACCGUUGAUUGUA (169) |
| | | AAAACCAUCGACCGUUGAUUGU (170) |
| | | CCAUCGACCGUUGAUUGUAC (171) |
| | | AUCGACCGUUGAUUGUACC (172) |
| | | AUCAAAACCAUCGACCGUUGA (173) |
| | | UCAAAACCAUCGACCGUUGAUUGUA (174) |
| | | AACCAUCGACCGUUGAUUG (175) |
| | | AAACCAUCGACCGUUGAUUG (176) |
| | | AAACCAUCGACCGUUGAU (177) |
| hsa-miR-181a-2* | ACCACUG (54) | ACCACUGACCGUUGACUGUAC (178) |
| | CACUGAC (55) | ACCACUGACCGUUGACUGUA (179) |
| | ACUGACC (56) | ACCACUGACCGUUGACUGU (180) |
| | CUGACCG (57) | AACCACUGACCGUUGACUGUAC (181) |
| | UGGGGUC (58) | AACCACUGACCGUUGACUGUA (182) |
| | AAAAAAC (59) | AACCACUGACCGUUGACUGU (183) |
| | AAAAACC (60) | ACCACUGACCGUUGACUGUACCU (184) |
| | | CCACUGACCGUUGACUGUAC (185) |
| | | ACCACUGACCGUUGACUG (186) |
| | | AACCACUGACCGUUGACUGUACC (187) |
| | | CCACUGACCGUUGACUGUACC (188) |
| | | CACUGACCGUUGACUGUAC (189) |
| | | CACUGACCGUUGACUGUA (190) |
| | | AACCACUGACCGUUGACUGUACCU (191) |
| | | CCACUGACCGUUGACUGUA (192) |
| | | UUGGGGUCCUUACAGACGACA (193) |
| | | ACUGACCGUUGACUGUACC (194) |
| | | ACUGACCGUUGACUGUAC (195) |
| | | CCACUGACCGUUGACUGUACCU (196) |
| | | CACUGACCGUUGACUGUACC (197) |
| | | GAAAAAACCACUGACCGUUGACUGU (198) |
| | | AAAAAACCACUGACCGUUGACUGU (199) |
| | | AACCACUGACCGUUGACUG (200) |
| | | AAAAAACCACUGACCGUUGACUGUA (201) |
| | | ACCACUGACCGUUGACUGUACCUUG (202) |
| hsa-miR-323-3p | CACAUUA (61) | GCACAUUACACGGUCGACCUCU (203) |
| | CAUUACA (62) | GCACAUUACACGGUCGACCU (204) |
| | AUUACAC (63) | GCACAUUACACGGUCGACCUC (205) |
| | UAUGGCG (64) | GCACAUUACACGGUCGACCUCUU (206) |
| | GCACAUU (65) | CACAUUACACGGUCGACCUC (207) |
| | | ACAUUACACGGUCGACCUCU (208) |
| | | GCACAUUACACGGUCGACC (209) |
| | | GCACAUUACACGGUCGACCUCUUUG (210) |
| | | CACAUUACACGGUCGACCUCUU (211) |
| | | GCACAUUACACGGUCGAC (212) |
| | | CACAUUACACGGUCGACCU (213) |
| | | GCACAUUACACGGUCGACCUCUUUU (214) |
| | | CACAUUACACGGUCGACC (215) |
| | | CAUUACACGGUCGACCUCU (216) |
| | | UUAUGGCGCACAUUACACGGUC (217) |
| | | CGCACAUUACACGGUCGACCUCU (218) |

TABLE 5-continued

IsomiR and seed sequences of miRNAs identified in screening (see Table 1) or referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
|---|---|---|
| hsa-miR-323-5p | CUGCUUG (66) | AGGUGGUCCGUGGCGCGUUC (219) |
| | UGCUUGG (67) | AGGUGGUCCGUGGCGCGUUCG (220) |
| | GCUGCUU (68) | GCUGCUUGGUACUUGGAGAG (221) |
| | AGGUGGU (69) | AGGUGGUCCGUGGCGCGUU (222) |
| | GUGGUCC (70) | CUGCUUGGUACUUGGAGAG (223) |
| | | UGCUGCUUGGUACUUGGAGAG (224) |
| | | GAGGUGGUCCGUGGCGCGUUC (225) |
| | | AGGUGGUCCGUGGCGCGUUCGCU (226) |
| | | GGUGGUCCGUGGCGCGUU (227) |
| | | AGGUGGUCCGUGGCGCGU (228) |
| | | GAGGUGGUCCGUGGCGCGUU (229) |
| hsa-miR-326 | CCUCAUC (71) | GCCUCAUCUGUCUGUUGGGCU (230) |
| | CUCAUCU (72) | CCUCAUCUGUCUGUUGGGCU (231) |
| | GCCUCAU (73) | AGCCUCAUCUGUCUGUUGGGCU (232) |
| | UCAUCUG (74) | CUCAUCUGUCUGUUGGGCU (233) |
| | CAUCUGU (75) | UCAUCUGUCUGUUGGGCU (234) |
| | CCCGAGG (76) | CCCCGAGGCGGAUUCACCAUGAG (235) |
| | GAGGCAG (77) | CCUCUGGGCCCUUCCUCCAGC (236) |
| | UGAAGGC (78) | CCCCGAGGCGGAUUCACC (237) |
| | | GCCUCAUCUGUCUGUUGGGC (238) |
| | | CCUCAUCUGUCUGUUGGG (239) |
| | | GUGAAGGCGGGUGGUGCUCAGAU (240) |
| | | GCCUCAUCUGUCUGUUGGG (241) |
| | | GGAGGCAGGGCCUUUGUGAAGGCGGG (242) |
| | | AGCCUCAUCUGUCUGUUGGG (243) |
| | | CCCCGAGGCGGAUUCACCAU (244) |
| hsa-miR-342-3p | CACACAG (79) | UCUCACACAGAAAUCGCACCCGUC (245) |
| | UCACACA (80) | UCUCACACAGAAAUCGCACCCG (246) |
| | ACACAGA (81) | UCACACAGAAAUCGCACCCGUCA (247) |
| | CACAGAA (82) | UCUCACACAGAAAUCGCACCCGUCA (248) |
| | CAGAAAU (83) | UCUCACACAGAAAUCGCACC (249) |
| | ACAGAAA (84) | UCACACAGAAAUCGCACCCGUC (250) |
| | UCUCACA (85) | UCACACAGAAAUCGCACCCGU (251) |
| | | CUCACACAGAAAUCGCACCCGU (252) |
| | | UCUCACACAGAAAUCGCACCC (253) |
| | | CUCACACAGAAAUCGCACCCGUC (254) |
| | | CACACAGAAAUCGCACCCGUCA (255) |
| | | UCACACAGAAAUCGCACCCG (256) |
| | | CUCACACAGAAAUCGCACCCG (257) |
| | | CUCACACAGAAAUCGCACCCGUCA (258) |
| | | UCUCACACAGAAAUCGCAC (259) |
| | | CACACAGAAAUCGCACCCGUC (260) |
| | | ACACAGAAAUCGCACCCGU (261) |
| | | CACACAGAAAUCGCACCCGU (262) |
| | | CUCACACAGAAAUCGCACCC (263) |
| | | ACAGAAAUCGCACCCGUC (264) |
| | | ACAGAAAUCGCACCCGUCA (265) |
| | | UCACACAGAAAUCGCACCC (266) |
| | | UCUCACACAGAAAUCGCA (267) |
| | | GUCUCACACAGAAAUCGCACCC (268) |
| | | ACACAGAAAUCGCACCCGUCA (269) |
| | | CACAGAAAUCGCACCCGU (270) |
| | | UCACACAGAAAUCGCACCCGUCAC (271) |
| | | UCACACAGAAAUCGCACC (272) |
| | | CACAGAAAUCGCACCCGUC (273) |
| hsa-miR-342-5p | GGGUGCU (86) | GGGGUGCUAUCUGUGAUUGAGGGACA (274) |
| | GCUAUCU (87) | GGGGUGCUAUCUGUGAUUGAGGGAC (275) |
| | GGUGCUA (88) | GGGGUGCUAUCUGUGAUUGAGGGA (276) |
| | UGUGAAA (89) | GGGGUGCUAUCUGUGAUUGAGG (277) |
| | GUGCUAU (90) | UGCUAUCUGUGAUUGAGGGACA (278) |
| | UGAAACU (91) | AGGGGUGCUAUCUGUGAUUGAGG (279) |
| | CUGUGAA (92) | GGGGUGCUAUCUGUGAUUGAGGG (280) |
| | CUAUCUG (93) | AGGGGUGCUAUCUGUGAUUGAGGGACA (281) |
| | UGCUAUC (94) | AGGGGUGCUAUCUGUGAUUGAGGGA (282) |
| | AUGGUUA (95) | GGGGUGCUAUCUGUGAUUGA (283) |
| | AUCUGUG (96) | UGCUAUCUGUGAUUGAGGGAC (284) |

TABLE 5-continued

IsomiR and seed sequences of miRNAs identified in screening (see Table 1) or referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
| --- | --- | --- |
| | GAAACUG (97) | GGGUGCUAUCUGUGAUUGAGGGA (285) |
| | UAUCUGU (98) | AGGGGUGCUAUCUGUGAUUGAGGG (286) |
| | GUGAAAC (99) | GGGUGCUAUCUGUGAUUGAGGGAC (287) |
| | | AGGGGUGCUAUCUGUGAUUGAG (288) |
| | | GGGUGCUAUCUGUGAUUGAGGG (289) |
| | | GGGUGCUAUCUGUGAUUGAGG (290) |
| | | UGCUAUCUGUGAUUGAGGGA (291) |
| | | GGGUGCUAUCUGUGAUUGAGGGACA (292) |
| | | AGGGGUGCUAUCUGUGAUUGAGGGAC (293) |
| | | CUGUGAAACUGGGCUCAAGGUG (294) |
| | | AGGGGUGCUAUCUGUGAUUG (295) |
| | | GGGGUGCUAUCUGUGAUUGAG (296) |
| | | UGCUAUCUGUGAUUGAGGGACAU (297) |
| | | CUGUGAAACUGGGCUCAAGGUGA (298) |
| | | GGUGCUAUCUGUGAUUGAGGGAC (299) |
| | | GUGAAACUGGGCUCAAGGUG (300) |
| | | GGGUGCUAUCUGUGAUUGAG (301) |
| | | GGGGUGCUAUCUGUGAUUG (302) |
| | | GCUAUCUGUGAUUGAGGGACA (303) |
| | | CCUGUGAAACUGGGCUCAAGGUG (304) |
| | | GUGCUAUCUGUGAUUGAGGGAC (305) |
| | | AGGGGUGCUAUCUGUGAUUGAGGGACAU (306) |
| | | UGCUAUCUGUGAUUGAGGG (307) |
| | | GGGUGCUAUCUGUGAUUG (308) |
| | | CAUGGUUAAUGGAAUUGUC (309) |
| | | GGGGUGCUAUCUGUGAUUGAGGGACAU (310) |
| | | GGGUGCUAUCUGUGAUUGA (311) |
| | | UAUCUGUGAUUGAGGGACA (312) |
| | | GUGAAACUGGGCUCAAGGUGA (313) |
| | | CCUGUGAAACUGGGCUCAAGGUGA (314) |
| | | GGUGCUAUCUGUGAUUGAGG (315) |
| | | CUAUCUGUGAUUGAGGGACA (316) |
| | | UGAAACUGGGCUCAAGGUG (317) |
| | | UGUGAAACUGGGCUCAAGGUGA (318) |
| hsa-miR-345 | UGACUCC (100) | GCUGACUCCUAGUCCAGGGCU (319) |
| | GACUCCU (101) | GCUGACUCCUAGUCCAGGGC (320) |
| | CCCUGAA (102) | GCUGACUCCUAGUCCAGG (321) |
| | CCUGAAC (103) | GCUGACUCCUAGUCCAGGG (322) |
| | | GCUGACUCCUAGUCCAGGGCUCGU (323) |
| | | GCUGACUCCUAGUCCAGGGCUCG (324) |
| | | CUGACUCCUAGUCCAGGGCU (325) |
| | | CUGACUCCUAGUCCAGGGC (326) |
| | | CUGACUCCUAGUCCAGGGCUC (327) |
| | | UGACUCCUAGUCCAGGGCUCG (328) |
| | | UGACUCCUAGUCCAGGGCU (329) |
| | | UGACUCCUAGUCCAGGGCUC (330) |
| | | GCCCUGAACGAGGGGUCUGGAG (331) |
| | | CCCUGAACGAGGGGUCUGGAG (332) |
| | | GCCCUGAACGAGGGGUCUGGA (333) |
| hsa-miR-371-3p | GUGCCGC (104) | AGUGCCGCCAUCUUUUGAGUGU (334) |
| | UGCCGCC (105) | GUGCCGCCAUCUUUUGAGUGU (335) |
| | GCCGCCA (106) | AAGUGCCGCCAUCUUUUGAGU (336) |
| | | AGUGCCGCCAUCUUUUGAGU (337) |
| | | AAGUGCCGCCAUCUUUUGAGUG (338) |
| | | GUGCCGCCAUCUUUUGAGUG (339) |
| | | UGCCGCCAUCUUUUGAGUGU (340) |
| | | AGUGCCGCCAUCUUUUGAGUGUU (341) |
| | | GUGCCGCCAUCUUUUGAGU (342) |
| hsa-miR-371-5p | UCAAACU (107) | ACUCAAACUGUGGGGGCACUUU (343) |
| | | ACUCAAACUGUGGGGGCACUUUC (344) |
| | | ACUCAAACUGUGGGGGCACUU (345) |
| | | ACUCAAACUGUGGGGGCACUUUCU (346) |
| | | CUCAAACUGUGGGGGCACUUUC (347) |
| | | ACUCAAACUGUGGGGGCAC (348) |
| | | CUCAAACUGUGGGGGCACUUUCU (349) |
| | | CUCAAACUGUGGGGGCACUUU (350) |
| | | ACUCAAACUGUGGGGGCA (351) |
| | | CUCAAACUGUGGGGGCACUU (352) |

TABLE 5-continued

IsomiR and seed sequences of miRNAs identified in screening
(see Table 1) or referred to in the application.
These isomiR sequences have been derived from small RNA high-
throughput deep sequencing analyses, and were obtained after
combining the data of 87 human tissue samples.

| Mature miRNA | Seed (SEQ ID NO) | IsomiR sequence (SEQ ID NO) |
|---|---|---|
| | | CUCAAACUGUGGGGGCAC (353) |
| | | CUCAAACUGUGGGGGCACU (354) |
| hsa-miR-3157 | UCAGCCA (363) | UUCAGCCAGGCUAGUGCAGUC (368) |
| | UUCAGCC (366) | CUUCAGCCAGGCUAGUGCAGUC (369) |
| | CAGCCAG (367) | UCAGCCAGGCUAGUGCAGUCU (370) |
| | | UUCAGCCAGGCUAGUGCAGU (371) |
| | | CUUCAGCCAGGCUAGUGCAGUCUG (372) |

The invention claimed is:

1. A method for treating, reverting, and/or delaying a disease or a condition associated with a squamous cell carcinoma wherein the disease or condition is head and neck squamous cell carcinoma (HNSCC) by administering to a subject in need thereof a miRNA-323 molecule, isomiR, or a precursor thereof, or a composition comprising said miRNA-323 molecule, isomiR, or a precursor thereof
wherein said miRNA-323 molecule or isomiR comprises at least 6 nucleotides of the 7 nucleotides present in the seed sequence identified as SEQ ID NO: 11, 12, 61, 62, 63, 64, 65, 66, 67, 68, 69 and/or 70 and/or has at least 70% identity over SEQ ID NO: 22, 23, 203, 204, 205, 206, 207, 208, 209, 210, 211, 212, 213, 214, 215, 216, 217, 218, 219, 220, 221 222, 223, 224, 225, 226, 227, 228 and/or 229 and has a length from 6 to 40 nucleotides,
wherein the precursor is a precursor of a miRNA-323 molecule or isomiR and has at least 70% identity with SEQ ID NO:3 and/or 31 and has a length of at least 50 nucleotides.

2. A method for treating, reverting, and/or delaying a disease or a condition associated with a squamous cell carcinoma, wherein the disease or condition is head and neck squamous cell carcinoma (HNSCC) by administering to a subject in need thereof a miRNA-323 and/or miRNA-342 molecule, isomiR, or a precursor thereof, or a composition comprising said miRNA-323 and/or miRNA-342 molecule, isomiR, or a precursor thereof
wherein said miRNA-323 molecule or isomiR comprises at least 6 nucleotides of the 7 nucleotides present in the seed sequence identified as SEQ ID NO: 11, 12, 61, 62, 63, 64, 65, 66, 67, 68, 69 and/or 70 and/or has at least 70% identity over SEQ ID NO: 22, 23, 203, 204, 205, 206, 207, 208, 209, 210, 211, 212, 213, 214, 215, 216, 217, 218, 219, 220, 221 222, 223, 224, 225, 226, 227, 228 and/or 229 and has a length from 6 to 40 nucleotides,
wherein said miRNA-342 molecule or isomiR comprises at least 6 of the 7 nucleotides present in the seed sequence identified as SEQ ID NO: 14, 15, 79, 80, 81, 82, 83, 84, 85, 86, 87, 88, 89, 90, 91, 92, 93, 94, 95, 96, 97, 98 and/or 99 and/or has at least 70% identity over SEQ ID NO: 25, 26, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 15 289, 290, 291, 292, 293, 294, 295, 296, 297, 298, 299, 300, 301, 302, 303, 304, 305, 306, 307, 308, 309, 310, 311, 312, 313, 314, 315, 316, 317 and/or 318 and has a length from 6 to 40 nucleotides,
wherein the precursor of a miRNA-342 molecule or isomiR has at least 70% identity with SEQ ID NO:5 and/or 33 and has a length of at least 50 nucleotides,
wherein the precursor of a miRNA-323 molecule or isomiR has at least 70% identity with SEQ ID NO:3 and/or 31 and has a length of at least 50 nucleotides.

* * * * *